US008394765B2

(12) United States Patent  
Roth et al.

(10) Patent No.: US 8,394,765 B2
(45) Date of Patent: Mar. 12, 2013

(54) METHODS OF TREATING OBESITY WITH TWO DIFFERENT ANTI-OBESITY AGENTS

(75) Inventors: Jonathan D. Roth, San Diego, CA (US); Christen M. Anderson, Encinitas, CA (US); Alain D. Baron, San Diego, CA (US)

(73) Assignees: Amylin Pharmaceuticals LLC, San Diego, CA (US); AstraZeneca Pharmaceuticals LP, Wilmington, DE (US)

( * ) Notice: Subject to any disclaimer, the term of this patent is extended or adjusted under 35 U.S.C. 154(b) by 239 days.

(21) Appl. No.: 11/940,317

(22) Filed: Nov. 14, 2007

(65) Prior Publication Data

US 2008/0207512 A1 Aug. 28, 2008

Related U.S. Application Data

(63) Continuation-in-part of application No. 11/665,675, filed as application No. PCT/US2005/039686 on Nov. 1, 2005.

(60) Provisional application No. 60/624,357, filed on Nov. 1, 2004.

(51) Int. Cl.
*A61K 38/00* (2006.01)
*A61K 38/16* (2006.01)
*A61K 38/22* (2006.01)

(52) U.S. Cl. ............ 514/4.8; 514/1.1; 514/5.8; 514/6.8; 514/6.9; 514/21.3

(58) Field of Classification Search ................... None
See application file for complete search history.

(56) References Cited

U.S. PATENT DOCUMENTS

| | | | |
|---|---|---|---|
| 3,914,250 A | 10/1975 | Kim | |
| 4,973,587 A | 11/1990 | Ward et al. | |
| 5,013,837 A | 5/1991 | Ward et al. | |
| 5,081,122 A | 1/1992 | Ward et al. | |
| 5,112,820 A | 5/1992 | Ward et al. | |
| 5,264,372 A | 11/1993 | Beaumont et al. | |
| 5,292,736 A | 3/1994 | Kumar et al. | |
| 5,462,960 A | 10/1995 | Barth et al. | |
| 5,521,283 A | 5/1996 | DeMarchi et al. | |
| 5,532,237 A | 7/1996 | Gallant et al. | |
| 5,552,522 A | 9/1996 | Basinski et al. | |
| 5,552,523 A | 9/1996 | Basinski et al. | |
| 5,552,524 A | 9/1996 | Basinski et al. | |
| 5,580,953 A | 12/1996 | Albrecht et al. | |
| 5,596,106 A | 1/1997 | Cullinan et al. | |
| 5,625,032 A | 4/1997 | Gaeta et al. | |
| 5,686,411 A | 11/1997 | Gaeta et al. | |
| 5,739,106 A | 4/1998 | Rink et al. | |
| 5,747,524 A | 5/1998 | Cullinan et al. | |
| 5,856,098 A | 1/1999 | Snodgrass et al. | |
| 6,001,836 A | 12/1999 | Poindexter et al. | |
| 6,007,998 A | 12/1999 | Rosenblum et al. | |
| 6,017,919 A | 1/2000 | Inaba et al. | |
| 6,028,084 A | 2/2000 | Barth et al. | |
| 6,114,304 A | 9/2000 | Kolterman et al. | |
| 6,124,331 A | 9/2000 | Marzabadi et al. | |
| 6,140,354 A | 10/2000 | Dax et al. | |
| 6,172,108 B1 | 1/2001 | Vega et al. | |
| 6,180,653 B1 | 1/2001 | Fukami et al. | |
| 6,191,160 B1 | 2/2001 | Gao et al. | |
| 6,214,853 B1 | 4/2001 | Marzabadi et al. | |
| 6,245,916 B1 | 6/2001 | Fauchere et al. | |
| 6,258,837 B1 | 7/2001 | Fukami et al. | |
| 6,262,112 B1 | 7/2001 | Mittendorf et al. | |
| 6,313,298 B1 | 11/2001 | Fukami et al. | |
| 6,326,375 B1 | 12/2001 | Fukami et al. | |
| 6,329,395 B1 | 12/2001 | Dugar et al. | |
| 6,335,345 B1 | 1/2002 | Fukami et al. | |
| 6,337,332 B1 | 1/2002 | Carpino | |
| 6,340,683 B1 | 1/2002 | Marzabadi et al. | |
| 6,344,474 B1 | 2/2002 | Maruani et al. | |
| 6,365,633 B1 | 4/2002 | Cheetham et al. | |
| 6,399,745 B1 | 6/2002 | Ertl et al. | |
| 6,410,511 B2 | 6/2002 | L'Italien et al. | |
| 6,458,924 B2 | 10/2002 | Knudsen et al. | |
| 6,469,054 B1 | 10/2002 | Mittendorf et al. | |
| 6,545,050 B1 | 4/2003 | Mittendorf et al. | |
| 6,624,334 B1 | 9/2003 | Biller et al. | |
| 6,624,941 B2 | 9/2003 | Takeuchi et al. | |
| 6,686,337 B2 | 2/2004 | Connor | |
| 6,777,388 B1 | 8/2004 | Grasso et al. | |
| 6,936,439 B2 | 8/2005 | Mann et al. | |
| 6,956,026 B2 | 10/2005 | Beeley et al. | |
| 7,141,561 B2 | 11/2006 | Schwink | |
| 7,402,663 B2 | 7/2008 | Flatt et al. | |
| 2001/0011071 A1 | 8/2001 | Knudsen et al. | |
| 2003/0073728 A1 | 4/2003 | van Poelje et al. | |
| 2003/0158177 A1 | 8/2003 | Ishihara et al. | |
| 2003/0220255 A1 | 11/2003 | Knudsen et al. | |
| 2004/0077628 A1 | 4/2004 | Ishihara et al. | |
| 2004/0116657 A1 | 6/2004 | Flatt et al. | |
| 2004/0122033 A1 | 6/2004 | Nargund et al. | |
| 2004/0132752 A1 | 7/2004 | Schwink et al. | |
| 2004/0214837 A1 | 10/2004 | Griffith et al. | |
| 2004/0214855 A1 | 10/2004 | Carpino et al. | |
| 2005/0069987 A1 | 3/2005 | Daley et al. | |
| 2005/0143303 A1 | 6/2005 | Quay et al. | |
| 2005/0171110 A1 | 8/2005 | Yu et al. | |
| 2006/0058224 A1* | 3/2006 | Yancopoulos et al. ............ 514/2 |
| 2006/0135559 A1 | 6/2006 | Sato et al. | |

FOREIGN PATENT DOCUMENTS

| CA | 2136893 | 6/1995 |
|---|---|---|
| CA | 2284051 | 10/1998 |

(Continued)

OTHER PUBLICATIONS

Bays, Harold Obesity Research, 2004, vol. 12, Issue 8, pp. 1197-1211.*
Anderson et al., "Ligands to the Melanocortin Receptors" (2001) Expert Opin. Ther. Patents 11:1583-1592.
Anderson et al. "[3H]Methoxymethyl-3-[(2-methyl-1,3-thiazol-4- . . . " (2002) J. Pharmacol. Exp. Ther. 303:1044-1051.

(Continued)

*Primary Examiner* — Robert Landsman
*Assistant Examiner* — Ian Dang

(57) ABSTRACT

Methods for treating obesity or obesity related disorders are disclosed. These methods include the use of anti-obesity agents directed to the forebrain in combination with anti-obesity agents directed to the hindbrain.

33 Claims, 28 Drawing Sheets

FOREIGN PATENT DOCUMENTS

| | | |
|---|---|---|
| EP | 0656354 | 6/1997 |
| EP | 1010691 | 6/2000 |
| EP | 0658546 | 5/2001 |
| EP | 1044970 | 1/2003 |
| JP | 13226269 | 8/2001 |
| WO | WO01/16234 | 8/1991 |
| WO | WO93/10146 | 5/1993 |
| WO | WO96/05309 | 2/1996 |
| WO | WO96/40912 | 2/1996 |
| WO | WO96/31526 | 10/1996 |
| WO | WO96/33159 | 10/1996 |
| WO | WO96/40912 | 12/1996 |
| WO | WO97/06816 | 2/1997 |
| WO | WO97/18833 | 5/1997 |
| WO | WO97/19682 | 6/1997 |
| WO | WO97/20820 | 6/1997 |
| WO | WO97/20821 | 6/1997 |
| WO | WO97/20822 | 6/1997 |
| WO | WO97/20823 | 6/1997 |
| WO | WO97/29079 | 8/1997 |
| WO | WO97/38014 | 10/1997 |
| WO | WO98/05351 | 2/1998 |
| WO | WO98/08512 | 3/1998 |
| WO | WO98/22128 | 5/1998 |
| WO | WO98/27063 | 6/1998 |
| WO | WO98/28427 | 7/1998 |
| WO | WO98/30231 A1 | 7/1998 |
| WO | WO98/31227 | 7/1998 |
| WO | WO98/33765 | 8/1998 |
| WO | WO98/37061 | 8/1998 |
| WO | WO99/07404 | 8/1998 |
| WO | WO98/41519 | 9/1998 |
| WO | WO98/43635 | 10/1998 |
| WO | WO98/43636 | 10/1998 |
| WO | WO99/25727 | 11/1998 |
| WO | WO98/55144 | 12/1998 |
| WO | WO99/02499 | 1/1999 |
| WO | WO99/14239 | 3/1999 |
| WO | WO99/25728 | 5/1999 |
| WO | WO99/43705 | 9/1999 |
| WO | WO99/51600 | 10/1999 |
| WO | WO00/10967 | 3/2000 |
| WO | WO00/10968 | 3/2000 |
| WO | WO00/20872 | 4/2000 |
| WO | WO00/21509 | 4/2000 |
| WO | WO00/25806 | 5/2000 |
| WO | WO02/068387 | 9/2000 |
| WO | WO00/64880 | 11/2000 |
| WO | WO00/66629 A1 | 11/2000 |
| WO | WO00/68197 | 11/2000 |
| WO | WO00/69849 | 11/2000 |
| WO | WO01/02379 | 1/2001 |
| WO | WO01/07409 | 2/2001 |
| WO | WO01/09120 | 2/2001 |
| WO | WO01/14376 | 3/2001 |
| WO | WO01/23387 | 4/2001 |
| WO | WO01/23388 | 4/2001 |
| WO | WO01/23389 | 4/2001 |
| WO | WO01/27060 | 4/2001 |
| WO | WO01/44201 | 6/2001 |
| WO | WO01/58869 | 8/2001 |
| WO | WO01/62737 | 8/2001 |
| WO | WO01/62738 | 8/2001 |
| WO | WO01/66548 | 9/2001 |
| WO | WO01/68609 | 9/2001 |
| WO | WO01/82925 | 11/2001 |
| WO | WO01/85098 | 11/2001 |
| WO | WO01/85173 | 11/2001 |
| WO | WO01/85690 | 11/2001 |
| WO | WO01/85714 | 11/2001 |
| WO | WO01/85730 | 11/2001 |
| WO | WO01/87834 | 11/2001 |
| WO | WO01/89528 | 11/2001 |
| WO | WO01/96302 | 12/2001 |
| WO | WO02/04433 | 1/2002 |
| WO | WO02/06245 | 1/2002 |
| WO | WO02/10169 | 2/2002 |
| WO | WO02/22592 | 3/2002 |
| WO | WO02/36596 | 5/2002 |
| WO | WO02/40456 | 5/2002 |
| WO | WO02/40457 | 5/2002 |
| WO | WO02/44152 | 6/2002 |
| WO | WO02/48124 | 6/2002 |
| WO | WO02/49648 | 6/2002 |
| WO | WO0248152 | 6/2002 |
| WO | WO02/051232 | 7/2002 |
| WO | WO02/051809 | 7/2002 |
| WO | WO02/051838 | 7/2002 |
| WO | WO02/051844 | 7/2002 |
| WO | WO02/067869 | 9/2002 |
| WO | WO02/068388 | 9/2002 |
| WO | WO02/076949 | 10/2002 |
| WO | WO03/000663 A1 | 1/2003 |
| WO | WO03/007949 | 1/2003 |
| WO | WO03/031410 | 4/2003 |
| WO | WO03/040117 | 5/2003 |
| WO | WO03/045920 A1 | 6/2003 |
| WO | WO03/047568 A1 | 6/2003 |
| WO | WO03/057235 A2 | 7/2003 |
| WO | WO03/066587 | 8/2003 |
| WO | WO03/068738 | 8/2003 |
| WO | WO03/094918 | 11/2003 |
| WO | WO2004/009015 A2 | 1/2004 |
| WO | WO2004/046324 A2 | 7/2004 |
| WO | WO2004/056324 A2 | 7/2004 |
| WO | WO2005/027978 A2 | 3/2005 |
| WO | WO2005/049088 | 6/2005 |
| WO | WO2005/077072 | 8/2005 |
| WO | WO96/14307 | 5/2006 |
| WO | WO2006/052608 | 5/2006 |
| WO | WO2006/083254 | 8/2006 |
| WO | WO2006/086769 | 8/2006 |
| WO | WO2006/105345 | 10/2006 |
| WO | WO2006/105527 | 10/2006 |
| WO | WO 2007/055728 | 5/2007 |
| WO | WO 2007/055743 | 5/2007 |

OTHER PUBLICATIONS

Anderson et al., "In vivo receptor occupancy of mGlu5 receptor antagonists . . . " (2003) J. Eur. J. Pharmacol. 473:35-40.

Batterham et al., "Gut hormone PYY3-36 physiologically inhibits food intake" (2002) Nature, 418:650-655.

Batterham et al., "Pancreatic Poly0peptide Reduces Appetite and Food Intake in Humans" (2003) J. Clin. Endocrinol. Metab. 88:3989-3992.

Bedarnek et al., "Ligands of the Melanocortin Receptors, 2002-2003 Update" (2004) Expert Opin. Ther. Patents 14:327-336.

Cabrele et al., "Molecular Characterization of the Ligand-Receptor . . . " (2000) J. Pept. Sci. 6:97-122.

Cooper et al., "Amylin Found in Amyloid in Human Type 2 Diabetes Mellitus . . . " (1988) Proc. Natl. Acad. Sci. USA 85:7763-7766.

Cosford et al., "[3H]-Methoxy-MTEP and [3H]-Methodxy-PEPy: Potent and Selective . . . " (2003) Bioorg. Med. Chem. Lett. 13(3):351-4.

Duhault et al., "Food Intake Regulation in Rodents Y5 or Yl, NPY . . . " (2000) Can. J Physiol. Pharm. 78:173-185.

Raposhino et al., Stimulation of the Gonadotropic Axis by the . . . (2000) Neuroendocrinology 71:2-7.

Reidmeister et al., "Substituted N-Phenylcarbamates as Histamine H3 Receptor Antagonists" (2000) Pharmazie 55:83-86.

Sasse et al. (2000) J. Med. Chem. 43:3335-3343.

Sasse et al., "Benzophenone Derivatives and Related Compounds as Potent Histamine H3-Receptor"(2001) Arch. Pharm.(Weinheim) 334:45-52.

Speake et al., "Recent Advances in the Development of Melanocortin-4 Receptor Agonists", (2002) Expert Opin. Ther. Patents 12:1631-163.

Wadden, Treatment of Obesity of Moderate and Severe Caloric Restriction . . . (1993) Ann. Intern. Med. 119:688-693.

Weintraub et al., "A Double Blind Clinical Trial in Weight Control . . . " (1984) Arch. Intern. Med. 144:1143-1148.

White-Smith et al., "Structure-Activity Analysis of N-Acetyl ) Leu 28,31] . . . " (1999) Neuropeptides 33:526-533.

Farooqi et al., "Effects of Recombinant Leptin Therapy in a Child with Congenital Leptin Deficiency" (1999) N. Engl. J. Med. 341:879-884.
Halford et al., "Serotonin (5-HT) Drugs: Effects on Appetite Expression and Use . . . " (2005) Curr. Drug Targets 6:201-213.
Heymsfield at al., "Recombinant Leptin for Weight Loss in Obese and Lean Adults", (1999) JAMA 282:1568-1575.
Kiec-Konowicz at al., "Importance of Lipophilic Group in Carbamates Having . . . " (2000) Pharmazie 55:349-355.
Lazewska at al., "Piperidine-Containing Histamine H3-Receptor Antagonists . . . " (2001) Pharmazie 56:927-932.
Leightgon et al., "Pancreatic Amylin & Calcitonin Gene-Related Peptide . . . " (1988) Nature 335:632-635.
Malis et al., "Influence of TASP-V, a Novel Neuropeptide Y(NPY) Y2, Agonists . . ." (1999) Br. J. Pharmacol. 126:989-996.
Mantozoros et al., "Editorial: Leptin as a Therapeutic Agent-Trials and Tribulations . . . " (2000) J. Clin. Endocrinol. Metab. 85:4000-4002.
Munson et al., "Ligand: A Versatle Computerized Approach for Characterization of Ligan-Binding Systems" (1980) Anal. Biochem. 107:220-239.
Nih, "Methods for Voluntary Weight Loss and Control" Technology Assessment Conference Panel (1992) Ann. Intern. Med. 116:942-949.
Eiden, Sandra, et al., "Salmon Calcitonin—A Potent Inhibitor of Food Intake in States of Impaired Leptin Signalling in Laboratory Rodents", Journal of Physiology (2002), 541.3, pp. 1041-1048.
Dingemans, et al., "Binge eating disorder: a review", International Journal of Obesity (2002) 26, pp. 299-307.
Reda, et al., "Amylin, Food Intake, and Obesity", Obesity Research, vol. 10, No. 10, Oct. 2002, pp. 1087-1091.
Gutzwiller, J.P., et al., "Interaction Between GLP-1 and CCK-33 in Inhibiting Food Intake and Appetite in Men", Am. J. Physiol. Regul. Integr. Comp. Physiol. Apr. 2004, vol. 287, pp. R562-R567.
Matson, C.A., et al., "Synergy Between Leptin and Cholecystokinin(CCK) to Control Daily Caloric Intake" Peptides, (1997) vol. 18, No. 8, pp. 1275-1278.
Matson, C.A., et al., "Cholecystokinin and Leptin Act Synergistically to Reduce Body Weight" Am J Physiol. Regul. Integ. Comp. Physiol. (2000) 278: R882-R890.
Repetto, et al., "Use of sibutramine in superobese patients undergoing to bariatric surgery", International Journal of Obesity, vol. 25, No. Supplement 2, May 2001, p. S114.
Muratori, et al., "Efficacy of sibutramine in subjects who regained weight after bariatric surgery", International Journal of Obesity, vol. 26, No. Supplement 1, Aug. 2002, p. S150.
Hanusch-Enserer, et al., "News in gut-brain communication: a role of peptide YY (PYY) in human obesity and following bariatric surgery?", European Journal of Clinical Investigation, Jul. 2005, vol. 35, No. 7, Jul. 2005, pp. 425-430.
Zilberstein, et al., "Topiramte after adjustable gastric banding in patients with binge eating and difficulty losing weight", Obesity Surgery: The Official Journal of the American Society for Bariatric Surgery and the Obesity Surgery Society of Australia and New Zealand 2004 June-July, vol. 14, No. 6, Jun. 2004, pp. 802-805.
Guerdjikova, et al., "Response of recurrent binge eating and weight gain to topiramate in patients with binge eating disorder after bariatric surgery", Obesity Surgery: The Official Journal of the American Society for Bariatric Surgery and the Obesity Surgery Society of Australia and New Zealand Feb. 2005, vol. 15, No. 2, Feb. 2005, pp. 273-277.
Halford, et al., "The psychopharmacology of appetite: Targets for potential anti-obesity agents", Current Medicinal Chemistry—Central Nervous System Agents, vol. 3, NR. 4, Dec. 2003, pp. 383-310.
Ratner, et al., "Adjunctive therapy with the amylin analogue pramlintide leads to a combined improvement in glycemic and weight control in insulin-treated subjects with type 2 diabetes", Diabetes Technology & Therapeutics, vol. 4, NR. 1, 2002, pp. 51-61.
Morley, et al., "Effects of amylin on appetite regulation and memory", Canadian Journal of Physiology and Pharmacology, Ottawa, Ont., CA, vol. 73, Jul. 1m 1995, pp. 1042-1046.
Hukshorn, et al.,"Weekly Subcutaneous Pegylated Recombinant Native Human Leptin (PEG-OB) Administration in Obese Men", The Journal of Clinical Endocrinology & Metabolism, vol. 85, No. 11, 2000, pp. 4003-4009.
Roth, et al., "Effects of prior or concurrent food restriction on amylin-induced changes in body weight and body composition in high-fat-fed female rats", Am J. Physiol Endocrinol Metal 293,Aug. 14, 2007, pp. 1112-1117.
Osto, et al., "Modulation of the satiating effect of amylin by central ghrelin, leptin and insulin", Physiology & Behavior 91, 2007, pp. 566-572.
Chicurel, M., "Whatever happened to leptin?", Nature, vol. 404, pp. 538-540 (2000).
Huckshorn et al., "Pegylated human recombinant leptin (PEG-OB) causes additional weight loss in severely energy-restricted, overweight men", Am J Clin Nutr, vol. 77, pp. 771-776 (2003).
Scarpace et al., "Leptin resistance exacerbates diet-induced obesity and is associated with diminished maximal leptin signaling capacity in rats", Diabetologia, vol. 48, pp. 1075-1083 (2005).
Tenenbaum, D, "Leptin's legacy", HHMI Bulletin, vol. 16(1), pp. 24-27 (Mar. 2003).
Batterham, et al., "The gut hormone peptide YY regulates appetite", 2003, Ann. N.Y. Acad. Sci. 994, pp. 162-168.
Shimosawa, et al., "Deficiency of adrenomedullin induces insulin resistance by increasing oxidative stress", Hypertension, vol. 5, May 2003, pp. 1080-1085.
Wasan, et al., "Emerging pharmacological approaches to the treatment of obesity", Journal of Pharmacy & Pharmaceutical Sciences, 2005, pp. 259-271.
Roth, et al., "Responsiveness to leptin restored by amylin in diet induced obese (DIO) rats: Magnitured and mechanisms of synergy", Diabetes, [Online] Jun. 2007, retrieved from the Internet: URL:http://professional.diabetes.org/Abstracts_Display.aspx?TYP=1 &CID=55418, 67th Annual Meeting of the American-Diabetes-Association; Chicago, IL, USA; Jun. 22-26, 2007, Abstract No. 0277-OR, 1pg.
Roth, et al., "Leptin responsiveness restored by amylin agonism in diet-induced obesity: Evidence from nonclinical and clinical studies", Proceedings of the National Academy of Sciences of the Unites States of America, vol. 105, No. 20, May 20, 2008, pp. 7257-7262.
Arnelo, et al., "Effects of Long-Term Infusion of Anorexic Concentrations of Islet Amyloid Polypeptide on Neurotransmitters and Neuropeptides in Rat Brain", Brain Res., 2000, vol. 887, pp. 391-398.
Boden, et al., Effect of Fasting on Serum Leptin in Normal Human Subjects, J. Clin Endocrinol Metab., 1996, vol. 81, pp. 3419-3423.
Grabler, et al., "Chronic infusion of the amylin antagonist AC 187 increases feeding in Zucker fa/fa rats but not in lean controls", Physiol Behav., 2004, vol. 81, pp. 481-488.
Morley, et al., "Modulation of food intake by peripherally administered amylin", Am J Physiol, 1994, vol. 267, pp. R178-R184.
Rushing, et al., "Amylin: a novel action in the brain to reduce body weight", Endocrinology, 2000, vol. 141, pp. 850-853.
EP Patent Application No. 05820773.9 (EP Patent No. 1814590), Notice of Opposition by Novo Nordisk A/S, filed Jan. 5, 2010, 51 pgs.

* cited by examiner

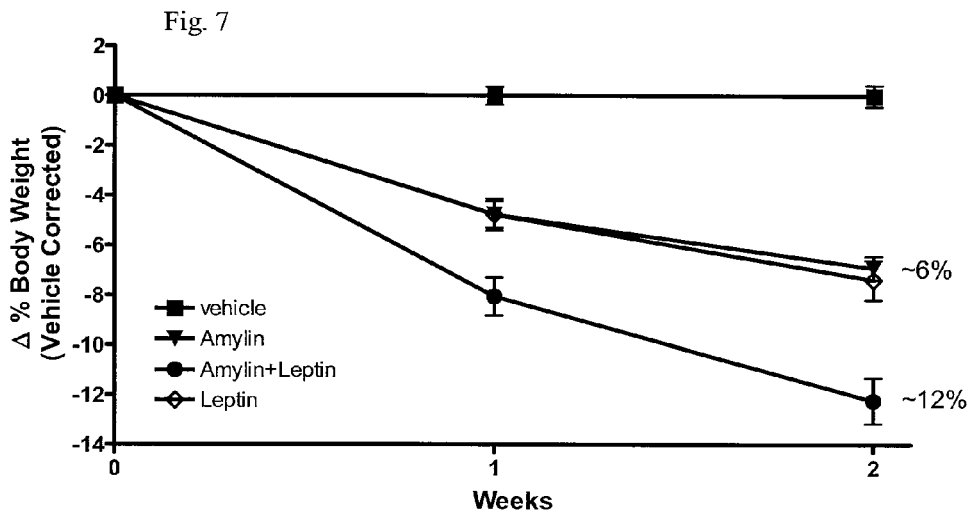
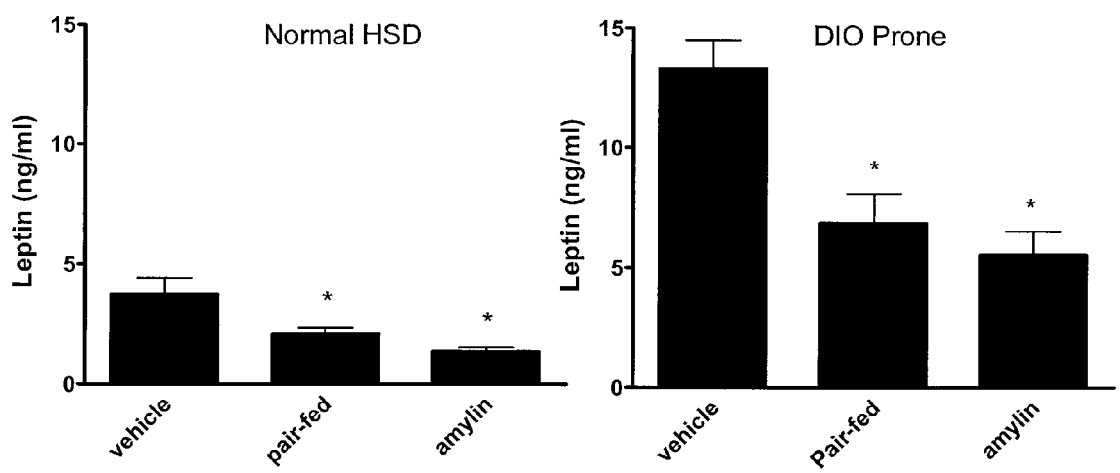

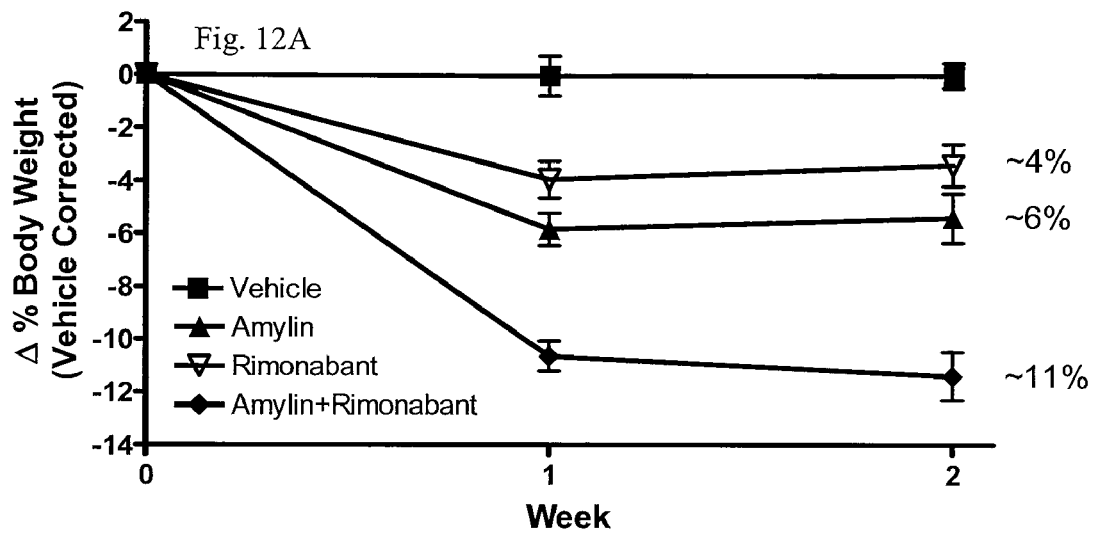
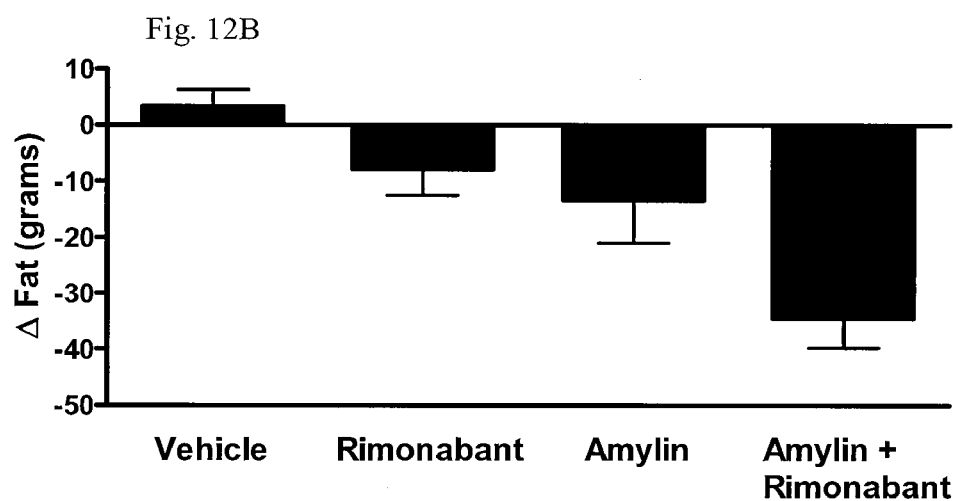
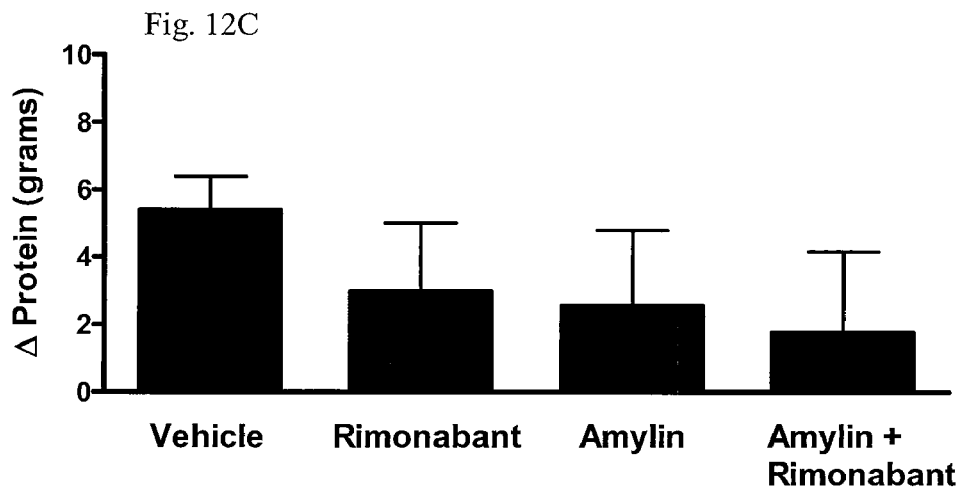

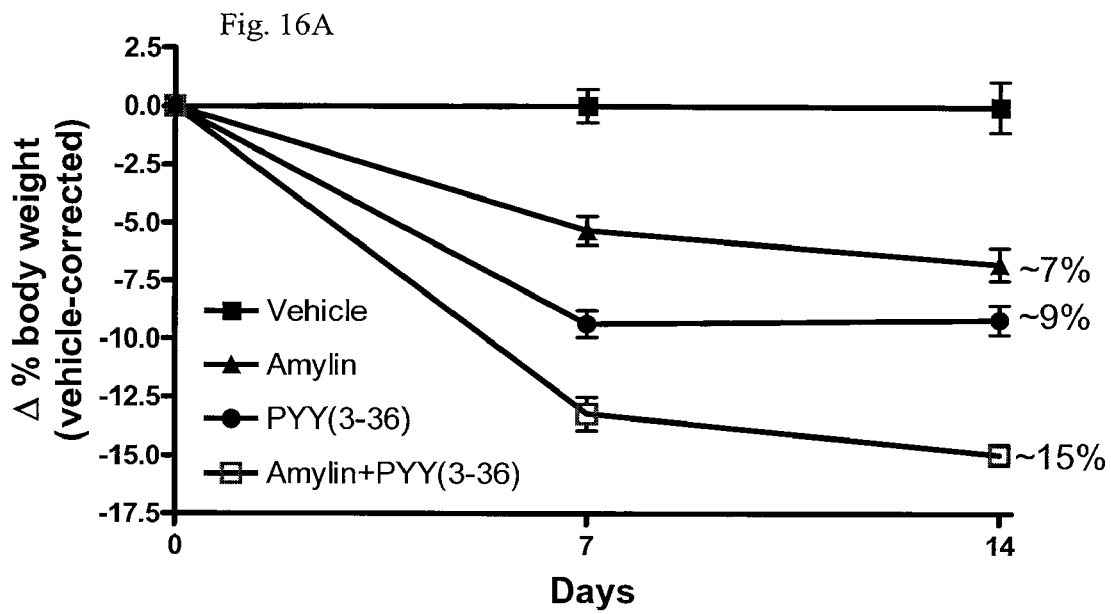
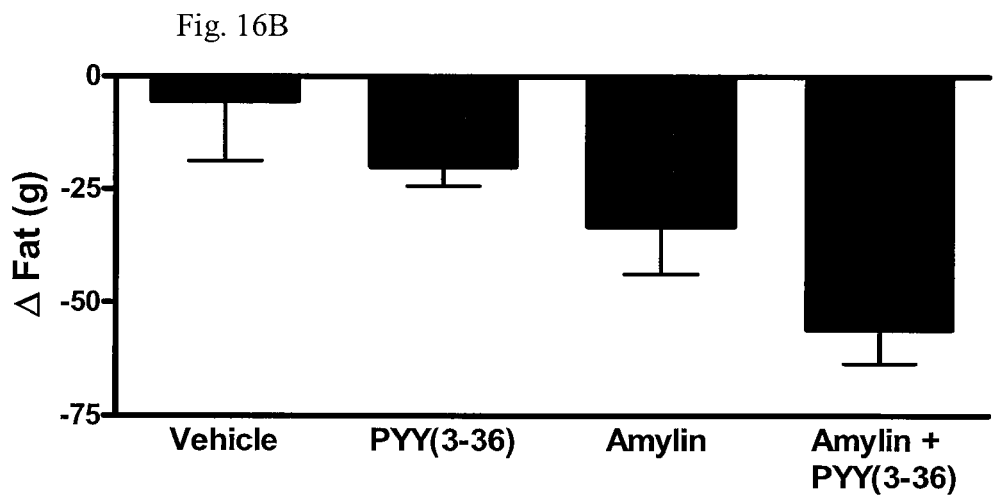
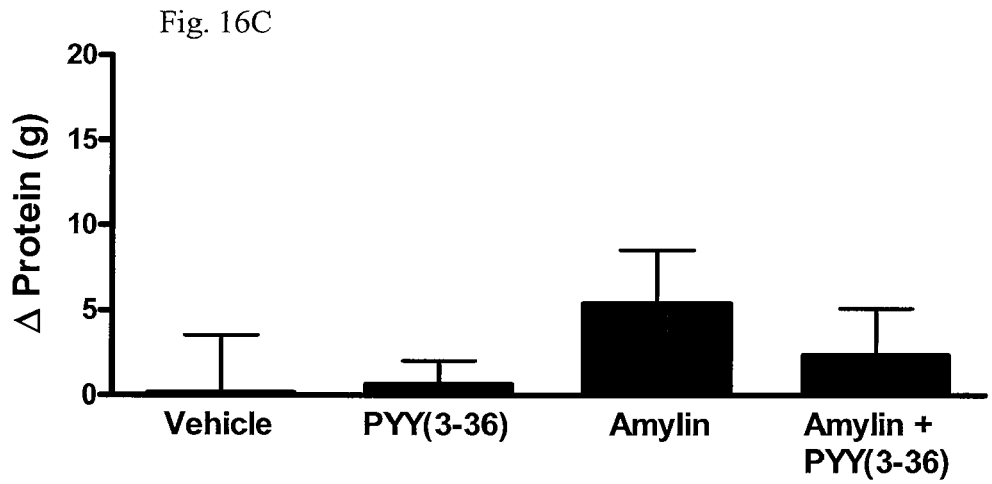

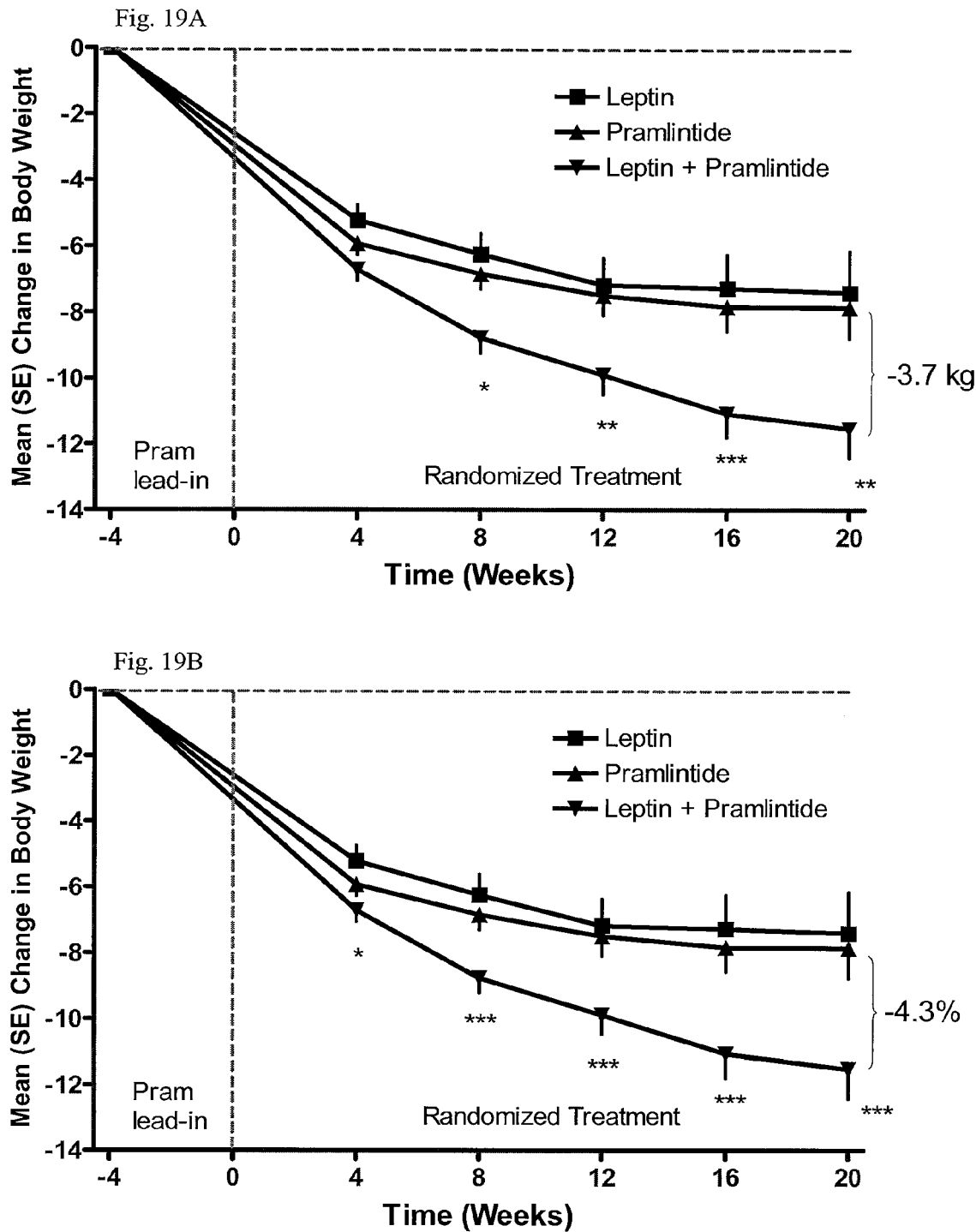

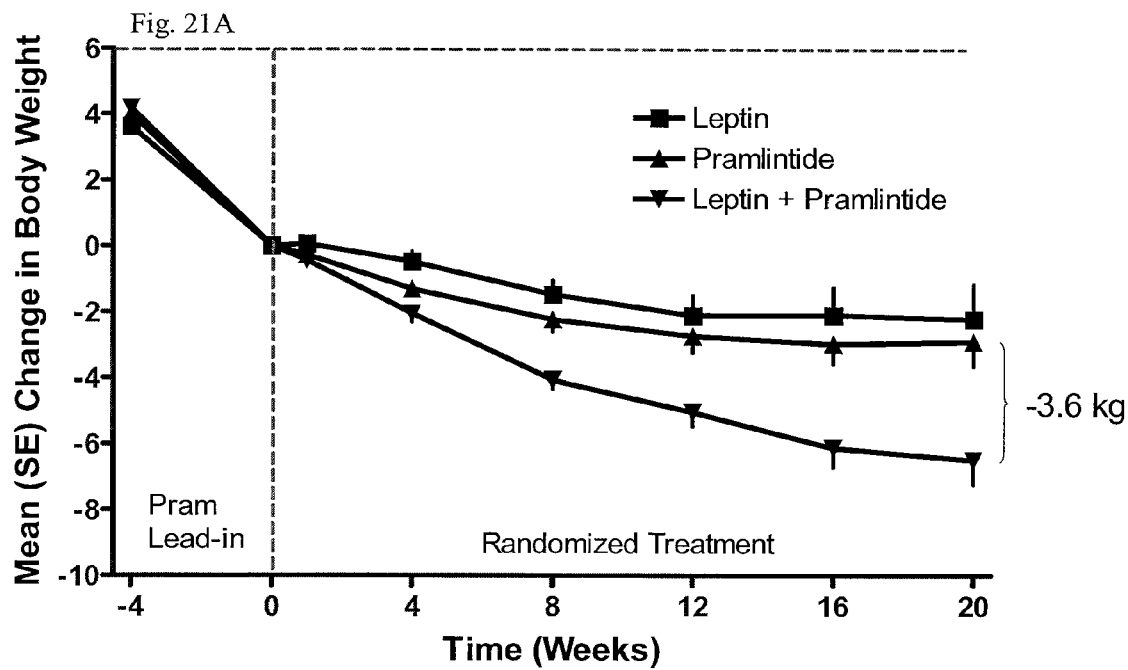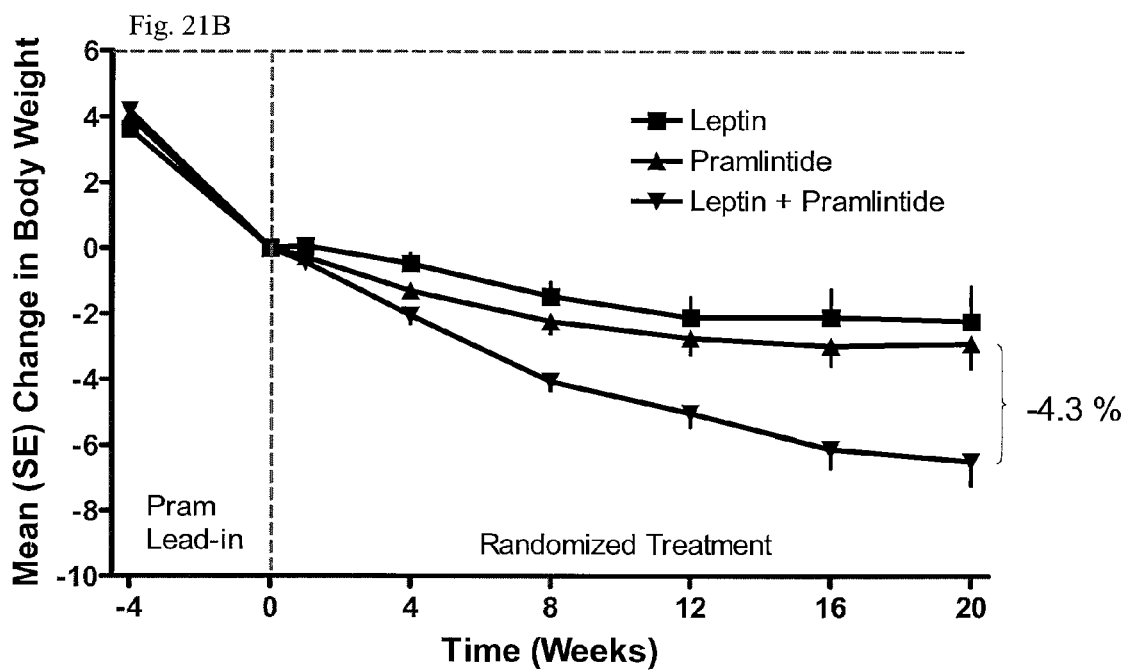

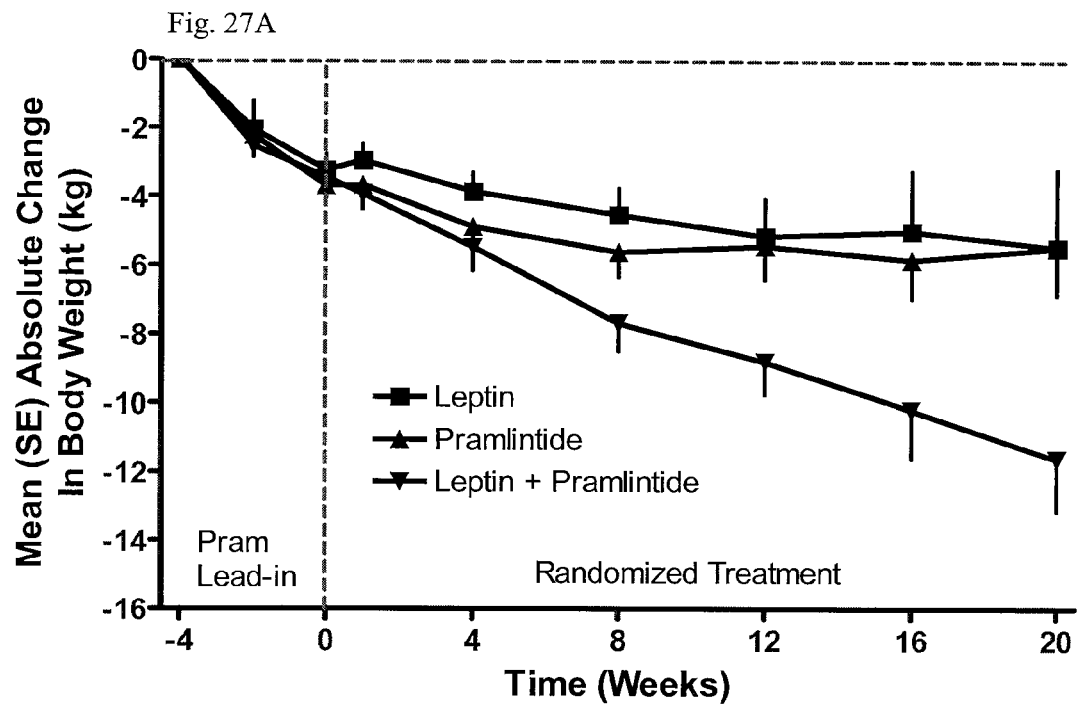
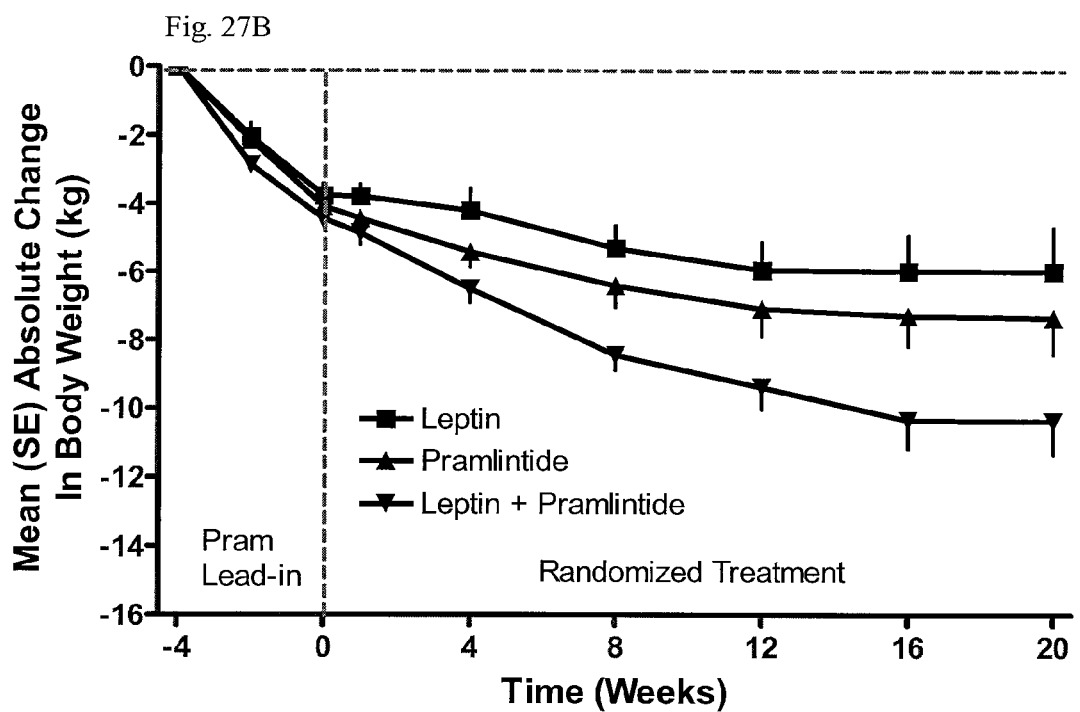

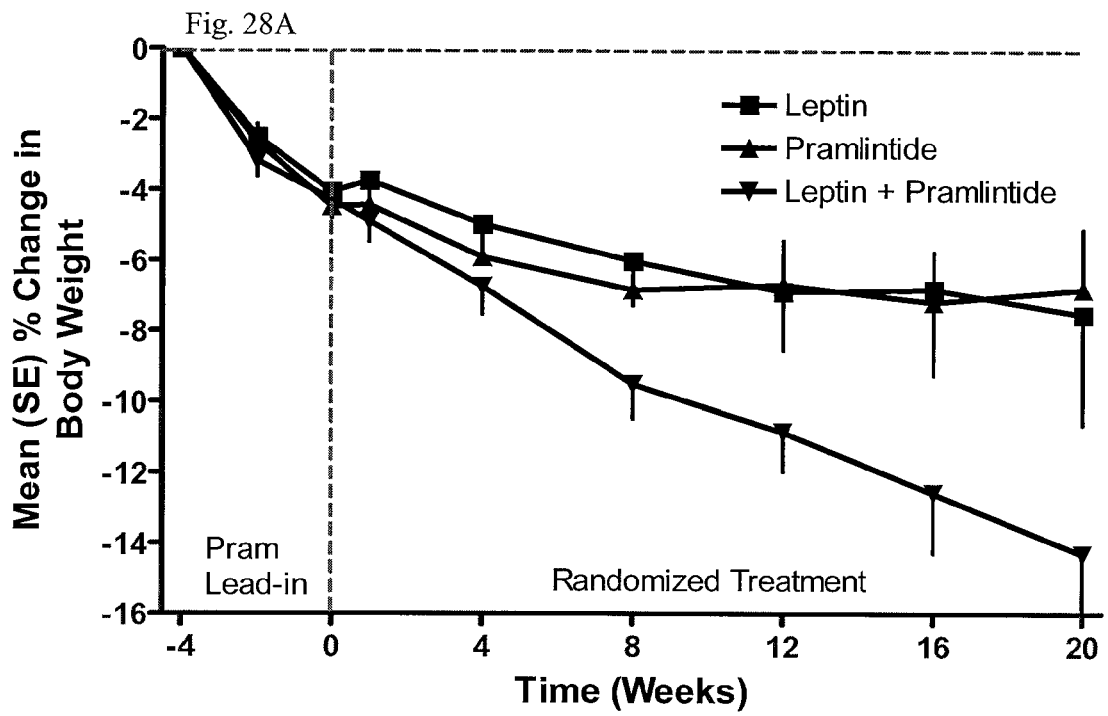
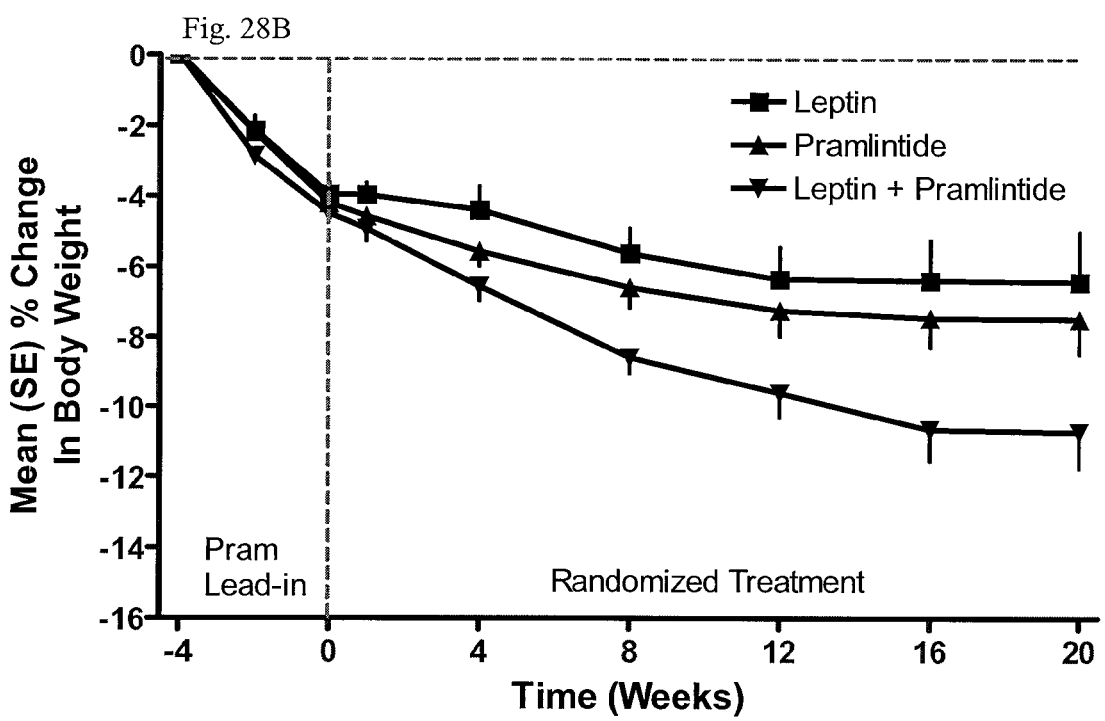

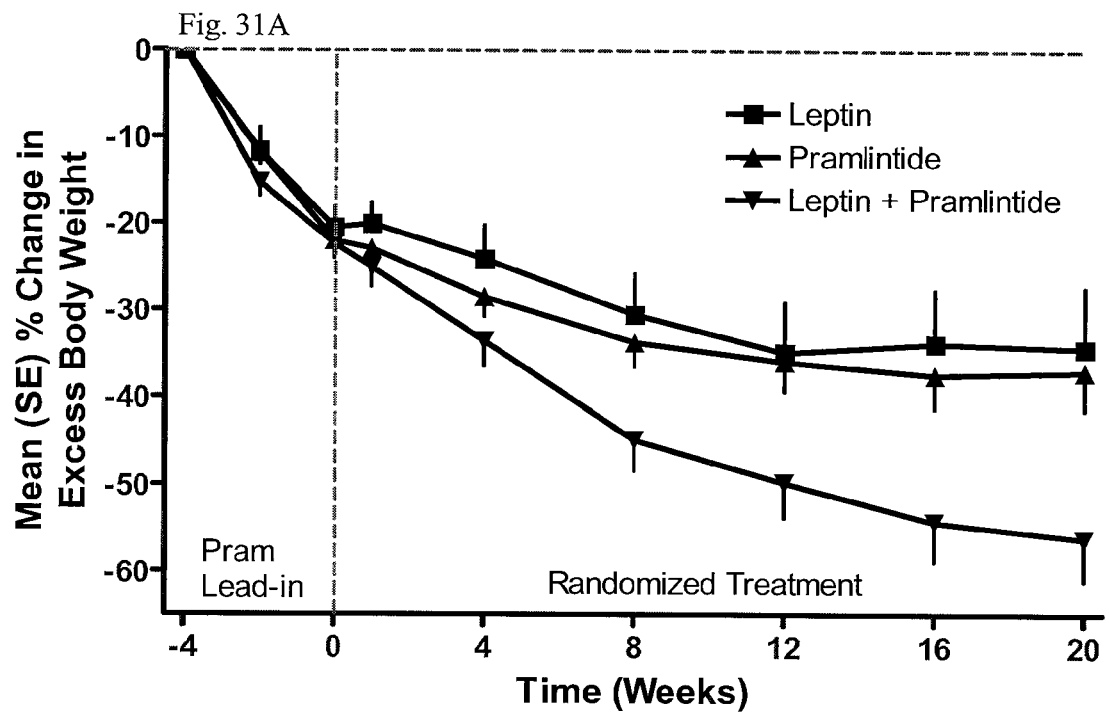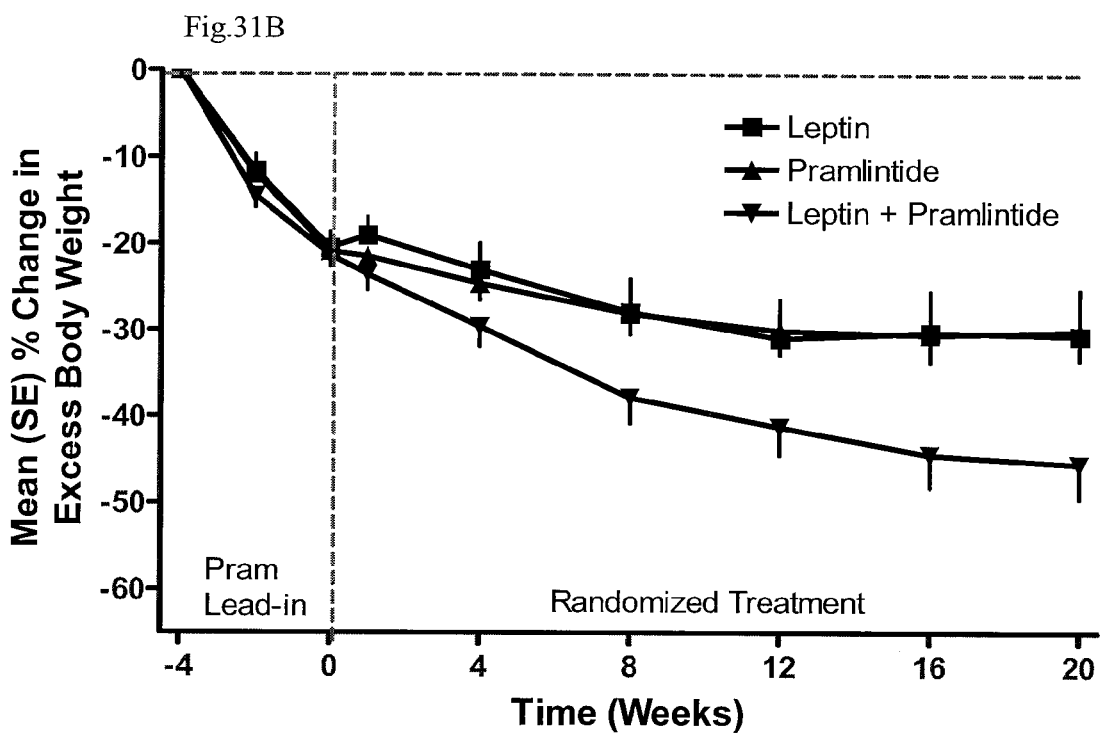

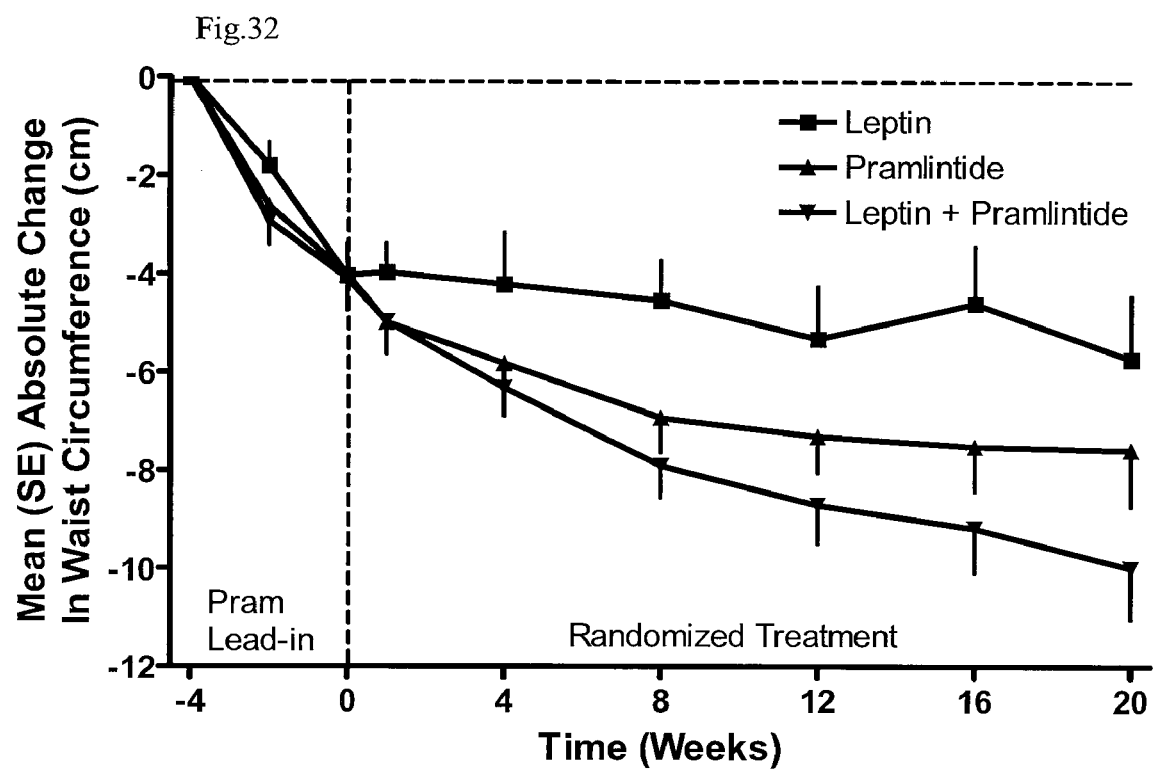

METHODS OF TREATING OBESITY WITH TWO DIFFERENT ANTI-OBESITY AGENTS

CROSS-REFERENCE TO RELATED APPLICATIONS

This application is a continuation-in-part of U.S. patent application Ser. No. 11/665,675, which is a national stage filing of International Application No. PCT/US2005/039686, filed Nov. 1, 2005, which claims the benefit of priority of U.S. Provisional Patent Application No. 60/624,357, filed Nov. 1, 2004, the entire contents of all of which are incorporated by reference herein and for all purposes.

FIELD OF THE INVENTION

The present invention relates to the medical field and in particular to the field of health, diet and nutrition. The invention relates to the use of anti-obesity agents.

BACKGROUND

Obesity and its associated disorders are common and very serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia (see, e.g., Kopelman, *Nature* 404: 635-43 (2000)).

Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al, *Br. Med. J.* 301: 835-7 (1990)). Obesity is also a risk factor for the group of conditions called insulin resistance syndrome, or "Syndrome X" and metabolic syndrome. The worldwide medical cost of obesity and associated disorders is enormous.

The pathogenesis of obesity is believed to be multifactoral. A problem is that, in obese subjects, nutrient availability and energy expenditure do not come into balance until there is excess adipose tissue. The central nervous system (CNS) controls energy balance and coordinates a variety of behavioral, autonomic and endocrine activities appropriate to the metabolic status of the animal. The mechanisms or systems that control these activities are broadly distributed across the forebrain (e.g., hypothalamus), hindbrain (e.g., brainstem), and spinal cord. Ultimately, metabolic (i.e., fuel availability) and cognitive (i.e., learned preferences) information from these systems is integrated and the decision to engage in appetitive (food seeking) and consummatory (ingestion) behaviors is either turned on (meal procurement and initiation) or turned off (meal termination). The hypothalamus is thought to be principally responsible for integrating these signals and then issuing commands to the brainstem. Brainstem nuclei that control the elements of the consummatory motor control system (e.g., muscles responsible for chewing and swallowing). As such, these CNS nuclei have literally been referred to as constituting the "final common pathway" for ingestive behavior.

Neuroanatomical and pharmacological evidence support that signals of energy and nutritional homeostasis integrate in forebrain nuclei and that the consummatory motor control system resides in brainstem nuclei, probably in regions surrounding the trigeminal motor nucleus. There are extensive reciprocal connection between the hypothalamus and brainstem. A variety of CNS-directed anti-obesity therapeutics (e.g., small molecules and peptides) focus predominantly upon forebrain substrates residing in the hypothalamus and/or upon hindbrain substrates residing in the brainstem.

Obesity remains a poorly treatable, chronic, essentially intractable metabolic disorder. Accordingly, a need exists for new therapies useful in weight reduction and/or weight maintenance in a subject. Such therapies would lead to a profound beneficial effect on the subject's health.

All patents, patent applications, and publications cited herein are hereby incorporated by reference in their entirety and for all purposes.

SUMMARY

The present invention provides methods and compositions useful in the control, treatment and prevention of obesity and obesity-related conditions, disorders, and diseases. The methods of the invention involve administration of at least two anti-obesity agents to a subject in amounts effective to control, treat and prevent obesity and obesity-related conditions, disorders and diseases.

In one aspect, the present invention provides methods for reducing nutrient availability in a subject. In another aspect, the invention provides methods for reducing weight of a subject. In one aspect, the present invention provides methods for inducing a synergistic anti-obesity effect among compounds.

In one aspect, the present invention provides methods for treating obesity in a subject comprising peripherally administering therapeutically effective amounts of at least two different anti-obesity agents, wherein at least one anti-obesity agent acts upon structures in the forebrain involved in food intake or body weight modulation and at least one anti-obesity agent that acts upon structures in the hindbrain involved in food intake or body weight modulation, wherein when one anti-obesity agent is a PYY(3-36) a PYY(3-36) analog, or a PYY(3-36) agonist, then another anti-obesity agent is not an amylin, an amylin agonist, an amylin analog, a CCK, a CCK analog, or a CCK agonist, and wherein when one anti-obesity agent is an exendin, an exendin derivative or an exendin agonist, then another anti-obesity agent is not an amylin, an amylin agonist, an amylin analog.

In certain embodiments, the methods of the invention include administration to a subject at least two different anti-obesity agents where at least one of the anti-obesity agents is selected from the group consisting of a NPY1 receptor antagonist, an NPY5 receptor antagonist, an NPY2 receptor agonist, an NPY4 receptor agonist, a leptin, a recombinant leptin, a leptin derivative, a leptin agonist, a CNTF, a CNTF agonist/modulator, a CNTF derivative, a MCH1R antagonist, a MCH2R antagonist, a melanocortin 4 agonist, a MC4 receptor agonist, a cannabinoid receptor (CB-1) antagonist/inverse agonist, a ghrelin antagonist, a 5HT2c agonist, a serotonin reuptake inhibitor, a serotonin transport inhibitor, an exendin, an exendin derivative, an exendin agonist, a GLP-1, a GLP-1 analog, a GLP-1 agonist, a DPP-IV inhibitor, an opioid antagonist, an orexin antagonist, a metabotropic glutamate subtype 5 receptor antagonist, a histamine 3 antagonist/inverse agonist, topiramate, a CCK, a CCK analog, a CCK agonist, an amylin, an amylin analog, and an amylin agonist.

In certain embodiments, the anti-obesity agent administered is phentermine, rimonabant, sibutramine or pramlintide (human $^{25,28,29}$Pro-amylin).

In certain embodiments, the invention provides a method of treating obesity in a subject comprising peripherally administering therapeutically effective amounts of at least two anti-obesity agents, wherein the first anti-obesity agent is selected from the group consisting of a NPY1 receptor antagonist, an NPY5 receptor antagonist, an NPY2 receptor agonist, an NPY4 receptor agonist, a leptin, a recombinant leptin, a leptin derivative, a leptin agonist, a CNTF, a CNTF agonist/modulator, a CNTF derivative, a MCH1R antagonist, a MCH2R antagonist, a melanocortin 4 agonist, a MC4 receptor agonist, a cannabinoid receptor (CB-1) antagonist/inverse agonist, a ghrelin antagonist, a 5HT2c agonist, a serotonin reuptake inhibitor, a serotonin transport inhibitor, an exendin, an exendin derivative, an exendin agonist, a GLP-1, a GLP-1 analog, a GLP-1 agonist, a DPP-IV inhibitor, an opioid antagonist, an orexin antagonist, a metabotropic glutamate subtype 5 receptor antagonist, a histamine 3 antagonist/inverse agonist, topiramate, wherein the second anti-obesity agent is selected from the group consisting of a CCK, a CCK analog, a CCK agonist, an amylin, an amylin analog, and an amylin agonist, wherein when the first anti-obesity agent is not a PYY(3-36) a PYY(3-36) analog, or a PYY(3-36) agonist, and wherein when the first anti-obesity agent is an exendin, an exendin derivative or an exendin agonist, then the second anti-obesity agent is not an amylin, an amylin agonist, an amylin analog.

In certain embodiments, the invention provides methods of treating obesity comprising administration of a first anti-obesity agent selected from an amylin, an amylin analog or an amylin agonist in combination with a second anti-obesity agent selected from a leptin, a recombinant leptin, a leptin derivative or a leptin agonist, wherein the administration of the agents result in a synergistic effect as compared to administration of either agent alone.

In certain embodiments, the invention provides methods whereby the subject reduces body weight by least 10%, the subject reduces body fat mass, the subject loses ectopic fat, or any combination thereof.

In some embodiments, the methods are direct to a subject which suffers from obesity, an obesity-related disorder, an obesity related disease, an obesity-related condition, diabetes, insulin-resistance syndrome, lypodystrpohy, nonalcoholic steatohepatitis, a cardiovascular disease, polycystic ovary syndrome, metabolic syndrome or a desire to lose body weight.

In one aspect, administration of the anti-obesity agents in combination may be simultaneous, concurrent, or sequential administration.

The present invention is also concerned with treatment of obesity and obesity-related conditions, disorders and diseases, and the use of the anti-obesity agents and compositions of the present invention for manufacture of a medicament useful for treating these conditions.

BRIEF DESCRIPTION OF THE DRAWINGS

FIG. 6A is a graph depicting an effect on body weight of administration of leptin (500 μg/kg/day) and amylin (100 μg/kg/day), either alone or in combination over two weeks. FIG. 6B is a graph depicting an effect on body fat of a two-week administration of leptin (500 μg/kg/day) and amylin (100 μg/kg/day), either alone or in combination. FIG. 6C is a graph depicting an effect on body protein of a two-week administration of leptin (500 μg/kg/day) and amylin (100 μg/kg/day), either alone or in combination.

FIG. 7 is a graph depicting an effect on body weight of administration of leptin alone (500 μg/kg/day), pair-fed leptin alone (500 μg/kg/day), and leptin (500 μg/kg/day and amylin (100 μg/kg/day) in combination over two weeks.

FIG. 8 shows graphs depicting serum leptin concentrations in normal HSD and in DIO prone animals that either received vehicle, were pair-fed to the amylin-treated group, or received amylin (100 μg/kg/day) for two weeks.

FIG. 9A is a graph depicting an effect on body weight of administration of vehicle or leptin (500 μg/kg/day) in normal animals. FIG. 9B is a graph depicting an effect on body weight of administration of vehicle or leptin (500 μg/kg/day) in DIO prone animals.

FIG. 10A is a graph depicting an effect on body weight of administration of sibutramine (3 mg/kg/day) and amylin (100 μg/kg/day), either alone or in combination over two weeks. FIG. 10B is a graph depicting an effect on body fat of a two-week administration of sibutramine (3 mg/kg/day) and amylin (100 μg/kg/day), either alone or in combination. FIG. 10C is a graph depicting an effect on body protein of a two-week administration of sibutramine (3 mg/kg/day) and amylin (100 μg/kg/day), either alone or in combination.

FIG. 11A is a graph depicting an effect on body weight of administration of phentermine (10 mg/kg/day) and amylin (100 μg/kg/day), either alone or in combination over two weeks. FIG. 11B is a graph depicting an effect on body fat of a two-week administration of phentermine (10 mg/kg/day) and amylin (100 μg/kg/day), either alone or in combination. FIG. 11C is a graph depicting an effect on body protein of a two-week administration of phentermine (10 mg/kg/day) and amylin (100 μg/kg/day), either alone or in combination.

FIGS. 12A-12C. FIG. 12A is a graph depicting an effect on body weight of administration of rimonabant (3 mg/kg/day) and amylin (100 μg/kg/day), either alone or in combination over two weeks. FIG. 12B is a graph depicting an effect on body fat of a two-week administration of rimonabant (3 mg/kg/day) and amylin (100 μg/kg/day), either alone or in combination. FIG. 12C is a graph depicting an effect on body protein of a two-week administration of rimonabant (3 mg/kg/day) and amylin (100 μg/kg/day), either alone or in combination.

FIG. 14A is a graph depicting the effect of administration of a CB-1 antagonist (1 mg/kg/day) and amylin (100 μg/kg/day), either alone or in combination, on body weight. FIG. 14B is a graph depicting the effect of administration of a CB-1 antagonist (3 mg/kg/day) and amylin (100 μg/kg/day), either alone or in combination, on body weight.

FIG. 15A is a graph depicting an effect on body weight of administration of an exendin-4 analog (10

μg/kg/day) and amylin (100 μg/kg/day), either alone or in combination over two weeks. FIG. 15B is a graph depicting an effect on body fat of a two-week administration of an exendin-4 analog (10 μg/kg/day) and amylin (100 μg/kg/day), either alone or in combination. FIG. 15C is a graph depicting an effect on body protein of a two-week administration of exendin-4 (10 μg/kg/day) and amylin (100 μg/kg/day), either alone or in combination.

FIGS. 16A-16C. FIG. 16A is a graph depicting an effect on body weight of administration of PYY(3-36) (1 mg/kg/day) and amylin (100 μg/kg/day), either alone or in combination over two weeks. FIG. 16B is a graph depicting an effect on body fat of a two-week administration of PYY(3-36) (1 mg/kg/day) and amylin (100 μg/kg/day), either alone or in combination. FIG. 16C is a graph depicting an effect on body protein of a two-week administration of PYY(3-36) (1 mg/kg/day) and amylin (100 μg/kg/day), either alone or in combination.

FIG. 18A: Absolute Change (kg). FIG. 18B: % Change. Doses are as described for FIG. 17 and in Example 8. The term "evaluable population" refers to randomized subjects who complied to protocol (N=93). Legend: metreleptin (boxes) (n=19 [Evaluable], 27 [ITT-LOCF]); pramlintide (triangle with base down) (n=38 [Evaluable], 55 [ITT-LOCF]); metreleptin+pramlintide (triangle with base up) (n=36 [Evaluable], 55 [ITT-LOCF]).

FIG. 19A and FIG. 19B demonstrate least squares change in body weight from enrollment for the evaluable population during the 24-week study described in Example 8. FIG. 19A: Absolute Change (kg). FIG. 19B: % Change. Evaluable population: N=93. Legend: metreleptin (boxes) (n=19); pramlintide (triangle with base down) (n=38); metreleptin+pramlintide (triangle with base up) (n=36). Statistics: * (P<0.05);  (P<0.01); * (P<0.001).

FIG. 20A: Absolute Change (kg). FIG. 20B: % Change. Evaluable population: N=93. Legend: as described for FIG. 19A and FIG. 19B.

FIG. 21A and FIG. 21B demonstrate mean change in body weight from baseline for the evaluable population during the 24-week study described in Example 8. FIG. 21A: Absolute Change (kg). FIG. 21B: % Change. Evaluable population: N=93. Legend: as described for FIG. 19A and FIG. 19B.

FIG. 23A: Weight Loss≧5%. FIG. 23B: Weight Loss≧10%. FIG. 23C: Weight Loss≧15%. Evaluable population: as described for FIG. 22.

FIG. 25A: female. FIG. 25B: male. Legend: leptin (boxes) (n=14[F], 5[M]); pramlintide (triangle with base down) (n=22[F], 16[M]); leptin+pramlintide (triangle with base up) (n=21[F], 15-[M]).

FIG. 26A: female. FIG. 26B: male. Legend: as described for FIG. 25A and FIG. 25B.

FIG. 27A and FIG. 27B demonstrate mean absolute change in body weight from enrollment by BMI category for the evaluable population during the 24-week study described in Example 8. FIG. 27A: BMI<30 kg/m$^2$. FIG. 27B: BMI≧30 kg/m$^2$. Legend: leptin (boxes) (n=5[<30], 14[≧30]); pramlintide (triangle with base down) (n=3[<30], [≧30]); leptin+pramlintide (triangle with base up) (n=9[<30], 27[≧30]).

FIG. 28A and FIG. 28B demonstrate mean percentage change in body weight from enrollment by BMI category for the evaluable population during the 24-week study described in Example 8. FIG. 28A: BMI<30 kg/m$^2$. FIG. 28B: BMI≧30 kg/m$^2$. Legend: as described for FIG. 27A and FIG. 27B.

FIG. 29A: Initial Weight Loss<5%. FIG. 29B: Initial Weight Loss≧5%. Legend: leptin (boxes) (n=16 [<5%1], 3[≧5%]); pramlintide (triangle with base down) (n=26[<5%], 12[≧5%]); leptin+pramlintide (triangle with base up) (n=25[<5%], 11[≧5%]).

FIG. 30A: Initial Weight Loss<5%. FIG. 30B: Initial Weight Loss≧5%. Legend: as described for FIG. 29A and FIG. 29B.

FIG. 31A and FIG. 31B demonstrate mean percentage change in total excess body weight from enrollment for the evaluable and ITT-LOCF populations during the 24-week study described in Example 8. FIG. 31A: Evaluable. FIG. 31B: ITT-LOCF. Legend: leptin (boxes) (n=19[Eval], 27[ITT-LOCF]); pramlintide (triangle with base down) (n=38[Eval], 56[ITT-LOCF]); leptin+pramlintide (triangle with base up) (n=36[Eval], 56[ITT-LOCF]). Statistics (based on LS means of combination vs. pramlintide monotherapy): *(P<0.05); (P<0.01); *(P<0.001). Percent change in excess body weight refers to change in weight (kg) from enrollment/excess body weight (kg) at enrollment×100, wherein excess body weight at enrollment refers to body weight (kg) at enrollment−24.9×height (m)$^2$.

FIG. 32 demonstrates mean change in waist circumference from enrollment for evaluable population during the 24-week study described in Example 8. Legend: leptin (boxes) (n=19 [Eval]); pramlintide (triangle with base down) (n=38[Eval]); leptin+pramlintide (triangle with base up) (n=36[Eval]). Statistics (based on LS means): *(P<0.05); **(P<0.01).

DETAILED DESCRIPTION

Figure 1:
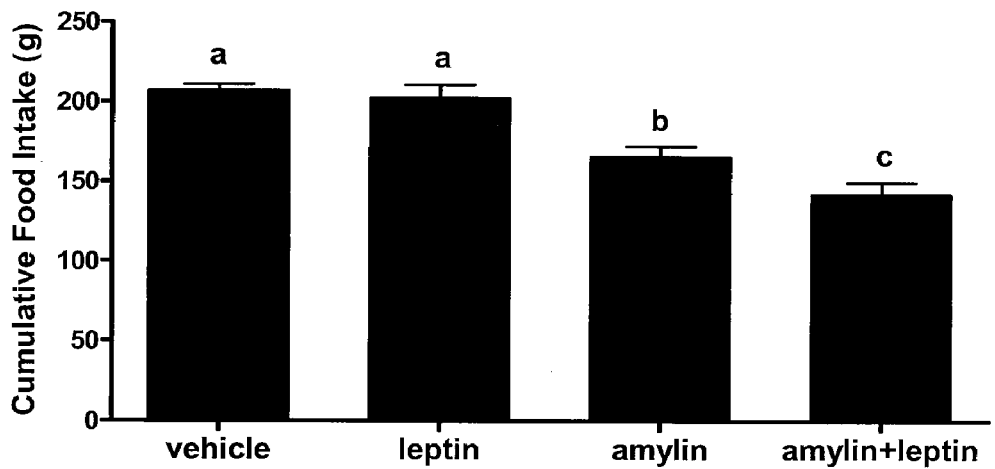
FIG. 1 is a graph depicting an effect of administration of leptin and amylin on food intake.

We have discovered that administration of an anti-obesity agent that acts upon structures in the forebrain involved in food intake and/or body weight modulation in combination with an anti-obesity agent that acts upon structures in the hindbrain involved in food intake and/or body weight modulation is surprisingly effective in reducing nutrient availability and in treating obesity and obesity related conditions, disorders, and diseases. It has been discovered that when administration of such anti-obesity agents is combined in this manner, the anti-obesity agents are more effective in reducing nutrient availability in the recipient than use of one of the agents alone. As shown herein, for example, a combination of anti-obesity agents can act synergistically to reduce nutrient availability, e.g., to reduce weight, reduce fat, reduce food intake, or any combination of these three.

Particular areas of the forebrain (telencephalonic- and diencephalonic-derived constituents of the brain) and hindbrain or brainstem (including the midbrain, pons and medulla) have been identified as being involved in controlling energy balance. Forebrain structures or nuclei residing in the hypothalamus involved in food intake and/or body weight modulation include, for example, the arcuate nucleus (ARC), the paraventricular nucleus (PVN), the dorsomedial hypothalamus (DMH), the ventromedial nucleus (VMH), and the lateral hypothalamus nucleus (LHA). Hindbrain structures or nuclei residing in the brainstem involved in food intake and/or body weight modulation include, for example, the nucleus of the solitary tract (NST), the area postrema (AP), and the lateral parabrachial nucleus (IPBN). Brainstem nuclei that control the elements of the consummatory motor control system are likely controlled by primary or second order projections from brainstem regions like the NST, AP, and IPBN. It is noteworthy that the AP, NST and IPBN have all been shown to (collectively and independently) possess their own integrative abilities.

A variety of CNS-directed anti-obesity agents act upon these forebrain structures residing in the hypothalamus involved in food intake and/or body weight modulation. In addition, CNS-directed anti-obesity agents act upon hindbrain structures residing in the brainstem involved in food intake and/or body weight modulation. Examples of such anti-obesity agents are described herein. See Table 1 for examples. Such agents include, for example, neuropeptide Y1 (NPY1) receptor antagonists, NPY5 receptor antagonists, leptin and leptin agonists, ciliary neurotrophic factor (CNTF) and CNTF agonists, melanin-concentrating hormone (MHC) and MCH antagonists, melacortins (MC) and MC agonists, cannabinoid receptor (CB-1) antagonists, serotonin (5-HT) and 5-HT agonists, peptide YY (PYY) and PYY agonists, exendin and exendin agonists, GLP-1 and GLP-1 agonist, DPP-IV inhibitors, ghrelin and ghrelin antagonists, cholecystokinin (CCK) and CCK agonists, and amylin and amylin agonists.

TABLE 1

Individual anti-obesity targets and location

| Signaling System | CNS Region | Food Intake Role | Anti-obesity agents |
|---|---|---|---|
| Neuropeptide Y (NPY) | Forebrain (ARC/PVN) | Increases intake | NPY1 and NPY5 receptor antagonists |
| Leptin | Forebrain (ARC) | Decreases intake | Leptin, or agonists |
| Ciliary neurotrophic factor (CNTF) | Forebrain (ARC) | Decreases intake | CNTF (Axokine ®) |
| Melanin-concentrating hormone (MCH) | Forebrain (ARC/PVN) | Increases intake | MCH antagonists |
| Melanocortins (MC) | Forebrain (PVN/ARC) | Agonists decrease intake | MC4 agonists |
| Cannabinoids (CB) | Forebrain (widespread) | Increase intake | Cannabinoid receptor antagonists |
| Serotonin (5-HT) | Forebrain (VMH) | Decrease intake | 5-HT2C agonists |
| Peptide YY (PYY) | Forebrain (ARC) | Decrease intake | PYY(3-36) agonists |
| Glucagon-like peptide-1 (GLP-1) | Forebrain (PVN) | Decrease intake | Exenatide and other GLP-1 ligands, DPP-IV inhibitors |
| Ghrelin | Forebrain (ARC) | Increase intake | Ghrelin antagonists |
| Cholecystokinin (CCK) | Hindbrain (AP) | Decrease intake | CCK agonists |
| Amylin | Hindbrain (AP) | Decrease intake | Amylin agonists, Pramlintide, amylin analogs |

In certain embodiments, the methods include a first compound that predominantly targets the energy balance centers of the hypothalamus, such as the ARC, PVN, VM, and LH. In certain embodiments, the methods include a second compound that predominantly targets the energy balance centers of the hindbrain such as the NST, the AP and the 1PBN.

In certain embodiments, these compounds are anti-obesity agents. In certain embodiments, the methods may include use of one or more predominantly forebrain acting anti-obesity agents. In other embodiments, the methods may include use of one or more predominantly hindbrain acting anti-obesity agents. Exemplary anti-obesity agents include an NPY1 receptor antagonist, an NPY5 receptor antagonist, a leptin or a leptin agonist or analog, a CNTF (e.g., AXOKINE®), an MCH antagonist, a MC4 agonist, a CB-1 antagonist (e.g., rimonabant), a 5-HT2C agonist, an NPY2 receptor agonist (e.g., a PYY(3-36) or a PYY(3-36) agonist), an exendin or an exendin agonist or analog, a GLP-1 or a GLP-1 agonist or analog, a DPP-IV inhibitor, a ghrelin antagonist, a CCK or a CCK agonist or analog, and an amylin or an amylin agonist or analog.

As exemplified herein, agonists and antagonists that are anti-obesity agents in the invention include, for example, molecules such peptides, polypeptides and small molecules agents.

The details of one or more embodiments of the invention are set forth in the accompanying drawings and the description below. Other features, objects, and advantages of the invention will be apparent from the description and drawings, and from the claims.

DEFINITIONS

An "anti-obesity agent" is a compound that is able to reduce nutrient availability to the body upon administration. A "weight-inducing agent" is a compound that would increase nutrient availability to the body. In one aspect, a weight-inducing agent is an antagonist of an anti-obesity agent.

As used herein, an anti-obesity agent that "acts on a forebrain structure involved in food intake and/or body weight modulation" stimulates or suppresses activity of a particular region, e.g., particular nuclei and/or neuronal circuits, in the forebrain. This forebrain stimulation or suppression leads to a reduction in nutrient availability to the body. An anti-obesity agent that "acts on a hindbrain structure involved in food intake and/or body weight modulation" stimulates or suppresses activity of a particular region, e.g., particular nuclei and/or neuronal circuits, in the hindbrain. This hindbrain stimulation or suppression results in a reduction in nutrient availability to the body.

"Reduced nutrient availability" is meant to include any means by which the body reduces the nutrients available to the body to store as fat. In other words, reducing nutrient availability may be by means that include, but are not limited to, reducing appetite, increasing satiety, affecting food choice/taste aversion, increasing metabolism, and/or decreasing or inhibiting food absorption. Exemplary mechanisms that may be affected include delayed gastric emptying or decreased absorption of food in the intestines.

"Increased nutrient availability" is meant to include any means by which the body increases the nutrients available to the body to store as fat. In other words, increasing nutrient availability may be by means that include, but are not limited to, increasing appetite, decreasing satiety, affecting food choice, decreasing taste aversion, decreasing metabolism, and/or increasing food absorption. Exemplary mechanisms that may be affected include decreasing gastric hypomotility or increasing absorption of food in the intestines.

While "obesity" is generally defined as a body mass index (BMI) over 30, for purposes of this disclosure, any subject, including those with a BMI of less than 30, who needs or wishes to reduce body weight or prevent body weight gain is included in the scope of "obese." Thus, subjects with a BMI of less than 30 and 25 and above (considered overweight) or below 25 are also included in the subjects of the invention. Morbid obesity refers to a BMI of 40 or greater.

With regard to the methods to reduce nutrient availability, as used herein, a "subject in need thereof" includes subjects who are overweight or obese or morbidly obese, or desirous of losing weight. In addition, subjects who are insulin resistant, glucose intolerant, or have any form of diabetes mellitus (e.g., type 1, 2 or gestational diabetes) can benefit from these methods to reduce nutrient availability.

With regard to the methods to increase nutrient availability, as used herein, a "subject in need thereof" includes subjects who are underweight or desirous of gaining weight.

A "subject" is meant to include any animal, including humans, primates, and other mammals including rats, mice, pets such as cats, dogs, livestock such as horses, cattle, sheep and goats, as well as chicken, turkey and any other animal for which body weight or altering body composition may be an issue.

By "metabolic rate" is meant the amount of energy liberated/expended per unit of time. Metabolism per unit time can be estimated by food consumption, energy released as heat, or oxygen used in metabolic processes. It is generally desirable to have a higher metabolic rate when one wants to loose weight. For example, a person with a high metabolic rate may be able to expend more energy (e.g., the body burns more calories) to perform an activity than a person with a low metabolic rate for that activity.

As used herein, "lean mass" or "lean body mass" refers to muscle and bone. Lean body mass does not necessarily indicate fat free mass. Lean body mass contains a small percentage of fat (roughly 3%) within the central nervous system (brain and spinal cord), marrow of bones, and internal organs. Lean body mass is measured in terms of density. Methods of measuring fat mass and lean mass include, but are not limited to, underwater weighing, air displacement plethysmograph, x-ray, DEXA scans, MRIs and CT scans. In certain embodiments, fat mass and lean mass is measured using underwater weighing as known in the art.

By "fat distribution" is meant the location of fat deposits in the body. Such locations of fat deposition include, for example, subcutaneous, visceral and ectopic fat depots.

By "subcutaneous fat" is meant the deposit of lipids just below the skin's surface. The amount of subcutaneous fat in a subject can be measured using any method available for the measurement of subcutaneous fat. Methods of measuring subcutaneous fat are known in the art, for example, those described in U.S. Pat. No. 6,530,886, the entirety of which is incorporated herein by reference.

By "visceral fat" is meant the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases.

By "ectopic fat storage" is meant lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body.

As used herein, and as well-understood in the art, "treatment" is an approach for obtaining beneficial or desired results, including clinical results. "Treating" or "palliating" a disease, disorder, or condition means that the extent and/or undesirable clinical manifestations of a condition, disorder, or a disease state are lessened and/or time course of the progression is slowed or lengthened, as compared to not treating the disorder. For example, in treating obesity, a decrease in body weight, e.g., at least a 5% decrease in body weight, is an example of a desirable treatment result. For purposes of this invention, beneficial or desired clinical results include, but are not limited to, alleviation or amelioration of one or more symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Further, treating does not necessarily occur by administration of one dose, but often occurs upon administration of a series of doses. Thus, a therapeutically effective amount, an amount sufficient to palliate, or an amount sufficient to treat a disease, disorder, or condition may be adminstered in one or more administrations.

As used herein, the term "therapeutically effective amount" means the amount of the active compounds in the composition that will elicit the biological or medical response in a tissue, system, subject, or human that is being sought by the researcher, veterinarian, medical doctor or other clinician, which includes alleviation of the symptoms of the disorder being treated. The novel methods of treatment of this invention are for disorders known to those skilled in the art.

As used herein, the term "prophylactically effective amount" means the amount of the active compounds in the composition that will elicit the biological or medical response in a tissue, system, subject, or human that is being sought by the researcher, veterinarian, medical doctor or other clinician, to prevent the onset of obesity or an obesity-related disorder, condition or disease in subjects as risk for obesity or the obesity-related disorder, condition or disease.

As used herein, the singular form "a", "an", and "the" includes plural references unless otherwise indicated or clear from context. For example, as will be apparent from context, "an" amylin agonist can include one or more amylin agonists.

As used herein, an "analog" refers to a peptide whose sequence was derived from that of a base reference peptide, e.g., amylin and calcitonin, and includes insertions, substitutions, extensions, and/or deletions of the reference amino acid sequence, for example having at least 50 or 55% amino acid sequence identity with the base peptide, in other cases, for example, having at least 70%, 80%, 90%, or 95% amino acid sequence identity with the base peptide. Such analogs may comprise conservative or non-conservative amino acid substitutions (including non-natural amino acids and L and D forms). Analogs include compounds having agonist and compounds having antagonist activity. Analogs, as herein defined, also include derivatives.

A "derivative" is defined as a reference peptide or analogs, described above, having a chemical modification of one or more of its amino acid side groups, α-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino include, without limitation, the desamino, N-lower alkyl, N-di-lower alkyl, and N-acyl modifications. Modifications of the terminal amino include, without limitation, the desamino, N-lower alkyl, N-di-lower alkyl, and N-acyl modifications, such as alkyl acyls, branched alkylacyls, alkylaryl-acyls. Modifications of the terminal carboxy group include, without limitation, the amide, lower alkyl amide, dialkyl amide, arylamide, alkylarylamide and lower alkyl ester modifications. Lower alkyl is C1-C4 alkyl. Furthermore, one or more side groups, or terminal groups, may be protected by protective groups known to the ordinarily-skilled synthetic chemist. The α-carbon of an amino acid may be mono- or dimethylated.

In general, with respect to an amino acid sequence, the term "modification" includes substitutions, insertions, elongations, deletions, and derivatizations alone or in combination. The polypeptides of the invention may include one or more modifications of a "non-essential" amino acid residue. In the context of the invention, a "non-essential" amino acid residue is a residue that can be altered, e.g., deleted or substituted, in the novel amino acid sequence without abolishing or substantially reducing the activity (e.g., the agonist activity) of the polypeptide (e.g., the analog polypeptide). The polypeptides of the invention may include deletions of 1, 2, 3, 4, 5, 6, 7, 8, 9, 10 or more non-essential amino acid residues. The polypeptides of the invention may include additions of at least of 1, 2, 3, 4, 5, 6, 7, 8, 9, 10 or more amino acids without abolishing or substantially reducing the activity of the polypeptide.

Substitutions include conservative amino acid substitutions. A "conservative amino acid substitution" is one in which the amino acid residue is replaced with an amino acid residue having a similar side chain, or physicochemical characteristics (e.g., electrostatic, hydrogen bonding, isosteric, hydrophobic features). The amino acids may be naturally occurring or nonnatural (unnatural). Families of amino acid residues having similar side chains are known in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, methionine, cysteine), nonpolar side chains (e.g., alanine, valine, leucine, isoleucine, proline, phenylalanine, tryptophan), β-branched side chains (e.g., threonine, valine, isoleucine) and aromatic side chains (e.g., tyrosine, phenylalanine, tryptophan, histidine). Substitutions may also include non-conservative changes.

By "amino acid" or "amino acid residue" is meant natural amino acids, unnatural amino acids, and modified amino acid. Unless stated to the contrary, any reference to an amino acid, generally or specifically by name, includes reference to both the D and the L stereoisomers if their structure allow such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), tryptophan (Trp), tyrosine (Tyr) and valine (Val). Unnatural amino acids include, but are not limited to homolysine, homoarginine, homoserine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline. Additional unnatural amino acids include modified amino acid residues which are chemically blocked, reversibly or irreversibly, or chemically modified on their N-terminal amino group or their side chain groups, as for example, N-methylated D and L amino acids or residues wherein the side chain functional groups are chemically modified to another functional group. For example, modified amino acids include methionine sulfoxide; methionine sulfone; aspartic acid-(beta-methyl ester), a modified amino acid of aspartic acid; N-ethylglycine, a modified amino acid of glycine; or alanine carboxamide, a modified amino acid of alanine. Additional residues that can be incorporated are described in Sandberg et al., *J. Med. Chem.* 41: 2481-91, 1998.

It should be noted that throughout the application that alternatives are written in Markush groups, for example, each amino acid position that contains more than one possible amino acid. It is specifically contemplated that each member of the Markush group should be considered separately, thereby comprising another embodiment of the invention, and the Markush group is not to be read as a single unit.

METHODS OF THE INVENTION

In a general aspect, the invention provides methods for reducing nutrient availability through administration of a combination of anti-obesity agents. Thus, the invention provides methods for treating obesity and obesity-related diseases, disorders, and/or conditions that would benefit from a reduction in nutrient availability. Given the increase in effectiveness when used in combinations, methods of the invention may allow for administration of lower dosages of one or more of the anti-obesity agents used in combination as compared to the use of the agent alone, such as in monotherapy.

The methods of the invention provide administration of a combination of anti-obesity agents. Administration of the agents "in combination" should be understood to mean providing each of the agents to a subject in need of treatment. Administration of the agents could occur as a single pharmaceutical dosage formulation containing all of the intended anti-obesity agents or in separately with each intended agent in its own dosage formulation.

Where separate dosage formulations are used, the individual anti-obesity agents can be administered at essentially the same time, i.e., concurrently, or at separately staggered times, i.e., sequentially prior to or subsequent to the administration of the other anti-obesity agent of the method. In some embodiments, administration in combination involves administration of separate dosage formulations during overlapping intervals. For example, anti-obesity agent 1 is administered from day 1 through day 30 and anti-obesity agent 2 is administered from day 20 through day 50. In other embodiments, administration in combination involves administration of separate dosage formulations in sequential, nonoverlapping intervals. For example, anti-obesity agent 1 is administered from day 1 through day 30 and anti-obesity agent 2 is administered from day 35 through day 50. The instant invention is therefore to be understood to include all such regimes of simultaneous, alternating, or completely separate treatments over the total treatment course, and the terms "administration," "administering," "administration in combination" and "administering in combination" are to be interpreted accordingly.

In certain embodiments, the invention provides methods for reducing nutrient availability through administration of at least one anti-obesity agent that acts upon forebrain structures involved in food intake and/or body weight modulation in combination with administration of at least one anti-obesity agent that acts upon hindbrain structures involved in food intake and/or body weight modulation. In some cases, the methods of the invention increase or enhance the effectiveness an anti-obesity agent that has limited effectiveness, if any, when used alone (monotherapy). In such cases, the methods of the invention increase or enhance the effectiveness an anti-obesity agent by, for example, preventing or delaying loss of effectiveness by continued use or increasing potency. Methods of the invention may allow for administration of lower dosages of one or more of the anti-obesity agents used in combination as compared to the use of either agent alone.

In one aspect, methods of the invention provide a synergistic anti-obesity effect among the administered agents. Accordingly, in certain embodiments, administration of a combination of anti-obesity agents results in an effect, e.g., a reduction in nutrient availability, reduction in body weight, reduction in food intake, increase in metabolism, which is greater than the combination of the results of administration of the anti-obesity agent alone (monotherapy).

In another aspect of the invention, methods are provided which reduce or eliminate a subject's resistance to an anti-obesity agent so that when the agent is administered, it will be able to elicit an anti-obesity response (e.g., reduce nutrient availability, reduce weight, reduce fat mass). For example, and without wishing to be bound by this or any other theory, it is theorized that leptin resistance may be due to the high levels of leptin found in obese subjects (i.e., the body has become desensitized to leptin). Therefore, one method of the invention comprises administering an anti-obesity agent other than leptin (e.g., amylin or an amylin agonist) to reduce weight of the subject so as to reduce or remove the leptin resistance. Once this has been achieved, leptin is then be administered, either alone or in combination with an anti-obesity agent (e.g., amylin or an amylin agonist), for a further anti-obesity effect. Other means of reducing weight to ameliorate leptin resistance are contemplated, such as diet, exercise, other diet drugs, and surgical devices.

In certain embodiments, the invention is directed to the delivery of a first anti-obesity agent that acts upon hindbrain structures involved in food intake and/or body weight modulation to prime the body before administration of a second anti-obesity agent that acts upon forebrain structures involved in food intake and/or body weight modulation. In certain embodiments, the administration of the first agent is for a number of days, weeks or even months before the administration of the second agent. At this point, the second agent may be administered alone or in combination with the first agent. In certain embodiments, the first anti-obesity agent is amylin or an amylin agonist and the second agent is a leptin or a leptin agonist. In some embodiments, the serum leptin concentration of a subject prior to administration of the anti-obesity agents is greater than 10 ng/ml, in other embodiments, it is greater than 20 ng/ml.

In certain embodiments, an amylin or an amylin agonist is administered to the subject at least 1 day, 2 days, 3 days, 5 days, 7 days, 10 days, 14 days, 21 days, 28 days or more prior to administration of a leptin or leptin agonist. In some embodiments, prior to administration of a leptin or a leptin agonist, an amylin or an amylin agonist is administered to the subject until the serum leptin concentration in the subject is about 4 ng/ml, less than 4 ng/ml, less than 2 ng/ml, less than 1 ng/ml, or less than about 0.5 ng/ml. In some embodiments, a leptin or a leptin agonist is administered in a replacement therapy amount to achieve near physiological concentrations of leptin in the plasma.

In another aspect of the present invention, methods for reducing the risk of developing metabolic disorders are provided, where the method comprises administering to the subject a combination of anti-obesity agents in effective amounts to reduce the weight of a subject.

In some embodiments of the invention, methods of the invention are used to increase the metabolic rate in a subject, decrease a reduction in the metabolic rate in a subject, or preserve the metabolic rate in a subject. In certain embodiments, the metabolic rate may involve the preferential use of the body's fat as an energy source over lean body tissue. In one aspect, lean body mass is not decreased following administration of the combination of anti-obesity agents. In another aspect, a reduction in the lean body mass is lessened or prevented following administration of the combination of anti-obesity agents. In still another aspect, lean body mass is increased following administration of the combination of anti-obesity agents. Such preference for fat as the energy source may be determined by comparing the amount of fatty tissue to lean body tissue, ascertained by measuring total body weight and fat content at the beginning and end of the treatment period. An increase in metabolic rate is a higher level of the use of calories or another energy source by a subject over a period of time compared with the level of use of calories or other energy source by the subject over another period of time under substantially similar or identical conditions without administration of the combination of anti-obesity agents. In certain embodiments, the metabolic rate is increased at least about 5% in a subject, in other embodiments, the metabolic rate is increased at least about 10%, 15%, 20% 25%, 30%, or 35% in a subject compared with the level of use of calories or other energy source by the subject over another period of time under substantially similar or identical conditions without administration of the combination of anti-obesity agents. The increase in metabolic rate can be measured using a respiratory calorimeter, for example. An effective amount of the anti-obesity agents as used in these embodiments is an amount of each agent effective to increase the metabolic rate in a subject when administered in combination compared to a subject not receiving the agents or only one of the agents.

In another embodiment, a method is provided to reduce a decrease in metabolic rate in a subject. Such a decrease in metabolic rate can be the result of any condition or nutritional or physical regimen that leads to a reduction in metabolic rate, for example, due to a reduced calorie diet, a restricted diet, or weight loss. A restricted diet includes allowances or prohibitions, or both on the types of food or the amounts of food or both permitted in a diet, not necessarily based on calories. For example, as in individual diets, the body compensates with a reduced metabolic rate based on the lower caloric intake. In essence, the body down-regulates the requirement for food, thereby subsisting on less food. As dieting continues, the threshold for caloric intake is reduced. When dieting has ended, the individual typically gains weight while eating a normal diet because of the lowered caloric intake threshold and lower-basal metabolic rate (NIH Technology Assessment Conference Panel (1992) *Ann. Intern. Med.* 116:942-949; Wadden (1993) *Ann. Intern. Med.* 119:688-693). In one aspect, a method is provided to reduce the loss of metabolic rate in a subject, where the loss of metabolic rate is the result of a reduced calorie diet or weight loss. By using such a method, the subject's reduction in metabolic rate is decreased by at least about 10%, 15%, 20% 25%, 30%, 35%, 40%, 50%, 60%, 70%, 80%, 90%, or 95% in a subject. For such methods, it may be desirable to administer the combination of anti-obesity agents at the time the condition or nutritional or physical regimen is initiated which leads to a loss or reduction in metabolic rate. However, it is also contemplated that administration of the agents is commenced before the condition or nutritional or physical regimen is initiated. In one instance, metabolic rate is measured using a respiratory calorimeter. An effective amount of the anti-obesity agents of as used in this embodiment is an amount of each agent effective to decrease the reduction of the metabolic rate in a subject when administered in combination.

In another aspect, methods for reducing metabolic plateaus are provided, where a method comprises administering effective amounts of anti-obesity agents in combination to a subject. In certain embodiments, the subject is losing weight, or has lost weight, for example, due to a reduced calorie diet, increased exercise or a combination thereof. By "metabolic plateau" is meant time intervals of steady metabolic rate while the body adjusts to changes in caloric or energy input. Changes in caloric input or expenditure can be the result of, for example, reduced calorie diets or increased physical activity. Such plateaus can be observed, for example, during a weight loss regimen when weight loss slows or stops. In certain embodiments, a method of the present invention reduces the duration of a metabolic plateau in a subject compared with the duration of metabolic plateaus in an otherwise identical subject over the same period of time under substantially similar or identical conditions without administration of the combination of anti-obesity agents. In other embodiments, a method of the present invention reduces the frequency of metabolic plateaus compared with the frequency of metabolic plateaus in an otherwise identical subject over the same period of time under substantially similar or identical conditions without administration of the combination of anti-obesity agents. In still other embodiments, a method of the present invention delays the onset of a metabolic plateau compared with the onset of a metabolic plateau in an otherwise identical subject over the same period of time under substantially similar or identical conditions without administration of the combination of anti-obesity agents. In certain embodiments, metabolic plateaus are identified by charting periods of reduced or no weight loss. In certain embodiments, at least one metabolic plateau is reduced. In other embodiments, at least two, three, four, five, six, seven, eight, nine, or ten metabolic plateaus are reduced. In another aspect, metabolic plateaus are delayed one day as compared to a subject not administered the combination of anti-obesity agents under identical or similar conditions. In other aspects, metabolic plateaus are delayed 2 days, 3 days, 4 days, 5 days, 6 days, 1 week, 10 days, 2 weeks or 3 weeks in a subject.

In yet other embodiments, a method is provided to preserve the metabolic rate in a subject. In certain embodiments, the subject may be at risk of losing metabolic rate, for example, due to the initiation of a reduced calorie diet, restricted diet, or anticipated weight loss. A preservation of metabolic rate is a maintenance of the level of the use of calories or another energy source by a subject over a period of time compared with the level of use of calories or other energy source by an otherwise identical subject over the same period of time under substantially similar or identical conditions without administration of the combination of anti-obesity agents. In one aspect, the metabolic rate is maintained within 15% of the subject's metabolic rate prior to the initiation of the event that results in the decrease in metabolic rate. In other aspects, the metabolic rate is maintained within 10%, within 7%, within 5%, within 3% or less of the subject's metabolic rate. In one aspect, the combination of anti-obesity agents is administered at the initiation of a reduced calorie diet, restricted diet, or exercise regimen.

Metabolic rates can be assessed using any method available for determining such rates, for example by using a respiratory calorimeter. Such methods and devices for assaying metabolic rates are known in the art and are described, for example, in U.S. Pat. Nos. 4,572,208, 4,856,531, 6,468,222, 6,616,615, 6,013,009, and 6,475,158. Alternatively, the metabolic rate of an animal can be assessed by measuring the amount of lean tissue versus fatty tissue catabolized by the animal following the diet period. Thus, total body weight and fat content can be measured at the end of the dietary period. In rats, a frequently used method to determine total body fat is to surgically remove and weigh the retroperitoneal fat pad, a body of fat located in the retroperitoneum, the area between the posterior abdominal wall and the posterior parietal peritoneum. The pad weight is considered to be directly related to percent body fat of the animal. Since the relationship between body weight and body fat in rats is linear, obese animals have a correspondingly higher percent of body fat and retroperitoneal fat pad weight.

In another aspect of the present invention, methods for reducing fat mass by increasing the metabolic rate in a subject are provided, where the methods comprise administering a combination of anti-obesity agents in amounts effective to reduce fat mass by increasing the subject's metabolic rate. Fat mass can be expressed as a percentage of the total body mass. In some aspects, the fat mass is reduced by at least 1%, at least 5%, at least 10%, at least 15%, at least 20%, or at least 25% over the course of treatment. In one aspect, the subject's lean mass is not decreased over the course of the treatment. In another aspect, the subject's lean mass is maintained or increased over the course of the treatment. In another aspect, the subject is on a reduced calorie diet or restricted diet. By "reduced calorie diet" is meant that the subject is ingesting fewer calories per day than compared to the same subject's normal diet. In one instance, the subject is consuming at least 50 fewer calories per day. In other instances, the subject is consuming at least 100, 150, 200, 250, 300, 400, 500, 600, 700, 800, 900, or 1000 fewer calories per day.

In certain embodiments of the present invention, a method for altering the fat distribution in a subject is provided where the method comprises administering a combination of anti-obesity agents in amounts effective to alter fat distribution in the subject. In one aspect, the alteration results from an increased metabolism of visceral or ectopic fat, or both in the subject. In some embodiments, the method involves the metabolism of visceral or ectopic fat or both at a rate of at least about 5%, 10%, 15%, 20%, 25%, 30%, 40%, or 50% greater than for subcutaneous fat. In one aspect, the methods result in a favorable fat distribution. In certain embodiments, favorable fat distribution is an increased ratio of subcutaneous fat to visceral fat, ectopic fat, or both. In one aspect, the method involves an increase in lean body mass, for example, as a result of an increase in muscle cell mass.

In other embodiments, methods for reducing the amount of subcutaneous fat in a subject are provided, wherein the method comprises administering, to a subject in need thereof, a combination of anti-obesity agents in amounts effective to reduce the amount of subcutaneous fat in the subject. In one instance, the amount of subcutaneous fat is reduced in a subject by at least about 5%. In other instances, the amount of subcutaneous fat is reduced by at least about 10%, 15%, 20%, 25%, 30% 40%, or 50% compared to the subject prior to administration of the anti-obesity agents.

The methods described herein can be used to reduce the amount of visceral fat in a subject. In one instance, the visceral fat is reduced in a subject by at least about 5%. In other instances, the visceral fat is reduced in the subject by at least about 10%, 15%, 20%, 25%, 30% 40%, or 50% compared to the subject prior to administration of the combination of anti-obesity agents. Visceral fat can be measured through any means available to determine the amount of visceral fat in a subject. Such methods include, for example, abdominal tomography by means of CT scanning and MRI. Other methods for determining visceral fat are described, for example, in U.S. Pat. Nos. 6,864,415, 6,850,797, and 6,487,445.

In certain embodiments, a method for preventing the accumulation of ectopic fat or reducing the amount of ectopic fat in a subject is provided, wherein the method comprises administering, to a subject in need thereof, a combination of anti-obesity agents in amounts effective to prevent accumulation of ectopic fat or to reduce the amount of ectopic fat in the subject. In one instance, the amount of ectopic fat is reduced in a subject by at least about 5% compared to the subject prior to administration of the combination of anti-obesity agents. In other instances, the amount of ectopic fat is reduced in a subject by at least about 10%, or by at least about 15%, 20%, 25%, 30% 40%, or 50%. Alternatively, the amount of ectopic fat is proportionally reduced 5%, 10%, 15%, 20%, 25%, 30%, 40%, 50%, 60%, 70%, 80%, 90%, or 100% in comparison to subcutaneous fat in a subject. Ectopic fat can be measured in a subject using any method available for measuring ectopic fat.

In other embodiments, methods are provided for producing a more favorable fat distribution in a subject, where the method comprises administering to a subject a combination of anti-obesity agents in amounts effective to produce a favorable fat distribution. In certain embodiments, administration of a combination of anti-obesity agents reduces the amount of visceral fat or ectopic fat, or both, in a subject. For example, administration of a combination of anti-obesity agents, where at least one anti-obesity agent that acts upon forebrain structures involved in food intake or body weight modulation or both in combination with administration of at least one anti-obesity agent that acts upon hindbrain structures involved in food intake or body weight modulation or both. In certain embodiments, the methods preferentially reduce the amount of visceral or ectopic fat, or a combination of both, over the reduction in subcutaneous fat. Such methods result in a higher ratio of subcutaneous fat to visceral fat or ectopic fat. Such improved ratios may result in a reduced risk of the development of cardiovascular diseases, polycystic ovary syndrome, metabolic syndrome, or any combinations thereof. In certain embodiments, ectopic or visceral fat is metabolized at a rate 5% greater than subcutaneous fat. In other embodiments, ectopic or visceral fat is metabolized at a rate at least 10% 15%, 20%, 25%, 30% 50%, 60%, 70%, 80%, 90%, or 100% greater than subcutaneous fat.

In still another aspect, methods of the invention include the use of a therapeutically effective amount of a combination of anti-obesity agents administered in combination with glucocortico steroids. Glucocortico steroids have the adverse effect of increasing fat mass and decreasing lean mass. Accordingly, it is contemplated that the anti-obesity agent combination can be used in conjunction with glucocortico steroids under conditions where glucocortico steroid use is beneficial.

Also provided are methods to reduce weight in a morbidly obese subject by first reducing the subject's weight to a level below that of being morbidly obese, then administering to the subject a combination of anti-obesity agents in effective amounts to further reduce the subject's weight. Methods for reducing a subject's weight to below that of morbid obesity include reducing caloric intake, increasing physical activity, drug therapy, bariatric surgery, such as gastric bypass surgery, or any combinations of the preceeding methods. In one aspect, administering the combination of anti-obesity agents further reduces the weight of the subject. In other embodiments, methods are provided for reducing the body mass index in a subject having a body mass index of 40 or less by administering a combination of anti-obesity agents in effective amounts to further reduce the subject's weight.

By reducing weight it is meant that the subject loses a portion of his/her total body weight over the course of treatment, whether the course of treatment be days, weeks, months or years. Alternatively, reducing weight can be defined as a decrease in proportion of fat mass to lean mass (in other words, the subject has lost fat mass, but maintained or gained lean mass, without necessarily a corresponding loss in total body weight). An effective amount of the anti-obesity agents administered in combination in these embodiments is an amount effective to reduce a subject's body weight over the course of the treatment, or alternatively an amount effective to reduce the subject's percentage of fat mass over the course of the treatment. In certain embodiments, the subject's body weight is reduced, over the course of treatment, by at least about 1%, by at least about 5%, by at least about 10%, by at least about 15%, or by at least about 20%. Alternatively, the subject's percentage of fat mass is reduced, over the course of treatment, by at least 1%, at least 5%, at least 10%, at least 15%, at least 20%, or at least 25%.

In certain embodiments, methods of reducing nutrient availability, e.g., reducing weight, in a subject comprise administering to the subject an effective amount of the anti-obesity agents in a bolus dose one or more times a day. A bolus dose is an intermittent dosage of medicine (as opposed to a continuous infusion). A subject can be administered one or more bolus doses per day. The bolus dose can be the same no matter when it is administered to the subject, or can be adjusted such that the subject is administered a larger bolus dose at certain times of the day as compared to others. Administration of an agent in certain formulations, e.g., sustained-release formulations, a bolus dose can be administered less frequently, for example, once every three days, once per week, twice a month, once every month. Furthermore, the time between bolus doses is preferably long enough to allow the drug administered in the previous bolus dose to clear the subject's blood stream.

In other embodiments, methods of reducing nutrient availability, e.g., reducing weight, in a subject comprise administering to the subject an effective amount of the anti-obesity agents in continuous doses. By continuous dose it is intended to mean the continuous infusion of the drug by, for example, intravenous injection or a transdermal patch. Alternatively, a continuous dose can be administered orally in the form of a controlled release capsule or tablet which releases the drug into the subject's system over a period of time. When administered by a continuous dose, the drug is released over a period of about 1 hour, in some cases the drug is released over a period of about 2, 3, 4, 5, 6, 7, 8, 9, 10, 11, 12, 18, or 24 hours.

By "administered in combination" is meant that the anti-obesity agents are administered as a single administration, simultaneously as separate doses, or as sequentially administered. Sequential administration refers to administering one of the anti-obesity agents either before or after an anti-obesity agent. In certain embodiments, the first anti-obesity agent is administered about 30 minutes before or after the at least one other anti-obesity agent, in other embodiments about 1, 2, 3, 4, 5, 6, 7, 8, 9, 10, 11, or 12 hours before or after the at least one other anti-obesity agents. Any of the administered anti-obesity agents can be administered as a bolus dose or as a continuous dose.

The present invention is further directed to methods of increasing thermogenesis in a subject, the method comprising administering to a subject in need thereof an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both. Thermogenesis is the process of liberating calories as heat by increasing the body's metabolic rate. Thermogenesis is activated by mechanisms, including supplements, nutrition, exercise, and exposure to cold.

The present invention is yet further directed to methods of increasing oxidative metabolism in a subject, the method comprising administering to a subject in need thereof an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both. Oxidative metabolism is the process by which oxygen is used to make energy from carbohydrates (sugars).

In another aspect, a method of inducing a feeling of fullness in a subject is provided, wherein the method comprises administering an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both to said subject.

In yet another aspect, a method of controlling hunger in a subject is provided, wherein the method comprises administering an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both to said subject.

In yet a further aspect, a method of prolonging a feeling of satiation in a subject is provided, wherein the method comprises administering an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both to said subject.

In yet a further aspect, a method of reducing caloric intake by reducing the size of a meal is provided, wherein the method comprises administering an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both to said subject.

In another aspect, a method of controlling food intake is provided, wherein the method comprises administering an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both to said subject.

In yet another aspect, a method for ensuring or assisting in compliance with a reduced calorie or restrictive diet is provided, wherein the method comprises administering an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both to said subject.

In a further aspect, a method of adjusting a subject's set point so that the body's propensity for homeostasis is adjusted to a healthier set point is provided, wherein the method comprises administering an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both to said subject.

In yet a further aspect, a method of maintaining weight loss or maintaining the weight lost is provided, wherein the method comprises administering an effective amount of at least one anti-obesity agent that acts upon forebrain structures involved in food intake, body weight modulation, or both in combination with administration of at least one anti-obesity agent that acts upon hindbrain structures involved in food intake, body weight modulation, or both to said subject. In other embodiments of this aspect of the invention, the weight loss is maintained by re-setting the subject's set point.

Furthermore, in certain embodiments, administration of the anti-obesity agents in combination results in a synergistic effect in any of the methods described herein. In addition, in certain embodiments, administration of the anti-obesity agents in combination results in a lower dosage requirement for at least one of the agents, with the same effect.

In certain embodiments, methods of the invention are of use in treating and/or preventing metabolic conditions or disorders that benefit from a reduction in nutrient availability. Accordingly, these methods may be useful in treating and/or preventing of obesity, diabetes (e.g., type 2 or non-insulin dependent diabetes, type 1 diabetes, and gestational diabetes), eating disorders, insulin-resistance syndrome, and cardiovascular disease.

In certain embodiments, methods of use in altering fat distribution, reducing fat mass, or both in a subject are provided. Accordingly, subjects for whom altering body composition is of benefit can also benefit from the present methods. Altered body composition, as intended herein, includes loss or maintenance of body fat, with minimization of loss, maintenance, or gain of lean body mass. In such situations, weight may increase as well as decrease. Accordingly, subjects may be lean, overweight, or obese as these terms are generally used in the art. Methods of the invention may also include reducing fat in non-adipose tissue while sparing lean mass. Uses for this method include treating diseases such as nonalcoholic steatohepatitis (NASH) or lipodystrophy.

Methods described herein use the administration of at least one anti-obesity agent that acts upon forebrain structures involved in food intake, body weight modulation, or both in combination with administration of at least one anti-obesity agent that acts upon hindbrain structures involved in food intake, body weight modulation, or both for the control, prevention and/or treatment of such conditions or disorders.

In another aspect, is provided methods that stimulate food intake, promote body weight gain, or both through administration of agents that act on the forebrain and hindbrain. In such methods, weight-inducing agents are administered to a subject in combination and in amounts effective to stimulate food intake, promote weight gain or both in the subject. These methods are particularly beneficial for diseases and disorders like cachexia and anorexia, and other wasting diseases characterized by loss of appetite, diminished food intake, and body weight loss in a subject. Exemplary weight-inducing agents include NPY1 receptor agonists, NPY5 receptor agonists, leptin antagonists, MCH agonists, MC4 antagonists, cannabinoid receptor agonists, 5-HT2C antagonists, exendin antagonists, GLP-1 antagonists, ghrelin agonists, CCK antagonists, and amylin antagonists. Accordingly, certain embodiments provide methods for stimulating food intake, promoting body weight gain or both in a subject in need thereof comprising administering to the subject at least two or more weight-inducing agents.

With regard to the administration of weight-inducing agents, the weight-inducing agents are administered as a single administration, simultaneously as separate doses, or as sequentially administered. Where separate dosage formulations are used, the individual weight-inducing agents can be administered at essentially the same time, i.e., concurrently, or at separately staggered times, e.g., sequentially prior to or subsequent to the administration of the other weight-inducing agent of the method. In certain embodiments, the first weight-inducing agent is administered about 30 minutes before or after the at least one other weight-inducing agent, in other embodiments about 1, 2, 3, 4, 5, 6, 7, 8, 9, 10, 11, or 12 hours before or after the at least one other weight-inducing agents. In some embodiments, administration in combination involves administration of separate dosage formulations during overlapping intervals. For example, weight-inducing agent 1 is administered from day 1 through day 30 and weight-inducing agent 2 is administered from day 20 through day 50. In other embodiments, administration in combination involves administration of separate dosage formulations in sequential, nonoverlapping intervals. For example, weight-inducing agent 1 is administered from day 1 through day 30 and weight-inducing agent 2 is administered from day 35 through day 50. The instant invention is therefore to be understood to include all such regimes of simultaneous, alternating, or completely separate treatments over the total treatment course. Any of the administered weight-inducing agents can be administered as a bolus dose or as a continuous dose.

Furthermore, in certain embodiments, administration of the weight-inducing agents in combination results in a synergistic effect in any of the aspects of the invention. In addition, in certain embodiments, administration of the weight-inducing agents in combination results in a lower dosage requirement for at least one of the agents, with the same effect.

Accordingly, in one embodiment is a method of treating obesity or reducing body weight in a subject in need thereof, comprising peripherally administering therapeutically effective amounts of at least two different anti-obesity agents, wherein at least one anti-obesity agent is an amylin, an amylin analog, or an amylin agonist and at least one anti-obesity agent is a leptin, a leptin derivative, or a leptin agonist, and the subject reduces body weight by least 10%, 12%, 15%, 20%, 30%, 40% or even 50%.

Further embodiments include the following.

EMBODIMENT 1

A method of treating obesity in a subject comprising peripherally administering therapeutically effective amounts of at least two different anti-obesity agents, wherein at least one anti-obesity agent is an amylin, an amylin analog, or an amylin agonist (i.e. an amylin agent) and the other is at least one anti-obesity agent that is a leptin, a leptin derivative, or a leptin agonist (i.e. a leptin agent); and wherein the subject reduces body weight by least 10%.

EMBODIMENT 2

A method of reducing body weight in a subject comprising peripherally administering therapeutically effective amounts of at least two different anti-obesity agents, wherein at least one anti-obesity agent is an amylin, an amylin analog, or an amylin agonist and at least one anti-obesity agent is a leptin, a leptin derivative, or a leptin agonist; and wherein the anti-obesity agents are administered in amounts effective to reduce the body weight of the subject by at least 10%.

EMBODIMENT 3

The method according to any one of embodiments 1 or 2 wherein the at least one anti-obesity amylin agent is an amylin agonist.

EMBODIMENT 4

The method according to embodiment 3 wherein the amylin agonist comprises an amylin analog.

EMBODIMENT 5

The method according to embodiment 4 wherein the amylin analog comprises pramlintide.

EMBODIMENT 6

The method according to any one of embodiments 1 to 5 wherein the at least one anti-obesity leptin agent is a leptin agonist.

EMBODIMENT 7

The method according to embodiments 6 wherein the leptin agonist comprises a leptin analog.

EMBODIMENT 8

The method according to embodiment 7 wherein the leptin analog comprises mature human leptin.

EMBODIMENT 9

The method according to embodiment 8 wherein the leptin analog comprises metreleptin.

EMBODIMENT 10

The method according to any one of embodiments 1 to 9 wherein the effective amount of the amylin agent and the effective amount of the leptin agent comprises an amount such that a greater amount of weight loss is achieved when the amylin agent is administered in combination with the leptin agent to said subject than the amount of weight loss achieved when either agent is administered alone.

EMBODIMENT 11

The method of embodiment 10 wherein the two agents are administered at the same time.

EMBODIMENT 12

The method of embodiment 11 wherein the two agents are mixed together.

EMBODIMENT 13

The method according to any one of embodiments 1 to 12 wherein the amylin analog or amylin agonist is administered at 90 to 400 micrograms twice daily.

EMBODIMENT 14

The method according to any one of embodiments 1 to 13 wherein the amylin analog or amylin agonist is administered at 150 to 375 micrograms twice daily.

EMBODIMENT 15

The method according to any one of embodiments 1 to 14 wherein the amylin analog or amylin agonist is administered at 180 to 360 micrograms twice daily.

EMBODIMENT 16

The method according to any one of embodiments 1 to 15 wherein the amylin analog or amylin agonist is administered at 360 micrograms twice daily.

EMBODIMENT 17

The method according to any one of embodiments 1 to 16 wherein the amylin analog or amylin agonist is administered at 180 micrograms twice daily.

EMBODIMENT 18

The method according to any one of embodiments 1 to 17 wherein the leptin, leptin analog or leptin agonist is administered at 1.0 to 6.0 milligrams twice daily.

EMBODIMENT 19

The method according to any one of embodiments 1 to 18 wherein the leptin, leptin analog or leptin agonist is administered at 1.25 to 5.0 milligrams twice daily.

EMBODIMENT 20

The method according to any one of embodiments 1 to 19 wherein the leptin, leptin analog or leptin agonist is administered at 2.0 to 3.0 milligrams twice daily.

EMBODIMENT 21

The method according to any one of embodiments 1 to 20 wherein the leptin, leptin analog or leptin agonist is administered at 1.25 milligrams twice daily

EMBODIMENT 22

The method according to any one of embodiments 1 to 21 wherein the leptin, leptin analog or leptin agonist is administered at 2.5 milligrams twice daily.

EMBODIMENT 23

The method according to any one of embodiments 1 to 12 wherein the amylin analog or amylin agonist is administered at 90 to 400 micrograms twice daily and the leptin, leptin analog or leptin agonist is administered at 1.0 to 6.0 milligrams twice daily.

EMBODIMENT 24

The method according to any one of embodiments 1 to 12 wherein the amylin analog or amylin agonist is administered at 180 to 360 micrograms twice daily and the leptin, leptin analog or leptin agonist is administered at 1.25 to 2.5 milligrams twice daily or 1.25 to 5.0 milligrams twice daily.

EMBODIMENT 25

The method according to any one of embodiments 1 to 24 wherein the two agents are adminstered at the same time.

EMBODIMENT 26

The method of any one of embodiments 1 to 25 wherein the leptin, leptin analog or leptin agonist is a dry formulation and the amylin, amylin analog or amylin agonist is a liquid formulation.

EMBODIMENT 27

The method of embodiment 26 wherein the leptin, leptin analog or leptin agonist dry formulation is reconstituted with the amylin, amylin analog or amylin agonist liquid formulation.

EMBODIMENT 28

The method of any one of embodiments 26 and 27 wherein the dry formulation is a lyophilized formulation.

EMBODIMENT 29

The method of any one of embodiments 1 to 28 wherein the amylin and leptin agents are formulated separately but packaged together.

EMBODIMENT 30

The method of any one of embodiments 1 to 29 wherein the amylin and leptin agents are in separate chambered cartridges.

EMBODIMENT 31

The method of any one of embodiments 1 to 30 wherein the amylin and leptin agents are in separate chambers of a chambered syringe prior to reconstitution of the leptin agent.

EMBODIMENT 32

The method according to any one of embodiments 1 to 31 further comprising at least one of an anti-obesity agent selected from the group consisting of a NPY1 receptor antagonist, an NPY5 receptor antagonist, an NPY2 receptor agonist, an NPY4 receptor agonist, a CNTF, a CNTF agonist/modulator, a CNTF derivative, a MCH1R antagonist, a MCH2R antagonist, a melanocortin 4 agonist, a MC4 receptor agonist, a cannabinoid receptor (CB-1) antagonist/inverse agonist, a ghrelin antagonist, a 5HT2c agonist, a serotonin reuptake inhibitor, a serotonin transport inhibitor, an exendin, an exendin derivative, an exendin agonist, a GLP-1, a GLP-1 analog, a GLP-1 agonist, a DPP-IV inhibitor, an opioid antagonist, an orexin antagonist, a metabotropic glutamate subtype 5 receptor antagonist, a histamine 3 antagonist/inverse agonist, topiramate, a CCK, a CCK analog, a CCK agonist and a PYY(3-36), a PYY(3-36) analog, and a PYY (3-36) agonist.

EMBODIMENT 33

The method according to embodiment 32 wherein the further at least one anti-obesity agent is phentermine, rimonabant, sibutramine or topiramate.

EMBODIMENT 34

The method according to any one of embodiments 1 to 33 wherein the subject reduces body fat mass.

EMBODIMENT 35

The method according to any one of embodiments 1 to 34, wherein the subject has at least one condition selected from the group consisting of obesity, an obesity-related disorder, an obesity related disease, being overweight, an obesity-related condition, diabetes, insulin-resistance syndrome, lypodystrpohy, nonalcoholic steatohepatitis, a cardiovascular disease, polycystic ovary syndrome, and metabolic syndrome.

EMBODIMENT 36

The method according to any one of embodiments 1 to 35 wherein the BMI is greater than 25.

EMBODIMENT 37

The method according to any one of embodiments 1 to 36 wherein the BMI is 25 to 35.

EMBODIMENT 38

The method according to any one of embodiments 1 to 37, wherein the BMI is 25 to 40.

EMBODIMENT 39

The method according to any one of embodiments 1 to 38, wherein the BMI is 25 to 45.

EMBODIMENT 40

The method according to any one of embodiments 1 to 39, wherein the BMI is 35 to 45.

EMBODIMENT 41

The method according to any one of embodiments 1 to 40, wherein the BMI is reduced to less than 30.

EMBODIMENT 42

The method according to any one of embodiments 1 to 41, wherein the BMI is reduced to less than 25.

EMBODIMENT 43

The method according to any one of embodiments 1 to 42, wherein the BMI is reduced to normal.

EMBODIMENT 44

The method according to any one of embodiments 1 to 43, wherein weight loss is achieved within 4 weeks of treatment.

EMBODIMENT 45

The method according to any one of embodiments 1 to 44, wherein weight loss is achieved within 8 weeks of treatment.

EMBODIMENT 46

The method according to any one of embodiments 1 to 45, wherein weight loss is achieved within 12 weeks of treatment.

EMBODIMENT 47

The method according to any one of embodiments 1 to 46, wherein weight loss is achieved within 20 weeks of treatment.

EMBODIMENT 48

The method according to any one of embodiments 1 to 47, wherein weight loss is achieved within 24 weeks of treatment.

EMBODIMENT 49

The method according to any one of embodiments 1 to 48, wherein the subject is human.

EMBODIMENT 50

The method according to any one of embodiments 1 to 49, wherein the subject is an obese human.

EMBODIMENT 51

The method according to any one of embodiments 1 to 50, wherein the subject is a human adult female.

EMBODIMENT 52

The method according to any one of embodiments 1 to 51, wherein the weight loss is reduced by at least 12%.

EMBODIMENT 3

The method according to any one of embodiments 1 to 52, wherein the weight loss is reduced by at least 15%.

EMBODIMENT 54

The method according to any one of embodiments 1 to 53, wherein the weight loss is reduced by at least 10% within 8 weeks of treatment.

EMBODIMENT 55

The method according to any one of embodiments 1 to 54, wherein the weight loss is reduced by at least 10% within 12 weeks of treatment.

EMBODIMENT 56

The method according to any one of embodiments 1 to 55, wherein the weight loss is reduced by at least 10% within 20 weeks of treatment.

EMBODIMENT 57

The method according to any one of embodiments 1 to 56, wherein the weight loss is reduced by at least 15% within 40 weeks of treatment.

EMBODIMENT 58

The method according to any one of embodiments 1 to 57, wherein the amylin agent and the leptin agent are administered within two hours prior to a meal.

EMBODIMENT 59

The method according to any one of embodiments 1 to 58, wherein the amylin agent and the leptin agent are adminstered within one hour prior to a meal.

EMBODIMENT 60

The method according to any one of embodiments 1 to 59, wherein the amylin agent and the leptin agent are adminstered within 15 minutes prior to a meal.

EMBODIMENT 61

The method according to any one of embodiments 1 to 60, wherein the amylin agent and the leptin agent are adminstered prior to breakfast.

EMBODIMENT 62

The method according to any one of embodiments 1 to 61, wherein the amylin agent and the leptin agent are adminstered prior to dinner.

EMBODIMENT 63

The method according to any one of embodiments 1 to 62, wherein the effective amount of the amylin agent achieves a blood plasma concentration of 500 to 2000 pg/ml.

EMBODIMENT 64

The method according to any one of embodiments 1 to 63 wherein the effective amount of the amylin agent achieves a blood plasma concentration of 750 to 1500 pg/ml.

EMBODIMENT 65

The method according to any one of embodiments 1 to 64, wherein the effective amount of the amylin agent achieves a maximal blood plasma concentration of about 1500 pg/ml.

EMBODIMENT 66

The method according to any one of embodiments 1 to 65, wherein the effective amount of the leptin agent achieves a blood plasma concentration of 20 to 100 pg/ml.

EMBODIMENT 67

The method according to any one of embodiments 1 to 66, wherein the effective amount of the leptin agent achieves a blood plasma concentration of 25 to 90 pg/ml.

EMBODIMENT 68

The method according to any one of embodiments 1 to 67, wherein the effective amount of the leptin agent achieves a blood plasma concentration of 25 to 90 pg/ml.

EMBODIMENT 69

The method according to any one of embodiments 1 to 68, wherein the effective amount of the amylin agent achieves a blood plasma concentration of 500 to 2000 pg/ml and the effective amount of the leptin agent achieves a blood plasma concentration of 20 to 100 pg/ml.

EMBODIMENT 70

The method of any one of embodiments 1 to 69, further comprising administering either the amylin or leptin agent alone to maintain or to continue the reduction in body weight.

EMBODIMENT 71

A method of reducing body weight in a subject comprising, administering at least an amylin, an amylin agonist or an amylin analog in an amount and time effective to sensitize the subject in need thereof to leptin, and then administering a leptin, a leptin derivative or a leptin agonist to reduce the body weight of the subject by at least 10%.

EMBODIMENT 72

A method of reducing body weight in a subject comprising, administering at least an amylin, an amylin agonist or an amylin analog and a leptin, a leptin derivative, or a leptin agonist to reduce the body weight of the subject by at least 10%, and then administering either an amylin, an amylin agonist or an amylin analog or a leptin, a leptin derivative, or a leptin agonist alone.

EMBODIMENT 73

A pharmaceutical composition for use in the method of any of the embodiments 1 to 72, wherein the composition comprises an effective amount of an amylin agonist and an effective amount of a leptin agonist.

EMBODIMENT 74

A pharmaceutical composition for the treatment of obesity or for effecting weight loss in a subject in need thereof, wherein said composition comprises an effective amount of an amylin agonist and an effective amount of a leptin agonist according to any one of embodiments 1 to 73.

EMBODIMENT 75

A pharmaceutical composition for the treatment of obesity or for effecting weight loss in a subject in need thereof, wherein the composition comprises an effective amount of an amylin agonist and an effective amount of a leptin agonist, and wherein the effective amount comprises an amount such that a greater amount of weight loss is achieved when the agents are administered in combination to said subject than the amount of weight loss achieved when either agent is administered alone.

EMBODIMENT 76

The use of a composition comprising an amylin agonist and a leptin agonist in the manufacture of a medicament for the treatment of obesity or for effecting weight loss, according to any one of embodiments 1 to 75.

Anti-obesity agents for use in the present invention include leptin, leptin derivatives, recombinant leptin, and leptin agonists. Leptin (derived from Greek leptos, meaning thin) is a hormone produced predominantly by fat cells. In obese humans, leptin blood levels generally correlate with the amount of fat stored in the body. Generally, the greater the amount of fat, the greater the amount of leptin. Serum leptin levels concentrations in the majority of humans with obesity are high, and without wishing to be bound by theory, a state of leptin resistance is thought to exist (Mantzoros et al. (2000) *J. Clin. Endocrinol. Metab.* 85:4000-4002). Despite therapeutic attempts at using leptin to treat obesity, the effect of recombinant human leptin has been limited, if any, in causing weight loss in obese individuals. Exceptions to this include the treatment of individuals with congenital leptin deficiency and the treatment of individuals with lipoatrophy. See, for example, Heymsfield et al. (1999) *JAMA* 282:1568-1575, Farooqi et al. (1999) *N. Engl. J. Med.* 341:879-884, and U.S. Pat. Publication No. 2005/0020496.

Exemplary leptins, leptin derivatives, recombinant leptins, and leptin agonists for use in the methods and compositions described herein include, but are not limited to, the amino acid sequence for mature, recombinant methionyl human leptin (herein called rmetHu-Leptin 1-146 or Metreleptin) having the amino acid sequence: MVPIQKVQD DTKTLIK-TIVTRINDISHTQSVSSKQKVTGLDFIPGLHPILTL SKMDQTLAVYQQILTSMPSRNVI-QISNDLENLRDLLHVLAF SKSCHLPWASGLETLD-SLGGVLEASGYSTEVVALSRLQGSL QDMLWQLDL-SPGC(SEQ ID NO:191).

In certain embodiments, leptin is administered in the form of replacement therapy so as to achieve near physiological concentrations of leptin in the plasma. It is estimated that the physiological replacement dose of leptin is about 0.02 mg/kg of body weight per day for males of all ages, about 0.03 mg/kg of body weight per day for females under 18 years and about 0.04 mg/kg of body weight per day for adult females. When attempting to achieve near physiological concentrations of leptin, one may, for example, treat a subject with 50 percent of the estimated replacement dose for the first month of treatment, 100 percent of the replacement dose for the second month of treatment, 200 percent of the replacement dose for the third month of treatment, etc. Serum leptin levels can be measured by methods known in the art, including, for example, using commercially available immunoassays.

It is one aspect of the invention that fat is reduced by means such as administration of amylin to treat leptin resistance. Once leptin resistance is ameliorated (lessened), leptin can be administered to further treat obesity.

Leptin proteins and leptin protein containing compositions appropriate for use in the methods and compositions described herein are known in the art and include, but are not limited to recombinant human leptin (PEG-OB, Hoffman La Roche) and recombinant methionyl human leptin (Amgen). Leptin proteins, analogs, derivatives, preparations, formulations, pharmaceutical compositions, doses, and administration routes have previously been described in the following patent publications and are hereby incorporated by reference in their entirety and for all purposes: U.S. Pat. Nos. 5,552,524; 5,552,523; 5,552,522; 5,521,283, 5,935,810; 6,001,968; 6,429,290; 6,350,730; 6,936,439; 6,420,339; 6,541,033; U.S. Pat. Publication Nos. 2005/0176107; 2005/0163799; and PCT Application Publication Nos. WO 96/05309, WO 96/40912; WO 97/06816, WO 00/20872, WO 97/18833, WO 97/38014, WO 98/08512, WO 98/28427, WO 98/46257, WO 00/09165, WO 00/47741, and WO 00/21574.

Leptin agonists and antagonists are known in the art. For example, leptin agonists are described in U.S. Pat. Publication Nos. 2004/0072219, 2003/049693, 2003/0166847, 2003/0092126, and U.S. Pat. Nos. 6,777,388 and 6,936,439. Leptin antagonists are described e.g. in U.S. Pat. Publication Nos. 2004/0048773, 2002/0160935 and U.S. Pat. No. 6,399,745. Means for testing for leptin agonism or antagonism are described e.g. in U.S. Pat. Nos. 6,007,998 and 5,856,098. These patents are exemplary and are incorporated herein by reference in their entirety and for all purposes.

Anti-obesity agents for use in the present invention also include amylin and amylin agonists. Amylin is a 37 amino acid peptide hormone that is co-secreted with insulin from pancreatic beta-cells in response to nutrient stimuli. Human amylin (rAmylin) has the following amino acid sequence: Lys-Cys-Asn-Thr-Ala-Thr-Cys-Ala-Thr-Gln-Arg-Leu-Ala-Asn-Phe-Leu-Val-His-Ser-Ser-Asn-Asn-Phe-Gly-Ala-Ile-Leu-Ser-Ser-Thr-Asn-Val-Gly-Ser-Asn-Thr-Tyr (SEQ ID NO:1). Rat amylin (rAmylin) has the following sequence: KCNTATCATQRLANFLVRSSNNLGPVLPPTNVGSNTY (SEQ ID NO:2). The use of amylins from any species is contemplated in the methods described herein.

It has surprisingly been found that modulation of effective amylin levels in vivo such as through the use of amylin, amylin agonists, and amylin antagonists, can modulate the effective levels of gbrelin in vivo.

Amylin agonists contemplated in the use of the invention include those described in U.S. Pat. Nos. 5,686,411, 6,114,304, and 6,410,511, which are herein incorporated by reference in their entirety and for all purposes. Such compounds include those having the formula I:

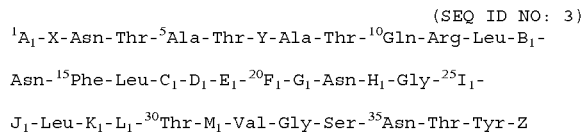

(SEQ ID NO: 3)
$^1A_1$-X-Asn-Thr-$^5$Ala-Thr-Y-Ala-Thr-$^{10}$Gln-Arg-Leu-$B_1$-Asn-$^{15}$Phe-Leu-$C_1$-$D_1$-$E_1$-$^{20}F_1$-$G_1$-Asn-$H_1$-Gly-$^{25}I_1$-$J_1$-Leu-$K_1$-$L_1$-$^{30}$Thr-$M_1$-Val-Gly-Ser-$^{35}$Asn-Thr-Tyr-Z wherein $A_1$ is Lys, Ala, Ser or hydrogen;
$B_1$ is Ala, Ser or Thr;
$C_1$ is Val, Leu or Ile;
$D_1$ is His or Arg;
$E_1$ is Ser or Thr;
$F_1$ is Ser, Thr, Gln or Asn;
$G_1$ is Asn, Gln or His;
$H_1$ is Phe, Leu or Tyr;
$I_1$ is Ala or Pro;
$J_1$ is Ile, Val, Ala or Leu;
$K_1$ is Ser, Pro, Leu, Ile or Thr;
$L_1$ is Ser, Pro or Thr;
$M_1$ is Asn, Asp, or Gln;

X and Y are independently selected amino acid residues having side chains which are chemically bonded to each other to form an intramolecular linkage; and Z is amino, alkylamino, dialkylamino, cycloalkylamino, arylamino, aralkylamino, alkyloxy, aryloxy or aralkyloxy.

Suitable side chains for X and Y include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond. Preferred alkyl chains include lower alkyl groups having from about 1 to about 6 carbon atoms.

An additional aspect of the present invention is directed to agonist analogues of SEQ ID NO:3 which are not bridged, and wherein X and Y are independently selected from Ala, Ser, Cys, Val, Leu and Ile or alkyl, aryl, or aralkyl esters and ethers of Ser or Cys.

Biologically active derivatives of the above agonist analogs are also included within the scope of this invention in which the stereochemistry of individual amino acids may be inverted from (L)/S to (D)/R at one or more specific sites.

Also included within the scope of this invention are the agonist analogs modified by glycosylation of Asn, Ser and/or Thr residues.

Biologically active agonist analogs of amylin are included within the scope of this invention which contain less peptide character. Such peptide mimetics may include, for example, one or more of the following substitutions for —CO—NH— amide bonds: depsipeptides (—CO—O—), iminomethylenes (—CH2-NH—), trans-alkenes (—CH=CH—), beta-enaminonitriles (—C(=CH—CN)—NH—), thioamides (—CS—NH—), thiomethylenes (—S—CH2- or —CH2-S—), methylenes (—CH2-C2-) and retro-amides (—NH—CO—).

Compounds of this invention form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include, for example, ammonium salts, alkali metal salts (such as sodium and potassium salts) and alkali earth salts (such as calcium and magnesium salts). Acetate, hydrochloride, and trifluoroacetate salts are preferred.

Throughout the application, the amino acid sequences may be referred to as amino acids at position a to position b adjacent to a reference peptide. For example, 1-7 hAmylin refers to the amino acid sequence from position 1 to position 7, inclusive, of human amylin (SEQ ID NO:1), the reference peptide in this example. Modification to the reference peptide may be shown as the position of modification adjacent to the modification. For example, ($^2$Asp $^7$Lys) 1-7 hAmylin represents the amino acid sequence at positions 1 to 7 of human amylin with a modification of the Cys to Asp at position 2 and a modification of the Cys to Lys at position 7. For another example, $^{18}$Arg$^{25,28}$ Pro-h-amylin represents the amino acid sequence of human amylin with a modification of the His to Arg at position 18, a modification of the Ala to Pro at position 25, and a modification of the Ser to Pro at position 28.

Exemplary compounds include, but are not limited to des-$^1$Lys-h-amylin (SEQ ID NO:4), $^{28}$Pro-h-amylin (SEQ ID NO:5), $^{25,28,29}$Pro-h-amylin (SEQ ID NO:6), $^{18}$Arg$^{25,28}$Pro-h-amylin (SEQ ID NO:7), and des-$^1$Lys$^{18}$Arg$^{25,28}$Pro-h-amylin (SEQ ID NO:8), all show amylin activity in vivo in treated test animals, (e.g., provoking marked hyperlactemia followed by hyperglycemia). In addition to having activities characteristic of amylin, certain of the preferred compounds of the invention have also been found to possess more desirable solubility and stability characteristics when compared to human amylin. Examples of these compounds include $^{25}$Pro$^{26}$Val$^{28,29}$ Pro-h-amylin (SEQ ID NO:9), $^{25,28,29}$Pro-h-amylin (SEQ ID NO:10), and $^{18}$Arg$^{25,28}$Pro-h-amylin (SEQ ID NO:7).

Other compounds include $^{18}$Arg$^{25,28,29}$Pro-h-amylin (SEQ ID NO:11), des-$^1$Lys$^{18}$Arg$^{25,28,29}$Pro-h-amylin (SEQ ID NO:12), des-$^1$ Lys$^{25,28,29}$Pro-h-amylin (SEQ ID NO:13), $^{25}$Pro$^{26}$Val$^{28,29}$Pro-h-amylin (SEQ ID NO:14), $^{23}$Leu$^{25}$Pro$^{26}$Val$^{28,29}$Pro-h-amylin (SEQ ID NO:15), $^{23}$Leu$^{25}$Pro$^{26}$Val$^{28}$Pro-h-amylin (SEQ ID NO:16), des-$^1$Lys$^{23}$ Leu$^{25}$Pro$^{26}$Val$^{28}$Pro-h-amylin (SEQ ID NO:17), $^{18}$Arg$^{23}$Leu$^{25}$Pro$^{26}$Val$^{28}$Pro-h-amylin (SEQ ID NO:18), $^{18}$Arg$^{23}$Leu$^{25,28,29}$Pro-h-amylin (SEQ ID NO:19), $^{18}$Arg$^{23}$Leu$^{25,28}$Pro-h-amylin (SEQ ID NO:20), $^{17}$Ile$^{23}$Leu$^{25,28,29}$Pro-h-amylin (SEQ ID NO:21), $^{17}$Ile$^{25,28,29}$Pro-h-amylin (SEQ ID NO:22), des-$^1$Lys$^{17}$Ile$^{23}$Leu$^{25,28,29}$Pro-h-amylin (SEQ ID NO:23), $^{17}$Ile$^{18}$Arg$^{23}$Leu-h-amylin (SEQ ID NO:24), $^{17}$Ile$^{18}$Arg$^{23}$Leu$^{26}$Val$^{29}$Pro-h-amylin (SEQ ID NO:25), $^{17}$Ile$^{18}$Arg$^{23}$Leu$^{25}$Pro$^{26}$Val$^{28,29}$Pro-h- amylin (SEQ ID NO:26), $^{13}$Thr$^{21}$His$^{23}$Leu$^{26}$Ala$^{28}$Leu$^{29}$Pro$^{31}$Asp-h-amylin (SEQ ID NO:27), $^{13}$Thr$^{21}$His$^{23}$Leu$^{26}$Ala$^{29}$Pro$^{31}$Asp-h-amylin (SEQ ID NO:28), des-$^{1}$Lys $^{13}$Thr$^{21}$His$^{23}$Leu$^{26}$Ala$^{28}$Pro$^{31}$Asp-h-amylin (SEQ ID NO:29), $^{13}$Thr$^{18}$Arg $^{21}$His$^{23}$Leu$^{26}$Ala$^{29}$Pro$^{31}$Asp-h-amylin (SEQ ID NO:30), $^{13}$Thr$^{18}$Arg$^{21}$His$^{23}$Leu$^{28,29}$Pro$^{31}$Asp-h-amylin (SEQ ID NO:31), and $^{13}$Thr$^{18}$Arg$^{21}$His$^{23}$Leu$^{25}$Pro$^{26}$Ala$^{28,29}$Pro$^{31}$Asp-h-amylin (SEQ ID NO:32).

Useful amylin agonist analogs include those identified in PCT Application Publication No. WO 93/10146, the contents of which is also hereby incorporated by reference.

Amylin agonists useful in the invention may also include fragments of amylin and its analogs as described above as well as those described in EP 289287, the contents of which are herein incorporated by reference. Amylin agonists may also be compounds having at least 60, 65, 70, 75, 80, 85, 90, 95, or 99% amino acid sequence identity to SEQ ID NO:1 having amylin activity. Amylin agonists also include small molecules, non-peptide molecules, for example those based on small molecule chemistry. "Amylin activity" as used herein includes the ability of amylin to affect ghrelin levels in a body. Amylin agonists also include analogs of amylin having insertions, deletions, extensions and/or substitutions in at least one or more amino acid positions of SEQ ID NO:1. The number of amino acid insertions, deletions, or substitutions may be not more than 5, 10, 15, 20, 25, or 30. Insertions, extensions, or substitutions may be with other natural amino acids, synthetic amino acids, peptidomimetics, or other chemical compounds. Amylin agonists, as contemplated in the invention may also be calcitonins, such as teleost calcitonins, and their analogs, as well as calcitonin-gene-related peptides (CGRP) and their analogs.

Amylin agonists also include polypeptides (referred to herein as LHC (loop helix C-terminus) peptides) described in U.S. Patent Application No. 60/543,275 and in PCT application No. PCT/US2005/004631, filed Feb. 11, 2005, each of which is incorporated herein by reference, as well as their analogs and derivatives. The LHC peptides for use in the invention act as an agonist for at least one biological effect of calcitonin, amylin, CGRP, or any combination of the three herein disclosed or bind to at least one of the receptors of amylin, calcitonin, or CGRP. Receptor binding activity and biological activity of exemplary LHC peptides are described in U.S. Patent Application No. 60/543,275 and in PCT application No. PCT/US2005/004631. In a general aspect, these polypeptide agonists have at least a loop region of amylin or calcitonin and analogs thereof, an α helix region of at least a portion of an α helix region of calcitonin or analogs thereof or an α helix region having a portion of an amylin α helix region and a calcitonin α helix region or their respective analogs, and a C-terminal tail of amylin or calcitonin or analogs thereof, with the proviso that the C-terminal tail of calcitonin or a calcitonin analog is not proline (Pro), hydroxyproline (Hyp), homoserine (Hse) or derivatives of Hse.

In certain embodiments, these LHC peptides have an amylin or amylin analog loop region, at least a portion of a calcitonin or calcitonin analog α helix region, and an amylin or amylin analog C-terminal tail. In other embodiments, these LHC peptides have a calcitonin or calcitonin analog loop region, at least a portion of a calcitonin or calcitonin analog α helix region, and an amylin or amylin analog C-terminal tail. In still other embodiments, these LHC peptides have an amylin or amylin analog loop region, at least a portion of an amylin or amylin analog α helix region and at least a portion of a calcitonin or calcitonin analog α helix region, and an amylin or amylin analog C-terminal tail. In yet other embodiments, these LHC peptides have a calcitonin or calcitonin analog loop region, at least a portion of an amylin or amylin analog α helix region and at least a portion of a calcitonin or calcitonin analog α helix region, and an amylin or amylin analog C-terminal tail. In still yet other embodiments, these LHC peptides have an amylin or amylin analog loop region, a portion or a calcitonin or calcitonin analog α helix region or at least a portion of an amylin or amylin analog α helix region and at least a portion of a calcitonin or calcitonin analog α helix region, and a calcitonin or calcitonin analog C-terminal tail.

In certain embodiments, the loop region of these LHC peptides may further comprise no more than one, two, three, or four modifications including substitutions, insertions, or deletions from the amylin or calcitonin loop, and analogs thereof. It is further contemplated that these LHC peptides may have additional modifications at the N-terminal portion of the loop comprising a N-cap region, that may have hydrophobic or hydrophilic characteristics such as acetyl, isocaproyl, 3,6-dioxyoctanoic acid, or 1-amino-4,7,10-trioxa-13-tridecanamine succinimic acid. Modifications may further include one, two, three or more additional amino acids. This is an area which allows for many modifications too numerous to mention, but would be understood by one of skill in the art based upon what is exemplified further in the present application.

These LHC peptides may also be further derivatized by chemical alterations such as amidation, glycosylation, acylation, sulfation, phosphorylation, acetylation, and cyclization. Such chemical alterations may be obtained through chemical or biochemical methodologies, as well as through in vivo processes, or any combination thereof. Derivatives of these LHC peptides may also include conjugation to one or more polymers or small molecule substituents. One type of polymer conjugation is linkage or attachment of polyethylene glycol ("PEG") polymers, polyamino acids (e.g., poly-his, poly-arg, poly-lys, etc.) and/or fatty acid chains of various lengths to the N- or C-terminus or amino acid residue side chains of the polypeptide. Small molecule substituents include short alkyls and constrained alkyls (e.g., branched, cyclic, fused, adamantyl), and aromatic groups. In addition, basic residues such as R and K may be replaced with homoR and homoK, citrulline, or ornithine to improve metabolic stability of the peptide. Polypeptides for use in the invention include acid as well as amide forms.

In certain embodiments, the α helix region of the LHC peptides comprise at least four consecutive amino acids of a calcitonin or calcitonin analog α helix region. In other embodiment, the α helix region comprises at least 5, 6, 7, or 8 consecutive amino acids of a calcitonin or calcitonin analog α helix region. In other embodiments, the α helix region comprises at least 10, 11, 12, 13, 14, 15, 16, 17, 18, 19, 20, 21 or more consecutive amino acids of a calcitonin or calcitonin analog α helix region. In certain embodiments, when the number of consecutive amino acids are less than 8, it is contemplated that the α helix region further comprises at least 4, 5, 6, 7, 9, 10, 11, or more consecutive amino acids of an amylin or amylin analog α helix region. In certain embodiments, it is envisioned that the less amino acids of calcitonin or calcitonin analog, the more amino acids of an amylin or amylin analog may be found in the α helix region of the novel compounds. The number of amino acids comprising the α helix region may be from about 10 to 23 amino acids. Accordingly, the α helix region may be 10, 11, 12, 13, 14, 15, 16, 17, 18, 19, 20, 21, 22, or 23 amino acids long. Moreover, the amino acids should provide for about three to about six α helical turns. It is further contemplated that the α helix region of the compounds may further comprise no more than one, two, three, four, five, six, seven, eight, nine or ten modifications including substitutions, insertions, or deletions from that of the calcitonin and/or amylin α helix region, and analogs thereof.

In certain embodiments, the C-terminal tail of the LHC peptides comprise at least the last six, five, or four amino acids of either amylin or calcitonin, and analogs thereof. In certain embodiments, the C-terminal tail of the novel compounds comprise at least a portion of the C-terminal end having a β turn. In certain embodiments, the β turn is introduced by the amino acid combination of Gly-Ser. Accordingly, the LHC peptides may have a C-terminal end comprising a portion of an amylin or calcitonin C-terminal tail (and analogs thereof) having Gly-Ser or starting at Gly-Ser.

In certain embodiments, the C-terminal tail of the LHC peptides may further comprise no more than one, two, or three, modifications including substitutions, insertions, or deletions from the amylin or calcitonin loop, and analogs thereof. It is further contemplated that the LHC peptides may have additional modifications at the C-terminal portion of the C-terminal tail which may include, for example, L-octylglycine, 4ABU (4-aminobutyric acid), 9Anc (9 amiononanoic acid), 3,6-dioxyoctanoic acid or 1-amino-4,7,10-trioxa-13-tridecanamine succinimic acid. Modification may further include one, two, three or more additional amino acids. The types of modification contemplated in this area would be understood by one of skill in the art based upon what is exemplified further in the present application.

In one aspect, a loop region is defined as that region found at the N-terminal end comprising at least 5 to 8 amino acids, wherein the first and last amino acid are capable of creating a bond, for example, residues at positions 2-7 of amylin or residues at positions 1-7 of calcitonin and their corresponding regions in their respective analogs. In another aspect, a α helix region is defined as the internal portion of amylin or calcitonin flanked by the loop region and the C-terminal tail which structurally forms an α helix, for example, residues at positions 8-23 of amylin or residues at positions 8-27 of calcitonin and their corresponding regions in their respective analogs. In yet another aspect, a C-terminal tail is defined as that region after the α helix, e.g., residues at positions 33-37 of amylin or longer such as residues at positions 27-37 or residues at positions 27 or 28 to 32 of calcitonin. Included in the LHC peptides are both the amide and acid forms of the disclosed compounds.

Amylin and calcitonin, as herein defined, includes all native and species variations. Examples of amylin and calcitonin include, but are not limited to:
human amylin (SEQ ID NO:1), rat amylin (SEQ ID NO:2), salmon calcitonin (sCT) CSNLSTCVLGKLSQELHKLQ-TYPRTNTGSGTP (SEQ ID NO:33), and human calcitonin (hCT) CGNLSTCMLGTYTQDFNKFHTFPQTAIGVGAP (SEQ ID NO:34).

In a general aspect, the LHC peptides comprise at least a loop region, an α helix region, and a C-terminal tail. The loop region comprises an amino sequence comprising the formula (II) X-Xaa1 sequence-Y wherein X and Y are capable of creating a bond and are independently selected residues having side chains which are, or are capable of being, chemically bonded to each other to form an intramolecular linkage such as, for example, a disulfide bond; an amide bond; a cyclic lactam formed, for example, by an alkyl acid and an alkyl amine; an alkyl amine or imine bridge formed, for example, by condensing and reducing an alkyl aldehydes or alkyl halides and alkylamines; and an alkyl, alkenyl, alkynyl, ether or thioether bond formed, for example, by connection of side chains. Alkyl chains may include lower alkyl groups having from about 1 to about 6 carbon atoms. In certain embodiments, the intramolecular linkage may be a disulfide, amide, imine, amine, alkyl and alkene bond. In certain embodiments, X and Y of formula (II) are independently selected from Ser, Asp, Glu, Lys, Orn (ornithine), or Cys. In certain embodiments, X and Y of formula (II) are Cys and Cys. In other embodiments, X and Y of formula (II) are Ser and Ser. In still other embodiments, X and Y of formula (II) are Asp and Lys or Lys and Asp.

The Xaa1 sequence of formula (II) comprises an amino acid sequence of 3, 4, 5, or 6 amino acids between X and Y. In certain embodiments, the Xaa1 sequence comprises an amino acid sequence having a region with one or more substituted or unsubstituted hydroxyl-containing residues next to Y. For example, the hydroxyl containing residue region may have at least 2 of the 3 amino acids adjacent Y that are either a Ser or Thr. The other amino acids in the Xaa1 sequence may be any amino acid. In certain embodiments, the Xaa1 sequence is 3 amino acids. In other embodiments, the Xaa1 sequence is 4 amino acids. In still other embodiments, the Xaa1 sequence is 5 amino acids. In yet other embodiments, the Xaa1 sequence is 6 amino acids. Accordingly, Xaa1 of formula (II) can be represented by Xaa2-Xaa3-Xaa4-Xaa5-Xaa6-Xaa7 (SEQ ID NO:35). In certain embodiments, Xaa2, Xaa3, Xaa4, any two, or all three may absent. In certain embodiments, Xaa5, Xaa6, and Xaa7 comprise the hydroxy-containing residue region. As such, at least two of the three amino acids can be a Ser, Hse, Thr, allo-Threonine (alloThr), d-Threonine (d-Thr), or other unnatural analog thereof. Xaa2 can be any amino acid or absent, Xaa3 can be any amino acid or absent, Xaa4 can be any amino acid or absent, Xaa5 can be any amino acid if Xaa6 is a Ser or Thr and Xaa7 is a Ser or Thr, Xaa6 can be any amino acid if Xaa5 is a Ser or Thr and Xaa7 is a Ser or Thr, Xaa7 can be any amino acid if Xaa5 is Ser or Thr and Xaa6 is Ser or Thr. Accordingly, in certain embodiment, Xaa1 can be represented as Xaa2 absent, Xaa3 is Ala, Gly, Ser, Asp or absent, Xaa4 is Asn, Ala, Asp, Gly or absent; Xaa5 is Ala, Leu, Thr, or Ser; Xaa6 is Ala, Ser, or Thr; and Xaa7 is Ala, Ser, Val, Hse, (S)-2-amino-3-hydroxy-methylbutanoic acid (Ahb), (2S, 3R)-2-amino-3hydroxy-methylpentanoic acid (Ahp), d-Thr, Thr, or a derivative thereof. In other embodiments Xaa1 can be represented as Xaa2 is absent, Xaa3 is Ser, Gly, or absent, Xaa4 is Asn or Asp, Xaa5 is Ala, Ser, Thr or Leu, Xaa6 is Ala, Thr or Ser, and Xaa7 is Ser, d-Thr, alloThr or Thr. In certain embodiments, the loop region of formula (II) comprises the above-described representations of Xaa1 wherein Xaa3 is Ala, wherein Xaa3 is Ser or wherein Xaa3 is Gly. Alternatively or additionally, the loop region comprises the above described representations of Xaa1 wherein Xaa4 is Ala, wherein Xaa4 is Asn, wherein Xaa4 is Asp, or wherein Xaa4 is Gly. Alternatively or additionally, the loop region comprises the above-described representations of Xaa1 wherein Xaa5 is Ala, wherein Xaa5 is Thr, or wherein Xaa5 is Leu. Alternatively or additionally, the loop region comprises the above described representations of Xaa1 wherein Xaa6 is Ser or wherein Xaa6 is Ala. Alternatively or additionally, the loop region comprises the above-described representations of Xaa1 wherein Xaa7 is Thr or wherein Xaa7 is d-Thr. It is further contemplated that no more than one, two, or three modifications such as substitutions, insertions, deletions, and/or derivatizations may be made to the loop region.

Examples of the loop region of the invention include, but are not limited to, CNTATC (SEQ ID NO:36); CATATC (SEQ ID NO:37); CDTATC (SEQ ID NO:38); CGTATC (SEQ ID NO:39); CNAATC (SEQ ID NO:40); CNTSTC (SEQ ID NO:41); CNTA-dThr-C (SEQ ID NO:42); CNTA- T(OPO3H2)-C (SEQ ID NO:43); CNTASC (SEQ ID NO:44); CNTAAC (SEQ ID NO:45); CNTAVC (SEQ ID NO:46); CNTA-Hse-C (SEQ ID NO:47); CNTA-Ahb-C (SEQ ID NO:48); CNTA-Ahp-C (SEQ ID NO:49); CSNL-STC (SEQ ID NO:50); CGNLSTC (SEQ ID NO:51); CANL-STC (SEQ ID NO:52); CSALSTC (SEQ ID NO:53); CSNASTC (SEQ ID NO:54); CSNLATC (SEQ ID NO:55); and CSNLSAC (SEQ ID NO:56). As previously noted, it is further contemplated that no more than one, two, or three modifications such as substitutions, insertions, deletions, and/or derivatizations may be made to the loop region.

The loop region of the LHC peptides may further comprise modifications or additional amino acids at the N-terminal end. Such modifications include the addition of compounds such as Lys, Ala, Phe, Ile, Ser, Octylglycine, Isocap, Fmoc-3,6-dioxyoctanoic acid, Fmoc-1-amino-4,7,10-trioxa-13-tridecanamine succinimic acid, acetyl, and/or groups for solubility, delivery, signaling. Exemplary modified loops include the addition of Lys to the sequence of Xaa1 or the addition of Ile to the sequence of Xaa1. For example, the modified loop region may be KCNTATC (SEQ ID NO:57). In certain embodiments, the additions and/or modifications at the N-terminal end of the loop region may change the loop region. For example, the loop region may be modified as follows: cyclo(2,7) 1-7 hAmylin, cyclo($^2$Asp $^7$Lys) 1-7 hAmylin, N-isocaproyl 1-7 hAmylin, N-3,6 dioxaoctanoyl 1-7 hAmylin, L-Octylglycine 1-7 hAmylin, Acetyl ($^2$Agy, $^7$Agy) 1-7 hAmylin wherein Agy is Allylglycine, Acetyl ($^1$Ala) 1-7 hAmylin, ($^1$Thr $^3$Asp) 1-7 hAmylin, Isocap ($^7$Ala) 5-7 sCT, Acetyl ($^2$Agy, $^7$Agy) 1-7 sCT, and cyclo (1,7) ($^1$Asp $^7$Lys) 1-7 sCT. Therefore, taking the example of Isocap ($^7$Ala) 5-7 sCT, certain embodiments comprise a modification at the N-terminal region of the loop region such that amino acids Xaa2 to Xaa5 are absent.

The α helix region of the LHC peptides may be about 8 to 23 amino acids in length. In certain embodiments, the α helix region is amphipathic. In certain embodiments, the α helix region comprises about 3 to 6 helical turns. In certain embodiments, the α helix region comprises 3, 4, 5, or 6 helical turns. In other embodiments, the α helix region is a rigid structure equivalent to about 3, 4, 5, or 6 helical turns. An example of an idealized helix is LLQQLQKLLQKLKQY (SEQ ID NO:58). In certain embodiments, the α helix is an amphipathic structure. Accordingly, characteristics of desirable amino acids that would provide this type of structure may be selected.

It has been found that the calcitonin α helix region, a combination of an amylin and a calcitonin α helix region, or parts thereof, and/or some CGRP elements are desirable in the α helix region of the LHC peptides. It is contemplated that, as with the loop region, the α helix region can be from any amylin or calcitonin, and analogs thereof. Accordingly, in certain embodiments, the α helix region is at least a portion of an α helix region of a calcitonin or calcitonin analog. In other embodiments, the α helix region is at least a portion of an α helix region of a calcitonin or calcitonin analog and at least a portion of an α helix of an amylin or amylin analog. In still other embodiments, the α helix region of the LHC peptides contain elements of CGRP. It is further contemplated that novel compounds may have no more than one, two, three, four, five, six, seven, eight, nine, or ten further modifications such as substitutions, insertions, deletions, and/or derivatizations.

In certain embodiments, the α helix region of the LHC may comprise α helix region type I. An α helix region type I comprises amino acids from position 8 of sCT to position 18, 19, 20, 21, 22, 23, 24, 25, 26, or 27 of sCT. Moreover, the α helix region type I may comprise more than one portion of a calcitonin or calcitonin analog α helix region of the same or different species, for example 8-21 sCT 19-27 sCT; 8-21 sCT 18-27 sCT; or 8-16 hCT 17-27 sCT; or ($^{11}$Arg) 8-16 hCT ($^{18}$Arg) 17-27 sCT. Alternatively or additionally, the above described α helix of 8-18 sCT to 8-27 sCT may further comprise the substitutions of one or more of ($^{10}$Aib), ($^{11}$Arg), ($^{11}$Orn), ($^{11}$hArg), ($^{11}$Cit), ($^{11}$hLys), ($^{11}$Lys(for)), ($^{17}$Aib), ($^{18}$Arg), ($^{18}$Orn), ($^{18}$hArg), ($^{18}$Cit), ($^{18}$hLys), ($^{11}$Lys(for)), ($^{11}$Lys(PEG5000)), ($^{22}$Leu), ($^{24}$Pro) or any combination thereof.

In certain embodiments, an α helix region type I of the LHC peptides can be represented by: X1 V L Xaa10 Xaa11 L S Q Xaa15 L Xaa17 Xaa18 L Q T Xaa22 P Xaa24 T N T X1 (SEQ ID NO:59), wherein Xaa10 is Gly or Aib;
Xaa11 is Lys, Arg, Orn, hArg, Cit, hLys, or Lys(for);
Xaa15 is Glu or Phe;
Xaa17 is His or Aib;
Xaa18 is Lys, Arg, Orn, hArg, Cit, hLys, Lys(for), Lys (PEG 5000);
Xaa22 is Try or Leu;
Xaa24 is Arg or Pro; or
X1 is absent or comprises 1-4 additional amino acids.

It should be remembered that each member of the Markush group, or a combination thereof, is another embodiment of the invention and is not to be read as a single unit. This is a shorthand method for stating, as an example, embodiments of the LHC peptides include an α helix region type I formula where, Xaa18 can be a Lys, Arg, Orn, hArg, Cit, hLys, or Lys(for), and each variation is a separate embodiment of the invention. Accordingly, the α helix region type I formula has embodiments wherein Xaa18 is Lys. It has other embodiments wherein Xaa18 is Arg, and so on. It is further contemplated that the α helix region may contain no more than one, two, three, four, five, six, seven, eight, nine, or ten modifications such as substitutions, insertions, deletions, and/or derivatizations. Accordingly, the compounds of α helix region type I may have further deletions at the C-terminal end. In certain embodiments, the amino acids of X1 are capable of forming an α helix turn.

Examples of an α helix region type I of the LHC peptides include, but are not limited to, 8-18 sCT, 8-21 sCT, 8-24 sCT, 8-27 sCT, ($^{11}$Arg) 8-18 sCT, ($^{18}$Arg) 8-18 sCT, ($^{11}$Arg$^{18}$Arg) 8-18 sCT, ($^{11}$Orn $^{18}$Orn) 8-18 sCT, ($^{11}$Arg $^{18}$Cit) 8-18 sCT, ($^{11}$hArg $^{18}$hArg) 8-18 sCT, ($^{11}$Arg $^{18}$Orn) 8-18 sCT, ($^{11}$Cit $^{18}$Arg) 8-18 sCT, ($^{11}$Cit $^{18}$Cit) 8-18 sCT, ($^{11}$hLys $^{18}$hLys) 8-18 sCT, ($^{10}$Aib $^{11}$Arg $^{17}$Aib $^{18}$Arg) 8-18 sCT, ($^{11}$Lys(for) $^{18}$Lys(for)) 8-18 sCT, ($^{10}$Aib $^{11}$Lys(for) $^{17}$Aib $^{18}$Lys(for)) 8-18 sCT, ($^{11}$Arg $^{18}$Lys(PEG 5000)) 8-18 sCT, ($^{11}$Arg) 8-21 sCT, ($^{18}$Arg) 8-21 sCT, ($^{11}$Arg $^{18}$Arg) 8-21 sCT, ($^{11}$Orn $^{18}$Orn) 8-21 sCT, ($^{11}$Arg $^{18}$Cit) 8-21 sCT, ($^{11}$hArg $^{18}$hArg) 8-21 sCT, ($^{11}$Arg $^{18}$Orn) 8-21 sCT, ($^{11}$Cit $^{18}$Arg) 8-21 sCT, ($^{11}$Cit $^{18}$Cit) 8-21 sCT, ($^{11}$hLys $^{18}$hLys) 8-21 sCT, ($^{10}$Aib $^{11}$Arg $^{17}$Aib $^{18}$Arg) 8-21 sCT, ($^{11}$Lys(for) $^{18}$Lys(for)) 8-21 sCT, ($^{10}$Aib $^{11}$Lys(for) $^{17}$Aib $^{18}$Lys(for)) 8-21 sCT, ($^{11}$Arg $^{18}$Lys(PEG 5000)) 8-21 sCT, ($^{11}$Arg) 8-24 sCT, ($^{18}$Arg) 8-24 sCT, ($^{11}$Arg $^{18}$Arg) 8-24 sCT, ($^{11}$Arg$^{18}$Arg $^{22}$Leu) 8-24 sCT, ($^{11}$Arg $^{18}$Arg $^{24}$Pro) 8-24 sCT, ($^{11}$Orn $^{18}$Orn) 8-24 sCT, ($^{11}$Arg $^{18}$Cit) 8-24 sCT, ($^{11}$hArg $^{18}$hArg) 8-24 sCT, ($^{11}$Arg $^{18}$Orn) 8-24 sCT, ($^{11}$Cit $^{18}$Arg) 8-24 sCT, ($^{11}$Cit $^{18}$Cit) 8-24 sCT, ($^{11}$hLys $^{18}$hLys) 8-24 sCT, ($^{10}$Aib $^{11}$Arg $^{17}$Aib $^{18}$Arg) 8-24 sCT, ($^{11}$Lys(for) $^{18}$Lys(for)) 8-24 sCT, ($^{10}$Aib $^{11}$Lys(for) $^{17}$Aib $^{18}$Lys(for)) 8-24 sCT, ($^{11}$Arg $^{18}$Lys(PEG 5000)) 8-24 sCT, ($^{11}$Arg) 8-27 sCT, ($^{18}$Arg) 8-27 sCT, ($^{11}$Arg $^{18}$Arg) 8-27 sCT, ($^{11}$Arg $^{18}$Arg $^{22}$Leu) 8-27 sCT, ($^{11}$Arg $^{11}$Arg $^{24}$Pro) 8-27 sCT, ($^{11}$Orn $^{18}$Orn) 8-27 sCT, ($^{11}$Arg $^{18}$Cit) 8-27 sCT, ($^{11}$hArg $^{18}$hArg) 8-27 sCT, ($^{11}$Arg $^{18}$Orn) 8-27 sCT, ($^{11}$Cit $^{18}$Arg)

8-27s CT, ($^{11}$Cit $^{18}$Cit) 8-27 sCT, ($^{11}$hLys $^{18}$hLys) 8-27 sCT, ($^{10}$Aib $^{11}$Arg $^{17}$Aib $^{18}$Arg) 8-27 sCT, ($^{11}$Lys(for) $^{18}$Lys(for)) 8-27 s CT, ($^{10}$Aib $^{11}$Lys(for) $^{17}$Aib $^{18}$Lys(for)) 8-27 sCT, ($^{11}$Arg $^{18}$Lys(PEG 5000)) 8-27 sCT, ($^{11}$Arg $^{18}$Arg) 8-21 sCT-19-27 s CT, and ($^{11}$Arg $^{18}$Arg) 8-21 sCT-(18Leu) 18-27 sCT.

In certain embodiments, the α helix region of the LHC peptides may comprise α helix region type II. An α helix region type II comprises a portion of an α helix region of an amylin or amylin analog and a portion of an α helix region of a calcitonin or calcitonin analog. The α helix region type II may comprise amino acids from position 8 of hAmylin to 11, 12, 13, 14, 15, 16, 17, 18 or 19 of hAmylin and amino acids from position 13, 14, 15, 16, 17, 18, and 19 of sCT to position 18, 19, 20, 21, 22, 23, 24, 25, 26, or 27 of sCT. Alternatively or additionally, the above described α helix region of amylin and calcitonin may further comprise the substitutions of one or more of ($^8$Val), ($^9$Leu), ($^9$Met), ($^{10}$Gly), ($^{10}$His), ($^{12}$Thr), ($^{13}$Thr), ($^{13}$Asn), ($^{13}$Phe), ($^{13}$Tyr), ($^{14}$Arg), ($^{14}$Ala), ($^{14}$Asp), ($^{14}$Glu), ($^{14}$Gln), ($^{14}$Thr), ($^{14}$Gly), ($^{15}$Leu), ($^{15}$Ser), ($^{15}$Glu), ($^{15}$Ala), ($^{15}$Tyr), ($^{16}$Asp), ($^{17}$Ser), ($^{17}$Phe), ($^{18}$Arg), ($^{17}$Aib), ($^{18}$Arg), ($^{18}$Orn), ($^{18}$hArg), ($^{18}$Cit), ($^{18}$hLys), ($^{18}$Lys(for)), ($^{18}$Lys(PEG5000)), ($^{19}$Phe), ($^{20}$His), ($^{21}$Asn), ($^{22}$Met), ($^{22}$Val), ($^{22}$Phe), ($^{22}$Leu), ($^{24}$Pro), or any combination thereof. In certain embodiments, the number of amino acids in the α helix region type II of the LHC peptides is at least 10 amino acids. In other embodiments, the number of amino acids in the α helix region type II of the LHC peptides is 11, 12, 13, 14, 15, 16, 17, 18, 19, 20, 21, 22, or 23. In other embodiments, the number of amino acids in the α helix region type II of the LHC peptides is 24 or more.

In certain embodiments, an α helix region type II of the LHC peptides can be represented by: X1 Xaa8 Xaa9 Xaa10 R Xaa12 Xaa13 Xaa14 Xaa15 Xaa16 Xaa17 Xaa18 Xaa19 Xaa20 Xaa21 Xaa22 P Xaa24 T N T X1 (SEQ ID NO:60) wherein
  Xaa8 is Ala or Val;
  Xaa9 is Thr, Met or Leu;
  Xaa10 is Gln, Gly, His;
  Xaa12 is Leu, or Thr;
  Xaa13 is Ala, Thr, Asn, Phe, Tyr, Ser, or Thr;
  Xaa14 is Asn, Arg, Ala, Asp, Glu, Gln, Thr, or Gly;
  Xaa15 is Phe, Leu, Ser, Glu, Ala, Asp, or Tyr;
  Xaa16 is Leu or Asp;
  Xaa17 is Val, His, Ser, Phe, or Aib;
  Xaa18 is His, Arg, Lys, Orn, hArg, Cit, hLys, Lys(for), or Lys(PEG5000);
  Xaa19 is Leu, Ser or Phe;
  Xaa20 is Gln or His;
  Xaa21 is Thr or Asn;
  Xaa22 is Tyr, Val, Phe, Leu or Met;
  Xaa24 is Arg or Pro; and
  X1 is absent or comprises 1-4 additional amino acids.

Again, each member in the Markush group, or a combination thereof is another embodiment of the invention and is not to be read as a single unit. It is further contemplated that the α helix region type II may contain no more than one, two, three, four, five, six, seven, eight, nine, or ten modifications such as substitutions, insertions, deletions, and/or derivatizations of the compounds described herein. For example, in certain embodiments, the α helix region type II may have deletions at the C-terminal end resulting in the deletion of position 27, 26, 25, 24, or 22. In other embodiments, however, the deletions do not remove amino acids of positions 19, 20, 21, or 22.

Examples of an α helix region of type II of the LHC peptides include, but are not limited to, ($^8$Val $^9$Leu $^{10}$Gly) 11-15 hAmylin 16-27 sCT, ($^8$Val $^9$Leu $^{10}$Gly) 11-15 hAmylin ($^{18}$Arg) 16-27 sCT, 8-12 hAmylin ($^{18}$Arg) 13-27 sCT, 8-18 hAmylin 19-23 sCT, 8-18 HAmylin 19-27 sCT, ($^{15}$Glu $^{18}$Arg) 8-18 hAmylin 19-24 sCT, ($^{14}$Arg $^{15}$Ser) 8-18 hAmylin 19-22 sCT, ($^{13}$Ala $^{14}$Ala $^{15}$Ala) 8-18 hAmylin 19-27 sCT, ($^{13}$Ala $^{14}$Asp $^{15}$Ala) 8-18 hAmylin 19-22 sCT, ($^{13}$Ala $^{14}$Asp) 8-18 hAmylin 19-23 sCT, ($^{13}$Ala $^{14}$Asp) 8-18 hAmylin 19-27 sCT, ($^{13}$Ala $^{14}$Ala) 8-18 hAmylin 19-22 sCT, ($^{13}$Ala $^{14}$Glu) 8-18 hAmylin 19-22 sCT, ($^{13}$Thr $^{14}$Asp $^{15}$Tyr) 8-18 hAmylin 19-22 sCT, ($^{13}$Ala $^{14}$Gln) 8-18 hAmylin 19-22 sCT, ($^{13}$Asn $^{14}$Glu $^{15}$Tyr) 8-18 hAmylin 19-27 sCT, ($^{13}$Phe $^{14}$Asp) 8-18 hAmylin 19-27 sCT, ($^{13}$Ala $^{14}$Asp) 8-18 hAmylin ($^{15}$Glu $^{18}$Arg) 8-18 hAmylin 19-24 sCT, ($^{19}$Phe $^{22}$Phe) 19-27 sCT, ($^{13}$Ala $^{14}$Asp) 8-18 hAmylin ($^{19}$Phe $^{20}$His $^{22}$Phe) 19-27 sCT, ($^{13}$Ala $^{14}$Asp) 8-18 hAmylin ($^{19}$Phe $^{22}$Phe) 19-27 sCT, ($^9$Thr $^{10}$His) 8-18 hAmylin 19-22 sCT, ($^9$Thr $^{10}$His $^{14}$Gly $^{15}$Leu $^{17}$Ser $^{18}$Arg) 8-19 hAmylin 20-23 sCT, 8-18 hAmylin ($^{21}$Asn $^{22}$Phe $^{23}$Val) 19-23 sCT, 8-18 hAmylin ($^{22}$Met) 19-27 sCT, 8-18 hAmylin ($^{22}$Val) 19-27 sCT, ($^9$Met $^{12}$Thr $^{13}$Tyr $^{14}$Thr $^{15}$Glu $^{16}$Asp $^{17}$Phe) 8-17 hAmylin ($^{18}$Arg) 18-20 sCT).

In other embodiments, novel compounds include variations of the above exemplary compounds with the α helix terminating at corresponding to 22, 23, 24, 25, 26 or 27 of sCT. In other words, compound 8-18 hAmylin 19-24 sCT is also specifically described as this compound is merely 8-18 hAmylin 19-27 sCT described above truncated to position 24. As another example, compound (13Ala 14Asp 15Ala) 8-18 hAmylin 19-23 is specifically described because of the above language applied to (13Ala 14Asp 15Ala) 8-18 hAmylin 19-22.

In certain embodiments, the C-terminal tail of the LHC peptides comprises amino acids from position 27, 28, 29, 30, 31, 32, or 33 to position 36 or 37 of hAmylin. In other embodiments, the C-terminal tail of the LHC peptides comprises amino acids from position 27 or 28 to position 32 of sCT; however, when the loop region is from a calcitonin or calcitonin analog and the α helix region is from a calcitonin or calcitonin analog, the last position of the C-terminal tail is not Pro, Hyp, Hse or derivatives of Hse. Alternatively or additionally, the above described α helix of amylin and calcitonin may further comprise the substitutions of one or more of ($^{27}$Tyr) hAmylin, ($^{29}$Arg) hAmylin, ($^{32}$Val) hAmylin, ($^{32}$Thr) hAmylin, ($^{34}$Glu) hAmylin, ($^{35}$Lys) hAmylin, ($^{36}$Phe) hAmylin, ($^{36}$Ala) hAmylin, ($^{37}$Phe) hAmylin, ($^{30}$Asn)sCT, ($^{32}$Tyr)$_s$ CT, or any combination thereof.

In certain embodiments, a C-terminal tail of the LHC peptides can be represented by Xaa28 Xaa29 Xaa30 Xaa31 Xaa32 Xaa33 G Xaa35 Xaa36 Xaa37 Xaa38 (SEQ ID NO:61), wherein
  Xaa28 is Lys, Tyr, or absent;
  Xaa29 is Ser, Pro, or absent;
  Xaa30 is Ser, Pro, Arg, or absent;
  Xaa31 is Thr, or absent;
  Xaa32 is Asn or absent;
  Xaa33 is Val, Thr, or absent;
  Xaa35 is Ser, Glu
  Xaa36 is Asn, Lys, or Gly;
  Xaa37 is Thr, Phe, or Ala;
  Xaa38 is Tyr, Phe, Pro, or absent;
with the proviso that when the loop region of the LHC agonist is from a calcitonin or calcitonin analog and the α helix region is from a calcitonin or calcitonin analog, the last position of the C-terminal tail is not Pro, Hyp, Hse or derivatives of Hse.

Again, each member of the Markush group, or a combination thereof, is another embodiment of the invention and is not to be read as a single unit. It is further contemplated that the C-terminal tail may contain no more than one, two, or three modifications such as substitutions, insertions, deletions, and/or derivatizations of the compounds described herein.

Examples of the C-terminal tail of an LHC agonist include, but are not limited to, 27-37 rAmylin, ($^{27}$Tyr $^{29}$Arg $^{32}$Thr) 27-37 rAmylin, ($^{29}$Arg $^{32}$Thr) 28-37 rAmylin, 30-37 hAmylin, ($^{32}$Thr) 30-37 hAmylin, ($^{35}$Lys $^{36}$Ala $^{37}$Phe) 30-37 hAmylin, 30-36 hAmylin, ($^{32}$Val) 30-36 hAmylin, ($^{34}$Glu $^{36}$Phe) 30-36 hAmylin, 31-37 hAmyin, 31-36 hAmylin, 33-36 hAmylin, 33-37 hAmylin, 28-32 sCT, ($^{30}$Asn $^{32}$Tyr) 28-32 sCT, and 27-32 sCT. In other embodiments, the C-terminal tail comprises the amino acid sequence KSNFVPTN (SEQ ID NO:62) or SNFVPTNV (SEQ ID NO:63).

It is further contemplated that no more than one, two, or three modifications such as substitutions, insertions, deletions, and/or derivatizations may be made to the C-terminal tail of the invention as described in the preceding paragraphs. The C-terminal tail of the LHC peptides may further comprise modifications or additional amino acids at the C-terminal end. Such modifications include the addition of compounds such as Lys, up to 4 Lys, L-Octylglycine, 4ABU (4-Aminobutyric acid), 9Anc (9-Amiononanoic acid), and/or groups for solubility, stability, or delivery. Examples include, but are not limited to, 33-37 hAmylin L-octylglycine, 33-37 hAmylin 4ABU, and 33-37 hAmylin 9Anc.

In a general aspect, LHC peptides for use in the invention comprise
(a) any of the LHC agonist loop regions as described herein;
(b) any of the LHC agonist α helix regions as described herein; and
(c) any LHC agonist C-terminal tails as described herein, with the proviso that when the loop region is from a calcitonin or calcitonin analog and the α helix region is from a calcitonin or calcitonin analog, the last position of the C-terminal tail is not Pro, Hyp, Hse or derivatives of Hse.

In another general aspect, LHC peptides for use in the invention comprise
(a) a loop region comprising formula (II) Xaa1 or Xaa1 with modifications at the N-terminal end;
(b) an α helix region comprising the α helix region type I or type II;
(c) a C-terminal tail represented by SEQ ID NO:61, with the proviso that when the loop region is from a calcitonin or calcitonin analog and the α helix region is from a calcitonin or calcitonin analog, the last position of the C-terminal tail is not Pro, Hyp, Hse or derivatives of Hse. The C-terminal end may comprise further modifications.

In yet another aspect, LHC peptides for use in the invention comprise an amino acid sequence of formula (III): Xaa1 X Xaa3 Xaa4 Xaa5 Xaa6 Y Xaa8 Xaa9 Xaa10 Xaa11 Xaa12 Xaa13 Xaa14 Xaa15 Xaa16 Xaa17 Xaa18 Xaa19 Xaa20 Xaa21 Xaa22 Xaa23 Xaa24 Xaa25 Xaa26 Xaa27 Xaa28 Xaa29 Xaa30 Xaa31 Xaa32 (SEQ ID NO:64) wherein Xaa1 is A, C, hC, D, E, F, I, L, K, hK, R, hR, S, Hse, T, G, Q, N, M, Y, W, P, Hyp, H, V or absent;
Xaa3 is A, D, E, N, Q, G, V, R, K, hK, hR, H, I, L, M, or absent;
Xaa4 is A, I, L, S, Hse, T, V, M, or absent;
Xaa5 is A, S, T, Hse, Y, V, I, L, or M;
Xaa6 is T, A, S, Hse, Y, V, I, L, or M;
Xaa8 is A, V, I, L, F, or M;
Xaa9 is L, T, S, Hse, V, I, or M;
Xaa10 is G, H, Q, K, R, N, hK, or hR;
Xaa11 is K, R, Q, N, hK, hR, or H;
Xaa12 is L, I, V, F, M, W, or Y;
Xaa13 is A, F, Y, N, Q, S, Hse, or T;
Xaa14 is A, D, E, G, N, K, Q, R, H, hR, or hK;
Xaa15 is A, D, E, F, L, S, Y, I, V, or M;
Xaa16 is L, F, M, V, Y, or I;
Xaa17 is H, Q, N, S, Hse, T, or V;
Xaa18 is K, hK, R, hR, H, u (Cit), or n (Orn);
Xaa19 is F, L, S, Hse, V, I, T, or absent;
Xaa20 is H, R, K, hR, hK, N, Q, or absent;
Xaa21 is T, S, Hse, V, I, L, Q, N, or absent;
Xaa22 is F, L, M, V, Y, or I;
Xaa23 is P or Hyp;
Xaa24 is P, Hyp, R, K, hR, hK, or H;
Xaa25 is T, S, Hse, V, I, L, F, or Y;
Xaa26 is N, Q, D, or E;
Xaa27 is T, V, S, F, I, or L;
Xaa28 is G or A; Xaa29 is S, Hse, T, V, I, L, or Y;
Xaa30 is E, G, K, N, D, R, hR, hK, H, or Q;
Xaa31 is A, T, S, Hse, V, I, L, F, or Y; and
Xaa32 is F, P, Y, Hse, S, T, or Hyp;
wherein X and Y are capable of creating a bond and are independently selected residues having side chains which are chemically bonded to each other to form an intramolecular linkage such as disulfide bonds; amide bond; alkyl acids and alkyl amines which may form cyclic lactams; alkyl aldehydes or alkyl halides and alkylamines which may condensed and be reduced to form an alkyl amine or imine bridge; or side chains which may be connected to form an alkyl, alkenyl, alkynyl, ether or thioether bond. Alkyl chains may include lower alkyl groups having from about 1 to about 6 carbon atoms. In certain embodiments, the intramolecular linkage may be a disulfide, amide, imine, amine, alkyl and alkene bond. In certain embodiments, X and Y are independently selected from Ser, Asp, Glu, Lys, Orn, or Cys. In certain embodiments, X and Y are Cys and Cys. In other embodiments, X and Y are Ser and Ser. In still other embodiments, X and Y are Asp and Lys or Lys and Asp.

In yet another aspect, LHC peptides for use in the invention comprise an amino acid sequence of formula (IV): Xaa1 Xaa2 Xaa3 Xaa4 Xaa5 Xaa6 Xaa7 Xaa8 Xaa9 Xaa10 Xaa11 Xaa12 Xaa13 Xaa14 Xaa15 Xaa16 Xaa17 Xaa18 Xaa19 Xaa20 Xaa21 Xaa22 P Xaa24 T N Xaa27 G S Xaa30 Xaa31 Xaa32 (SEQ ID NO:65) wherein
Xaa1 is A, C, D, F, I, K, S, T, or absent;
Xaa2 is C, D, S, or absent;
Xaa3 is A, D, N, or absent;
Xaa4 is A, L, T, or absent;
Xaa5 is A or S;
Xaa6 is T, A, S, or V;
Xaa7 is C, K, or A;
Xaa8 is A, V, L, or M;
Xaa9 is L or T;
Xaa10 is G, H, or Q;
Xaa11 is K, R, Q, or hArg;
Xaa12 is L, W, or Y;
Xaa13 is A, F, N, Q, S, or T;
Xaa14 is A, D, E, G, N, K, Q, or R;
Xaa15 is A, D, E, F, L, S, or Y;
Xaa16 is L, or F;
Xaa17 is H, Q, S, or V;
Xaa18 is K, R, hArg, u (Cit), or n (Orn);
Xaa19 is F, L, S, or absent;
Xaa20 is H, Q, or absent;
Xaa21 is T, N, or absent;
Xaa22 is F, L, M, V, or Y;
Xaa24 is P or R;
Xaa27 is T or V;

Xaa30 is E, G, K, or N;
Xaa31 is A or T; and
Xaa32 is F, P, or Y.

In yet another aspect, LHC peptides for use in the invention comprise an amino acid sequence of formula (V): Xaa1 Xaa2 Xaa3 Xaa4 Xaa5 T Xaa7 Xaa8 Xaa9 Xaa10 Xaa11 L Xaa13 Xaa14 Xaa15 L Xaa17 Xaa18 Xaa19 Xaa20 Xaa21 Xaa22 P Xaa24 T N Xaa27 G S Xaa30 Xaa31 Xaa32, (SEQ ID NO:66) wherein Xaa1 is A, C, F, I, K, S, or absent;
Xaa2 is C, D, or S;
Xaa3 is A, D or N;
Xaa4 is A, L or T;
Xaa5 is A or S;
Xaa7 is C or K;
Xaa8 is A or V;
Xaa9 is L or T;
Xaa10 is G, H, or Q;
Xaa11 is K, R, or hArg;
Xaa13 is A, F, N, S, or T;
Xaa14 is A, D, E, G, N, Q, or R;
Xaa15 is A, E, F, L, S, or Y;
Xaa17 is H, S, or V;
Xaa18 is K, R, hArg, u (Cit), or n (Orn);
Xaa19 is F, L, or S;
Xaa20 is H or Q;
Xaa21 is T or N;
Xaa22 is F, L, M, V, or Y;
Xaa24 is P or R;
Xaa27 is T, or V;
Xaa30 is E, G, K, or N;
Xaa31 is A, or T; and
Xaa32 is F, P, or Y.

In a general aspect, the sequence of formula (III), (IV), or (V) further comprises 1, 2, 3, 4, 5, 6, 7, 8, 9, 10, 11, 12, or more modifications of substitutions, insertions, deletions, elongations and/or derivatizations. In certain embodiments, the sequence of formula (III), (IV), or (V) comprises a Val inserted between amino acids at positions 22 and 23. In other embodiments, the sequence of formula (III), (IV), or (V) comprises a Gln inserted between positions 22 and 23. In still other embodiments, the sequence of formula (III), (IV), or (V) comprises a sequence of Gln-Thr-Tyr between positions 22 and 23. In yet other embodiments, the sequence of formula (III), (IV), or (V) comprises a sequence of Leu-Gln-Thr-Tyr (SEQ ID NO:67) between positions 22 and 23. In another general aspect, the modifications of formula (III), (IV), or (V) may be at the N-terminal end. In certain embodiments, the N-terminal portion of formula (III), (IV), or (V) has an added octylglycine. In other embodiments, the N-terminal portion of formula (III), (IV), or (V) has an added isocap.

In yet another aspect, LHC peptides for use in the invention comprise an amino acid sequence of formula (VI): Xaa1 Xaa2 Xaa3 Xaa4 Xaa5 Xaa6 Xaa7 Xaa8 Xaa9 Xaa10 Xaa11 Xaa12 Xaa13 Xaa14 Xaa15 Xaa16 Xaa17 Xaa18 Xaa19 Xaa20 Xaa21 Xaa22 P Xaa24 T N Xaa27 G S Xaa30 Xaa31 Xaa32 (SEQ ID NO:68) wherein Xaa1 is A, C, D, F, K, T, or absent;
Xaa2 is A, C, D, S, or absent;
Xaa3 is A, D, N, or absent;
Xaa4 is A, L, T, or absent;
Xaa5 is A or S;
Xaa6 is A, S, T, or V;
Xaa7 is A, C, or K;
Xaa8 is A, L, M, or V;
Xaa9 is L or T;
Xaa10 is G, H, or Q;
Xaa11 is K, Q, or R;
Xaa12 is L, W, or Y;
Xaa13 is A, N, Q, S, or T;
Xaa14 is A, D, E, G, K, N, Q, or R;
Xaa15 is A, D, E, F, L, S, or Y;
Xaa16 is F or L;
Xaa17 is H, Q, S or V;
Xaa18 is K, or R;
Xaa19 is F, L, S, or absent;
Xaa20 is H, K, Q, or absent;
Xaa21 is Q, T, or absent;
Xaa22 is F, L, or Y;
Xaa24 is P or R;
Xaa27 is T or V;
Xaa30 is E, K or N;
Xaa31 is A or T; and
Xaa32 is F, Y, or absent.

In a general aspect, the sequence of formula (VI) further comprises 1, 2, 3, 4, 5, 6, 7, 8, 9, 10, 11, 12, or more modifications of substitutions, insertions, deletions, elongations and/or derivatizations. In certain embodiments, the sequence of formula (III), (IV), (V) or (VI) comprises a deletion at position 24.

In yet another aspect, LHC peptides for use in the invention comprise an amino acid sequence comprising:

a) a loop region comprising formula (II) Xaa1; wherein Xaa1 comprises an amino sequence of X Xaa2 Xaa3 Xaa4 Xaa5 Xaa6 Xaa7 Y (SEQ ID NO: 69) wherein, Xaa2 is any amino acid or absent;
Xaa3 is Ala, Gly, Ser, Asp or absent;
Xaa4 is Asn, Ala, Asp, Gly or absent;
Xaa5 is Ala, Leu, Thr, or Ser;
Xaa6 is Ala, Ser, or Thr; and
Xaa7 is Ala, Ser, Val, Hse, (S)-2-amino-3-hydroxy-methylbutanoic acid (Ahb), (2S,3R)-2-amino-3hydroxy-methylpentanoic acid (Ahp), d-Thr, Thr, or a derivative thereof;

X and Y are amino acids capable of creating a bond and are independently selected residues having side chains which can be chemically bonded to each other to form an intramolecular linkage such as a disulfide bond; an amide bond; a cyclic lactam formed by an alkyl acid and an alkyl amine; an alkyl amine or imine bridge formed by condensing and reducing an alkyl aldehydes or alkyl halides and alkylamines; and an alkyl, alkenyl, alkynyl, ether or thioether bond formed by connection of side chains;

b) an α helix region type I comprising the sequence X1 V L Xaa10 Xaa11 L S Q Xaa15 L Xaa17 Xaa18 L Q T Xaa22 P Xaa24 T N T X1 (SEQ ID NO:70), wherein Xaa10 is Gly or Aib;
Xaa11 is Lys, Arg, Orn, hArg, Cit, hLys, or Lys(for);
Xaa15 is Glu or Phe;
Xaa17 is His or Aib;
Xaa18 is Lys, Arg, Orn, hArg, Cit, hLys, Lys(for), Lys (PEG 5000);
Xaa22 is Try or Leu;
Xaa24 is Arg or Pro; and
X1 is absent or comprises 1-4 additional amino acids; and c) a C-terminal tail comprising the sequence Xaa28 Xaa29 Xaa30 Xaa31 Xaa32 Xaa33 G Xaa35 Xaa36 Xaa37 Xaa38 (SEQ ID NO:71), wherein Xaa28 is Lys, Tyr, or absent;
Xaa29 is Ser, Pro, or absent;
Xaa30 is Ser, Pro, Arg, or absent;
Xaa31 is Thr, or absent;
Xaa32 is Asn or absent;
Xaa33 is Val, Thr, or absent;
Xaa35 is Ser, Glu Xaa36 is Asn, Lys, or Gly;
Xaa37 is Thr, Phe, or Ala;
Xaa38 is Tyr, Phe, Pro, or absent;
with the proviso that when the loop region is from a calcitonin or calcitonin analog and the α helix region is from a calcitonin or calcitonin analog, the last position of the C-terminal tail is not Pro, Hyp, Hse or derivatives of Hse.

In yet another aspect, LHC peptides for use in the invention comprise an amino acid sequence comprising:
a) a loop region comprising Xaa1;
a) a loop region comprising the formula (II) Xaa1; wherein Xaa1 comprises an amino sequence of X Xaa2 Xaa3 Xaa4 Xaa5 Xaa6 Xaa7 Y (SEQ ID NO:72) wherein,
   Xaa2 is any amino acid or absent;
   Xaa3 is Ala, Gly, Ser, Asp or absent;
   Xaa4 is Asn, Ala, Asp, Gly or absent;
   Xaa5 is Ala, Leu, Thr, or Ser;
   Xaa6 is Ala, Ser, or Thr; and
   Xaa7 is Ala, Ser, Val, Hse, Ahb, Ahp, d-Thr, Thr, or a derivative thereof;
   X and Y are amino acids capable of creating a bond and are independently selected residues having side chains which can be chemically bonded to each other to form an intramolecular linkage such as a disulfide bond; an amide bond; a cyclic lactam formed by an alkyl acid and an alkyl amine; an alkyl amine or imine bridge formed by condensing and reducing an alkyl aldehydes or alkyl halides and alkylamines; and an alkyl, alkenyl, alkynyl, ether or thioether bond formed by connection of side chains;
b) an α helix region type II comprising the sequence X1 Xaa8 Xaa9 Xaa10 R Xaa12 Xaa13 Xaa14 Xaa15 Xaa16 Xaa17 Xaa18 Xaa19 Xaa20 Xaa21 Xaa22 P Xaa24 T N T X1 (SEQ ID NO:73) wherein
   Xaa8 is Ala or Val;
   Xaa9 is Thr, Met or Leu;
   Xaa10 is Gln, Gly, His;
   Xaa12 is Leu, or Thr;
   Xaa13 is Ala, Thr, Asn, Phe, Tyr, Ser, or Thr;
   Xaa14 is Asn, Arg, Ala, Asp, Glu, Gln, Thr, or Gly;
   Xaa15 is Phe, Leu, Ser, Glu, Ala, Asp, or Tyr;
   Xaa16 is Leu or Asp;
   Xaa17 is Val, His, Ser, Phe, or Aib;
   Xaa18 is His, Arg, Lys, Orn, hArg, Cit, hLys, Lys(for), or Lys(PEG5000);
   Xaa19 is Leu, Ser or Phe;
   Xaa20 is Gln or His;
   Xaa21 is Thr or Asn;
   Xaa22 is Tyr, Val, Phe, Leu or Met;
   Xaa24 is Arg or Pro; and
   X1 is absent or comprises 1-4 additional amino acids; and
c) a C-terminal tail comprising the sequence Xaa28 Xaa29 Xaa30 Xaa31 Xaa32 Xaa33 G Xaa35 Xaa36 Xaa37 Xaa38 (SEQ ID NO:74), wherein
   Xaa28 is Lys, Tyr, or absent;
   Xaa29 is Ser, Pro, or absent;
   Xaa30 is Ser, Pro, Arg, or absent;
   Xaa31 is Thr, or absent;
   Xaa32 is Asn, or absent;
   Xaa33 is Val, Thr, or absent;
   Xaa35 is Ser, or Glu
   Xaa36 is Asn, Lys, or Gly;
   Xaa37 is Thr, Phe, or Ala;
   Xaa38 is Tyr, Phe, Pro, or absent.

In still another aspect, LHC peptides use in the invention include:

```
                                              (SEQ ID NO: 75)
KCNTATCVLGKLSQELHRLQTYPRTNTGSNTY (SEQ ID NO: 76)
KCNTATCVLGRLSQELHRLQTLPRTNTGSNTY (SEQ ID NO: 77)
KCNTATCVLGRLSQELHRLQTYPPTNTGSNTY (SEQ ID NO: 78)
KCNTATCVLGRLSQELHRLQTYPRTNVGSNTY (SEQ ID NO: 79)
KCNTATCVLGRLSQELHRLQTLPPTNVGSNTY (SEQ ID NO: 80)
KCNTATCVLGRLANFLHRLQTYPRTNTGSNTY (SEQ ID NO: 81)
ACNTATCVLGRLSQELHRLQTYPRTNTGSNTY (SEQ ID NO: 82)
KCNAATCVLGRLSQELHRLQTYPRTNTGSNTY (SEQ ID NO: 83)
KCNTAACVLGRLSQELHRLQTYPRTNTGSNTY (SEQ ID NO: 84)
CANLSTCVLGRLSQELHRLQTYPRTNTGSNTY (SEQ ID NO: 85)
isocaproyl-STAVLGRLSQELHRLQTYPRTNTGSNTY (SEQ ID NO: 86)
CSNASTCVLGRLSQELHRLQTYPRTNTGSNTY (SEQ ID NO: 87)
CSNLATCVLGRLSQELHRLQTYPRTNTGSNTY (SEQ ID NO: 88)
CSNLSACVLGRLSQELHRLQTYPRTNTGSNTY (SEQ ID NO: 89)
KCNTATCVLGRLSQELHKLQTYPRTNTGSNTY (SEQ ID NO: 90)
KCNTATCVLGRLSQELHRLQTYPRTNTGSGTP (SEQ ID NO: 91)
CSALSTCVLGRLSQELHRLQTYPRTNTGSNTY (SEQ ID NO: 92)
Ac-(Agy)SNLST(Agy)VLGRLSQELHRLQTYPRTNTGSNTY (SEQ ID NO: 192)
Ac-K(Agy)NTAT(Agy)VLGRLSQELHRLQTYPRTNTGSNTY (SEQ ID NO: 93)
Isocaproyl-STAVL(Aib)RLSQELRLQTYPRTNTGSGTP (SEQ ID NO: 94)
Isocaproyl-STAVLG[K(For)]LSQELH[K(For)]LQTYPRTNTGS
GTP (SEQ ID NO: 95)
Isocaproyl-STAVL(Aib)[K(For)]LSQEL(Aib)[K(For)]LQT
YPRTNTGSNTY (SEQ ID NO: 96)
Isocaproyl-STAVL(Aib)[K(For)]LSQEL(Aib)[K(For)]LQT
YPRTNVGSNTY (SEQ ID NO: 97)
KCNTATCLLQQLQKLLQKLKQYPRTNTGSNTY (SEQ ID NO: 98)
KCNTASCVLGRLSQELHRLQTYPRTNTGSNTY
```

-continued (SEQ ID NO: 99)
KCNTAVCVLGRLSQELHRLQTYPRTNTGSNTY (SEQ ID NO: 100)
KCNTATCVLGRLSQELHRYPRTNTGSNTY (SEQ ID NO: 101)
KCNTATCVLGK(For)LSQELHK(For)LQTYPRTNTGSNTY (SEQ ID NO: 102)
KCNTA(d-Thr)CVLGRLSQELHRLQTYPRTNTGSNTY (SEQ ID NO: 103)
KCNTA(dAh)CVLGRLSQELHRLQTYPRTNTGSNTY (SEQ ID NO: 104)
Ac-ACNTATCVLGRLSQELHK(PEG5000)LQTYPRTNTGSNTY (SEQ ID NO: 105)
KCNTATCVLGRLSQELHRLQTLQTYPRTNTGSNTY (SEQ ID NO: 106)
KCNTATCVLGRLSQELHRLQTLLQTYPRTNTGSNTY (SEQ ID NO: 107)
KCNTATCVLGKLSQELHKLQTYPRTNTGSNTY (SEQ ID NO: 108)
KCNTSTCVLGRLSQELHRLQTYPRTNTGSNTY (SEQ ID NO: 109)
KCNTATCATQRLSQELHRLQTYPRTNTGSNTY (SEQ ID NO: 110)
KCNTATCATQRLSQELHRLQTYPRTNVGSNTY (SEQ ID NO: 111)
KCNTSTCATQRLANELVRLQTYPRTNVGSNTY (SEQ ID NO: 112)
KCNTA(Hse)CVLGRLSQELHRLQTYPRTNTGSNTY (SEQ ID NO: 113)
KCNTA(Ahb)CVLGRLSQELHRLQTYPRTNTGSNTY (SEQ ID NO: 114)
KCNTA(Ahp)CVLGRLSQELHRLQTYPRTNTGSNTY (SEQ ID NO: 115)
KCNTAT(OPO3H2)CVLGRLSQELHRLQTYPRTNTGSNTY (SEQ ID NO: 116)
KCNTATCVLG(Orn)LSQELH(Orn)LQTYPRTNTGSNTY (SEQ ID NO: 117)
KCNTATCVLG(Cit)LSQELH(Cit)LQTYPRTNTGSNTY (SEQ ID NO: 118)
KCNTATCVLG(homoK)LSQELH(homoK)LQTYPRTNTGSNTY (SEQ ID NO: 119)
L-OctylglycineKCNTATCVLGRLSQELHRLQTYPRTNTGSNTY (SEQ ID NO: 120)
N-3,6-dioxaoctanoyl-CNTATCVLGRLSQELHRLQTVPRTNTGSNT
Y (SEQ ID NO: 121)
KCNTATCMLGRYTQDFHRLQTYPRTNTGSNTY (SEQ ID NO: 122)
DSNLSTKVLGRLSQELHRLQTYPRTNTGSNTY (SEQ ID NO: 123)
KDNTATKVLGRLSQELHRLQTYPRTNTGSNTY (SEQ ID NO: 124)
CNTATCVLGRLSQELHRLQTYPRTNTGSNTY -continued (SEQ ID NO: 125)
KCNTATCVLGRLSQELHRLQTYPRTNTGSNTY(9Anc)

(SEQ ID NO: 126)
KCNTATCVLGRLSQELHRLQTYPRTNTGSNTY(L-octylglycine)

(SEQ ID NO: 127)
N-isocaproyl-KCNTATCVLGRLSQELHRLQTYPRTNTGSNTY (SEQ ID NO: 128)
KCNTATCVLG(homoR)LSQELH(homoR)LQTYPRTNTGSNTY (SEQ ID NO: 129)
FCNTATCVLGRLSQELHRLQTYPRTNTGSNTY (SEQ ID NO: 130)
KCNTATCVLGRLSQELH(Cit)LQTYPRTNTGSNTY (SEQ ID NO: 131)
KCNTATCVLGRLSQELH(Orn)LQTYPRTNTGSNTY (SEQ ID NO: 132)
ICNTATCVLGRLSQELHRLQTYPRTNTGSNTY (SEQ ID NO: 133)
1-Octylglycine-CNTATCVLGRLSQELHRLQTYPRTNTGSNTY (SEQ ID NO: 134)
Isocaproyl-CNTATCVLGRLSQELHRLQTYPRTNTGSNTY (SEQ ID NO: 135)
KCNTATCVLG(Cit)LSQELHRLQTYPRTNTGSNTY (SEQ ID NO: 136)
KCNTATCVLGRLSQELHRLQTYPRTNTGSNTY(4ABU)

(SEQ ID NO: 137)
Isocaproyl-KCNTATCVLGRLSQELHRLQTYPRTNTGSNTY(4ABU)

(SEQ ID NO: 138)
KCNTSTCATQRLANELVRLQTYPRTNVGSEAF (SEQ ID NO: 139)
KCNTATCVLGRLSQELHRLQTYPTNVGSEAF (SEQ ID NO: 140)
KCNTATCVLGRLSRSLHRLQTYPRTNTGSNTY (SEQ ID NO: 141)
KCNTATCVTHRLSQELHRLQTYPRTNTGSNTY (SEQ ID NO: 142)
KCNTATCVLGRLADFLHRLQTYPRTNTGSNTY (SEQ ID NO: 143)
CNTATCVLGRLSQELHRLQTYPRTNTGSNT (SEQ ID NO: 144)
KCNTATCVLGRLSQELHRLQNFVPRTNTGSNTY (SEQ ID NO: 145)
KCNTATCVLGRLSQELHRLQTYPRTNTGSETF (SEQ ID NO: 146)
ACDTATCVLGRLSQELHRLQTYPRTNTGSNTY (SEQ ID NO: 147)
KCNTATCVLGRLSQELHRLQTYPRTNTGSKAF (SEQ ID NO: 148)
KCDTATCVTHRLAGLLSRSQTYPRTNTGSNTY (SEQ ID NO: 149)
KCNTATCVLGRLADALHRLQTYPRTNTGSNTY (SEQ ID NO: 150)
KCNTATCVLGRLAAFLHRLQTYPRTNTGSNTY (SEQ ID NO: 151)
SCNTATCVLGRLADFLHRLQTYPRTNTGSNTY

KCNTATCVLGRLSQELHRLQTMPRTNTGSNTY (SEQ ID NO: 152)

KCNTATCVLGRLSQELHRLQTVPRTNTGSNTY (SEQ ID NO: 153)

KCNTATCVLGRLNEYLHRLQTYPRTNTGSNTY (SEQ ID NO: 154)

SCNTATCVLGRLSQELHRLQTYPRTNTGSNTY (SEQ ID NO: 155)

KCNTATCVLGRLTEFLHRLQTYPRTNTGSNTY (SEQ ID NO: 156)

KCNTATCVLGRLAEFLHRLQTYPRTNTGSNTY (SEQ ID NO: 157)

KCNTATCVLGRLTDYLHRLQTYPRTNTGSNTY (SEQ ID NO: 158)

KCNTATCVLGRLAQFLHRLQTYPRTNTGSNTY (SEQ ID NO: 159)

KCNTATCVLGRLADFLHRFQTFPRTNTGSNTY (SEQ ID NO: 160)

KCNTATCVLGRLADFLHRFHTFPRTNTGSNTY (SEQ ID NO: 161)

KCNTATCVLGRLADFLHRFQTFPRTNTGSGTP (SEQ ID NO: 162)

CNTATCVLGRLADFLHRLQTYPRTNTGSNTY (SEQ ID NO: 163)

KCDTATCVLGRLSQELHRLQTYPRTNTGSNTY (SEQ ID NO: 164)

KCNTATCVLGRLFDFLHRLQTYPRTNTGSNTY (SEQ ID NO: 165)

KCNTATCVLGRLAAALHRLQTYPRTNTGSNTY (SEQ ID NO: 166)

TCDTATCVLGRLSQELHRLQTYPRTNTGSNTY (SEQ ID NO: 167)

CSNLSTCATQRLANELVRLQTYPRTNVGSNTY (SEQ ID NO: 168)

KCNTATCATQRLANELVRLQTYPRTNVGSNTY (SEQ ID NO: 169)

CSNLSTCVLGRLSQELHRLQTYPRTNTGSNTY (SEQ ID NO: 170)

KCNTATCVLGRLSQELHRLQTYPRTNTGSNTY (SEQ ID NO: 171)

In still another aspect, LHC peptides for use in the invention include biologically active fragments of SEQ ID NOS:75 to 171. Biologically active fragments may comprise deletions of 1, 2, 3, 4, 5, 6, 7, 8, 9, 10, 11, 12, 13, 14, 15 or more amino acids. In certain embodiments, the amino acid sequences of SEQ ID NOs:75 to 171 comprise at least 1, 2, 3, 4, 5, 6, 7, 8, 9, 10 or more modifications such as substitutions, insertions, deletions, and/or derivatizations. In other embodiments, the amino acid sequences of SEQ ID NOs:75 to 171 have no more than 1, 2, 3, 4, 5, 6, 7, 8, 9, or 10 modifications such as substitutions, insertions, deletions, and/or derivatizations. In still another aspect of the invention, compounds of the invention include those having at least 75, 80, 85, 90, 95, or 97% amino acid sequence identity to any of SEQ ID NOs: 75 to 171. Percent identity is determined by analysis with the AlignX® module in Vector NTI® (Invitrogen; Carlsbad Calif.). It is intended that each percent identity described, or reference to biologically active fragments or modifications be applied to each SEQ ID NO: individually. For example, each embodiment described, fragments, modification, or % identity is applicable to SEQ ID NO:75, 76, 77, 78, 44, etc., or to any group of SEQ ID NOs.

In general, amylin agonists or amylin agonist analogs are recognized as referring to compounds which, by directly or indirectly interacting or binding with one or more receptors, mimics an action of amylin. Accordingly, compounds of the invention may act as an agonist for at least one biological effect of calcitonin, amylin, CGRP, or any combination of the three herein disclosed or bind to at least one of the receptors of amylin, calcitonin, or CGRP. Conversely, amylin antagonists by directly or indirectly interacting or binding with one or more receptors, suppresses an action of amylin. Such interactions or binding events include those that affect ghrelin levels.

Amylin antagonists contemplated in the use of the invention include AC66 (sCT[8-32]) (SEQ ID NO:172) and derivatives such as AC187 (Ac 30Asn, 32Tyr-sCT[8-32]) (SEQ ID NO:173) a 25 amino acid peptide fragment of salmon calcitonin, developed as a selective amylin receptor antagonist over CGRP receptors. Other useful antagonists include antagonists described in U.S. Pat. Nos. 5,625,032 and 5,580,953, which are incorporated herein by reference. Such antagonist compounds include those comprising formula (VII): X—R1-Thr-Gln-R2-Leu-Ala-Asn-R3-Leu-Val-Arg-Leu-Gln-Thr-Tyr-Pro-Arg-Thr-Asn-Val-Gly-R4-Asn-Thr-Tyr-NH2 (SEQ ID NO:174)
wherein
R1 is Ala or a bond;
R2 is Arg, Gln, Lys, Asn or Leu;
R3 is Gln, Glu, Asn, Asp or Phe;
R4 is Ala or Ser; and
X is hydrogen or an acetyl group.

Amylin antagonists may be acetylated or non-acetylated at the N-terminus and include acid as well as amide forms of the molecule. Examples of amylin antagonists include, but are not limited to, acetyl-Ala Thr Gln Arg Leu Ala Asn Glu Leu Val Arg Leu Gln Thr Tyr Pro Arg Thr Asn Val Gly Ser Asn Thr Tyr (SEQ ID NO:175), Ala Thr Gln Gln Leu Ala Asn Gln Leu Val Arg Leu Gln Thr Tyr Pro Arg Thr Asn Val Gly Ser Asn Thr Tyr (SEQ ID NO:176), Ala Thr Gln Leu Leu Ala Asn Gln Leu Val Arg Leu Gln Thr Tyr Pro Arg Thr Asn Val Gly Ser Asn Thr Tyr (SEQ ID NO:177), Ala Thr Gln Arg Leu Ala Asn Gln Leu Val Arg Leu Gln Thr Tyr Pro Arg Thr Asn Val Gly Ser Asn Thr Tyr (SEQ ID NO:178), Ala Thr Gln Leu Leu Ala Asn Glu Leu Val Arg Leu Gln Thr Tyr Pro Arg Thr Asn Val Gly Ser Asn Thr Tyr (SEQ ID NO:179), Ala Thr Gln Gln Leu Ala Asn Glu Leu Val Arg Leu Gln Thr Tyr Pro Arg Thr Asn Val Gly Ser Asn Thr Tyr (SEQ ID NO:180).

Methods of testing compounds for amylin activity are known in the art. Exemplary screening methods and assays for testing amylin agonists or antagonists are described in the Examples, particularly Example 4 herein, and in U.S. Pat. Nos. 5,264,372 and 5,686,411, which are incorporated herein by reference.

Activity as amylin agonists and/or analogs can be confirmed and quantified by performing various screening assays, including the nucleus accumbens receptor binding assay, followed by the soleus muscle assay, a gastric emptying assay, or by the ability to induce hypocalcemia or reduce postprandial hyperglycemia in mammals.

The receptor binding assay, a competition assay that measures the ability of compounds to bind specifically to membrane-bound amylin receptors, is described in U.S. Pat. Nos. 5,264,372 and 5,686,411, the disclosures of which are incorporated herein by reference. A preferred source of the membrane preparations used in the assay is the basal forebrain which comprises membranes from the nucleus accumbens and surrounding regions. Compounds being assayed compete for binding to these receptor preparations with 125I Bolton Hunter rat amylin. Competition curves, wherein the amount bound (B) is plotted as a function of the log of the concentration of ligand, are analyzed by computer using analyses by nonlinear regression to a 4-parameter logistic equation (IN-PLOT program; GraphPad Software, San Diego, Calif.) or the ALLFIT program of DeLean et al. (ALLFIT, Version 2.7 (NIH, Bethesda, Md. 20892)). Munson and Rodbard (1980) *Anal. Biochem.* 107:220-239.

Assays of biological activity of amylin agonists/analogs in the soleus muscle may be performed using previously described methods (Leighton et al. (1988) *Nature* 335:632-635; Cooper et al. (1988) *Proc. Natl. Acad. Sci. USA* 85:7763-7766), in which amylin agonist activity may be assessed by measuring the inhibition of insulin-stimulated glycogen synthesis. In brief, an exemplary method includes soleus muscle strips prepared from 12-h fasted male Wistar rats. The tendons of the muscles are ligated before attachment to stainless steel clips. Muscle strips are pre-incubated in Erlenmeyer flasks containing 3.5 ml Krebs-Ringer bicarbonate buffer, 7 mM N-2-hydroxyethyl-peperazine-N'-2-ethane-sulphonic acid, pH 7.4, and 5.5 mM pyruvate. Flasks are sealed and gassed continuously with $O_2$ and $CO_2$ in the ratio 19:1 (v/v). After pre-incubation of muscles in this medium for 30 min at 37° C. in an oscillating water bath, the muscles strips are transferred to similar vials containing identical medium (except pyruvate) with added [U-14C] glucose (0.5 µCi/ml) and insulin (100 µU/ml). The flasks are sealed and re-gassed for an initial 15 min in a 1-h incubation. At the end of the incubation period, muscles are blotted and rapidly frozen in liquid N2. The concentration of lactate in the incubation medium can be determined spectrophotometrically and [U-14C] glucose incorporation in glycogen measured. Amylin antagonist activity is assessed by measuring the resumption of insulin-stimulated glycogen synthesis in the presence of 100 nM rat amylin and an amylin antagonist.

Methods of measuring the rate of gastric emptying are disclosed in, for example, Young et al. In a phenol red method, conscious rats receive by gavage an acoloric gel containing methyl cellulose and a phenol red indicator. Twenty minutes after gavage, animals are anesthetized using halothane, the stomach exposed and clamped at the pyloric and lower esophageal sphincters, removed and opened into an alkaline solution. Stomach content may be derived from the intensity of the phenol red in the alkaline solution, measured by absorbance at a wavelength of 560 nm. In a tritiated glucose method, conscious rats are gavaged with tritiated glucose in water. The rats are gently restrained by the tail, the tip of which is anesthetized using lidocaine. Tritium in the plasma separated from tail blood is collected at various timepoints and detected in a beta counter. Test compounds are normally administered about one minute before gavage.

Amylin agonist and antagonist compounds may exhibit activity in the receptor binding assay on the order of less than about 1 to 5 nM, preferably less than about 1 nM and more preferably less than about 50 pM. In the soleus muscle assay, amylin agonist compounds may show EC50 values on the order of less than about 1 to 10 micromolar. In the soleus muscle assay, amylin antagonists may show $IC_{50}$ values on the order of less than about 1 to 2 micromolar. In the gastric emptying assays, preferred agonist compounds show $ED_{50}$ values on the order of less than 100 µg/rat. Antagonist compounds would show no effect or the opposite effect in the gastric emptying assay.

In one exemplary method of making the compounds, compounds of the invention may be prepared using standard solid-phase peptide synthesis techniques and preferably an automated or semiautomated peptide synthesizer. Typically, using such techniques, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein. Other methods of synthesizing or expressing amylin and amylin agonists and purifying them are known to the skilled artisan.

Anti-obesity agents for use in the present invention also include exendin peptide hormones and exendin agonists. Native exendin peptide hormones are known in art, as are functional peptide analogs and derivatives. Certain native peptides, peptide analogs and derivatives are described herein, however it should be recognized that any known exendin peptides that exhibit hormonal activity known in the art may be used in conjunction with the present invention. Exemplary exendin peptides include exendin-3 (His Ser Asp Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser (SEQ ID NO:181)) and exendin-4 (His Gly Glu Gly Thr Phe Thr Ser Asp Leu Ser Lys Gln Met Glu Glu Glu Ala Val Arg Leu Phe Ile Glu Trp Leu Lys Asn Gly Gly Pro Ser Ser Gly Ala Pro Pro Pro Ser (SEQ ID NO:182)).

Any exendin peptide analog or derivative known in the art may be used in conjunction with the present invention. In certain embodiments, the exendin peptide analogs and derivatives have at least one hormonal activity of a native exendin peptide. In certain embodiments, the exendin peptide analogs are agonists of a receptor which a native exendin peptide is capable of specifically binding. Exendin compounds include exendin peptide analogs in which one or more naturally occurring amino acids are eliminated or replaced with another amino acid(s). As known in the art, such exendin analogs are may be amidated or may be in the acid form.

In certain embodiments, an exendin analog can have one or more amino acid substitutions, deletions, inversion, or additions compared to a native or naturally occurring exendin. Thus, exendin analogs can have an amino acid sequence that has one or more amino acid substitutions, additions or deletions as compared with a naturally occurring exendin, for example, exendin-4. In certain embodiments, an exendin analog has an amino acid sequence that has about 30 or less, 25 or less, 20 or less, 15 or less, 10 or less, 5 or less, 4 or less, 3 or less, 2 or less, or 1 or less substitutions, additions, or deletions as compared to a naturally occurring exendin, such as exendin-4

Exemplary exendin compounds include agonist analogs of exendin-4, including, but are not limited to, $^{14}$Leu, $^{25}$Phe-exendin-4 (His Gly Glu Gly Thr Phe Thr Ser Asp Leu Ser Lys Gln Leu Glu Glu Glu Ala Val Arg Leu Phe Ile Glu Phe Leu Lys Asn Gly Gly Pro Ser Ser Gly Ala Pro Pro Pro Ser (SEQ ID NO:183), $^5$Ala, $^{14}$Leu, Phe-exendin-4 (His Gly Glu Gly Ala Phe Thr Ser Asp Leu Ser Lys Gln Leu Glu Gln Glu Ala Val Arg Leu Phe Ile Glu Phe Leu Lys Asn Gly Gly Pro Ser Ser Gly Ala Pro Pro Pro Ser (SEQ ID NO:184)), and $^{14}$Leu, $^{22}$Ala, $^{25}$Pheexendin-4 (His Gly Glu Gly Thr Phe Thr Ser Asp Leu Ser Lys Gln Leu Glu Glu Glu Ala Val Arg Leu Ala Ile Glu Phe Leu Lys Asn Gly Gly Pro Ser Ser Gly Ala Pro Pro Pro Ser (SEQ ID NO:185)). Other exemplary exendin analogs include, but are not limited to, exendin-4 (1-30) (His Gly Glu Gly Thr Phe Thr Ser Asp Leu Ser Lys Gln Met Glu Glu Glu Ala Val Arg Leu Phe Ile Glu Trp Leu Lys Asn Gly Gly (SEQ ID NO:186)), exendin-4 (1-28) amide (His Gly Glu Gly Thr Phe Thr Ser Asp Leu Ser Lys Gln Met Glu Glu Glu Ala Val Arg Leu Phe Ile Glu Trp Leu Lys Asn-NH2 (SEQ ID NO:187)), 14Leu, 25Phe exendin-4 (1-28) amide (His Gly Glu Gly Thr Phe Thr Ser Asp Leu Ser Lys Gln Leu Glu Glu Glu Ala Val Arg Leu Phe Ile Glu Phe Leu Lys Asn-NH2 (SEQ ID NO:188)), and 14Leu,22Ala,25Phe exendin-4 (1-28) amide (His Gly Glu Gly Thr Phe Thr Ser Asp Leu Ser Lys Gln Leu Glu Glu Glu Ala Val Arg Leu Ala Ile Glu Phe Leu Lys Asn-NH2 (SEQ ID NO:189)).

Additional exemplary exendin agonists are described in U.S. patent application Ser. No. 10/181,102 and PCT Application No. PCT/US98/16387, both which claim the benefit of U.S. patent application Ser. No. 60/055,404, filed Aug. 8, 1997, all of which are herein incorporated by reference. Exemplary exendin agonists include compounds of the formula (I), formula (II) and formula (III) of U.S. patent application Ser. No. 10/181,102 and PCT Application No. PCT/US98/16387.

Other exendin agonists are described in U.S. patent application Ser. No. 09/554,533 and PCT Application Serial No. PCT/US98/24210, both of which claim the benefit of U.S. Provisional Application No. 60/065,442 filed Nov. 14, 1997, all of which are herein incorporated by reference. Still other exendin agonists are described in U.S. patent application Ser. No. 09/554,531 and PCT Application Serial No. PCT/US98/24273, both of which claim the benefit of U.S. Provisional Application No. 60/066,029 filed Nov. 14, 1997, all of which are herein incorporated by reference. Still other exendin agonists are described in PCT Application Serial No. PCT/US97/14199, filed Aug. 8, 1997, which is a continuation-in-part of U.S. patent application Ser. No. 08/694,954 filed Aug. 8, 1996, both of which are hereby incorporated by reference. Still other exendin agonists are described in U.S. Pat. No. 6,956,026, which claims priority to U.S. Provisional Application No. 60/034,905 filed Jan. 7, 1997, both of which are hereby incorporated by reference. Yet other exendin analogs and derivatives are described in US 2004/0209803 A1, filed Dec. 19, 2003, which is hereby incorporated by reference.

Anti-obesity agents in the present invention also include ciliary neurotrophic factor (CNTF), CNTF-related polypeptides, modified CNTF polypeptides, CNTF agonists, and CNTF analogs, including, but not limited to AXOKINE® (Regeneron). CNTF, CNTF-related polypeptides, and CNTF and/or CNTF-related polypeptide containing compositions appropriate for use in the methods of the invention are known in the art. CNTF polypeptides, CNTF-related polypeptides, modified CNTF polypeptides, CNTF agonists, analogs, derivatives, preparations, formulations, pharmaceutical compositions, doses, and administration routes have previously been described, for example, in U.S. Pat. Nos. 6,680,291 and 6,767,894, and in PCT Application Publication Nos. WO 94/09134, WO 98/22128, and WO 99/43813, which are hereby incorporated by reference in their entirety.

Anti-obesity agents in the present invention also include serotonin (5HT) transport inhibitors, including, but not limited to, paroxetine, fluoxetine, fenfluramine, fluvoxamine, sertraline, and imipramine. Anti-obesity agents in the present invention also include selective serotonin reuptake inhibitors, including, but not limited to dexfenfluramine, fluoxetine, sibutramine (e.g., MERIDIA®) and those described in U.S. Pat. No. 6,365,633 and PCT Patent Application Publication Nos. WO 01/27060 and WO 01/162341, which are hereby incorporated by reference in their entirety. Such 5HT transport inhibitors and serotonin reuptake inhibitors, analogs, derivatives, preparations, formulations, pharmaceutical compositions, doses, and administration routes have previously been described.

Anti-obesity agents for use in the present invention also include selective serotonin agonists and selective 5-HT2C receptor agonists, including, but not limited to, U.S. Pat. No. 3,914,250; and PCT Application Publication Nos. WO 02/36596, WO 02/48124, WO 02/10169, WO 01/66548, WO 02/44152; WO 02/51844, WO 02/40456, and WO 02/40457, which are hereby incorporated by reference in their entirety. Such selective serotonin agonists and 5-HT2C receptor agonists, compositions containing such agonists, and administration routes appropriate for use in the methods of the invention are known in the art. See, for example, Halford et al. (2005) Curr. Drug Targets 6:201-213 and Weintraub et al. (1984) Arch. Intern. Med. 144:1143-1148.

Anti-obesity agents for use in the present invention also include antagonists/inverse agonists of the central cannabinoid receptors (the CB-1 receptors), including, but not limited to, rimonabant (Sanofi Synthelabo), and SR-147778 (Sanofi Synthelabo). CB-1 antagonists/inverse agonists, derivatives, preparations, formulations, pharmaceutical compositions, doses, and administration routes have previously been described, for example, in U.S. Pat. Nos. 6,344,474, 6,028,084, 5,747,524, 5,596,106, 5,532,237, 4,973,587, 5,013,837, 5,081,122, 5,112,820, 5,292,736, 5,624,941; European Patent Application Nos. EP-656 354 and EP-658546; and PCT Application Publication Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, and WO 02/076949, which are hereby incorporated by reference in their entirety.

Anti-obesity agents for use in the present invention also include melanocortins and melanocortin agonists. Melanacortins are peptides from the pro-opiomelanocortin gene, including α-melanocyte-stimulating hormone (α-MSH) and adrenocorticotrophic hormone (ACTH), and five melanocortin receptors are known, MC1-5R. MC4R appears to play a role in energy balance and obesity. See, for example, Anderson et al. (2001) Expert Opin. Ther. Patents 11: 1583-1592, Speake et al. (2002) Expert Opin. Ther. Patents 12:1631-1638, Bednarek et al. (2004) Expert Opin. Ther. Patents 14:327-336. Melanocortin agonists, including, but not limited to, MC4R agonists, and composition containing such agonist appropriate for use in the methods of the invention are known in the art. MCR agonists, MC4R agonists, derivatives, preparations, formulation, pharmaceutical compositions, doses, and administration routes have previously been described, for example, in the following PCT patent applications, which are hereby incorporated by reference in their entirety: WO 03/007949, WO 02/068388, WO 02/068387, WO 02/067869, WO 03/040117, WO 03/066587, WO 03/068738, WO 03/094918, and WO 03/031410.

Anti-obesity agents for use in the present invention also include metabotropic glutamate subtype 5 receptor (mGluR5) antagonists, including, but are not limited to, compounds such as 2-methyl-6-(phenylethynyl)-pyridine (MPEP) and (3-[(2-methyl-1,3-thiazol-4-yl)ethynyl]pyridine) (MTEP) and those compounds described in Anderson et al. (2003) J. Eur. J. Pharmacol. 473:35-40; Cosford et al.

(2003) *Bioorg. Med. Chem. Lett.* 13(3):351-4; and Anderson et al. (2002) *J. Pharmacol. Exp. Ther.* 303:1044-1051.

Anti-obesity agents for use in the present invention also include topiramate (TOPIMAX® (Ortho McNeil Pharmaceuticals), indicated as an anti-convulsant and an anti-convulsant, but also shown to increase weight loss.

Anti-obesity agents for use in the present invention also include neuropeptide Y1 (NPY1) antagonists and NPY5 antagonists. NPY1 and NPY5 antagonists are known in the art. See, for example Duhault et al. (2000) *Can. J Physiol. Pharm.* 78:173-185, and U.S. Pat. Nos. 6,124,331, 6,214,853, and 6,340,683. NPY1 and NPY5 antagonists, derivatives, preparations, formulation, pharmaceutical compositions, doses, and administration routes have previously been described. NPY1 antagonists useful in the present invention, include: U.S. Pat. No. 6,001,836; and PCT Application Publication Nos. WO 96/14307, WO 01/23387, WO 99/51600, WO 01/85690, WO 01/85098, WO 01/85173, and WO 01/89528, which are hereby incorporated by reference in their entirety. NPY5 antagonists useful in the present invention, include, but are not limited to, the compounds described in: U.S. Pat. Nos. 6,140,354, 6,191,160, 6,258,837, 6,313,298, 6,337,332, 6,329,395, 6,340,683, 6,326,375, and 6,335,345; European Patent Nos. EP-01010691, and EP-01044970; and PCT Patent Publication Nos. WO 97/19682, WO 97/20820, WO 97/20821, WO 97/20822, WO 97/20823, WO 98/27063, WO 00/64880, WO 00/68197, WO 00/69849, WO 01/09120, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, WO 02/49648, and WO 01/14376.

Anti-obesity agents for use in the present invention also include melanin-concentrating hormone (MCH) antagonists including melanin-concentrating hormone 1 receptor (MCH1R) antagonists, such as T-226296 (Takeda) and melanin-concentrating hormone 2 receptor (MCH2R) antagonists. MCH receptor antagonists, derivatives, preparations, formulation, pharmaceutical compositions, doses, and administration routes have previously been described, for example, in U.S. Patent Application Publication Nos. 2005/0009815, 2005/0026915, 2004/0152742, 2004/0209865; PCT Patent Application Publication Nos. WO 01/82925, WO 01/87834, WO 02/06245, WO 02/04433, and WO 02/51809; and Japanese Patent Application No. JP 13226269, which are hereby incorporated by reference in their entirety.

Anti-obesity agents for use in the present invention also include opioid antagonists, including, but not limited to those described in PCT Application No. WO 00/21509. Specific opioid antagonists useful in the present invention include, but are not limited to, nalmefene (REVEX®), 3-methoxynaltrexone naloxone, naltrexone, naloxonazine, beta-funaltrexamine, delta1 ([D-Ala2,Leu5,Cys6]-enkephalin (DALCE), naltrindole isothiocyanate, and nor-binaltorphamine.

Anti-obesity agents for use in the present invention also include orexin antagonists, including, but not limited to, those described in PCT Patent Application Nos. WO 01/96302, WO 01/68609, WO 02/51232, and WO 02/51838. Specific orexin antagonists useful in the present invention include, but are not limited to, SB-334867-A.

Anti-obesity agents for use in the present invention also include neuropeptide Y2 (NPY2) agonists, including, but not limited to, compounds such as PYY3-36 (e.g., Batterham et al. (2003) *Nature* 418:650-654), NPY3-36, and other Y2 agonists such as N acetyl [Leu(28,31)] NPY 24-36 (White-Smith et al. (1999) *Neuropeptides* 33:526-533, TASP-V (Malis et al. (1999) *Br. J. Pharmacol.* 126:989-996), cyclo-(28/32)-Ac-[Lys28-Glu32]-(25-36)-pNPY (Cabrele et al. (2000) *J. Pept.* *Sci.* 6:97-122). Anti-obesity agents in the present invention also include neuropeptide Y4 (NPY4) agonists including, but not limited to, compounds such as pancreatic peptide (PP) (e.g., Batterham et al. (2003) *J. Clin. Endocrinol. Metab.* 88:3989-3992) and other Y4 agonists such as 1229U91 (Raposinho et al. (2000) *Neuroendocrinology* 71:2-7). NPY2 agonists and NPY4 agonists, derivatives, preparations, formulations, pharmaceutical compositions, doses, and administration routes have previously been described, for example, in U.S. Pat. Publication No. 2002/0141985 and PCT Application Publication No. WO 2005/077094.

Anti-obesity agents for use in the present invention also include histamine 3 (H3) antagonist/inverse agonists including but not limited to, those described in PCT Application No. WO 02/15905, O-[3-(1H-imidazol-4-yl)propanol]carbamates (Kiec-Kononowicz et al. (2000) *Pharmazie* 55:349-355), piperidine-containing histamine H3-receptor antagonists (Lazewska et al. (2001) *Pharmazie* 56:927-932), benzophenone derivatives and related compounds (Sasse et al. (2001) *Arch. Pharm.* (Weinheim) 334:45-52), substituted N-phenylcarbamates (Reidemeister et al. (2000) *Pharmazie* 55:83-86), and proxifan derivatives (Sasse et al. (2000) *J. Med. Chem.* 43:3335-3343). Specific H3 antagonists/inverse agonists useful in the present invention include, but are not limited to, thioperamide, 3-(1H-imidazol-4-yl)propyl N-(4-pentenyl) carbamate, clobenpropit, iodophenpropit, imoproxifan, and GT2394 (Gliatech).

Anti-obesity agents for use in the present invention also include cholecystokinin (CCK) and CCK agonists. Cholecystokinin-A (CCK-A) agonists useful in the present invention include, but are not limited to, those described U.S. Pat. No. 5,739,106. Specific CCK-A agonists include, but are not limited to, AR-R 15849, GI 181771, JMV-180, A-71378, A-71623 and SR146131.

Anti-obesity agents for use in the present invention also include ghrelin antagonists such as those described in PCT Application Publication Nos. WO 01/87335 and WO 02/08250. Ghrelin antagonists are also known as GHS (growth hormone secretagogue receptor) antagonists. The compositions and methods of the present invention therefore comprehend the use GHS antagonists in place of ghrelin antagonists.

Dosage/Formulation

Anti-obesity agents and weight-inducing agents (herein referred to in this section as the "compounds") may be administered alone or in combination with pharmaceutically acceptable carriers or excipients, in either single or multiple doses. These pharmaceutical compounds may be formulated with pharmaceutically acceptable carriers or diluents as well as any other known adjuvants and excipients in accordance with conventional techniques such as those disclosed in Remington's Pharmaceutical Sciences by E. W. Martin. See also Wang et al. (1988) *J. of Parenteral Sci. and Tech.*, Technical Report No. 10, Supp. 42:2 S.

In general, the compounds may be formulated into a stable, safe pharmaceutical composition for administration to a patient. Pharmaceutical formulations contemplated for use in the methods of the invention may comprise approximately 0.01 to 1.0% (w/v), in certain cases 0.05 to 1.0%, of the compound, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group consisting of m-cresol, benzyl alcohol, methyl, ethyl, propyl and butyl parabens and phenol. Such a preservative is generally included if the formulated peptide is to be included in a multiple use product.

In particular embodiments of the present invention, a pharmaceutical formulation of the present invention may contain a range of concentrations of the compound, e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in these embodiments. A sufficient amount of water for injection may be used to obtain the desired concentration of solution.

Additional tonicifying agents such as sodium chloride, as well as other known excipients, may also be present, if desired. In some cases, such excipients are useful in maintenance of the overall tonicity of the compound. An excipient may be included in the presently described formulations at various concentrations. For example, an excipient may be included in the concentration range from about 0.02% to about 20% w/w, preferably between about 0.02% and 0.5% w/w, about 0.02% to about 10% w/v, or about 1% to about 20% w/w. In addition, similar to the present formulations themselves, an excipient may be included in solid (including powdered), liquid, semi-solid or gel form.

The pharmaceutical formulations may be composed in various forms, e.g., solid, liquid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the formulations of peptidic anti-obesity agents, for example, water or an aqueous/organic solvent mixture or suspension.

The stability of a peptide formulation for use in the present invention is enhanced by maintaining the pH of the formulation in the range of about 3.0 to about 7.0 when in liquid form. In certain embodiments, the pH of the formulation is maintained in the range of about 3.5 to 5.0, or about 3.5 to 6.5, in some embodiments from about 3.7 to 4.3, or about 3.8 to 4.2. In some embodiments, pH may be about 4.0. While not seeking to be bound by this theory, it is presently understood that where the pH of the pharmaceutical formulation exceeds 5.5, chemical degradation of the peptide may be accelerated such that the shelf life is less than about two years.

In certain embodiments, the buffer with the anti-obesity agents is an acetate buffer (preferably at a final formulation concentration of from about 1-5 to about 60 mM), phosphate buffer (preferably at a final formulation concentration of from about 1-5 to about to about 30 mM) or glutamate buffer (preferably at a final formulation concentration of from about 1-5 to about to about 60 mM). In some embodiments, the buffer is acetate (preferably at a final formulation concentration of from about 5 to about 30 mM).

A stabilizer may be included in the formulations of anti-obesity agents but, and importantly, is not necessarily needed. If included, however, a stabilizer useful in the practice of the present invention is a carbohydrate or a polyhydric alcohol. A suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic patient, i.e., the carbohydrate is not metabolized to form unacceptably large concentrations of glucose in the blood. Such carbohydrates are well known in the art as suitable for diabetics. Sucrose and fructose are suitable for use with the compound in non-diabetic applications (e.g. treating obesity).

In certain embodiments, if a stabilizer is included, the compound is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, and 8000). Mannitol is the preferred polyhydric alcohol in some embodiments. Another useful feature of the lyophilized formulations of the present invention is the maintenance of the tonicity of the lyophilized formulations described herein with the same formulation component that serves to maintain their stability. In some embodiments, mannitol is the preferred polyhydric alcohol used for this purpose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), in some embodiments range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid. A detailed description of each preservative is set forth in Remington's Pharmaceutical Sciences by Martin.

Pramlintide does not have a tendency to adsorb onto the glass in a glass container when in a liquid form, therefore, a surfactant is not required to further stabilize the pharmaceutical formulation. However, with regard to compounds which do have such a tendency when in liquid form, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the peptide may optionally be present in the range of about 0.001 to 0.3% (w/v) of the total formulation and include polysorbate 80 (i.e., polyoxyethylene (20) sorbitan monooleate), CHAPS® (i.e., 3-[(3-cholamidopropyl) dimethylammonio]1-propanesulfonate), Brij® (e.g., Brij 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations preferably may be isotonic or substantially isotonic.

A preferred vehicle for parenteral products is water. Water of suitable quality for parenteral administration can be prepared either by distillation or by reverse osmosis. Water for injection is the preferred aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation of the present invention.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type I-33) or its equivalent (Wheaton Glass Co.). Other vendors of similar borosilicate glass vials and cartridges acceptable for manufacture include Kimbel Glass Co., West Co., Bünder Glas GMBH and Form a Vitrum. The biological and chemical properties of the compound may be stabilized by formulation and lyophilization in a Wheaton Type I-33 borosilicate serum vial to a final concentration of 0.1 mg/ml and 10 mg/ml of the compound in the presence of 5% mannitol, and 0.02% Tween 80.

For formulations to be delivered by injection, in order to permit introduction of a needle from a hypodermic syringe into a multiple-dose vial and provide for resealing as soon as the needle is withdrawn, the open end of each vial is preferably sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. For formulations comprising peptidic anti-obesity agents, these stoppers are compatible with the peptide as well as the other components of the formulation. The inventors have also discovered that these stoppers pass the stopper integrity test when tested using patient use patterns, e.g., the stopper can withstand at least about 100 injections. Alternatively, the peptide can be lyophilized in to vials, syringes or cartridges for subsequent reconstitution. Liquid formulations of the present invention can be filled into one or two chambered cartridges, or one or two chamber syringes.

Each of the components of the pharmaceutical formulation described above is known in the art and is described in Pharmaceutical Dosage Forms: Parenteral Medications, Vol. 1, 2nd ed., Avis et al. Ed., Mercel Dekker, New York, N.Y. 1992, which is incorporated by reference in its entirety herein.

The manufacturing process for the above liquid formulations generally involves compounding, sterile filtration and filling steps. The compounding procedure involves dissolution of ingredients in a specific order (preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolacctone, ozone, chloropicrin, peracetic acid methyl bromide and the like), exposure to a radiation source, and aseptic handling. Filtration is the preferred method of sterilization for liquid formulations of the present invention. The sterile filtration involves filtration through 0.45 µm and 0.22 µm (1 or 2) which may be connected in series. After filtration, the solution is filled into appropriate vials or containers.

In certain embodiments, the anti-obesity agents are administered peripherally to the subjects. In some embodiments, the liquid pharmaceutical formulations of the present invention are intended for parenteral administration. Suitable routes of administration include intramuscular, intravenous, subcutaneous, intradermal, intraarticular, intrathecal and the like. In some embodiments, the subcutaneous route of administration is preferred. In certain embodiments, mucosal delivery is also preferred. These routes include, but are not limited to, oral, nasal, sublingual, pulmonary and buccal routes which may include administration of the peptide in liquid, semi-solid or solid form. For formulations comprising peptidic anti-obesity agents, administration via these routes requires substantially more peptide to obtain the desired biological effects due to decreased bioavailability compared to parenteral delivery. In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368, 630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842.

The compounds may be provided in dosage unit form containing an amount of the compound with or without insulin or glucose (or a source of glucose) that will be effective in one or multiple doses to control the effects of ghrelin. Therapeutically effective amounts of the compounds for the treatment of ghrelin-associated diseases or disorders are those sufficient to treat, prevent, or ameliorate the physiological effects of undesirable levels of ghrelin.

As will be recognized by those in the field, an effective amount of the anti-obesity agents will vary with many factors including the age and weight of the patient, the patient's physical condition, the condition to be treated, and other factors. An effective amount of the anti-obesity agents will also vary with the particular combination administered. As described herein, administration of the agents in combination may allow for a reduced amount of any of the administered agents to be an effective amount.

However, typical doses may contain from a lower limit of about 1 µg, 5 µg, 10 µg, 50 µg to 100 µg to an upper limit of about 100 µg, 500 µg, 5 mg, 10 mg, 50 mg or 100 mg of the pharmaceutical compound per day. Also contemplated are other dose ranges such as 0.1 µg to 1 mg of the compound per dose. The doses per day may be delivered in discrete unit doses, provided continuously in a 24 hour period or any portion of that the 24 hours. The number of doses per day may be from 1 to about 4 per day, although it could be more. Continuous delivery can be in the form of continuous infusions. The terms "QID," "TID," "BID" and "QD" refer to administration 4, 3, 2 and 1 times per day, respectively. Exemplary doses and infusion rates include from 0.005 nmol/kg to about 20 nmol/kg per discrete dose or from about 0.01/pmol/kg/min to about 10 pmol/kg/min in a continuous infusion. These doses and infusions can be delivered by intravenous administration (i.v.) or subcutaneous administration (s.c.). Exemplary total dose/delivery of the pharmaceutical composition given i.v. may be about 2 µg to about 8 mg per day, whereas total dose/delivery of the pharmaceutical composition given s.c may be about 6 µg to about 6 mg per day.

Leptin and leptin derivatives may be administered, for example, at a daily dosage of from about 0.01 mg/kg to about 20 mg/kg, in some cases, from about 0.01 mg/kg to about 0.3 mg/kg. Administration may be by injection of a single dose or in divided doses.

Sibutramine may be administered, for example, at a daily dosage of from about 0.01 mg/kg to about 10 mg/kg, in some cases from about 0.01 mg/kg to about 1 mg/kg in a single dose or in divided doses 2 to 3 times per day, or in sustained release form. In some instances, sibutramine may be administered the single daily dose of 5 mg, 10 mg, 15 mg, 20 mg or 30 mg orally.

Rimonabant may be administered, for example, at a daily dosage of from about 0.01 mg/kg to about 8 mg/kg, in some instances from about 0.3 mg/kg to about 3 mg/kg of body weight in a single dose or in divided doses 2 to 3 times per day, or in sustained release form.

The following Examples are provided to illustrate, but not limit, the invention.

EXAMPLES

Example 1

Diet-induced obesity (DIO) in the in the Sprague-Dawley rat is a valuable model for the study of obesity and regulation of energy homeostasis. These rats were developed from a line of (Crl:CD®(SD)BR) rats that are prone to become obese on a diet relatively high in fat and energy. See, for example, Levin (1994) *Am. J. Physiol.* 267:R527-R535, Levin et al. (1997) *Am. J. Physiol.* 273:R725-R730. DIO male rats were obtained from Charles River Laboratories, Inc. (Wilmington, Mass.). The rats were housed individually in shoebox cages at 22° C. in a 12/12-hour light dark cycle. Rats were maintained ad-libitum on a moderately high fat diet (32% kcal from fat; Research Diets D1226B) for 6-7 weeks prior to drug treatment. At the end of the fattening period (prior to drug administration), the animals typically achieve a mean body weight of about 500 g.

The DIO animals were divided into four treatment groups. Each group was implanted with subcutaneous osmotic minipumps (DURECT Corp., Cupertino, Calif.) designed to deliver vehicle, leptin (500 µg/kg/day), amylin (100 µg/kg/day) or leptin (500 µg/kg/day)+amylin (100 µg/kg/day) for a 14 day period. As described herein, amylin acts on structures in the hindbrain involved in food intake and/or body weight modulation and leptin acts on structures in the hypothalamus involved in food intake and/or body weight modulation. Food intake and body weight were recorded daily. Body composition was measured prior to and after drug treatment using NMR (Echo Medical Systems, Houston, Tex.). Indirect calorimetry was used to measure changes in energy expenditure on days 4, 5 and 6 of drug treatment (Oxymax; Columbus Instruments, Columbus, Ohio). All data are represented as mean±SEM. Analysis of variance (ANOVA) and post-hoc tests were used to test for group difference. A P-value<0.05 was considered significant. Statistical analysis and graphing were performed using PRISM® 4 for Windows (GraphPad Software, Inc., San Diego, Calif.). In some early studies, SYSTAT® for Windows (Systat Software, Inc., Point Richmond Calif.) was used for analysis.

Figure 2:
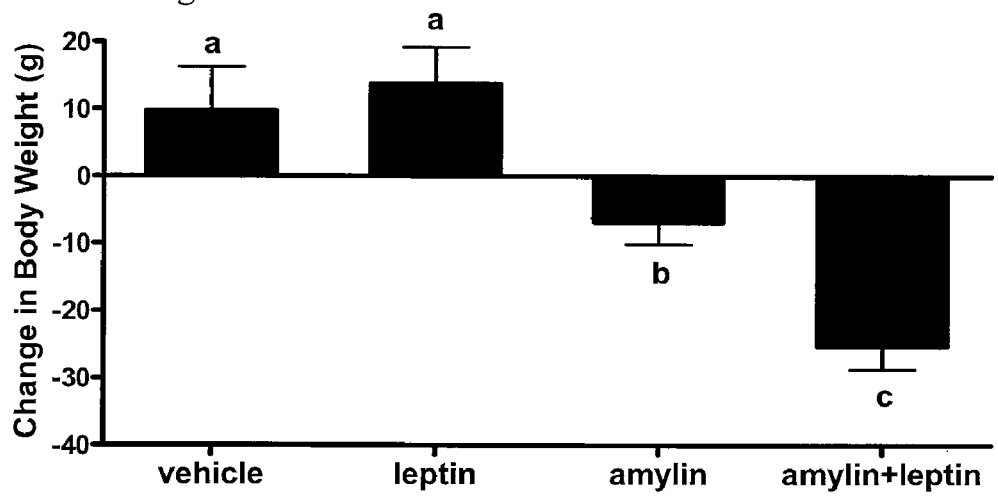
FIG. 2 is a graph depicting an effect of administration of leptin and amylin on body weight.

FIGS. 1 and 2 show the effects of amylin and leptin on cumulative food intake and total changes in body weight after 14 days of drug administration. Of particular interest is that (1) leptin, the forebrain acting agent, was ineffective on its own in this obesity model (no effect on either food intake or body weight), and (2) rats treated with the combination of amylin and leptin consumed significantly less food and lost significantly more weight relative to rats treated with either vehicle or amylin or leptin alone (p<0.05; different letters indicate that groups differed significantly from one another).

Figure 3:
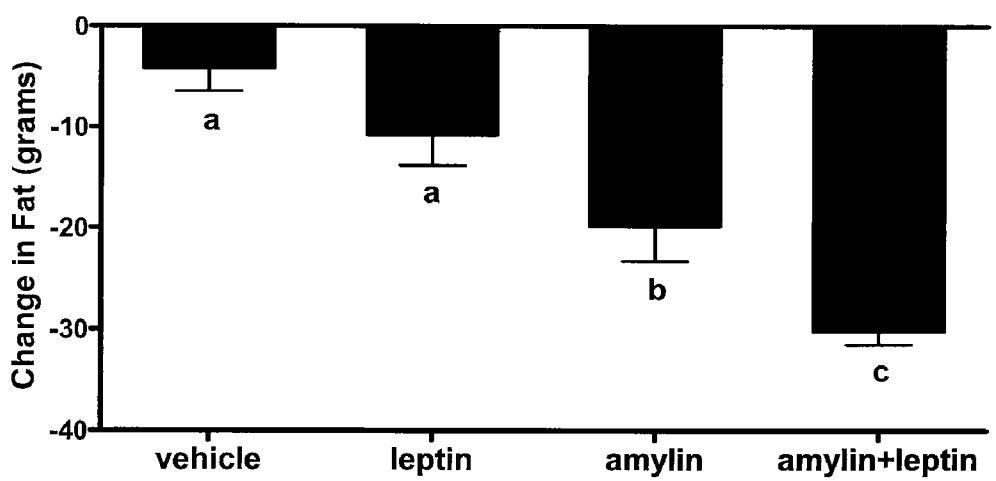
FIG. 3 is a graph depicting an effect of administration of leptin and amylin on body composition.
Figure 4:
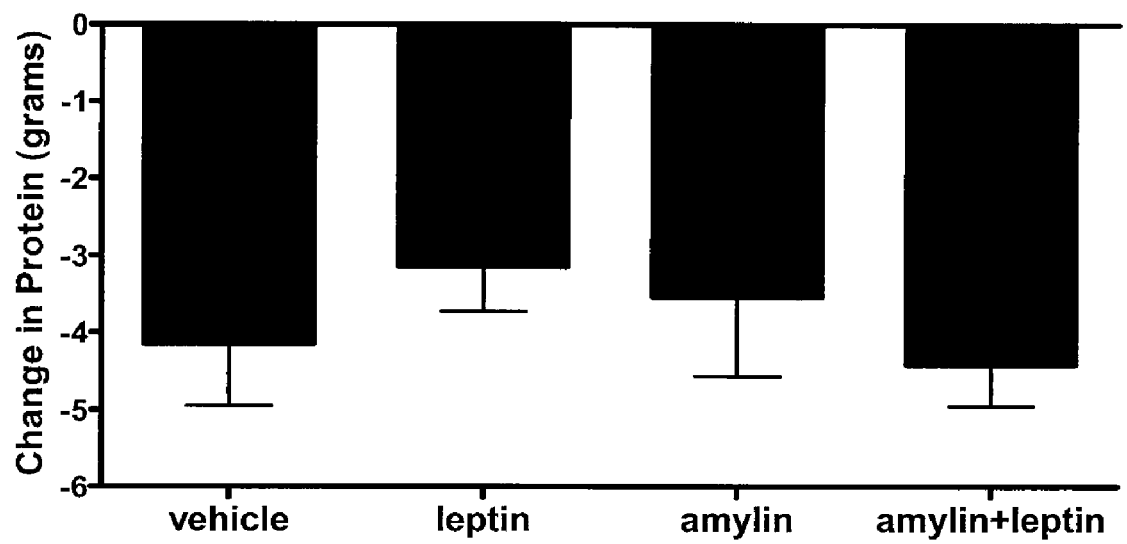
FIG. 4 is a graph depicting an effect of administration of leptin and amylin on body composition.

Similar effects were observed on body composition. FIG. 3 depicts changes in body fat produced by the treatments and FIG. 4 depicts changes in body protein produced by the treatments. Fat loss in animals treated with the combination of amylin+leptin was significantly greater than that in animals treated with either individual agent or vehicle (p<0.05). These changes in body fat were not accompanied by significant decreases in lean tissue (p>0.05; FIG. 4).

Figure 5:
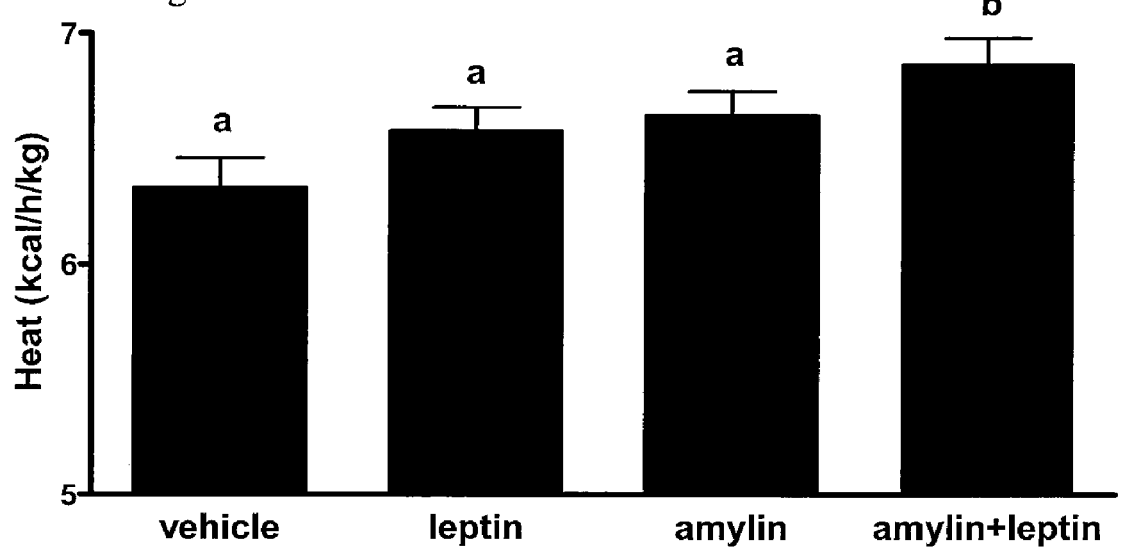
FIG. 5 is a graph depicting an effect of administration of leptin and amylin on energy expenditure.

FIG. 5 depicts changes in energy expenditure during the dark cycle of the treatment groups. While drug (or diet)-induced reduction in food intake and body weight is often accompanied by a slowing of metabolic rate (Heat, kcal/h/kg), rats treated with the combination of leptin and amylin had a significantly higher metabolic rate during the dark cycle relative to the other groups (p<0.05). Thus, simultaneously targeting hindbrain and forebrain feeding centers with the amylin+leptin combination resulted in a significant and sustained reduction in food intake, body weight and body fat while increasing metabolic rate. In addition, the reductions in body weight and body fat were not accompanied by a reduction in lean tissue mass.

Example 2

Another series of experiments were performed to further explore the synergistic effects of the combination of amylin and leptin on changes in body weight and body composition. In-bred DIO (Levin) rats were obtained from Charles Rivers Labs for these studies. These rats were developed by Barry Levin from a line of Crl:CD® (SD)BR rats that are prone to become obese on a diet relatively high in fat and energy. They were housed individually in shoebox cages at 22 C in a 12/12-hour light dark cycle. Rats were maintained ad-libitum on a moderately high fat diet (32% kcal from fat; Research Diets D1226B) for approximately 6 weeks prior to drug treatment and throughout the experiment with the exception of pair-fed controls (PF). PF rats were restricted to the intake of either the amylin-treated group. Prior to drug administration rats had typically attained a mean body weight of 500 g.

The animals were divided into treatment groups counterbalanced for body weight and were implanted with subcutaneous osmotic mini-pumps (Durect Corp., Cupertino, Calif.). Each rat was implanted with two mini-pumps containing drug or the appropriate vehicle. Rat amylin (AC0128; Lot#28) was dissolved in 50% DMSO in sterile water and murine leptin (Peprotech, catalog#450-31) was dissolved in sterile water. The pumps were designed to deliver vehicle, amylin at 100 µg/kg/day or murine leptin at 500 µg/kg/day for a 14 day period.

Each group was implanted with subcutaneous osmotic mini-pumps (DURECT Corp., Cupertino, Calif.) designed to deliver vehicle, leptin (500 µg/kg/day), amylin (100 µg/kg/day) or leptin (500 µg/kg/day)+amylin (100 µg/kg/day) for a 14 day period. Body weight and food intake were recorded daily. Body composition was measured prior to and after drug treatment using NMR (Echo Medical Systems, Houston, Tex.). For body composition measurements, rats were briefly placed (~1 min) in a well-ventilated plexiglass tube that was then inserted into a specialized rodent NMR machine. Rats were scanned prior to pump implantation and on the final day of the experiment. This enabled the calculation of changes in actual grams of fat and dry lean tissue (e.g., grams of body fat after treatment−grams of body fat at baseline=change in grams of body fat) and changes in % body composition for fat and dry lean tissue (e.g., % body fat after treatment−% body fat at baseline=change in % body fat).

Figure 6A:
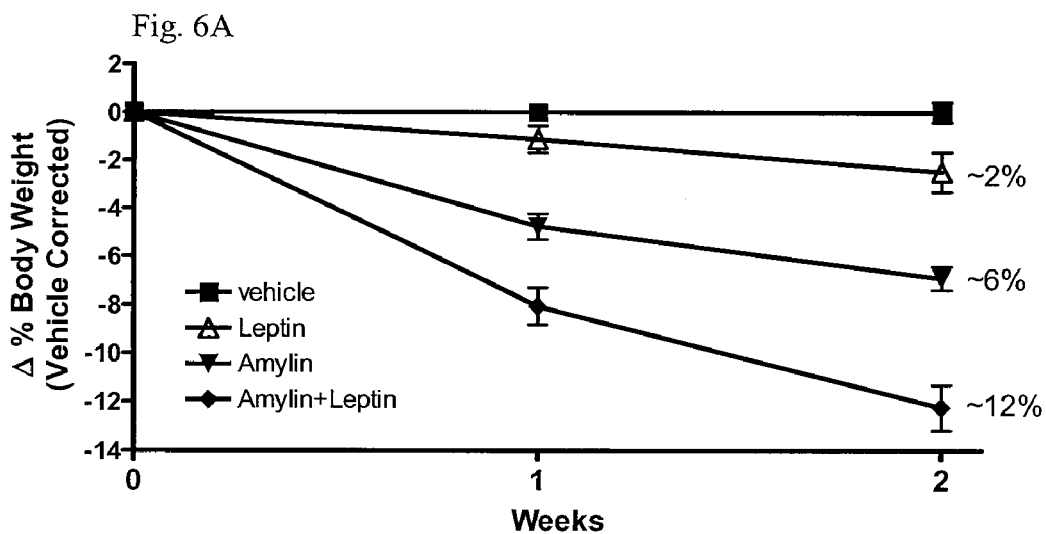
FIGS. 6A-6C.
Figure 6B:
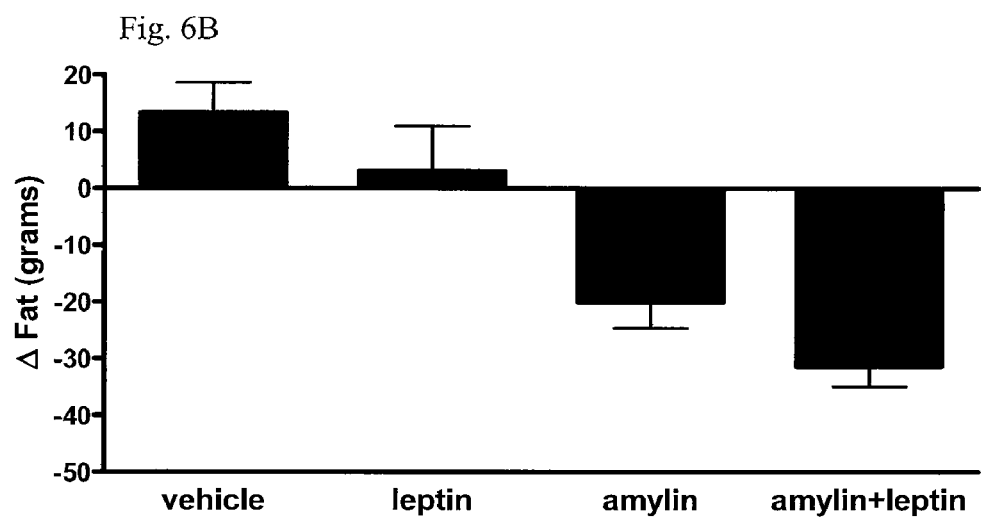
Figure 6C:
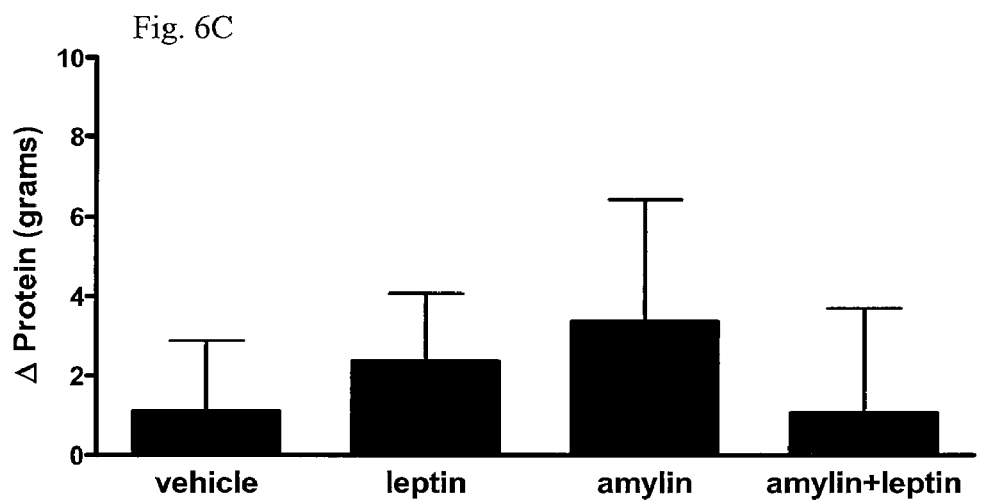

The graph in FIG. 6A depicts vehicle-corrected changes in percent body weight of the treatment groups over the two weeks of treatment. In this experiment, leptin administration resulted in an overall 2% decrease in body weight and amylin administration resulted in an overall 6% decease in body weight. Notably, the percent decrease in body weight in response to administration of a combination of amylin and leptin was about 12%, an effect greater than the combined effect from the individual agents administered alone. Accordingly, amylin and leptin acted synergistically to reduce body weight. FIGS. 6B and 6C depict changes in body fat and changes in body protein, respectively, produced after the two weeks of treatment. Again, the reduction in body fat as a result of the combination of agents is more than the combined reduction in body fat as a result of the individual agents. These changes in body fat were not accompanied decreases in body protein but rather by a gain in percent protein. These results support a metabolic effect of the combination of agents as well as a weight reducing effect.

Amylin is known to have an anorectic effect on a recipient. In order to examine the effect of amylin+leptin in the context of an anorectic effect of amylin, a pair-feeding experiment was performed. DIO rats and drug treatment groups were established as described above. DIO rats in the vehicle, amylin, and amylin+leptin treatment groups had ad libitum access to food, while intake in the pair-fed leptin treatment was restricted to the amount consumed by the amylin-treated group. Body weight was recorded daily for the two weeks of treatment. As shown in FIG. 7, the amylin treatment group and the pair-fed, leptin treatment group both had approximately a 6% decrease in body weight relative to vehicle control. This result is consistent with the previous result of leptin having little or no effect on body weight in the DIO animals. The combination of amylin+leptin results in a decrease of about 12% in body weight relative to vehicle control. Accordingly, the pair-fed experiment demonstrates that the combination of amylin+leptin reduces body weight over and above that conferred by caloric restriction.

Example 3

As discussed herein, serum leptin levels in the majority of humans with obesity are high, and a state of leptin resistance is thought to exist in these individuals. Plasma leptin levels and leptin resistance were examined in normal Harlan Sprague-Dawley (HSD) and in DIO prone rats.

DIO prone and normal HSD rats were divided into three treatment groups. Two groups were implanted with subcutaneous osmotic mini-pumps (DURECT Corp., Cupertino, Calif.) designed to deliver vehicle or amylin (100 µg/kg/day) and the third group was pair-fed to the amount consumed by the amylin-treated group for a 14 day period. Serum leptin levels were determined by immunoassays using a commercial kit (Linco Research, Inc., St. Charles, Mo.). As shown in FIG. 8, the serum leptin level in the DIO prone animals is approximately three-times higher than that in the normal HSD animals. Thus, DIO prone rats are hyper-leptinemic. Both amylin treatment and caloric restriction to the amount of food eaten by the amylin-treated animals significantly reduced plasma leptin levels in both the DIO prone and the normal animals.

Figure 9A:
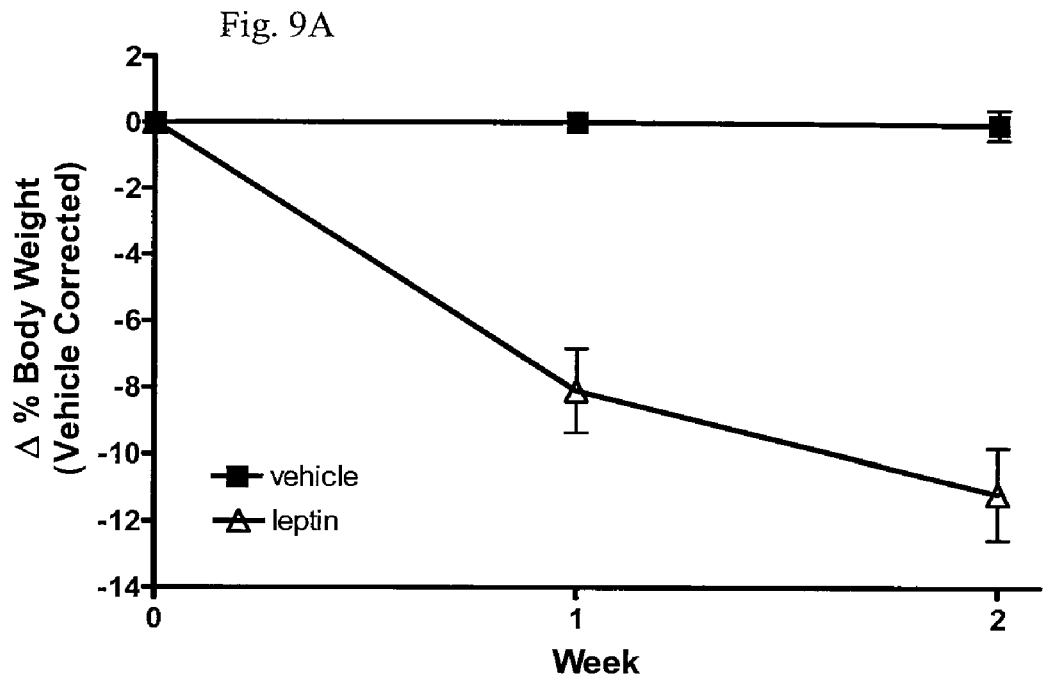
FIGS. 9A-9B.
Figure 9B:
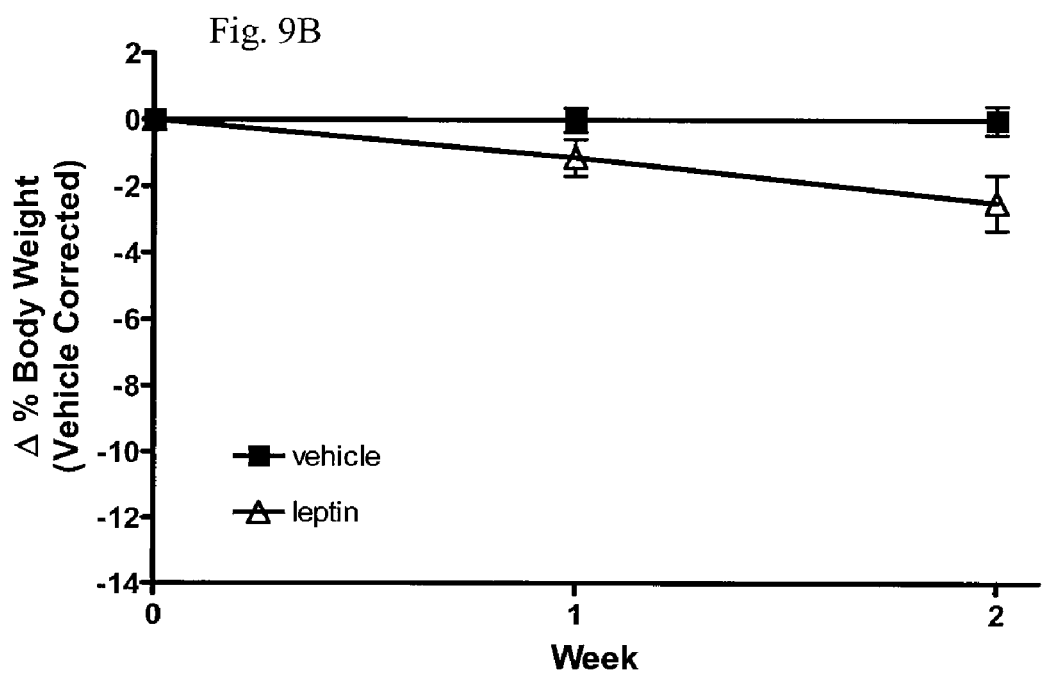

Normal, lean HSD rats were divided into two treatment groups. Each group was implanted with subcutaneous osmotic mini-pumps (DURECT Corp., Cupertino, Calif.) designed to deliver either vehicle or leptin (500 µg/kg/day) for a 14 day period and body weight was recorded weekly. As shown in FIG. 9, the ineffective dose of leptin (500 mg/kg/day) in DIO prone animals, elicited a significant and sustained reduction in body weight in normal HSD rats. The DIO prone animals described herein appear resistant to the weight reducing effect of leptin.

Example 4

To demonstrate effects of the combination of amylin and a serotonergic/noradrenergic reuptake inhibitor on changes in body weight and body composition, DIO male rats were fattened and divided into four treatment groups, as described in Example 2. Rat amylin was dissolved in 50% DMSO in sterile water and sibutramine was dissolved in sterile water. Each group was implanted with subcutaneous osmotic mini-pumps designed to deliver vehicle, sibutramine (3 mg/kg/day) or amylin (100 µg/kg/day) for a 14 day period. Body weight and food intake were recorded daily. Body composition was measured prior to and after drug treatment using NMR (Echo Medical Systems, Houston, Tex.). For body composition measurements, rats were briefly placed (~1 min) in a well-ventilated plexiglass tube that was then inserted into a specialized rodent NMR machine. Rats were scanned prior to pump implantation and on the final day of the experiment.

This enabled the calculation of changes in actual grams of fat and dry lean tissue (e.g., grams of body fat after treatment−grams of body fat at baseline=change in grams of body fat) and changes in % body composition for fat and dry lean tissue (e.g., % body fat after treatment−% body fat at baseline=change in % body fat).

Figure 10A:
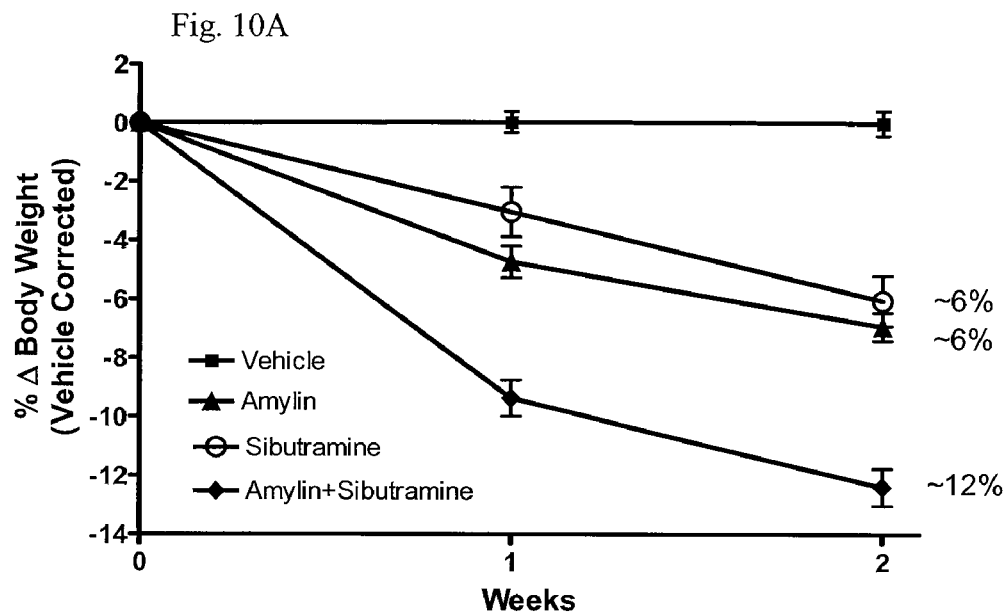
FIGS. 10A-10C.
Figure 10B:
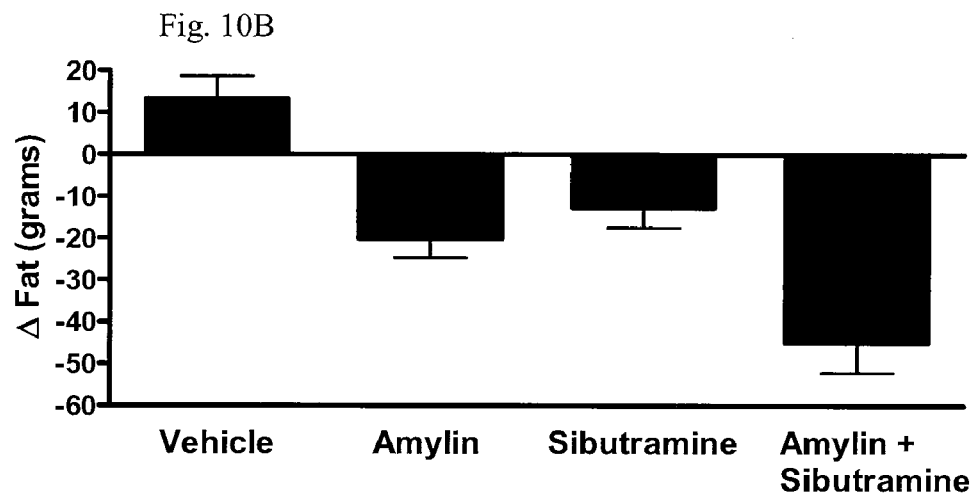
Figure 10C:
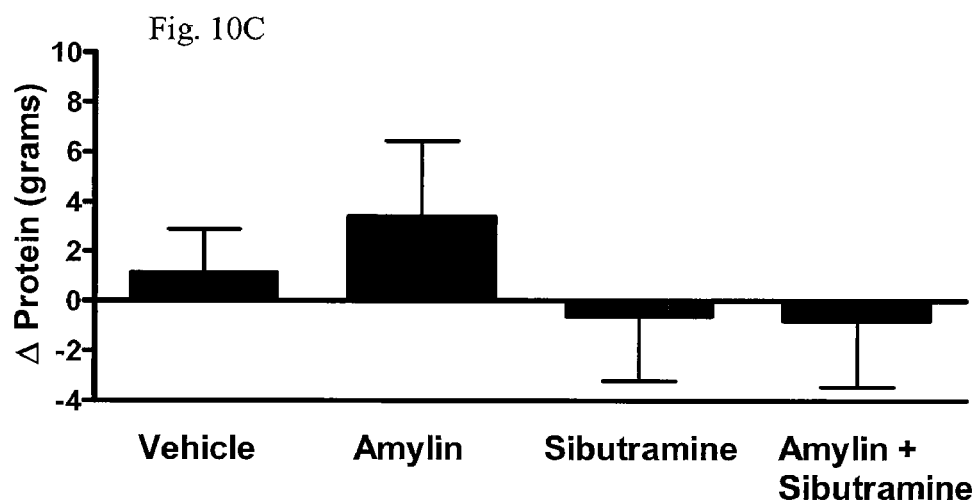

The graph in FIG. 10A depicts vehicle-corrected changes in percent body weight of the treatment groups over the two weeks of treatment. Sibutramine administration alone and amylin administration alone resulted in about a 6% decease in body weight. The percent decrease in body weight in response to administration of a combination of amylin and sibutramine was about 12%. FIGS. 10B and 10C depict changes in body fat and changes in body protein, respectively, produced after the two weeks of treatment. Fat mass loss was evident with the treatment of either amylin alone or sibutramine alone, and a synergistic effect was obtained when both amylin and sibutramine were administered in combination (FIG. 10B). Administration of amylin alone resulted in an increase in lean (protein) mass. Lean (protein) mass was relatively unchanged when sibutramine was administered alone or in combination with amylin (FIG. 10C). These results support a metabolic effect of the combination of agents as well as a weight reducing effect.

The combination of amylin and catecholaminergic agonist, phentermine, were also tested for effects on changes in body weight and body composition. Phentermine is classically referred to as a catecholaminergic agonist as it actually hits NA/5-HT receptors. DIO male rats were fattened and divided into four treatment groups, as described above. Each group was implanted with subcutaneous osmotic mini-pumps and/or inserted with an oral gavage, designed to deliver vehicle, phentermine (10 mg/kg/day), amylin (100 µg/kg/day) or phentermine (10 mg/kg/day)+amylin (100 µg/kg/day) for a 14 day period. The mini-pump contained either vehicle (50% DMSO in water) or amylin while the oral gavage administered either sterile water or phentermine. Body weight was recorded daily and body composition was measured prior to and after drug treatment using NMR.

Figure 11A:
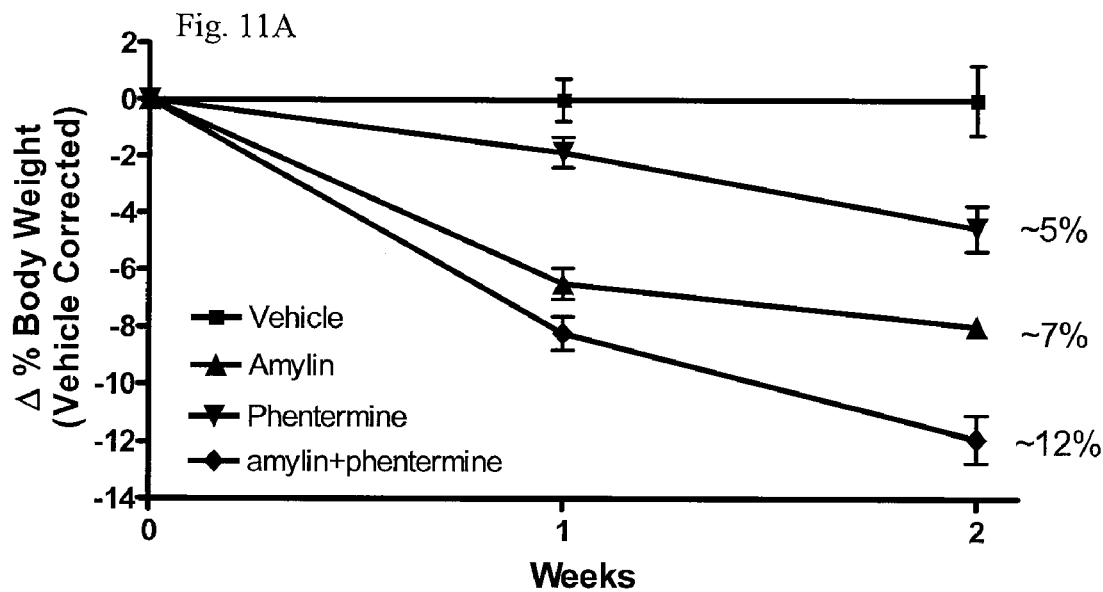
FIGS. 11A-11C.
Figure 11B:
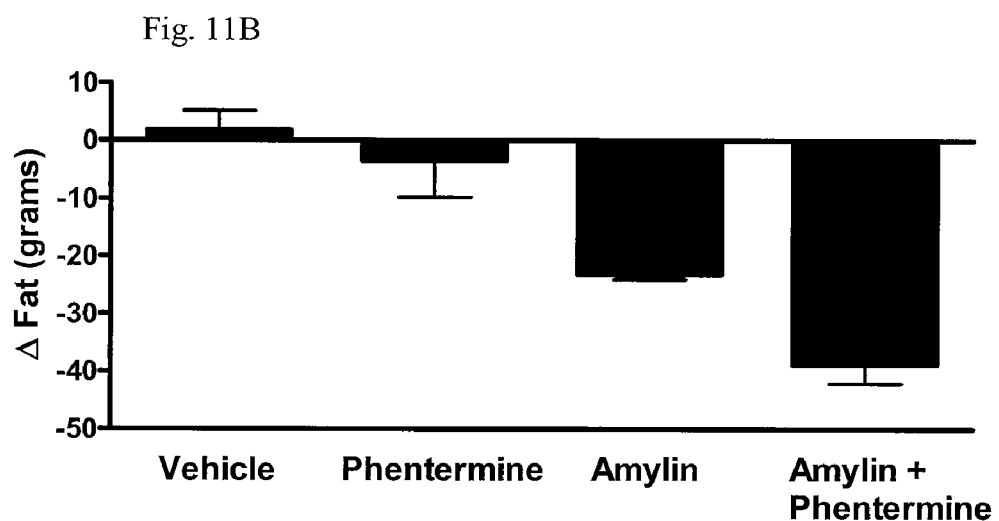
Figure 11C:
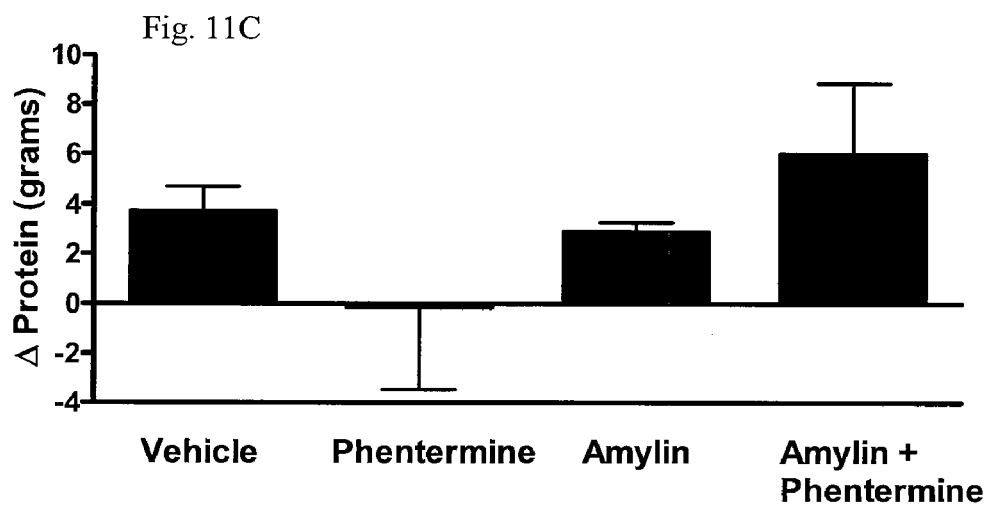

The graph in FIG. 11A depicts vehicle-corrected changes in percent body weight of the treatment groups over the two weeks of treatment. Phentermine administration alone resulted in about a 5% decrease in body weight and amylin administration alone resulted in about a 7% decease in body weight. The percent decrease in body weight in response to administration of a combination of amylin and phentermine was about 12%. FIGS. 11B and 11C depict changes in body fat and changes in body protein, respectively, produced after the two weeks of treatment. A modest amount of fat mass loss was evident with the treatment of phentermine alone and a greater amount of fat mass loss was evident with the treatment of amylin alone. When amylin and phentermine were administered in combination, a synergistic effect was obtained (FIG. 11B). Lean (protein) mass was unchanged or tended to be lost when phentermine was administered alone. Administration of amylin alone preserved lean (protein) mass and the combination of amylin and phentermine tended to have the greatest increase in lean (protein) mass, even while the animals underwent about 12% loss in body weight (FIG. 11C). These results support a metabolic effect of the combination of agents as well as a weight reducing effect.

Example 5

To demonstrate effects of the combination of amylin and a CB-1 antagonist on changes in body weight and body composition, in-bred DIO (Levin) rats were obtained from Charles Rivers Labs. These rats were developed by Barry Levin from a line of Crl:CD®(SD)BR rats that are prone to become obese on a diet relatively high in fat and energy. They were housed individually in shoebox cages at 22 C in a 12/12-hour light dark cycle. Rats were maintained ad-libitum on a moderately high fat diet (32% kcal from fat; Research Diets D1226B) for approximately 6 weeks prior to drug treatment and throughout the experiment. Prior to drug administration rats had typically attained a mean body weight of 500 g. Rats were habituated to oral gavage for 1 week prior to treatment. Rimonabant was administered at a range of doses (0.1, 0.3, 1.0, 3.0. 10 mg/kg/day) by oral gavage. Amylin (dissolved in 50% DMSO sterile water) or vehicle was administered by mini-pump (100 µg/kg/day). Rimonabant was always delivered just prior to lights out. Food intake and body weight were measured at 1 and 2 weeks post-treatment. Body composition was measured prior to and after drug treatment using NMR (Echo Medical Systems, Houston, Tex.). For body composition measurements, rats were briefly placed (~1 min) in a well-ventilated plexiglass tube that was then inserted into a specialized rodent NMR machine. Rats were scanned prior to pump implantation and on the final day of the experiment. This enabled the calculation of changes in actual grams of fat and dry lean tissue (e.g., grams of body fat after treatment−grams of body fat at baseline=change in grams of body fat) and changes in % body composition for fat and dry lean tissue (e.g., % body fat after treatment−% body fat at baseline=change in % body fat).

The graph in FIG. 12A depicts vehicle-corrected changes in percent body weight of the treatment groups over the two weeks of treatment. Rimonabant administration alone resulted in about a 4% decrease in body weight and amylin administration alone resulted in about a 6% decease in body weight. The percent decrease in body weight in response to administration of a combination of amylin and rimonabant was about 11%. FIGS. 12B and 12C depict changes in body fat and changes in body protein, respectively, produced after the two weeks of treatment. Fat mass loss was evident with the treatment of either amylin alone or rimonabant alone, and a synergistic effect was obtained when both amylin and rimonabant were administered in combination (FIG. 12B). Administration of amylin alone, rimonabant alone, and amylin+rimonabant in combination resulted in a relatively equivalent increase in lean (protein) mass (FIG. 12C). These results support a metabolic effect of the combination of agents as well as a weight reducing effect.

Figure 13:
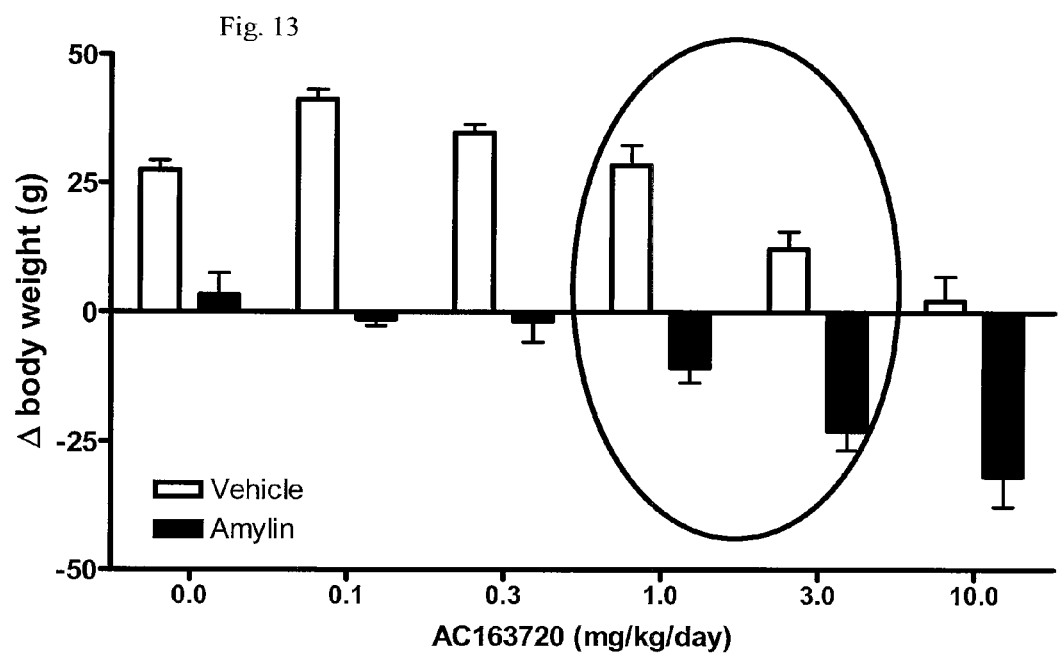
FIG. 13 is a graph depicting the effect of administration of a range of doses of a CB-1 antagonist, either alone or in combination with amylin (100 μg/kg/day), on body weight. The time course of the combinations in the circled area are depicted in FIGS. 14 A and B.
Figure 14A:
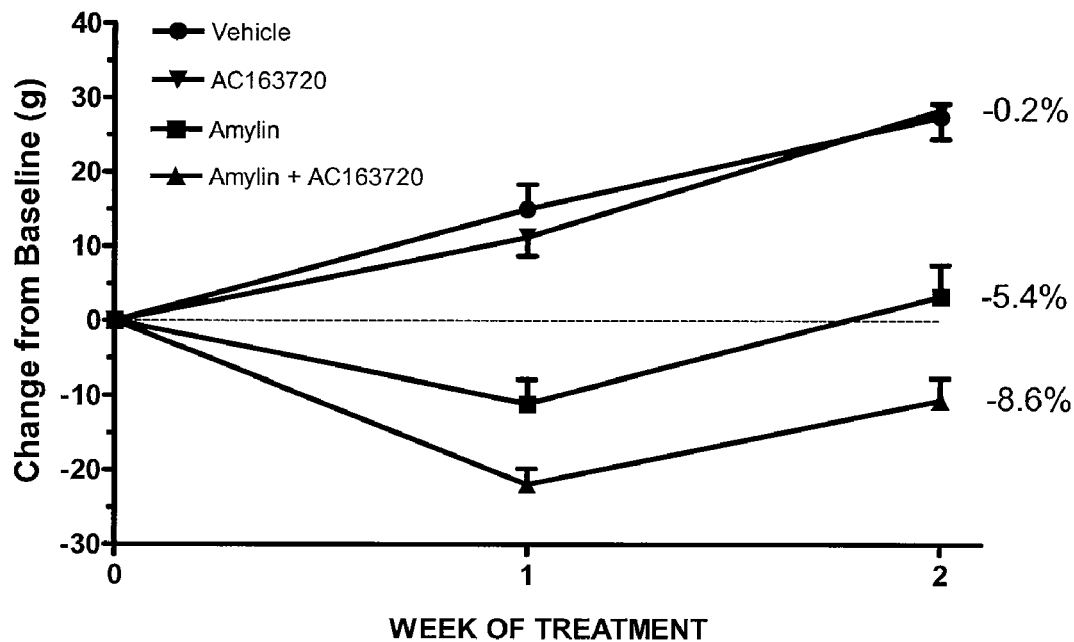
FIGS. 14A-14B.
Figure 14B:
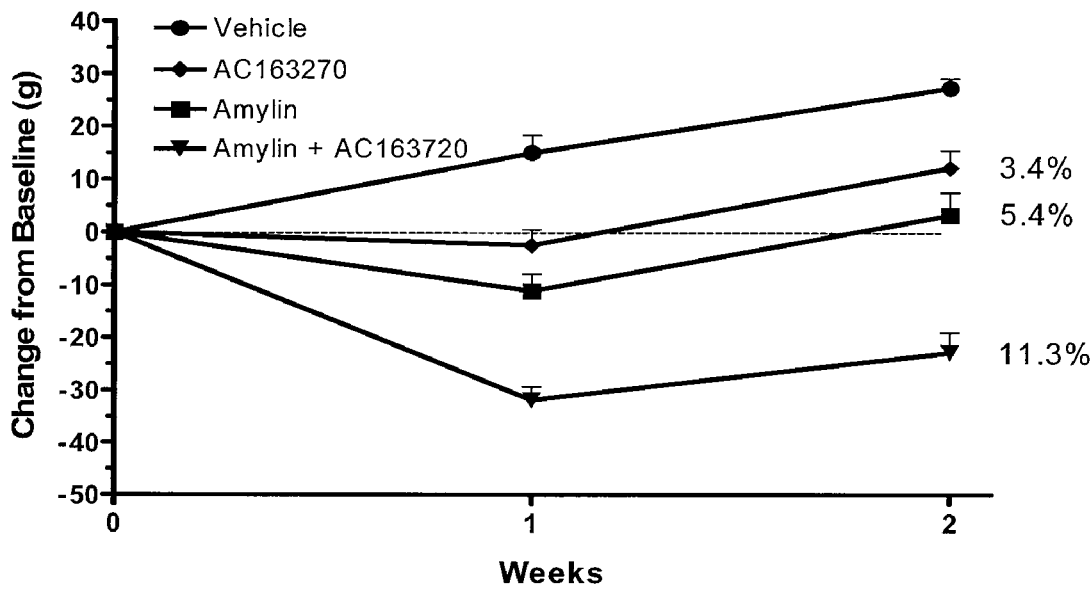

In another assay, the CB-1 antagonist rimonanbant (AC163720) was administered in combination with amylin. DIO prone rats were maintained ad-libitum on a moderately high fat diet (32% kcal from fat; Research Diets D 1226B) for 6 weeks prior to drug treatment. At the end of the fattening period they typically have a mean body weight of 500 g. Rats were then divided into treatment groups and implanted with one subcutaneous mini-pump (Durect Corp) and inserted with an oral gavage. The mini-pump contained either vehicle (50% DMSO in water) or amylin (100 µg/kg/day) while the oral gavage administered either sterile water or a range of doses of rimonabant (AC163720) (0.1, 0.3, 1.0, 3.0, 10.0 mg/kg/day). Change in body weight after 2 weeks is depicted in FIG. 13 and two of these combinations (circled) are highlighted in FIGS. 14A and 14B in more detail.

Example 6

To demonstrate effects of the combination of amylin and an exendin analog, $^{14}$Leu-exendin-4: His Gly Glu Gly Thr Phe Thr Ser Asp Leu Ser Lys Gln Leu Glu Glu Glu Ala Val Arg Leu Phe Ile Glu Trp Leu Lys Asn Gly Gly Pro Ser Ser Gly Ala Pro Pro Pro Ser (SEQ ID NO:190), on changes in body weight and body composition, DIO male rats were fattened and divided into four treatment groups, as described above. Prior to drug administration rats had typically attained a mean body weight of 500 g Exendin-4 analog was administered by minipump at a range of doses (0.3, 1, 3, 10, 30 µg/kg/day). Amylin (dissolved in 50% DMSO in water) or vehicle was administered by mini-pump (100 µg/kg/day). Body weight and food intake was recorded daily. Body composition was measured prior to and after drug treatment using NMR (Echo Medical Systems, Houston, Tex.). For body composition measurements, rats were briefly placed (~1 min) in a well-ventilated plexiglass tube that was then inserted into a specialized rodent NMR machine. Rats were scanned prior to pump implantation and on the final day of the experiment. This enabled the calculation of changes in actual grams of fat and dry lean tissue (e.g., grams of body fat after treatment–grams of body fat at baseline=change in grams of body fat) and changes in % body composition for fat and dry lean tissue (e.g., % body fat after treatment–% body fat at baseline=change in % body fat).

Figure 15A:
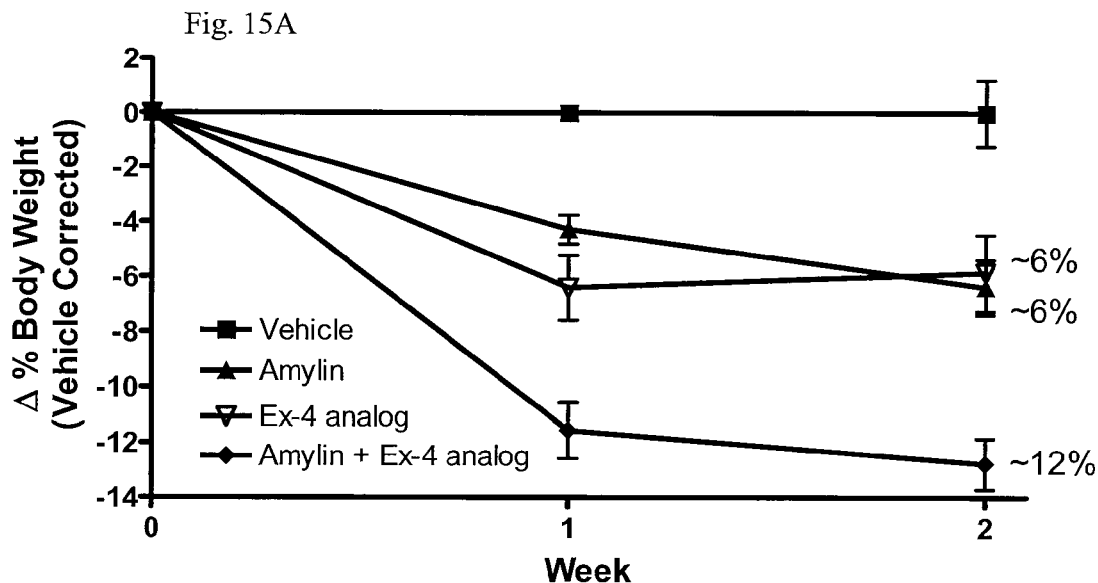
FIGS. 15A-15C.
Figure 15B:
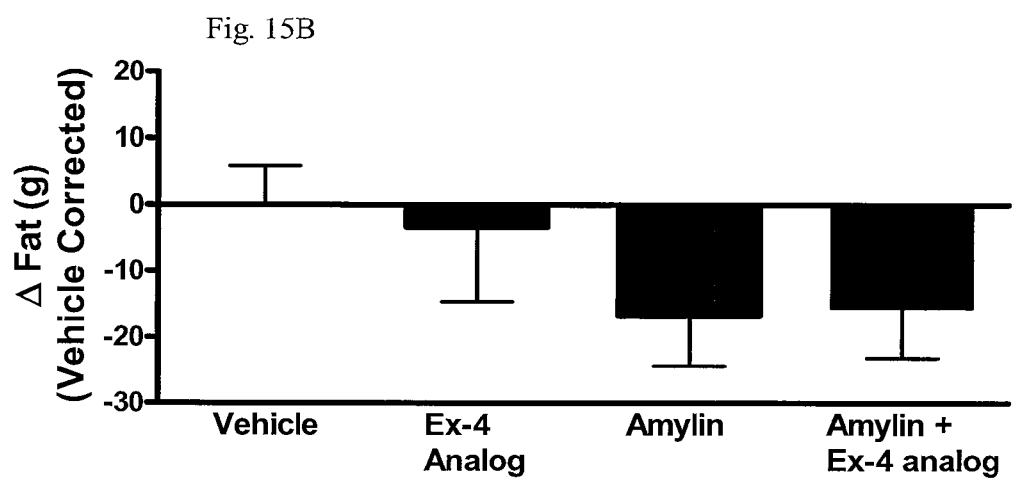
Figure 15C:
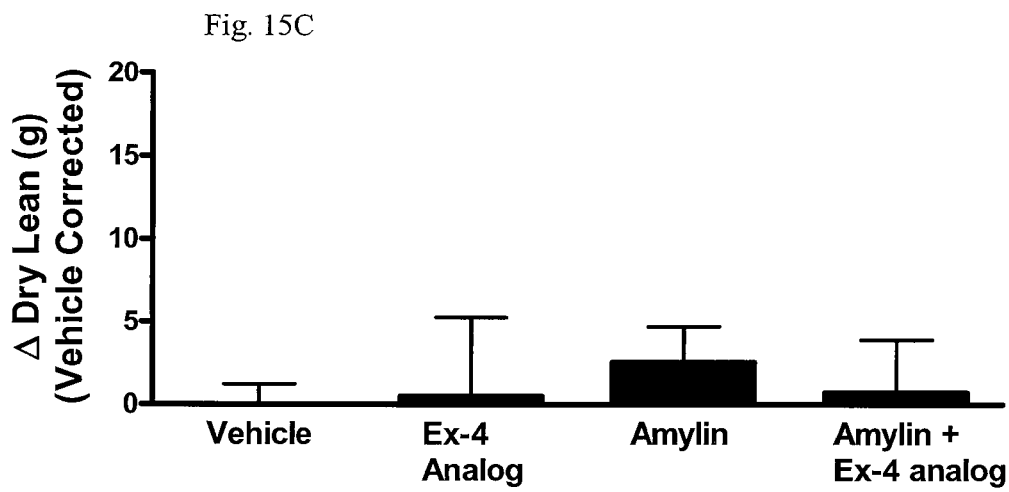

The graph in FIG. 15A depicts vehicle-corrected changes in percent body weight of the treatment groups over the two weeks of treatment. Exendin-4 analog administration alone and amylin administration alone each resulted in about a 6% decrease in body weight. The percent decrease in body weight in response to administration of a combination of amylin and Exendin-4 analog was about 12%. FIGS. 15B and 15C depict changes in body fat and changes in body protein, respectively, produced after the two weeks of treatment. Fat mass loss was evident with the treatment of Exendin-4 analog alone. Administration of amylin alone and amylin+Exendin-4 analog in combination resulted in a relatively equivalent decrease in fat mass (FIG. 15B). Administration of amylin alone, Exendin-4 analog alone, and amylin+AC3174 in combination resulted in a relatively equivalent increase in lean (protein) mass (FIG. 15C). These results support a metabolic effect of the combination of agents as well as a weight reducing effect.

Example 7

To demonstrate effects of the combination of amylin and PYY agonists on changes in body weight and body composition, DIO male rats were fattened and divided into four treatment groups, as described above. Each group was implanted with subcutaneous osmotic mini-pumps, designed to deliver vehicle, PYY(3-36) (1000 µg/kg/day), amylin (100 µg/kg/day) or PYY(3-36) (1000 µg/kg/day)+amylin (100 µg/kg/day) for a 14 day period. PYY(3-36) was administered by mini-pump at a range of doses (100, 200, 400, 800, 1000 µg/kg/day). Amylin 100 µg/kg/day (dissolved in 50% DMSO sterile water), PYY(3-36) (dissolved in 50% DMSO sterile water) or vehicle was administered by mini-pump. Food intake and body weight was recorded daily. Body composition was measured prior to and after drug treatment using NMR (Echo Medical Systems, Houston, Tex.). For body composition measurements, rats were briefly placed (~1 min) in a well-ventilated plexiglass tube that was then inserted into a specialized rodent NMR machine. Rats were scanned prior to pump implantation and on the final day of the experiment. This enabled the calculation of changes in actual grams of fat and dry lean tissue (e.g., grams of body fat after treatment–grams of body fat at baseline change in grams of body fat) and changes in % body composition for fat and dry lean tissue (e.g., % body fat after treatment–% body fat at baseline=change in % body fat).

The graph in FIG. 16A depicts vehicle-corrected changes in percent body weight of the treatment groups over the two weeks of treatment. PYY(3-36) administration alone resulted in about a 9% decrease in body weight and amylin administration alone resulted in about a 7% decrease in body weight. The percent decrease in body weight in response to administration of a combination of amylin and PYY(3-36) was about 15%. FIGS. 16B and 16C depict changes in body fat and changes in body protein, respectively, produced after the two weeks of treatment. Increasing amount of fat mass loss was evident with the treatment of PYY(3-36) alone, amylin alone, and amylin+PYY(3-36) in combination (FIG. 16B). Administration of amylin alone and amylin+PYY(3-36) in combination resulted in an increase in lean (protein) mass (FIG. 16C). These results support a metabolic effect of the combination of agents as well as a weight reducing effect.

Example 8

To evaluate inter alia the safety, tolerability and effect of the combination of an amylin agonist (pramlintide) and a leptin (metreleptin) on changes in body weight, a 24-week, randomized, double-blind, active-drug-controlled, multi-center study was conducted under USFDA approved protocols. Secondary objectives of the study were the determination of the pharmacokinetics of pramlintide and leptin, waist circumference, rate of change in body weight, and patient reported outcomes including for example without limitation perception of well-being related to weight change and mood. The study enrolled overweight and obese subjects with defined BMI (27 to 35 mg/m$^2$), with enrollment statistics as provided in Table 2. At the end of the 24-week study, pramlintide/metreleptin combination treatment reduced body weight on average 12.7%, significantly more than treatment with pramlintide alone (8.4%, p<0.001). Subjects treated with pramlintide/metreleptin lost an average of 25 pounds from the start of the 24-week study compared with an average of 17 pounds for subjects treated with pramlintide alone. Furthermore, subject receiving pramlintide/metreleptin had continuous weight loss through the end of the study compared to those treated with pramlintide alone, whose weight had stabilized towards the end of the 24-week study. Demographics of the subject population are provided in Table 3.

TABLE 2

Subject Disposition of 24-Week Study

| | Leptin | Pramlintide | Leptin + Pramlintide | Non-randomized |
|---|---|---|---|---|
| Enrolled | 27 | 56 | 56 | 38 |
| Completed Study | 19 | 37 | 38 | 0 |
| Week 16 evaluable | 19 | 38 | 36 | 0 |
| Withdrew prior to completion (%) | 29.6 | 33.9 | 32.1 | 100.0 |

TABLE 3

Subject Demographics for 24-week study

| Enrolled (N = 177) | Leptin | Pramlintide | Leptin + Pramlintide | Non-Randomized |
|---|---|---|---|---|
| Enrolled (n) | 27 | 56 | 56 | 38 |
| Sex (% female) | 63 | 63 | 63 | 63 |
| Race (C/B/A/H/O, %) | 82/19/0/0/0 | 82/13/0/4/2 | 88/5/4/4/0 | 61/24/8/8/0 |
| Age (y) | 40.5 ± 8.1 | 38.3 ± 9.1 | 38.5 ± 8.4 | 37.9 ± 7.5 |
| Height (cm) | 171 ± 10 | 170 ± 9 | 171 ± 9 | 170 ± 12 |
| Weight (kg) | 93.8 ± 14.3 | 91.7 ± 11.1 | 93.9 ± 12.8 | 94.5 ± 16.0 |
| BMI (kg/m2) | 32.0 ± 2.1 | 31.5 ± 2.0 | 32.0 ± 2.1 | 32.5 ± 1.9 |
| <30 kg/m2 (%) | 22 | 21 | 23 | 8 |
| Total Excess Body Weight (kg) | 21.0 ± 7.2 | 19.2 ± 6.3 | 20.8 ± 6.9 | 22.4 ± 7.4 |

In an initial lead-in phase, all subjects received dietary instructions and treatment with pramlintide at 180 mcg BID for two weeks, followed by pramlintide at 360 mcg BID for two weeks. Subjects who completed the 4-week lead-in period and who lost 2-8 percent body weight during this period were eligible to continue the study. The term "enrolled" (Table 2) refers to subjects (N=177) receiving at least one dose of pramlintide during the lead-in period. The term "non-randomized" refers to subjects not continuing in the study past the lead-in period. The term "evaluable" refers to subjects who completed Visit 9 (Week 16) study procedures and adequately complied with the study protocol.

After the 4-week lead-in period, for the remaining 20 weeks of the study the subjects were randomized in a 2:2:1 ratio to one of three groups with BID treatment of 1) pramlintide 360 mcg/metreleptin 5 mg ("Leptin+Pramlintide"); 2) pramlintide 360 mcg/placebo ("Pramlintide"); or 3) metreleptin 5 mg/placebo ("Leptin").

Changes in the enrolled population over the 4-week lead-in period are provided in Table 4.

TABLE 4

Changes Over Lead-in Period for 24-Week Study

| Enrolled (N = 177) | Leptin | Pramlintide | Leptin + Pramlintide | Non-Randomized |
|---|---|---|---|---|
| Enrolled (n) | 27 | 56 | 56 | 38 |
| Mean Change in Body Weight (kg) | −3.97 | −3.65 | −4.01 | n/a |
| % Weight Loss During Lead-in | | | | |
| <5% | 78% | 77% | 71% | n/a |
| ≧5% | 22% | 23% | 29% | n/a |
| Endogenous Leptin Concentration (pg/mL) | | | | |
| Enrollment (Week −4) | 28.7 ± 15.8 | 25.2 ± 13.8 | 25.7 ± 15.2 | 28.5 ± 14.7 |
| Baseline (Day 1) | 22.8 ± 13.8 | 18.1 ± 12.3 | 19.5 ± 12.4 | n/a |

Figure 17:
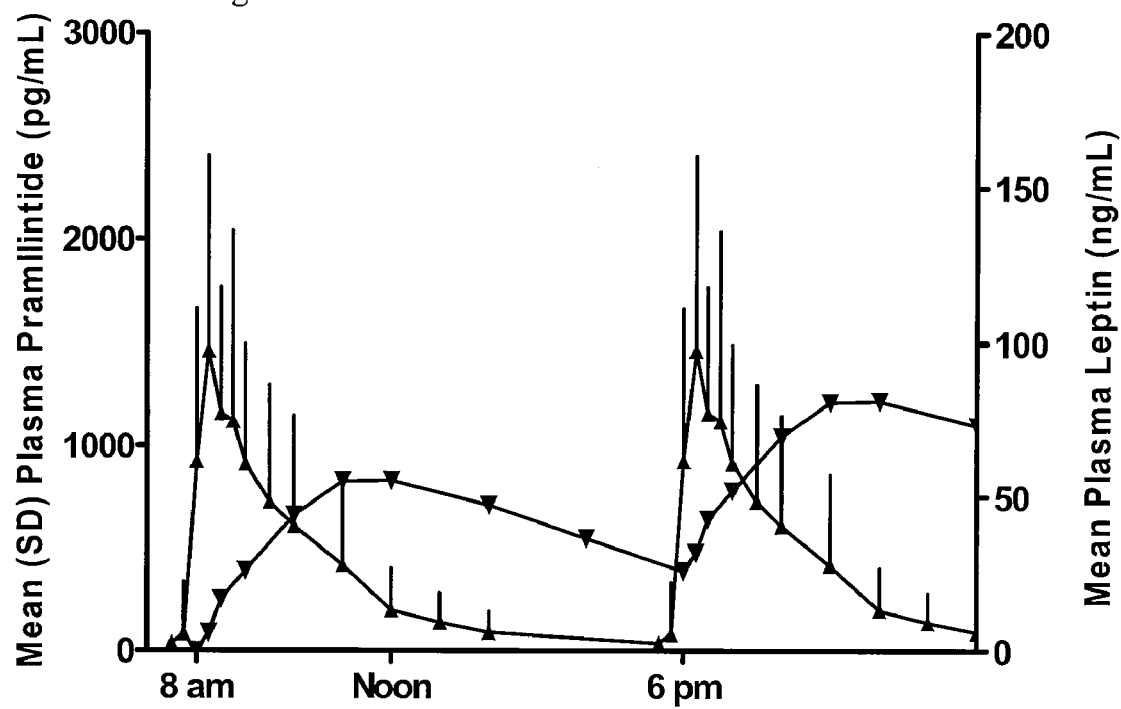
FIG. 17 provides the mean plasma concentrations of pramlintide and metreleptin in subjects (N=31) enrolled in a 24-week study of the effects of the combination of an amylin agonist and a leptin (Example 8). Metreleptin and pramlintide were administered at 5 mg BID and 360 microgram (mcg) BID, respectively, within 15 min prior to breakfast and dinner. Assay for metreleptin and pramlintide were conducted by routine methods known in the art. Legend: metreleptin (triangle with base up); pramlintide (triangle with base down).

Dose selection and timing was informed by pharmacokinetic studies for example as provided in FIG. 17, which demonstrates the mean plasma concentration of metreleptin and pramlintide administered at 5 mg BID and 360 mcg BID, respectively, with administration within 15 min prior to breakfast and dinner.

Figure 18A:
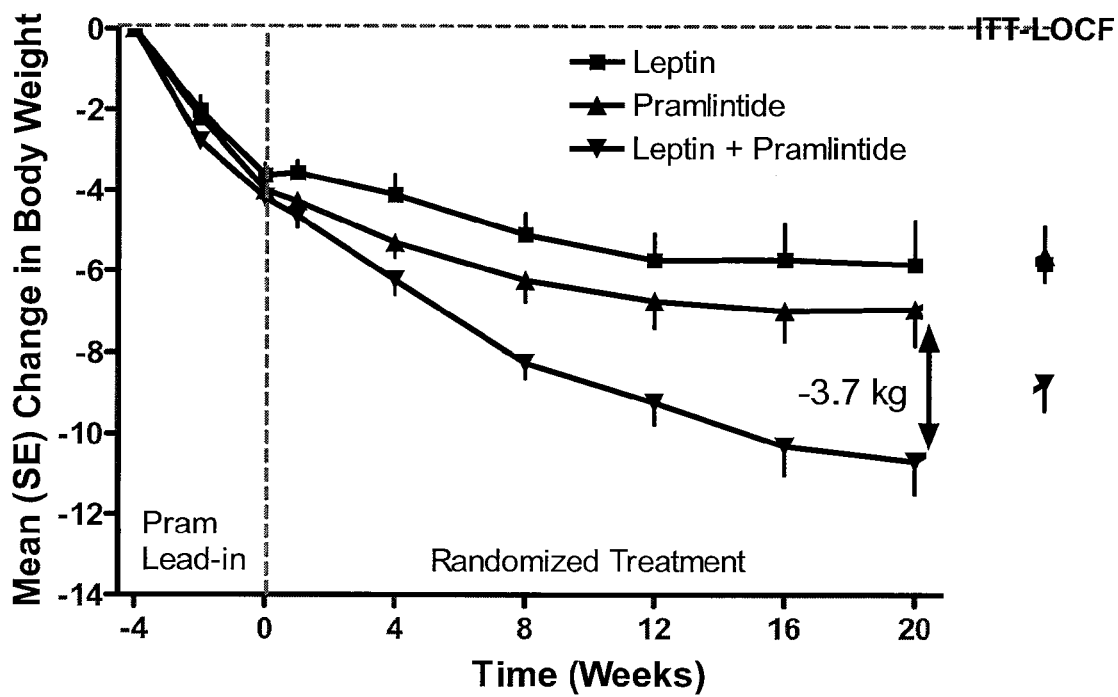
FIG. 18A and FIG. 18B show the mean change in body weight from enrollment for the evaluable population over the course of a 24-week study (Example 8.)
Figure 18B:
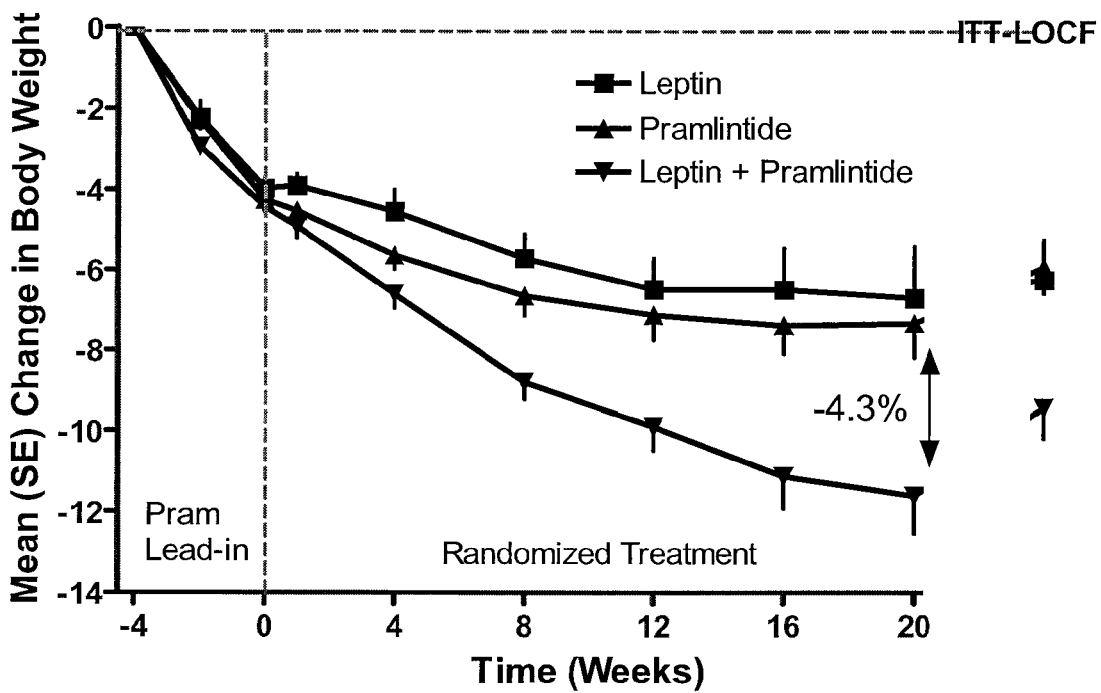
Figure 20A:
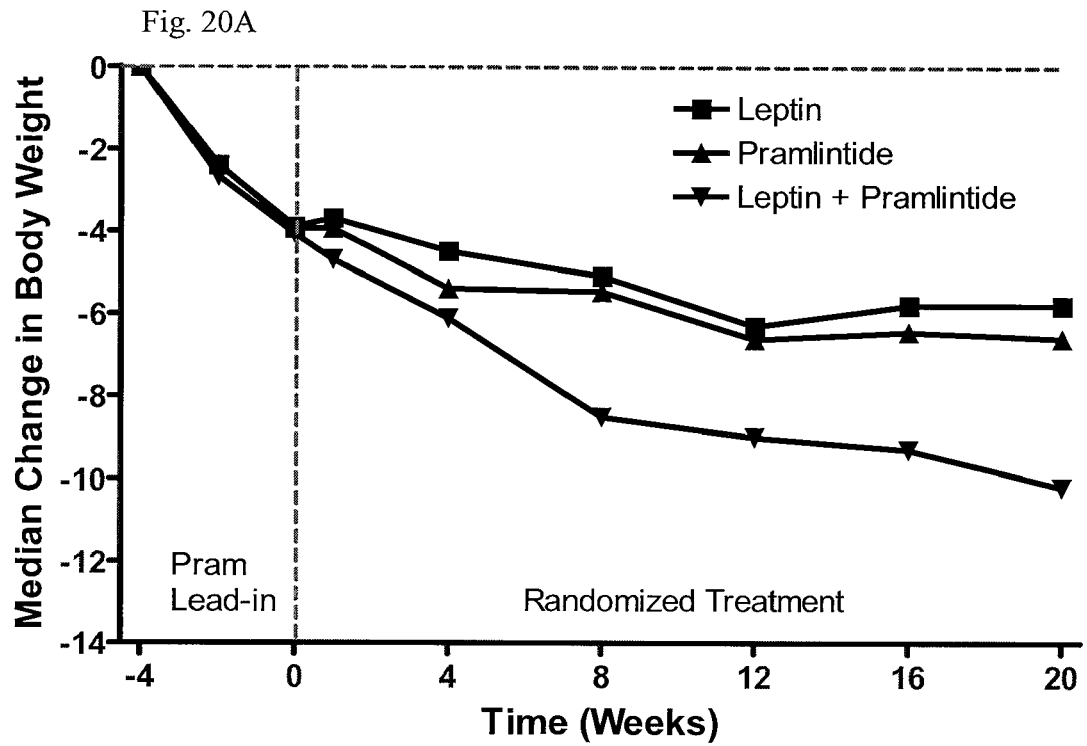
FIG. 20A and FIG. 20B demonstrate median change in body weight from enrollment for the evaluable population during the 24-week study described in Example 8.
Figure 20B:
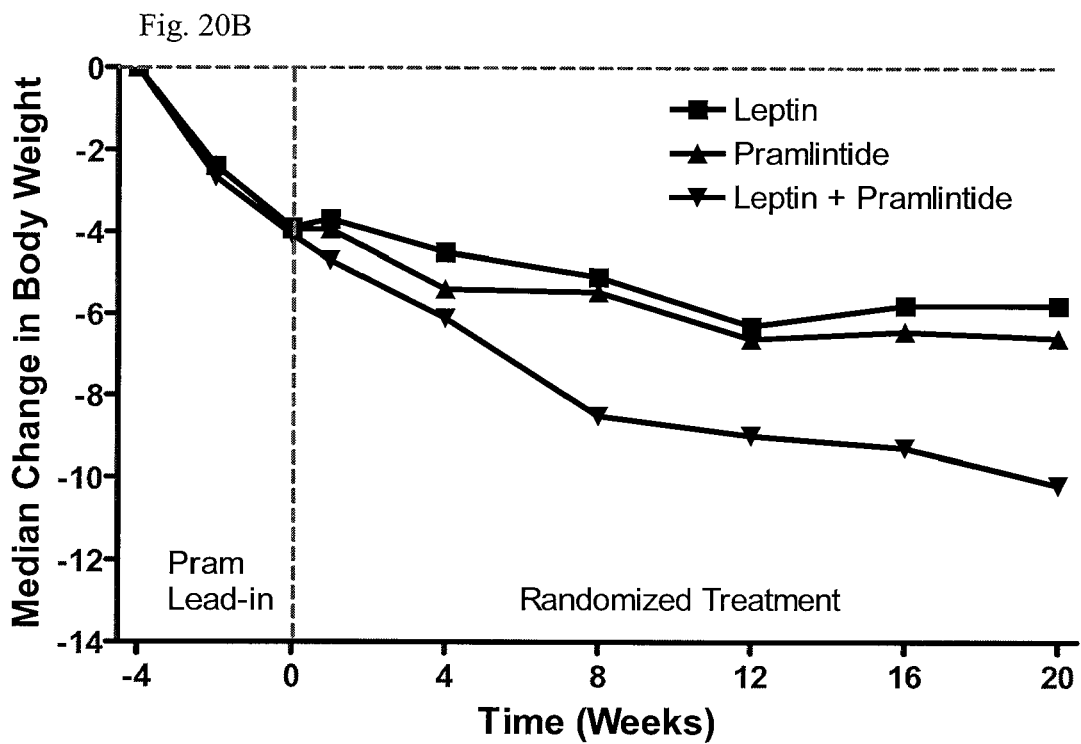
Figure 22:
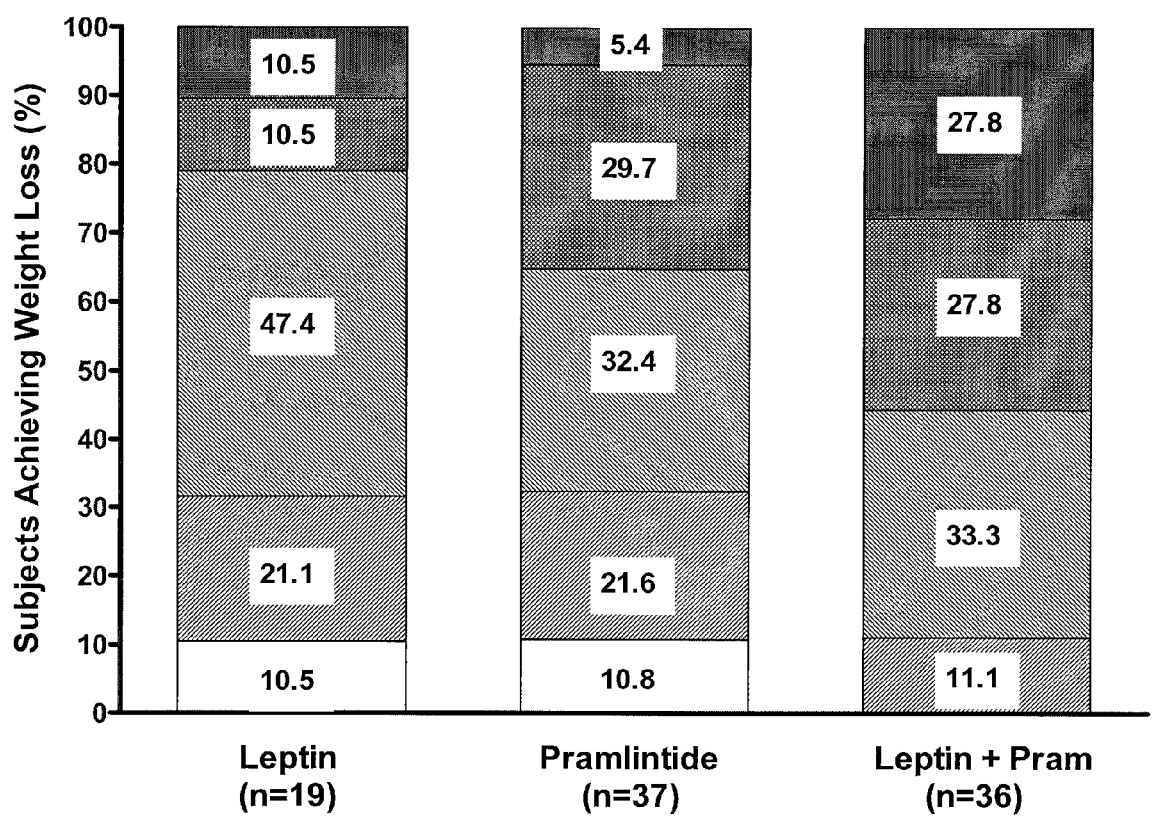
FIG. 22 demonstrates categorical change in body weight from enrollment to week 20 for the Week 20 evaluable population during the 24-week study described in Example 8. The term "Week 20 evaluable" refers to randomized subjects who complied to protocol and completed Week 20. Evaluable population: leptin (n=19); pramlintide (n=37); leptin+pramlintide (n=36). Legend: blank (no weight loss); diagonal lower left to upper right (0 to −5%); diagonal upper left to lower right (−5 to −10%); crosshatched (−10 to −15%); checked (≧−15%).
Figure 23A:
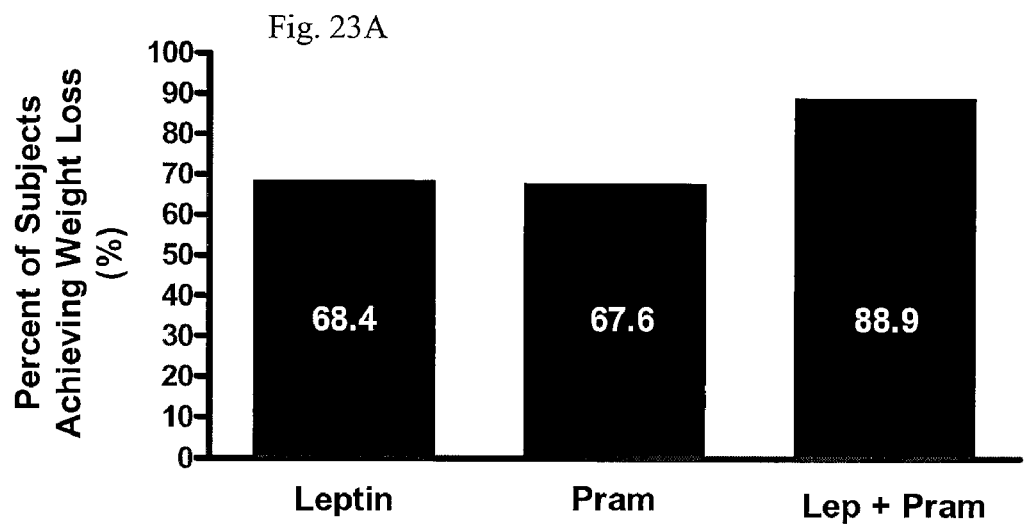
FIG. 23A, FIG. 23B and FIG. 23C demonstrate categorical change in body weight from enrollment to week 20 for the Week 20 evaluable population during the 24-week study based on weight loss described in Example 8.
Figure 23B:
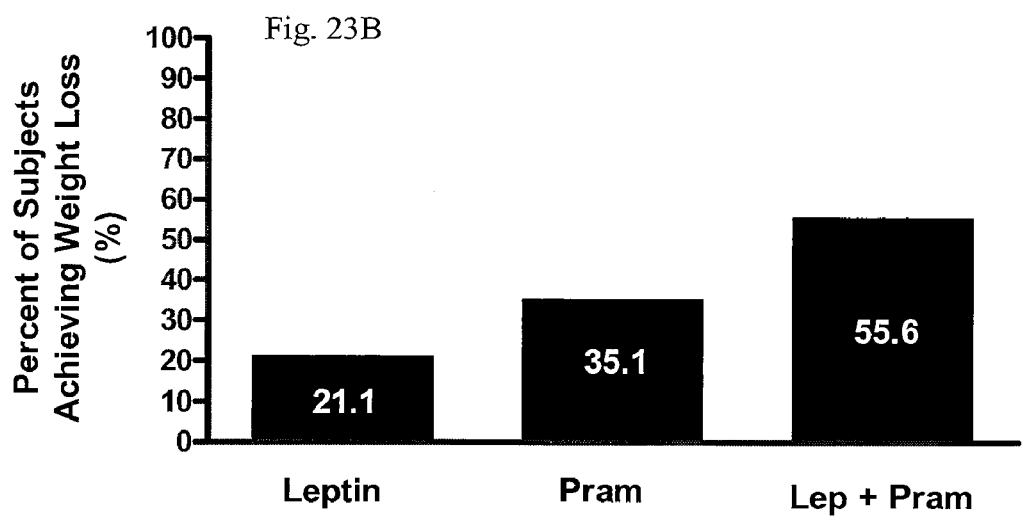
Figure 23C:
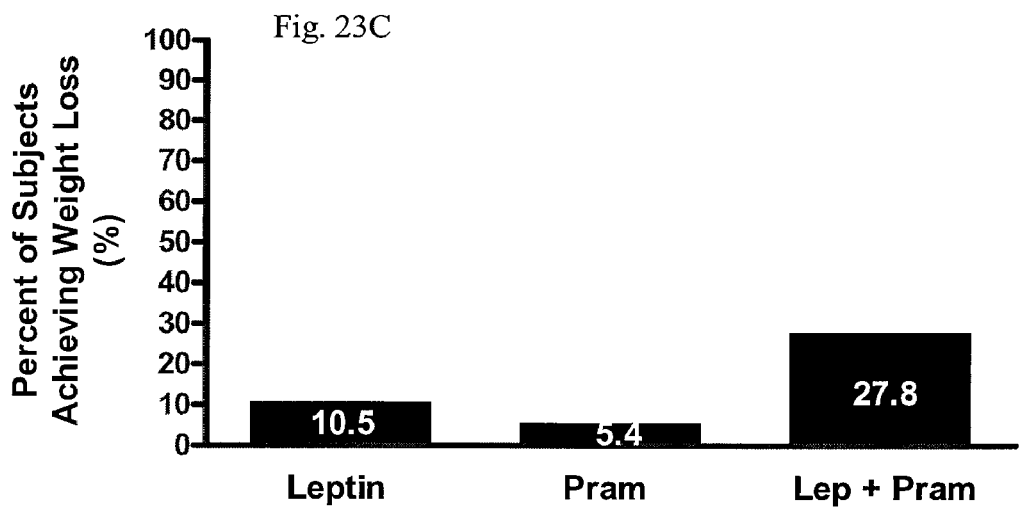
Figure 24:
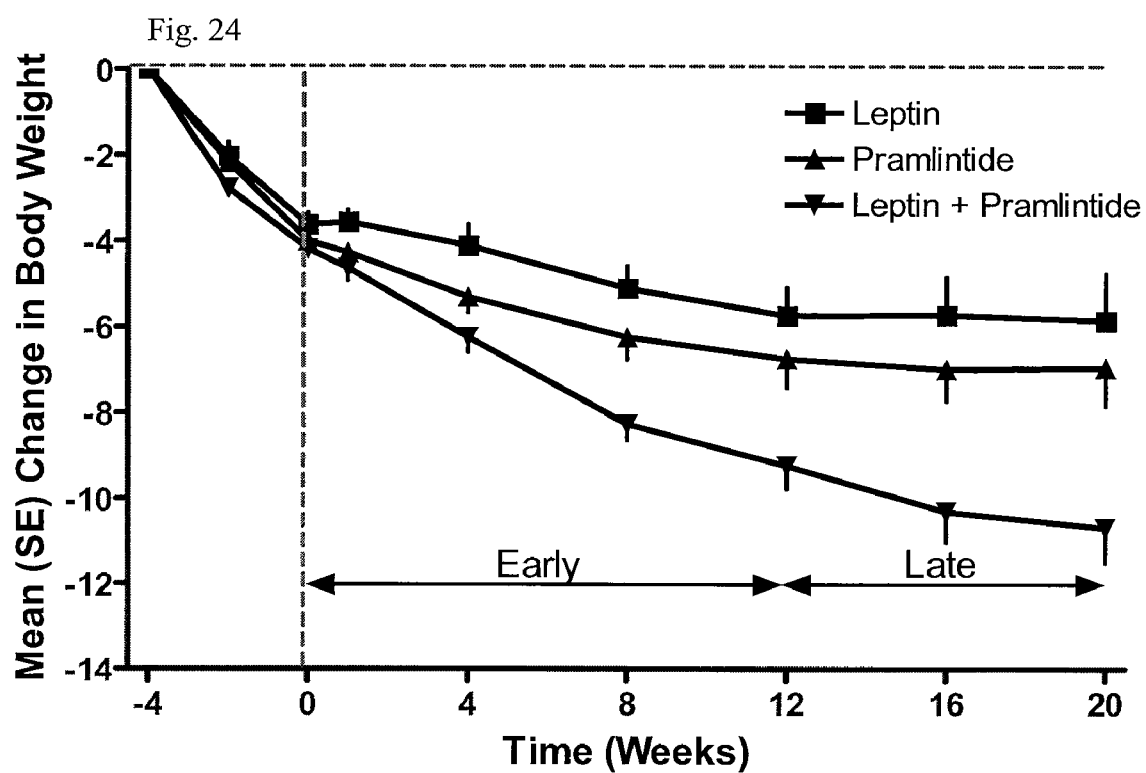
FIG. 24 demonstrates rate of change in body weight during early rate (0-12 weeks) and late rate (12-20 weeks) in the 24-week study described in Example 8. Early and late rates of change between the combination arm and monotherapy arms are significantly different (p-value<0.05). Late rate of change in the combination arm is significant (p-value=0.0005). Late rate of change in monotherapy arms is not significant (p>0.05). Evaluable population is as described for FIG. 22. Rate of change (kg/week): leptin (−0.19±0.05 early; −0.01±0.08 late); pramlintide (−0.23±0.04 early; −0.02±0.04 late); leptin+pramlintide (−0.44±0.03 early; −0.18+0.06 late).
Figures 25A, 25B:
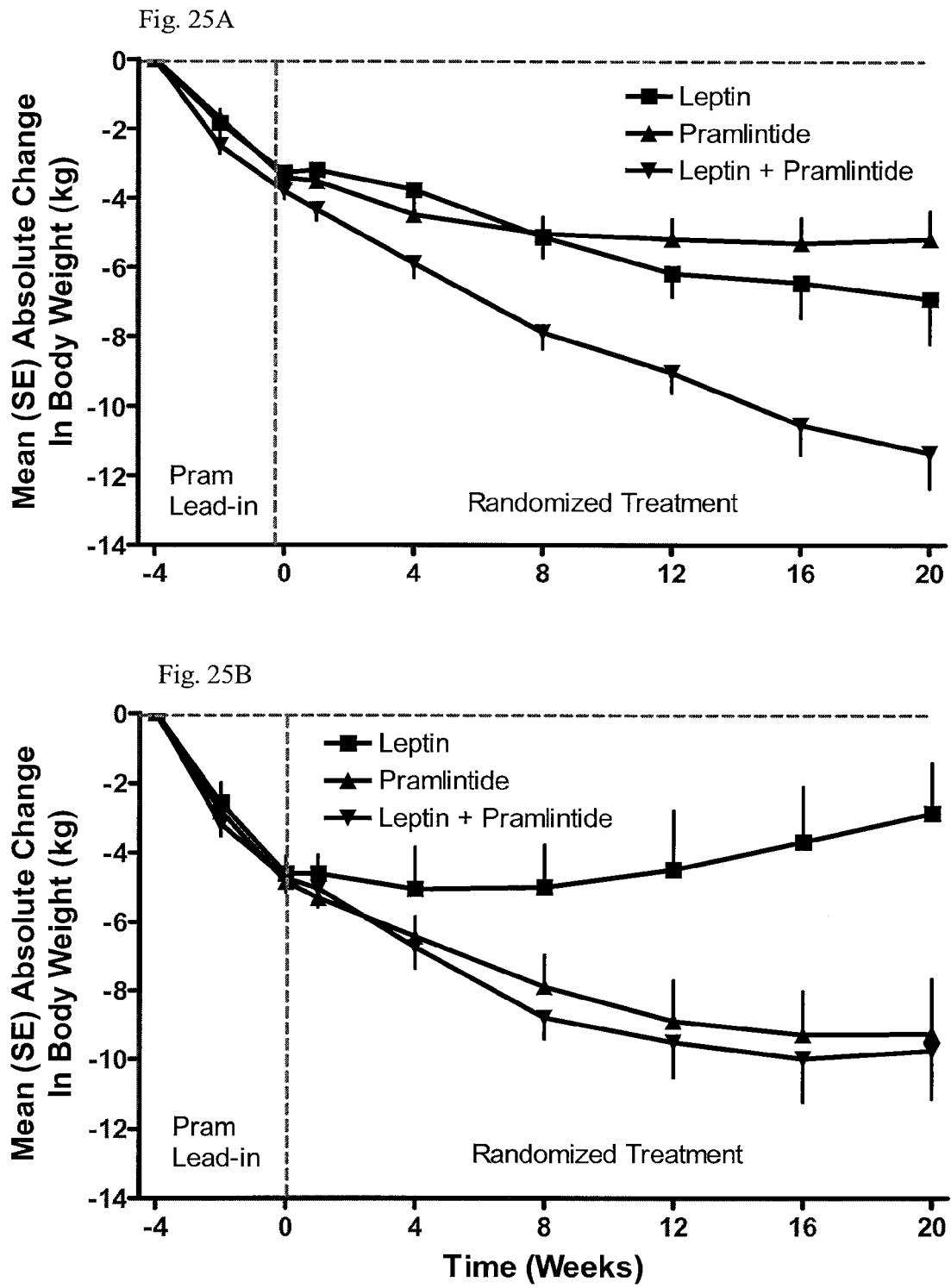
FIG. 25A and FIG. 25B demonstrate mean absolute change in body weight from enrollment by sex for the evaluable population during the 24-week study described in Example 8.
Figure 26A:
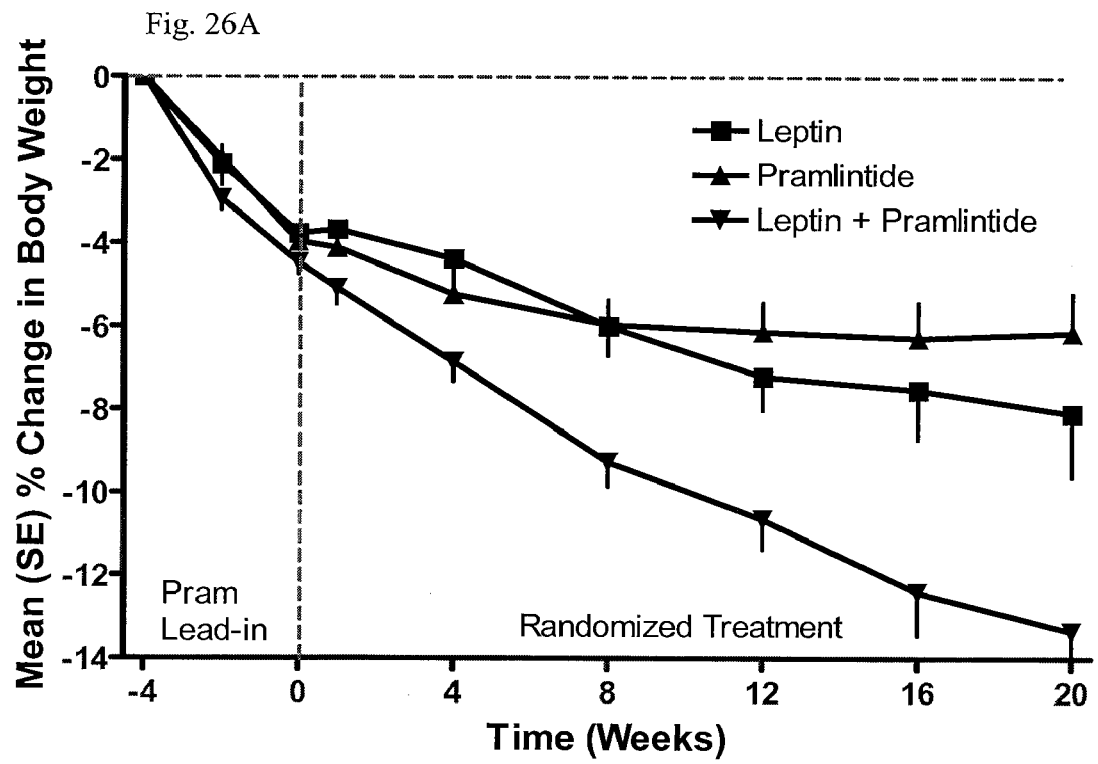
FIG. 26A and FIG. 26B demonstrate mean percentage change in body weight from enrollment by sex for the evaluable population during the 24-week study described in Example 8.
Figure 26B:
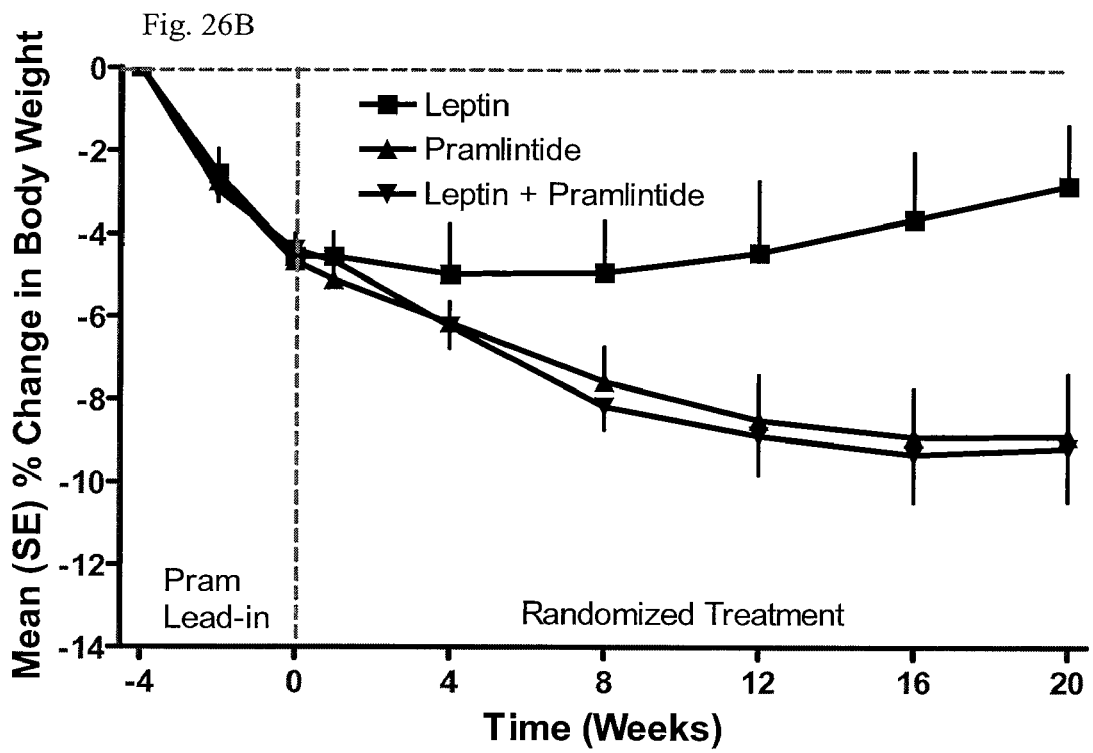
Figure 29A:
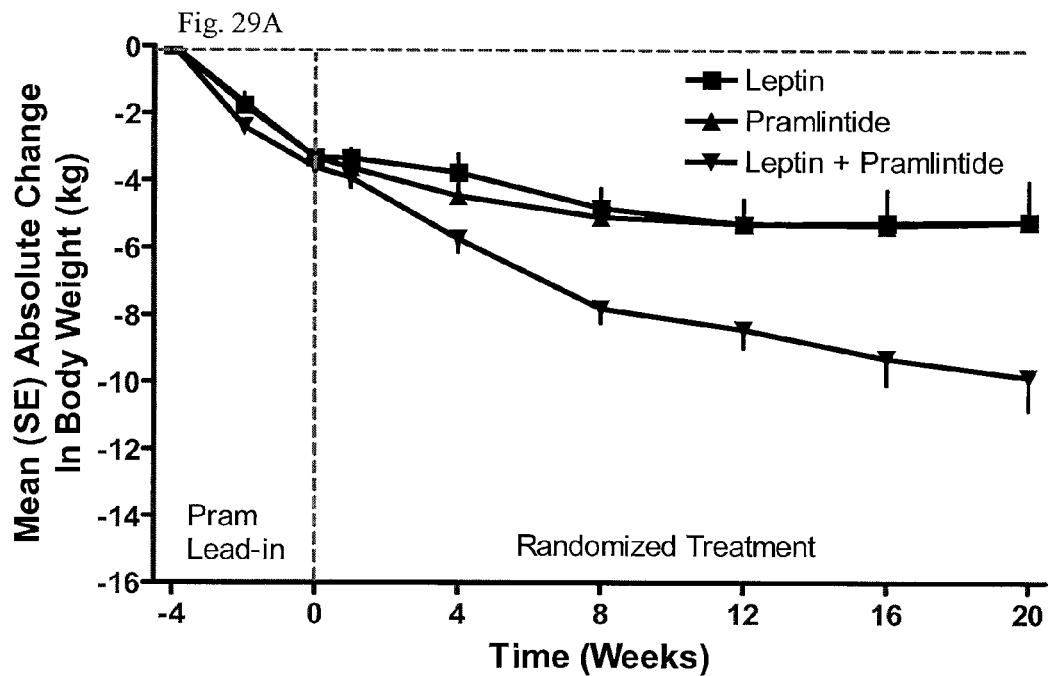
FIG. 29A and FIG. 29B demonstrate mean absolute change in body weight from enrollment by initial weight loss for the evaluable population during the 24-week study described in Example 8.
Figure 29B:
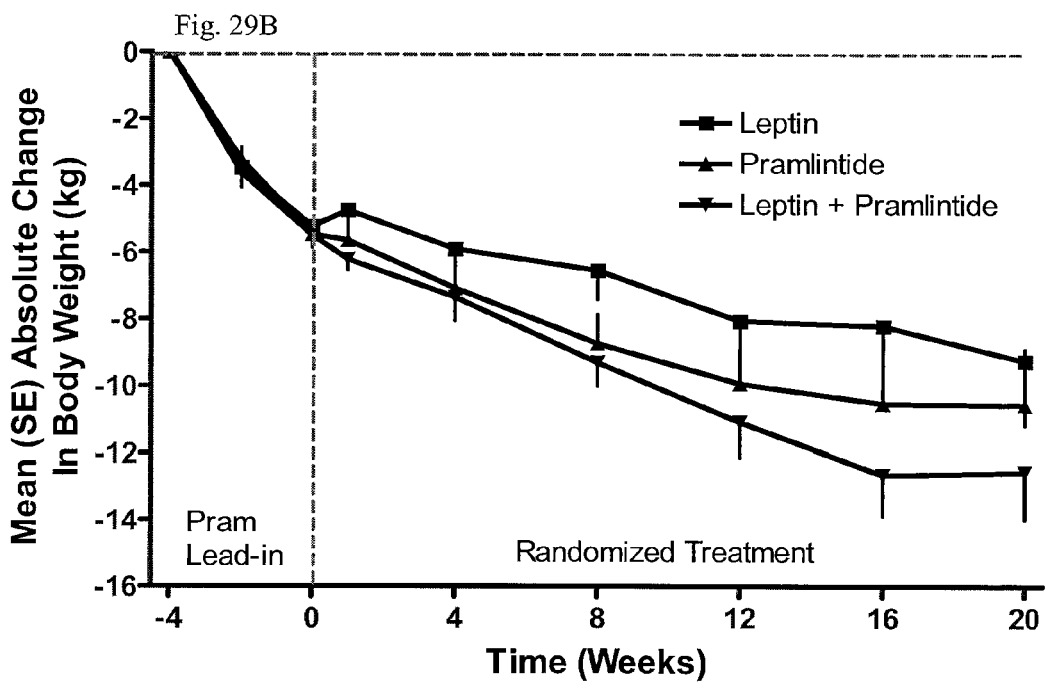
Figure 30A:
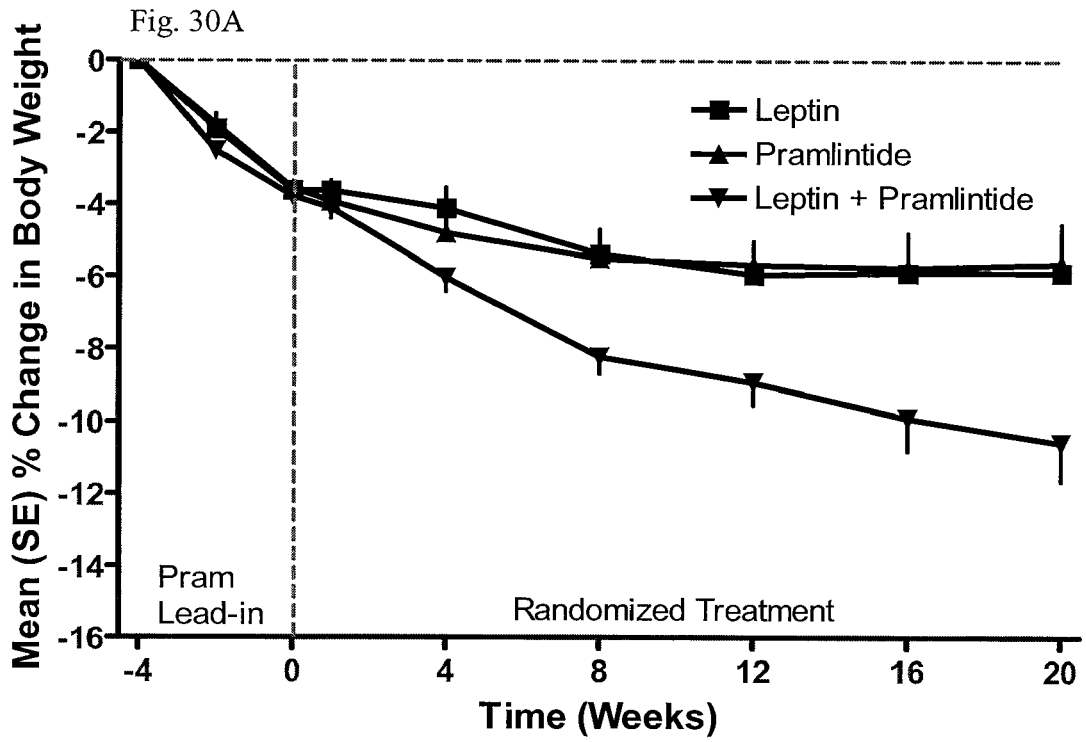
FIG. 30A and FIG. 30B demonstrate mean percentage change in body weight from enrollment by initial weight loss for the evaluable population during the 24-week study described in Example 8.
Figure 30B:
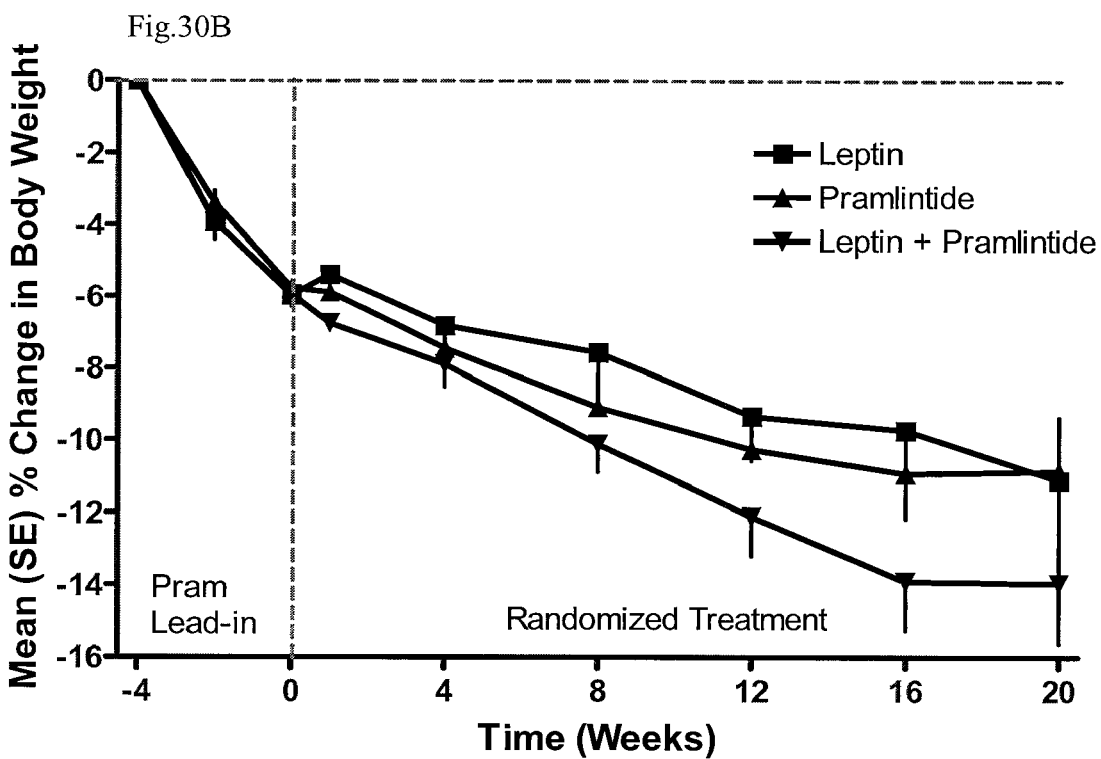

The results of the 24-week study with respect to mean change in body weight from enrollment is provided in FIG. 18A and FIG. 18B. The results of the 24-week study with respect to least squares mean change in body weight from enrollment is provided in FIG. 19A and FIG. 19B. The results of the 24-week study with respect to median change in body weight from enrollment is provided in FIG. 20A and FIG. 20B. The results of the 24-week study with respect to mean change in body weight from baseline is provided in FIG. 21A and FIG. 21B. The results of the 24-week study with respect to categorical change in body weight from enrollment to week is provided in FIG. 22. Another representation of the results of the 24-week study with respect to categorical change in body weight from enrollment to week 20 is provided in FIG. 23A, FIG. 23B and FIG. 23C, wherein weight loss stratification (e.g., ≧5%, 10%, 15%) is employed in separate panels of the figure. The results of rate of change in body weight for early rate (0-12 weeks) and late rate (12-20 weeks) is provided in FIG. 24. FIG. 24 demonstrates that while the weight reduction effects of metreleptin and pramlintide alone in the 24-week study approached a late rate of zero, the metreleptin+pramlintide combination still resulted in decreased weight toward the end of the 24-week study. The results of the 24-week study with respect to mean absolute change in body weight from enrollment by sex is provided in FIG. 25A and FIG. 25B. The results of the 24-week study with respect to mean percentage change in body weight from enrollment by sex is provided in FIG. 26A and FIG. 26B. The mean BMI for the female and male cohorts was 28.97 and 27.32, respectively. The results of the 24-week study with respect to mean absolute change in body weight from enrollment by BMI category is provided in FIG. 27A and FIG. 27B. The results of the 24-week study with respect to mean percentage change in body weight from enrollment by BMI category is provided in FIG. 28A and FIG. 28B. The results of the 24-week study with respect to mean absolute change in body weight from enrollment by initial weight loss is provided in FIG. 29A and FIG. 29B. The results of the 24-week study with respect to mean percentage change in body weight from enrollment by initial weight loss is provided in FIG. 30A and FIG. 30B. The results of the 24-week study with respect to mean percentage change in total excess body weight from enrollment is provided in FIG. 31A and FIG. 31B. The term "ITT" refers to subjects randomized who received study mediation. The term "LOCF" in the context of subjects randomized who received study medication refers to "last observation carried forward." The results of the 24-week study with respect to mean change in waist circumference from enrollment is provided in FIG. 32 for evaluable subjects.

While the foregoing description discloses the present invention, with examples provided for the purpose of illustration, it will be understood that the practice of the present invention encompasses all of the usual variations, adaptations, or modifications as being within the scope of the claimed invention. Therefore, descriptions and examples should not be construed as limiting the scope of the invention, which is delineated by the appended claims.

---

What is claimed is:

1. A method of treating obesity in an obese leptin resistant subject comprising peripherally administering therapeutically effective amounts of two different anti-obesity agents, wherein one anti-obesity agent is pramlintide and one anti-obesity agent is metreleptin; and wherein the subject reduces body weight, thereby treating the obesity.

2. A method of reducing body weight in an obese leptin resistant subject comprising peripherally administering therapeutically effective amounts of two different anti-obesity agents,
wherein one anti-obesity agent is pramlintide and one anti-obesity agent is metreleptin; and
wherein the anti-obesity agents are administered in amounts effective to reduce the body weight of the subject.

3. The method according to claim 1 to 2, wherein the effective amount of the pramlintide and the effective amount of said metreleptin comprises an amount such that a greater amount of weight loss is achieved when said pramlintide is administered in combination with said metreleptin to said subject than the amount of weight loss achieved when either agent is administered alone.

4. The method of claim 1 or 2, wherein said pramlintide and said metreleptin are administered at the same time.

5. The method of claim 1 or 2, wherein said pramlintide and said metreleptin are mixed together.

6. The method according to claim 1 or 2 wherein body fat mass of the subject is reduced.

7. The method according to claim 1 or 2, wherein the subject has at least one condition selected from the group consisting of overweight, diabetes, insulin-resistance syndrome, nonalcoholic steatohepatitis, a cardiovascular disease, polycystic ovary syndrome, and metabolic syndrome.

8. The method according to claim 7, wherein the condition is being overweight.

9. The method according to claim 7, wherein the condition is diabetes.

10. The method according to claim 7, wherein the condition is insulin-resistance syndrome.

11. The method according to claim 7, wherein the condition is nonalcoholic steatohepatitis.

12. The method according to claim 7, wherein the condition is a cardiovascular disease.

13. The method according to claim 7, wherein the condition is polycystic ovary syndrome.

14. The method according to claim 7, wherein the condition is metabolic syndrome.

15. The method according to claim 1 or 2, wherein the subject is human.

16. The method according to claim 15, wherein the subject is a human adult female.

17. The method according to claim 1 or 2 wherein said subject reduces body weight by at least 5%.

18. The method according to claim 1 or 2 wherein said subject reduces body weight by at least 10%.

19. A method of treating obesity in an obese leptin resistant subject consisting essentially of peripherally administering therapeutically effective amounts of two different anti-obesity agents, wherein one anti-obesity agent is pramlintide and one anti-obesity agent is metreleptin; and wherein the subject reduces body weight, thereby treating the obesity.

20. A method of reducing body weight in an obese leptin resistant subject consisting essentially of peripherally administering therapeutically effective amount of two different anti-obesity agents, wherein one anti-obesity agent is pramlintide and one anti-obesity agent is metreleptin; and wherein the anti-obesity agents are administered in amounts effective to reduce the body weight of the subject.

21. The method according to claim 19 or 20, wherein the effective amount of said pramlintide and the effective amount of said metreleptin comprises and amount of such that a greater amount of weight loss is achieved when said pramlintide is administered in combination with said metreleptin to said subject than the amount of weight loss achieved when either agent is administered alone.

22. The method of claim 19 or 20, wherein said pramlintide and said metreleptin are administered at the same time.

23. The method of claim 19 or 20, wherein said pramlintide and said metreleptin are mixed together.

24. A method of treating obesity in an obese leptin resistant subject consisting of peripherally administering: a pharmaceutically formulation comprising a therapeutically effective amount of pramlintide; and a pharmaceutical formulation comprising a therapeutically effective amount of metreleptin; wherein the body weight of the subject is reduced, thereby treating the obesity.

25. The method according to claim 24, wherein the effective amount of said pramlintide and the effective amount of said metreleptin comprises an amount such that a greater amount of weight loss is achieved when said pramlintide is administered in combination with said metreleptin to said subject than the amount of weight loss achieved when either agent is administered alone.

26. The method of claim 24 wherein the subject is human.

27. The method of claim 24 or 26, wherein said pramlintide and said metreleptin are mixed together.

28. The method of claim 24 or 26, wherein said pramlintide and said metreleptin are administered at the same time.

29. A method of treating obesity in an obese leptin-resistant subject, consisting of: peripherally administering a pharmaceutically formulation comprising a therapeutically effective amount of pramlintide and a therapeutically effective amount of metreleptin; wherein the body weight of the subject is reduced, thereby treating the obesity.

30. A method of reducing body weight in an obese leptin-resistant subject consisting of: peripherally administering a pharmaceutically formulation comprising a therapeutically effective amount of pramlintide and a therapeutically effective amount of metreleptin; wherein the therapeutically effective amounts are effective to reduce the body weight of the subject.

31. The method of claim 29 wherein the subject is human.

32. The method of claim 30 wherein the subject is human.

33. The method according to any one of claims 29, 30, 31, and 32, wherein the therapeutically effective amount of said pramlintide and the effective amount of said metreleptin comprises an amount such that a greater amount of weight loss is achieved when said pramlintide is administered in combination with said metreleptin to said subject than the amount of weight loss achieved when either agent is administered alone.

* * * * *

UNITED STATES PATENT AND TRADEMARK OFFICE
CERTIFICATE OF CORRECTION

PATENT NO.        : 8,394,765 B2
APPLICATION NO.   : 11/940317
DATED             : March 12, 2013
INVENTOR(S)       : Roth et al.

Page 1 of 2

It is certified that error appears in the above-identified patent and that said Letters Patent is hereby corrected as shown below:

On the Title Page item [56]
Page 2, Column 1 (Foreign Patent Documents)
--Line 9, Delete "WO WO96/40912 2/1996" and insert -- "WO WO96/40912 12/1996" --

On the Title Page item [56]
Page 2, Column 2 (Other Publications)
--Line 5, Delete "Poly0peptide" and insert -- Polypeptide" --
--Line 14, Delete "Methodxy" and insert -- "Methoxy" --
--Line 17, Delete "Yl" and insert -- "Y1" --

On the Title Page item [56]
Page 3 Column 1 (Other Publications)
--Line 6, Delete "at" after the word "Heymsfield" and insert -- "et" --
--Line 8, Delete "at" after the word "Kiec-Konowicz" and insert -- "et" --
--Line 10, Delete "at" after the word "Lazewska" and insert -- "et --
--Line 19, Delete "Versatle" and insert -- "Versatile" --
--Line 20, Delete "Ligan" and insert -- "Ligand" --
--Line 51, Delete "Topiramte" and insert -- "Topiramate" --

On the Title Page item [56]
Page 3, Column 2 (Other Publications)
--Line 5, Delete "1m" before 1995 and insert -- "1" --
--Line 36, Delete "Magnitured" and insert -- "Magnitude" --
--Line 38, Delete "diabites" and insert -- "diabetes" --

In the Claims
--Line 53, In Claim 3, delete "to" after the word "claim 1" and insert -- "or" --
--Line 54, In Claim 3, delete "of the" after the word "amount" and insert -- "of said" --

Signed and Sealed this
Twenty-fourth Day of June, 2014

Michelle K. Lee
*Deputy Director of the United States Patent and Trademark Office*

In the Claims
--Line 37, In Claim 7, delete "of" after the word "consisting" and insert -- "of being" --
--Line 40, In Claim 8, delete "the" after the word "wherein" and insert -- "said" --
--Line 42, In Claim 9, delete "the" after the word "wherein" and insert -- "said" --
--Line 44, In Claim 10, delete "the" after the word "wherein" and insert -- "said" --
--Line 46, In Claim 11, delete "the" after the word "wherein" and insert -- "said" --
--Line 48, In Claim 12, delete "the" after the word "wherein" and insert -- "said" --
--Line 50, In Claim 13, delete "the" after the word "wherein" and insert -- "said" --
--Line 52, In Claim 14, delete "the" after the word "wherein" and insert -- "said" --

In the Claims
--Line 3, In Claim 20, delete "amount" and insert -- "amounts" --
--Line 10, In Claim 21, delete "and amount of" and insert -- "an amount" --

UNITED STATES PATENT AND TRADEMARK OFFICE
CERTIFICATE OF CORRECTION

PATENT NO.           : 8,394,765 B2                                      Page 1 of 2
APPLICATION NO.      : 11/940317
DATED                : March 12, 2013
INVENTOR(S)          : Roth et al.

It is certified that error appears in the above-identified patent and that said Letters Patent is hereby corrected as shown below:

On the Title Page item [56]
Page 2, Column 1 (Foreign Patent Documents)
--Line 9, Delete "WO WO96/40912 2/1996" and insert -- "WO WO96/40912 12/1996" --

On the Title Page item [56]
Page 2, Column 2 (Other Publications)
--Line 5, Delete "Poly0peptide" and insert -- Polypeptide" --
--Line 14, Delete "Methodxy" and insert -- "Methoxy" --
--Line 17, Delete "Yl" and insert -- "Y1" --

On the Title Page item [56]
Page 3, Column 1 (Other Publications)
--Line 6, Delete "at" after the word "Heymsfield" and insert -- "et" --
--Line 8, Delete "at" after the word "Kiec-Konowicz" and insert -- "et" --
--Line 10, Delete "at" after the word "Lazewska" and insert -- "et --
--Line 19, Delete "Versatle" and insert -- "Versatile" --
--Line 20, Delete "Ligan" and insert -- "Ligand" --
--Line 51, Delete "Topiramte" and insert -- "Topiramate" --

On the Title Page item [56]
Page 3, Column 2 (Other Publications)
--Line 5, Delete "1m" before 1995 and insert -- "1" --
--Line 36, Delete "Magnitured" and insert -- "Magnitude" --
--Line 38, Delete "diabites" and insert -- "diabetes" --

This certificate supersedes the Certificate of Correction issued June 24, 2014.

Signed and Sealed this
Fifth Day of August, 2014

Michelle K. Lee
*Deputy Director of the United States Patent and Trademark Office*

CERTIFICATE OF CORRECTION (continued)
U.S. Pat. No. 8,394,765 B2

In the Claims
Column 181
--Line 53, In Claim 3, delete "to" after the word "claim 1" and insert -- "or" --
--Line 54, In Claim 3, delete "of the" after the word "amount" and insert -- "of said" --

In the Claims
Column 182
--Line 37, In Claim 7, delete "of" after the word "consisting" and insert -- "of being" --
--Line 40, In Claim 8, delete "the" after the word "wherein" and insert -- "said" --
--Line 42, In Claim 9, delete "the" after the word "wherein" and insert -- "said" --
--Line 44, In Claim 10, delete "the" after the word "wherein" and insert -- "said" --
--Line 46, In Claim 11, delete "the" after the word "wherein" and insert -- "said" --
--Line 48, In Claim 12, delete "the" after the word "wherein" and insert -- "said" --
--Line 50, In Claim 13, delete "the" after the word "wherein" and insert -- "said" --
--Line 52, In Claim 14, delete "the" after the word "wherein" and insert -- "said" --

In the Claims
Column 183
--Line 3, In Claim 20, delete "amount" and insert -- "amounts" --
--Line 10, In Claim 21, delete "and amount of" and insert -- "an amount" --

UNITED STATES PATENT AND TRADEMARK OFFICE
CERTIFICATE OF CORRECTION

| | | |
|---|---|---|
| PATENT NO. | : 8,394,765 B2 | Page 1 of 1 |
| APPLICATION NO. | : 11/940317 | |
| DATED | : March 12, 2013 | |
| INVENTOR(S) | : Roth et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 199 days.

Signed and Sealed this
Sixteenth Day of December, 2014

Michelle K. Lee
*Deputy Director of the United States Patent and Trademark Office*

SEQUENCE LISTING

```
<160> NUMBER OF SEQ ID NOS: 192

<210> SEQ ID NO 1
<211> LENGTH: 37
<212> TYPE: PRT
<213> ORGANISM: Homo sapiens

<400> SEQUENCE: 1

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 2
<211> LENGTH: 37
<212> TYPE: PRT
<213> ORGANISM: Rattus norvegicus

<400> SEQUENCE: 2

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 3
<211> LENGTH: 37
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Lys, Ala, Ser, or absent
<220> FEATURE:
<221> NAME/KEY: MISC_FEATURE
<222> LOCATION: (2)..(2)
<223> OTHER INFORMATION: variable amino acid
<220> FEATURE:
<221> NAME/KEY: MISC_FEATURE
<222> LOCATION: (2)..(7)
<223> OTHER INFORMATION: residues 2 and 7 are independently selected
      amino acid residues having side chains which are chemically
      bonded to each other to form an intramolecular linkage
<220> FEATURE:
<221> NAME/KEY: MISC_FEATURE
<222> LOCATION: (7)..(7)
<223> OTHER INFORMATION: variable amino acid
<220> FEATURE:
<221> NAME/KEY: MISC_FEATURE
```

```
<222> LOCATION: (13)..(13)
<223> OTHER INFORMATION: Ala, Ser, or Thr
<220> FEATURE:
<221> NAME/KEY: MISC_FEATURE
<222> LOCATION: (17)..(17)
<223> OTHER INFORMATION: Val, Leu or Ile
<220> FEATURE:
<221> NAME/KEY: MISC_FEATURE
<222> LOCATION: (18)..(18)
<223> OTHER INFORMATION: His or Arg
<220> FEATURE:
<221> NAME/KEY: MISC_FEATURE
<222> LOCATION: (19)..(19)
<223> OTHER INFORMATION: Ser or Thr
<220> FEATURE:
<221> NAME/KEY: MISC_FEATURE
<222> LOCATION: (20)..(20)
<223> OTHER INFORMATION: Ser, Thr, Gln, or Asn
<220> FEATURE:
<221> NAME/KEY: MISC_FEATURE
<222> LOCATION: (21)..(21)
<223> OTHER INFORMATION: Asn, Gln, or His
<220> FEATURE:
<221> NAME/KEY: MISC_FEATURE
<222> LOCATION: (23)..(23)
<223> OTHER INFORMATION: Phe, Leu, or Tyr
<220> FEATURE:
<221> NAME/KEY: MISC_FEATURE
<222> LOCATION: (25)..(25)
<223> OTHER INFORMATION: Ala or Pro
<220> FEATURE:
<221> NAME/KEY: MISC_FEATURE
<222> LOCATION: (26)..(26)
<223> OTHER INFORMATION: Ile, Val, Ala, or Leu
<220> FEATURE:
<221> NAME/KEY: MISC_FEATURE
<222> LOCATION: (28)..(28)
<223> OTHER INFORMATION: Ser, Pro, Leu, Ile, or Thr
<220> FEATURE:
<221> NAME/KEY: MISC_FEATURE
<222> LOCATION: (29)..(29)
<223> OTHER INFORMATION: Ser, Pro, or Thr
<220> FEATURE:
<221> NAME/KEY: MISC_FEATURE
<222> LOCATION: (31)..(31)
<223> OTHER INFORMATION: Asn, Asp, or Gln

<400> SEQUENCE: 3

Xaa Xaa Asn Thr Ala Thr Xaa Ala Thr Gln Arg Leu Xaa Asn Phe Leu
1               5                   10                  15

Xaa Xaa Xaa Xaa Xaa Asn Xaa Gly Xaa Xaa Leu Xaa Xaa Thr Xaa Val
            20                  25                  30

Gly Ser Asn Thr Tyr
        35

<210> SEQ ID NO 4
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 4

Cys Asn Thr Ala Thr Cys Ala Thr Gln Arg Leu Ala Asn Phe Leu Val
1               5                   10                  15

His Ser Ser Asn Asn Phe Gly Ala Ile Leu Ser Ser Thr Asn Val Gly
            20                  25                  30

Ser Asn Thr Tyr
        35

<210> SEQ ID NO 5
<211> LENGTH: 37
```

```
<212> TYPE: PRT
<213> ORGANISM: Artificial Sequence
<220> FEATURE:
<223> OTHER INFORMATION: Synthetic peptide construct

<400> SEQUENCE: 5

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Pro Ser Thr Asn Val
            20                  25                  30

Gly Ser Asn Thr Tyr
        35

<210> SEQ ID NO 6
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 6

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 7
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 7

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Ser Thr Asn Val
            20                  25                  30

Gly Ser Asn Thr Tyr
        35

<210> SEQ ID NO 8
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 8

Cys Asn Thr Ala Thr Cys Ala Thr Gln Arg Leu Ala Asn Phe Leu Val
1               5                   10                  15

His Arg Ser Asn Asn Phe Gly Pro Ile Leu Pro Ser Thr Asn Val Gly
            20                  25                  30

Ser Asn Thr Tyr
        35

<210> SEQ ID NO 9
<211> LENGTH: 37
<212> TYPE: PRT
<213> ORGANISM: Artificial Sequence
<220> FEATURE:
<223> OTHER INFORMATION: Synthetic peptide construct
```

-continued

<400> SEQUENCE: 9

Lys Cys Asn Thr Ala Thr Cys Ala Thr Gln Arg Leu Ala Asn Phe Leu
1               5                   10                  15

Val His Ser Ser Asn Asn Phe Gly Pro Val Leu Pro Pro Thr Asn Val
                20                  25                  30

Gly Ser Asn Thr Tyr
            35

<210> SEQ ID NO 10
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 10

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
                20                  25                  30

Gly Ser Asn Thr Tyr
            35

<210> SEQ ID NO 11
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 11

Lys Cys Asn Thr Ala Thr Cys Ala Thr Gln Arg Leu Ala Asn Phe Leu
1               5                   10                  15

Val Arg Ser Ser Asn Asn Phe Gly Pro Ile Leu Pro Pro Thr Asn Val
                20                  25                  30

Gly Ser Asn Thr Tyr
            35

<210> SEQ ID NO 12
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 12

Cys Asn Thr Ala Thr Cys Ala Thr Gln Arg Leu Ala Asn Phe Leu Val
1               5                   10                  15

Arg Ser Ser Asn Asn Phe Gly Pro Ile Leu Pro Pro Ser Asn Val Gly
                20                  25                  30

Ser Asn Thr Tyr
            35

<210> SEQ ID NO 13
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 13

Cys Asn Thr Ala Thr Cys Ala Thr Gln Arg Leu Ala Asn Phe Leu Val

```
                1               5                  10                  15
His Ser Ser Asn Asn Phe Gly Pro Ile Leu Pro Pro Ser Asn Val Gly
                        20                  25                  30

Ser Asn Thr Tyr
            35

<210> SEQ ID NO 14
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 14

Lys Cys Asn Thr Ala Thr Cys Ala Thr Gln Arg Leu Ala Asn Phe Leu
1               5                  10                  15

Val His Ser Ser Asn Asn Phe Gly Pro Val Leu Pro Pro Thr Asn Val
                20                  25                  30

Gly Ser Asn Thr Tyr
                35

<210> SEQ ID NO 15
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 15

Lys Cys Asn Thr Ala Thr Cys Ala Thr Gln Arg Leu Ala Asn Phe Leu
1               5                  10                  15

Val His Ser Ser Asn Asn Leu Gly Pro Val Leu Pro Pro Thr Asn Val
                20                  25                  30

Gly Ser Asn Thr Tyr
                35

<210> SEQ ID NO 16
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 16

Lys Cys Asn Thr Ala Thr Cys Ala Thr Gln Arg Leu Ala Asn Phe Leu
1               5                  10                  15

Val His Ser Ser Asn Asn Leu Gly Pro Val Leu Pro Ser Thr Asn Val
                20                  25                  30

Gly Ser Asn Thr Tyr
                35

<210> SEQ ID NO 17
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 17

Cys Asn Thr Ala Thr Cys Ala Thr Gln Arg Leu Ala Asn Phe Leu Val
1               5                  10                  15

His Ser Ser Asn Asn Leu Gly Pro Val Leu Pro Ser Thr Asn Val Gly
                20                  25                  30
```

```
Ser Asn Thr Tyr
        35

<210> SEQ ID NO 18
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 18

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Ser Thr Asn Val
            20                  25                  30

Gly Ser Asn Thr Tyr
        35

<210> SEQ ID NO 19
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 19

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Pro Thr Asn Val
            20                  25                  30

Gly Ser Asn Thr Tyr
        35

<210> SEQ ID NO 20
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 20

Lys Cys Asn Thr Ala Thr Cys Ala Thr Gln Arg Leu Ala Asn Phe Leu
1               5                   10                  15

Val Arg Ser Ser Asn Asn Leu Gly Pro Ile Leu Pro Ser Thr Asn Val
            20                  25                  30

Gly Ser Asn Thr Tyr
        35

<210> SEQ ID NO 21
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 21

Lys Cys Asn Thr Ala Thr Cys Ala Thr Gln Arg Leu Ala Asn Phe Leu
1               5                   10                  15

Ile His Ser Ser Asn Asn Leu Gly Pro Ile Leu Pro Pro Thr Asn Val
            20                  25                  30

Gly Ser Asn Thr Tyr
        35
```

<210> SEQ ID NO 22
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 22

Lys Cys Asn Thr Ala Thr Cys Ala Thr Gln Arg Leu Ala Asn Phe Leu
1               5                   10                  15

Ile His Ser Ser Asn Asn Phe Gly Pro Ile Leu Pro Pro Thr Asn Val
            20                  25                  30

Gly Ser Asn Thr Tyr
        35

<210> SEQ ID NO 23
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 23

Cys Asn Thr Ala Thr Cys Ala Thr Gln Arg Leu Ala Asn Phe Leu Ile
1               5                   10                  15

His Ser Ser Asn Asn Leu Gly Pro Ile Leu Pro Pro Thr Asn Val Gly
            20                  25                  30

Ser Asn Thr Tyr
        35

<210> SEQ ID NO 24
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 24

Lys Cys Asn Thr Ala Thr Cys Ala Thr Gln Arg Leu Ala Asn Phe Leu
1               5                   10                  15

Ile Arg Ser Ser Asn Asn Leu Gly Ala Ile Leu Ser Ser Thr Asn Val
            20                  25                  30

Gly Ser Asn Thr Tyr
        35

<210> SEQ ID NO 25
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 25

Lys Cys Asn Thr Ala Thr Cys Ala Thr Gln Arg Leu Ala Asn Phe Leu
1               5                   10                  15

Ile Arg Ser Ser Asn Asn Leu Gly Ala Val Leu Ser Pro Thr Asn Val
            20                  25                  30

Gly Ser Asn Thr Tyr
        35

<210> SEQ ID NO 26
<211> LENGTH: 37
<212> TYPE: PRT

```
<213> ORGANISM: Artificial Sequence
<220> FEATURE:
<223> OTHER INFORMATION: Synthetic peptide construct

<400> SEQUENCE: 26

Lys Cys Asn Thr Ala Thr Cys Ala Thr Gln Arg Leu Ala Asn Phe Leu
1               5                   10                  15

Ile Arg Ser Ser Asn Asn Leu Gly Pro Val Leu Pro Pro Thr Asn Val
            20                  25                  30

Gly Ser Asn Thr Tyr
        35

<210> SEQ ID NO 27
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 27

Lys Cys Asn Thr Ala Thr Cys Ala Thr Gln Arg Leu Thr Asn Phe Leu
1               5                   10                  15

Val His Ser Ser His Asn Leu Gly Ala Ala Leu Leu Pro Thr Asp Val
            20                  25                  30

Gly Ser Asn Thr Tyr
        35

<210> SEQ ID NO 28
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 28

Lys Cys Asn Thr Ala Thr Cys Ala Thr Gln Arg Leu Thr Asn Phe Leu
1               5                   10                  15

Val His Ser Ser His Asn Leu Gly Ala Ala Leu Ser Pro Thr Asp Val
            20                  25                  30

Gly Ser Asn Thr Tyr
        35

<210> SEQ ID NO 29
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 29

Cys Asn Thr Ala Thr Cys Ala Thr Gln Arg Leu Thr Asn Phe Leu Val
1               5                   10                  15

His Ser Ser His Asn Leu Gly Ala Ala Leu Pro Ser Thr Asp Val Gly
            20                  25                  30

Ser Asn Thr Tyr
        35

<210> SEQ ID NO 30
<211> LENGTH: 37
<212> TYPE: PRT
<213> ORGANISM: Artificial Sequence
<220> FEATURE:
<223> OTHER INFORMATION: Synthetic peptide construct
```

-continued

```
<400> SEQUENCE: 30

Lys Cys Asn Thr Ala Thr Cys Ala Thr Gln Arg Leu Thr Asn Phe Leu
1               5                   10                  15

Val Arg Ser Ser His Asn Leu Gly Ala Ala Leu Ser Pro Thr Asp Val
            20                  25                  30

Gly Ser Asn Thr Tyr
        35

<210> SEQ ID NO 31
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 31

Lys Cys Asn Thr Ala Thr Cys Ala Thr Gln Arg Leu Thr Asn Phe Leu
1               5                   10                  15

Val Arg Ser Ser His Asn Leu Gly Ala Ile Leu Pro Pro Thr Asp Val
            20                  25                  30

Gly Ser Asn Thr Tyr
        35

<210> SEQ ID NO 32
<211> LENGTH: 37
<212> TYPE: PRT
<213> ORGANISM: Artificial Sequence
<220> FEATURE:
<223> OTHER INFORMATION: Synthetic peptide construct

<400> SEQUENCE: 32

Lys Cys Asn Thr Ala Thr Cys Ala Thr Gln Arg Leu Thr Asn Phe Leu
1               5                   10                  15

Val Arg Ser Ser His Asn Leu Gly Pro Ala Leu Pro Pro Thr Asp Val
            20                  25                  30

Gly Ser Asn Thr Tyr
        35

<210> SEQ ID NO 33
<211> LENGTH: 32
<212> TYPE: PRT
<213> ORGANISM: Oncorhynchus sp.

<400> SEQUENCE: 33

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 34
<211> LENGTH: 32
<212> TYPE: PRT
<213> ORGANISM: Homo sapiens

<400> SEQUENCE: 34

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 35
<211> LENGTH: 6
```

```
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Any amino acid or absent
<220> FEATURE:
<221> NAME/KEY: MISC_FEATURE
<222> LOCATION: (2)..(2)
<223> OTHER INFORMATION: Any amino acid or absent
<220> FEATURE:
<221> NAME/KEY: MISC_FEATURE
<222> LOCATION: (3)..(3)
<223> OTHER INFORMATION: Any amino acid or absent
<220> FEATURE:
<221> NAME/KEY: MISC_FEATURE
<222> LOCATION: (4)..(4)
<223> OTHER INFORMATION: Any amino acid, see specification for detailed
      description of substitutions and embodiments
<220> FEATURE:
<221> NAME/KEY: MISC_FEATURE
<222> LOCATION: (5)..(5)
<223> OTHER INFORMATION: Any amino acid, see specification for detailed
      description of substitutions and embodiments
<220> FEATURE:
<221> NAME/KEY: MISC_FEATURE
<222> LOCATION: (6)..(6)
<223> OTHER INFORMATION: Any amino acid, see specification for detailed
      description of substitutions and embodiments

<400> SEQUENCE: 35

Xaa Xaa Xaa Xaa Xaa Xaa
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide construct

<400> SEQUENCE: 36

Cys Asn Thr Ala Thr Cys
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide construct

<400> SEQUENCE: 37

Cys Ala Thr Ala Thr Cys
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide construct

<400> SEQUENCE: 38

Cys Asp Thr Ala Thr Cys
1               5

<210> SEQ ID NO 39
<211> LENGTH: 6
<212> TYPE: PRT
```

```
<213> ORGANISM: Artificial Sequence
<220> FEATURE:
<223> OTHER INFORMATION: Synthetic peptide construct

<400> SEQUENCE: 39

Cys Gly Thr Ala Thr Cys
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide construct

<400> SEQUENCE: 40

Cys Asn Ala Ala Thr Cys
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide construct

<400> SEQUENCE: 41

Cys Asn Thr Ser Thr Cys
1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (5)..(5)
<223> OTHER INFORMATION: D-Thr

<400> SEQUENCE: 42

Cys Asn Thr Ala Xaa Cys
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (5)..(5)
<223> OTHER INFORMATION: Thr(OPO3H2)

<400> SEQUENCE: 43

Cys Asn Thr Ala Xaa Cys
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide construct

<400> SEQUENCE: 44

Cys Asn Thr Ala Ser Cys
```

```
<210> SEQ ID NO 45
<211> LENGTH: 6
<212> TYPE: PRT
<213> ORGANISM: Artificial Sequence
<220> FEATURE:
<223> OTHER INFORMATION: Synthetic peptide construct

<400> SEQUENCE: 45

Cys Asn Thr Ala Ala Cys
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide construct

<400> SEQUENCE: 46

Cys Asn Thr Ala Val Cys
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (5)..(5)

<400> SEQUENCE: 47

Cys Asn Thr Ala Xaa Cys
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (5)..(5)
<223> OTHER INFORMATION: Ahb

<400> SEQUENCE: 48

Cys Asn Thr Ala Xaa Cys
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (5)..(5)
<223> OTHER INFORMATION: Ahp

<400> SEQUENCE: 49

Cys Asn Thr Ala Xaa Cys
1               5

<210> SEQ ID NO 50
```

<211> LENGTH: 7
<212> TYPE: PRT
<213> ORGANISM: Artificial Sequence
<220> FEATURE:
<223> OTHER INFORMATION: Synthetic peptide construct

<400> SEQUENCE: 50

Cys Ser Asn Leu Ser Thr Cys
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide construct

<400> SEQUENCE: 51

Cys Gly Asn Leu Ser Thr Cys
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide construct

<400> SEQUENCE: 52

Cys Ala Asn Leu Ser Thr Cys
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide construct

<400> SEQUENCE: 53

Cys Ser Ala Leu Ser Thr Cys
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide construct

<400> SEQUENCE: 54

Cys Ser Asn Ala Ser Thr Cys
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic peptide construct

<400> SEQUENCE: 55

Cys Ser Asn Leu Ala Thr Cys
1               5

<210> SEQ ID NO 56
<211> LENGTH: 7
<212> TYPE: PRT

```
<213> ORGANISM: Artificial Sequence
<220> FEATURE:
<223> OTHER INFORMATION: Synthetic peptide construct

<400> SEQUENCE: 56

Cys Ser Asn Leu Ser Ala Cys
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide construct

<400> SEQUENCE: 57

Lys Cys Asn Thr Ala Thr Cys
1               5

<210> SEQ ID NO 58
<211> LENGTH: 15
<212> TYPE: PRT
<213> ORGANISM: Artificial Sequence
<220> FEATURE:
<223> OTHER INFORMATION: Synthetic peptide construct

<400> SEQUENCE: 58

Leu Leu Gln Gln Leu Gln Lys Leu Leu Gln Lys Leu Lys Gln Tyr
1               5                   10                  15

<210> SEQ ID NO 59
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Variable amino acid or absent
<220> FEATURE:
<221> NAME/KEY: MISC_FEATURE
<222> LOCATION: (2)..(2)
<223> OTHER INFORMATION: Variable amino acid or absent
<220> FEATURE:
<221> NAME/KEY: MISC_FEATURE
<222> LOCATION: (3)..(3)
<223> OTHER INFORMATION: Variable amino acid or absent
<220> FEATURE:
<221> NAME/KEY: MISC_FEATURE
<222> LOCATION: (4)..(4)
<223> OTHER INFORMATION: Variable amino acid or absent
<220> FEATURE:
<221> NAME/KEY: MISC_FEATURE
<222> LOCATION: (7)..(7)
<223> OTHER INFORMATION: Gly or Aib
<220> FEATURE:
<221> NAME/KEY: MISC_FEATURE
<222> LOCATION: (8)..(8)
<223> OTHER INFORMATION: Lys, Arg, Orn, homo-Arg, Cit, homo-Lys, or
      Lys(for)
<220> FEATURE:
<221> NAME/KEY: MISC_FEATURE
<222> LOCATION: (12)..(12)
<223> OTHER INFORMATION: Glu or Phe
<220> FEATURE:
<221> NAME/KEY: MISC_FEATURE
<222> LOCATION: (14)..(14)
<223> OTHER INFORMATION: His or Aib
<220> FEATURE:
<221> NAME/KEY: MISC_FEATURE
<222> LOCATION: (15)..(15)
<223> OTHER INFORMATION: Lys, Arg, Orn, homo-Arg, Cit, homo-Lys,
      Lys(for), or Lys(PEG 5000)
```

```
<220> FEATURE:
<221> NAME/KEY: MISC_FEATURE
<222> LOCATION: (19)..(19)
<223> OTHER INFORMATION: Tyr or Leu
<220> FEATURE:
<221> NAME/KEY: MISC_FEATURE
<222> LOCATION: (21)..(21)
<223> OTHER INFORMATION: Arg or Pro
<220> FEATURE:
<221> NAME/KEY: MISC_FEATURE
<222> LOCATION: (24)..(24)
<223> OTHER INFORMATION: Variable amino acid or absent
<220> FEATURE:
<221> NAME/KEY: MISC_FEATURE
<222> LOCATION: (25)..(25)
<223> OTHER INFORMATION: Variable amino acid or absent
<220> FEATURE:
<221> NAME/KEY: MISC_FEATURE
<222> LOCATION: (26)..(36)
<223> OTHER INFORMATION: Variable amino acid or absent
<220> FEATURE:
<221> NAME/KEY: MISC_FEATURE
<222> LOCATION: (27)..(27)
<223> OTHER INFORMATION: Variable amino acid or absent

<400> SEQUENCE: 59

Xaa Xaa Xaa Xaa Val Leu Xaa Xaa Leu Ser Gln Xaa Leu Xaa Xaa Leu
1               5                   10                  15

Gln Thr Xaa Pro Xaa Thr Asn Thr Xaa Xaa Xaa Xaa
            20                  25

<210> SEQ ID NO 60
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Variable amino acid or absent
<220> FEATURE:
<221> NAME/KEY: MISC_FEATURE
<222> LOCATION: (2)..(2)
<223> OTHER INFORMATION: Variable amino acid or absent
<220> FEATURE:
<221> NAME/KEY: MISC_FEATURE
<222> LOCATION: (3)..(3)
<223> OTHER INFORMATION: Variable amino acid or absent
<220> FEATURE:
<221> NAME/KEY: MISC_FEATURE
<222> LOCATION: (4)..(4)
<223> OTHER INFORMATION: Variable amino acid or absent
<220> FEATURE:
<221> NAME/KEY: MISC_FEATURE
<222> LOCATION: (5)..(5)
<223> OTHER INFORMATION: Ala or Val
<220> FEATURE:
<221> NAME/KEY: MISC_FEATURE
<222> LOCATION: (6)..(6)
<223> OTHER INFORMATION: Thr, Met or Leu
<220> FEATURE:
<221> NAME/KEY: MISC_FEATURE
<222> LOCATION: (7)..(7)
<223> OTHER INFORMATION: Gln, Gly, or His
<220> FEATURE:
<221> NAME/KEY: MISC_FEATURE
<222> LOCATION: (8)..(8)
<223> OTHER INFORMATION: Leu or Thr
<220> FEATURE:
<221> NAME/KEY: MISC_FEATURE
<222> LOCATION: (9)..(9)
<223> OTHER INFORMATION: Leu or Thr
<220> FEATURE:
<221> NAME/KEY: MISC_FEATURE
<222> LOCATION: (10)..(10)
<223> OTHER INFORMATION: Ala, Thr, Asn, Phe, Tyr, Ser, or Thr
```

```
<220> FEATURE:
<221> NAME/KEY: MISC_FEATURE
<222> LOCATION: (11)..(11)
<223> OTHER INFORMATION: Asn, Arg, Ala, Asp, Glu, Gln, Thr, or Gly
<220> FEATURE:
<221> NAME/KEY: MISC_FEATURE
<222> LOCATION: (12)..(12)
<223> OTHER INFORMATION: Phe, Leu, Ser, Glu, Ala, Asp, or Tyr
<220> FEATURE:
<221> NAME/KEY: MISC_FEATURE
<222> LOCATION: (13)..(13)
<223> OTHER INFORMATION: Leu or Asp
<220> FEATURE:
<221> NAME/KEY: MISC_FEATURE
<222> LOCATION: (14)..(14)
<223> OTHER INFORMATION: Val, His, Ser, Phe, or Aib
<220> FEATURE:
<221> NAME/KEY: MISC_FEATURE
<222> LOCATION: (15)..(15)
<223> OTHER INFORMATION: His, Arg, Lys, Orn, homo-Arg, Cit, homo-Lys,
      Lys(for), or Lys(PEG5000)
<220> FEATURE:
<221> NAME/KEY: MISC_FEATURE
<222> LOCATION: (16)..(16)
<223> OTHER INFORMATION: Leu, Ser, or Phe
<220> FEATURE:
<221> NAME/KEY: MISC_FEATURE
<222> LOCATION: (17)..(17)
<223> OTHER INFORMATION: Gln or His
<220> FEATURE:
<221> NAME/KEY: MISC_FEATURE
<222> LOCATION: (18)..(18)
<223> OTHER INFORMATION: Thr or Asn
<220> FEATURE:
<221> NAME/KEY: MISC_FEATURE
<222> LOCATION: (19)..(19)
<223> OTHER INFORMATION: Tyr, Val, Phe, Leu or Met
<220> FEATURE:
<221> NAME/KEY: MISC_FEATURE
<222> LOCATION: (21)..(21)
<223> OTHER INFORMATION: Arg or Pro
<220> FEATURE:
<221> NAME/KEY: MISC_FEATURE
<222> LOCATION: (25)..(25)
<223> OTHER INFORMATION: Variable amino acid or absent
<220> FEATURE:
<221> NAME/KEY: MISC_FEATURE
<222> LOCATION: (26)..(26)
<223> OTHER INFORMATION: Variable amino acid or absent
<220> FEATURE:
<221> NAME/KEY: MISC_FEATURE
<222> LOCATION: (27)..(27)
<223> OTHER INFORMATION: Variable amino acid or absent
<220> FEATURE:
<221> NAME/KEY: MISC_FEATURE
<222> LOCATION: (28)..(28)
<223> OTHER INFORMATION: Variable amino acid or absent

<400> SEQUENCE: 60

Xaa Xaa Xaa Xaa Xaa Xaa Xaa Arg Xaa Xaa Xaa Xaa Xaa Xaa Xaa Xaa
1               5                   10                  15

Xaa Xaa Xaa Pro Xaa Thr Asn Thr Xaa Xaa Xaa Xaa
            20                  25

<210> SEQ ID NO 61
<211> LENGTH: 11
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Lys, Tyr, or absent
<220> FEATURE:
<221> NAME/KEY: MISC_FEATURE
<222> LOCATION: (2)..(2)
```

```
<223> OTHER INFORMATION: Ser, Pro, or absent
<220> FEATURE:
<221> NAME/KEY: MISC_FEATURE
<222> LOCATION: (3)..(3)
<223> OTHER INFORMATION: Ser, Pro, Arg, or absent
<220> FEATURE:
<221> NAME/KEY: MISC_FEATURE
<222> LOCATION: (4)..(4)
<223> OTHER INFORMATION: Thr or absent
<220> FEATURE:
<221> NAME/KEY: MISC_FEATURE
<222> LOCATION: (5)..(5)
<223> OTHER INFORMATION: Asn or absent
<220> FEATURE:
<221> NAME/KEY: MISC_FEATURE
<222> LOCATION: (6)..(6)
<223> OTHER INFORMATION: Val, Thr, or absent
<220> FEATURE:
<221> NAME/KEY: MISC_FEATURE
<222> LOCATION: (8)..(8)
<223> OTHER INFORMATION: Ser or Glu
<220> FEATURE:
<221> NAME/KEY: MISC_FEATURE
<222> LOCATION: (9)..(9)
<223> OTHER INFORMATION: Asn, Lys, or Gly
<220> FEATURE:
<221> NAME/KEY: MISC_FEATURE
<222> LOCATION: (10)..(10)
<223> OTHER INFORMATION: Thr, Phe, or Ala
<220> FEATURE:
<221> NAME/KEY: MISC_FEATURE
<222> LOCATION: (11)..(11)
<223> OTHER INFORMATION: Tyr, Phe, Pro, or absent

<400> SEQUENCE: 61

Xaa Xaa Xaa Xaa Xaa Xaa Gly Xaa Xaa Xaa Xaa
1               5                   10

<210> SEQ ID NO 62
<211> LENGTH: 8
<212> TYPE: PRT
<213> ORGANISM: Artificial Sequence
<220> FEATURE:
<223> OTHER INFORMATION: Synthetic peptide construct

<400> SEQUENCE: 62

Lys Ser Asn Phe Val Pro Thr Asn
1               5

<210> SEQ ID NO 63
<211> LENGTH: 8
<212> TYPE: PRT
<213> ORGANISM: Artificial Sequence
<220> FEATURE:
<223> OTHER INFORMATION: Synthetic peptide construct

<400> SEQUENCE: 63

Ser Asn Phe Val Pro Thr Asn Val
1               5

<210> SEQ ID NO 64
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Ala, Cys, hCys, Asp, Glu, Phe, Ile, Leu, Lys,
      homo-Lys, Arg, homo-Arg, Ser, Hse, Thr, Gly, Gln, Asn, Met, Tyr,
      Trp, Pro, Hyp, His, Val, or absent
<220> FEATURE:
<221> NAME/KEY: MISC_FEATURE
```

-continued

```
<222> LOCATION: (2)..(2)
<223> OTHER INFORMATION: variable amino acid
<220> FEATURE:
<221> NAME/KEY: MISC_FEATURE
<222> LOCATION: (2)..(7)
<223> OTHER INFORMATION: residues 2 and 7 are independently selected
      residues having side chains which are chemically bonded to each
      other to form an intramolecular linkage
<220> FEATURE:
<221> NAME/KEY: MISC_FEATURE
<222> LOCATION: (3)..(3)
<223> OTHER INFORMATION: Ala, Asp, Glu, Asn, Gln, Gly, Val, Arg, Lys,
      homo-Lys, homo-Arg, His, Ile, Leu, Met, or absent
<220> FEATURE:
<221> NAME/KEY: MISC_FEATURE
<222> LOCATION: (4)..(4)
<223> OTHER INFORMATION: Ala, Ile, Leu, Ser, Hse, Thr, Val, Met, or
      absent
<220> FEATURE:
<221> NAME/KEY: MISC_FEATURE
<222> LOCATION: (5)..(5)
<223> OTHER INFORMATION: Ala, Ser, Thr, Hse, Tyr, Val, Ile, Leu or Met
<220> FEATURE:
<221> NAME/KEY: MISC_FEATURE
<222> LOCATION: (6)..(6)
<223> OTHER INFORMATION: Thr, Ala, Ser, Hse, Tyr, Val, Ile, Leu or Met
<220> FEATURE:
<221> NAME/KEY: MISC_FEATURE
<222> LOCATION: (7)..(7)
<223> OTHER INFORMATION: variable amino acid
<220> FEATURE:
<221> NAME/KEY: MISC_FEATURE
<222> LOCATION: (8)..(8)
<223> OTHER INFORMATION: Ala, Val, Ile, Leu, Phe or Met
<220> FEATURE:
<221> NAME/KEY: MISC_FEATURE
<222> LOCATION: (9)..(9)
<223> OTHER INFORMATION: Leu, Thr, Ser, Hse, Val, Ile or Met
<220> FEATURE:
<221> NAME/KEY: MISC_FEATURE
<222> LOCATION: (10)..(10)
<223> OTHER INFORMATION: Gly, His, Gln, Lys, Arg, Asn, homo-Lys, or
      homo-Arg
<220> FEATURE:
<221> NAME/KEY: MISC_FEATURE
<222> LOCATION: (11)..(11)
<223> OTHER INFORMATION: Lys, Arg, Gln, Asn, homo-Lys, homo-Arg, or His
<220> FEATURE:
<221> NAME/KEY: MISC_FEATURE
<222> LOCATION: (12)..(12)
<223> OTHER INFORMATION: Leu, Ile, Val, Phe, Met, Trp, or Tyr
<220> FEATURE:
<221> NAME/KEY: MISC_FEATURE
<222> LOCATION: (13)..(13)
<223> OTHER INFORMATION: Ala, Phe, Tyr, Asn, Gln, Ser, Hse, or Thr
<220> FEATURE:
<221> NAME/KEY: MISC_FEATURE
<222> LOCATION: (14)..(14)
<223> OTHER INFORMATION: Ala, Asp, Glu, Gly, Asn, Lys, Gln, Arg, His,
      homo-Arg, or homo-Lys
<220> FEATURE:
<221> NAME/KEY: MISC_FEATURE
<222> LOCATION: (15)..(15)
<223> OTHER INFORMATION: Ala, Asp, Glu, Phe, Leu, Ser, Tyr, Ile, Val,
      or Met
<220> FEATURE:
<221> NAME/KEY: MISC_FEATURE
<222> LOCATION: (16)..(16)
<223> OTHER INFORMATION: Leu, Phe, Met, Val, Tyr, or Ile
<220> FEATURE:
<221> NAME/KEY: MISC_FEATURE
<222> LOCATION: (17)..(17)
<223> OTHER INFORMATION: His, Gln, Asn, Ser, Hse, Thr, or Val
<220> FEATURE:
<221> NAME/KEY: MISC_FEATURE
<222> LOCATION: (18)..(18)
<223> OTHER INFORMATION: Lys, homo-Lys, Arg, homo-Arg, His, Cit, or Orn
<220> FEATURE:
<221> NAME/KEY: MISC_FEATURE
<222> LOCATION: (19)..(19)
```

```
<223> OTHER INFORMATION: Phe, Leu, Ser, Hse, Val, Ile, Thr, or absent
<220> FEATURE:
<221> NAME/KEY: MISC_FEATURE
<222> LOCATION: (20)..(20)
<223> OTHER INFORMATION: His, Arg, Lys, homo-Arg, homo-Lys, Asn, Gln,
      or absent
<220> FEATURE:
<221> NAME/KEY: MISC_FEATURE
<222> LOCATION: (21)..(21)
<223> OTHER INFORMATION: Thr, Ser, Hse, Val, Ile, Leu, Gln, Asn, or
      absent
<220> FEATURE:
<221> NAME/KEY: MISC_FEATURE
<222> LOCATION: (22)..(22)
<223> OTHER INFORMATION: Phe, Leu, Met, Val, Tyr, or Ile
<220> FEATURE:
<221> NAME/KEY: MISC_FEATURE
<222> LOCATION: (23)..(23)
<223> OTHER INFORMATION: Pro or Hyp
<220> FEATURE:
<221> NAME/KEY: MISC_FEATURE
<222> LOCATION: (24)..(24)
<223> OTHER INFORMATION: Pro, Hyp, Arg, Lys, homo-Arg, homo-Lys, or His
<220> FEATURE:
<221> NAME/KEY: MISC_FEATURE
<222> LOCATION: (25)..(25)
<223> OTHER INFORMATION: Thr, Ser, Hse, Val, Ile, Leu, Phe, or Val
<220> FEATURE:
<221> NAME/KEY: MISC_FEATURE
<222> LOCATION: (26)..(26)
<223> OTHER INFORMATION: Asn, Gln, Asp, or Glu
<220> FEATURE:
<221> NAME/KEY: MISC_FEATURE
<222> LOCATION: (27)..(27)
<223> OTHER INFORMATION: Thr, Val, Ser, Phe, Ile, or Leu
<220> FEATURE:
<221> NAME/KEY: MISC_FEATURE
<222> LOCATION: (28)..(28)
<223> OTHER INFORMATION: Gly or Ala
<220> FEATURE:
<221> NAME/KEY: MISC_FEATURE
<222> LOCATION: (29)..(29)
<223> OTHER INFORMATION: Ser, Hse, Thr, Val, Ile, Leu, or Tyr
<220> FEATURE:
<221> NAME/KEY: MISC_FEATURE
<222> LOCATION: (30)..(30)
<223> OTHER INFORMATION: Glu, Gly, Lys, Asn, Asp, Arg, homo-Arg,
      homo-Lys, His or Gln
<220> FEATURE:
<221> NAME/KEY: MISC_FEATURE
<222> LOCATION: (31)..(31)
<223> OTHER INFORMATION: Ala, Thr, Ser, Hse, Val, Ile, Leu, Phe, or Tyr
<220> FEATURE:
<221> NAME/KEY: MISC_FEATURE
<222> LOCATION: (32)..(32)
<223> OTHER INFORMATION: Phe, Pro, Tyr, Hse, Ser, Thr, or Hyp

<400> SEQUENCE: 64

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

<210> SEQ ID NO 65
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Ala, Cys, Asp, Phe, Ile, Lys, Ser, Thr, or
      absent
<220> FEATURE:
<221> NAME/KEY: MISC_FEATURE
<222> LOCATION: (2)..(2)
```

```
<223> OTHER INFORMATION: Cys, Asp, Ser, or absent
<220> FEATURE:
<221> NAME/KEY: MISC_FEATURE
<222> LOCATION: (3)..(3)
<223> OTHER INFORMATION: Ala, Asp, Asn, or absent
<220> FEATURE:
<221> NAME/KEY: MISC_FEATURE
<222> LOCATION: (4)..(4)
<223> OTHER INFORMATION: Ala, Leu, Thr, or absent
<220> FEATURE:
<221> NAME/KEY: MISC_FEATURE
<222> LOCATION: (5)..(5)
<223> OTHER INFORMATION: Ala or Ser
<220> FEATURE:
<221> NAME/KEY: MISC_FEATURE
<222> LOCATION: (6)..(6)
<223> OTHER INFORMATION: Thr, Ala, Ser, or Val
<220> FEATURE:
<221> NAME/KEY: MISC_FEATURE
<222> LOCATION: (7)..(7)
<223> OTHER INFORMATION: Cys, Lys, or Ala
<220> FEATURE:
<221> NAME/KEY: MISC_FEATURE
<222> LOCATION: (8)..(8)
<223> OTHER INFORMATION: Ala, Val, Leu, or Met
<220> FEATURE:
<221> NAME/KEY: MISC_FEATURE
<222> LOCATION: (9)..(9)
<223> OTHER INFORMATION: Leu or Thr
<220> FEATURE:
<221> NAME/KEY: MISC_FEATURE
<222> LOCATION: (10)..(10)
<223> OTHER INFORMATION: Gly, His, or Gln
<220> FEATURE:
<221> NAME/KEY: MISC_FEATURE
<222> LOCATION: (11)..(11)
<223> OTHER INFORMATION: Lys, Arg, Gln, or homo-Arg
<220> FEATURE:
<221> NAME/KEY: MISC_FEATURE
<222> LOCATION: (12)..(12)
<223> OTHER INFORMATION: Leu, Trp, or Tyr
<220> FEATURE:
<221> NAME/KEY: MISC_FEATURE
<222> LOCATION: (13)..(13)
<223> OTHER INFORMATION: Ala, Phe, Asn, Gln, Ser, or Thr
<220> FEATURE:
<221> NAME/KEY: MISC_FEATURE
<222> LOCATION: (14)..(14)
<223> OTHER INFORMATION: Ala, Asp, Glu, Gly, Asn, Lys, Gln, or Arg
<220> FEATURE:
<221> NAME/KEY: MISC_FEATURE
<222> LOCATION: (15)..(15)
<223> OTHER INFORMATION: Ala, Asp, Glu, Phe, Leu, Ser, or Tyr
<220> FEATURE:
<221> NAME/KEY: MISC_FEATURE
<222> LOCATION: (16)..(16)
<223> OTHER INFORMATION: Leu or Phe
<220> FEATURE:
<221> NAME/KEY: MISC_FEATURE
<222> LOCATION: (17)..(17)
<223> OTHER INFORMATION: His, Gln, Ser, or Val
<220> FEATURE:
<221> NAME/KEY: MISC_FEATURE
<222> LOCATION: (18)..(18)
<223> OTHER INFORMATION: Lys, Arg, homo-Arg, Cit, or Orn
<220> FEATURE:
<221> NAME/KEY: MISC_FEATURE
<222> LOCATION: (19)..(19)
<223> OTHER INFORMATION: Phe, Leu, Ser, or absent
<220> FEATURE:
<221> NAME/KEY: MISC_FEATURE
<222> LOCATION: (20)..(20)
<223> OTHER INFORMATION: His, Gln, or absent
<220> FEATURE:
<221> NAME/KEY: MISC_FEATURE
<222> LOCATION: (21)..(21)
<223> OTHER INFORMATION: Thr, Asn, or absent
<220> FEATURE:
<221> NAME/KEY: MISC_FEATURE
<222> LOCATION: (22)..(22)
```

```
<223> OTHER INFORMATION: Phe, Leu, Met, Val, or Tyr
<220> FEATURE:
<221> NAME/KEY: MISC_FEATURE
<222> LOCATION: (24)..(24)
<223> OTHER INFORMATION: Pro or Arg
<220> FEATURE:
<221> NAME/KEY: MISC_FEATURE
<222> LOCATION: (27)..(27)
<223> OTHER INFORMATION: Thr or Val
<220> FEATURE:
<221> NAME/KEY: MISC_FEATURE
<222> LOCATION: (30)..(30)
<223> OTHER INFORMATION: Glu, Gly, Lys, or Asn
<220> FEATURE:
<221> NAME/KEY: MISC_FEATURE
<222> LOCATION: (31)..(31)
<223> OTHER INFORMATION: Ala or Thr
<220> FEATURE:
<221> NAME/KEY: MISC_FEATURE
<222> LOCATION: (32)..(32)
<223> OTHER INFORMATION: Phe, Pro, or Tyr

<400> SEQUENCE: 65

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 66
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Ala, Cys, Phe, Ile, Lys, Ser, or absent
<220> FEATURE:
<221> NAME/KEY: MISC_FEATURE
<222> LOCATION: (2)..(2)
<223> OTHER INFORMATION: Cys, Asp, or Ser
<220> FEATURE:
<221> NAME/KEY: MISC_FEATURE
<222> LOCATION: (3)..(3)
<223> OTHER INFORMATION: Ala, Asp or Asn
<220> FEATURE:
<221> NAME/KEY: MISC_FEATURE
<222> LOCATION: (4)..(4)
<223> OTHER INFORMATION: Ala, Leu or Thr
<220> FEATURE:
<221> NAME/KEY: MISC_FEATURE
<222> LOCATION: (5)..(5)
<223> OTHER INFORMATION: Ala or Ser
<220> FEATURE:
<221> NAME/KEY: MISC_FEATURE
<222> LOCATION: (7)..(7)
<223> OTHER INFORMATION: Cys or Lys
<220> FEATURE:
<221> NAME/KEY: MISC_FEATURE
<222> LOCATION: (8)..(8)
<223> OTHER INFORMATION: Ala or Val
<220> FEATURE:
<221> NAME/KEY: MISC_FEATURE
<222> LOCATION: (9)..(9)
<223> OTHER INFORMATION: Leu or Thr
<220> FEATURE:
<221> NAME/KEY: MISC_FEATURE
<222> LOCATION: (10)..(10)
<223> OTHER INFORMATION: Gly, His, or Gln
<220> FEATURE:
<221> NAME/KEY: MISC_FEATURE
<222> LOCATION: (11)..(11)
<223> OTHER INFORMATION: Lys, Arg, or homo-Arg
<220> FEATURE:
<221> NAME/KEY: MISC_FEATURE
<222> LOCATION: (13)..(13)
```

```
<223> OTHER INFORMATION: Ala, Phe, Asn, Ser, or Thr
<220> FEATURE:
<221> NAME/KEY: MISC_FEATURE
<222> LOCATION: (14)..(14)
<223> OTHER INFORMATION: Ala, Asp, Glu, Gly, Asn, Gln, or Arg
<220> FEATURE:
<221> NAME/KEY: MISC_FEATURE
<222> LOCATION: (15)..(15)
<223> OTHER INFORMATION: Ala, Glu, Phe, Leu, Ser, or Tyr
<220> FEATURE:
<221> NAME/KEY: MISC_FEATURE
<222> LOCATION: (17)..(17)
<223> OTHER INFORMATION: His, Ser, or Val
<220> FEATURE:
<221> NAME/KEY: MISC_FEATURE
<222> LOCATION: (18)..(18)
<223> OTHER INFORMATION: Lys, Arg, homo-Arg, Cit, or Orn
<220> FEATURE:
<221> NAME/KEY: MISC_FEATURE
<222> LOCATION: (19)..(19)
<223> OTHER INFORMATION: Phe, Leu, or Ser
<220> FEATURE:
<221> NAME/KEY: MISC_FEATURE
<222> LOCATION: (20)..(20)
<223> OTHER INFORMATION: His or Gln
<220> FEATURE:
<221> NAME/KEY: MISC_FEATURE
<222> LOCATION: (21)..(21)
<223> OTHER INFORMATION: Thr or Asn
<220> FEATURE:
<221> NAME/KEY: MISC_FEATURE
<222> LOCATION: (22)..(22)
<223> OTHER INFORMATION: Phe, Leu, Met, Val, or Tyr
<220> FEATURE:
<221> NAME/KEY: MISC_FEATURE
<222> LOCATION: (24)..(24)
<223> OTHER INFORMATION: Pro or Arg
<220> FEATURE:
<221> NAME/KEY: MISC_FEATURE
<222> LOCATION: (27)..(27)
<223> OTHER INFORMATION: Thr or Val
<220> FEATURE:
<221> NAME/KEY: MISC_FEATURE
<222> LOCATION: (30)..(30)
<223> OTHER INFORMATION: Glu, Gly, Lys, or Asn
<220> FEATURE:
<221> NAME/KEY: MISC_FEATURE
<222> LOCATION: (31)..(31)
<223> OTHER INFORMATION: Ala or Thr
<220> FEATURE:
<221> NAME/KEY: MISC_FEATURE
<222> LOCATION: (32)..(32)
<223> OTHER INFORMATION: Phe, Pro, or Tyr

<400> SEQUENCE: 66

Xaa Xaa Xaa Xaa Xaa Thr Xaa Xaa Xaa Xaa Xaa Leu Xaa Xaa Xaa Leu
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 67
<211> LENGTH: 4
<212> TYPE: PRT
<213> ORGANISM: Artificial Sequence
<220> FEATURE:
<223> OTHER INFORMATION: Synthetic peptide construct

<400> SEQUENCE: 67

Leu Gln Thr Tyr
1

<210> SEQ ID NO 68
<211> LENGTH: 32
<212> TYPE: PRT
<213> ORGANISM: Artificial Sequence
```

-continued

```
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Ala, Cys, Asp, Phe, Lys, Thr, or absent
<220> FEATURE:
<221> NAME/KEY: MISC_FEATURE
<222> LOCATION: (2)..(2)
<223> OTHER INFORMATION: Ala, Cys, Asp, Ser, or absent
<220> FEATURE:
<221> NAME/KEY: MISC_FEATURE
<222> LOCATION: (3)..(3)
<223> OTHER INFORMATION: Ala, Asp, Asn, or absent
<220> FEATURE:
<221> NAME/KEY: MISC_FEATURE
<222> LOCATION: (4)..(4)
<223> OTHER INFORMATION: Ala, Leu, Thr, or absent
<220> FEATURE:
<221> NAME/KEY: MISC_FEATURE
<222> LOCATION: (5)..(5)
<223> OTHER INFORMATION: Ala or Ser
<220> FEATURE:
<221> NAME/KEY: MISC_FEATURE
<222> LOCATION: (6)..(6)
<223> OTHER INFORMATION: Ala, Ser, Thr, or Val
<220> FEATURE:
<221> NAME/KEY: MISC_FEATURE
<222> LOCATION: (7)..(7)
<223> OTHER INFORMATION: Ala, Cys, or Lys
<220> FEATURE:
<221> NAME/KEY: MISC_FEATURE
<222> LOCATION: (8)..(8)
<223> OTHER INFORMATION: Ala, Leu, Met, or Val
<220> FEATURE:
<221> NAME/KEY: MISC_FEATURE
<222> LOCATION: (9)..(9)
<223> OTHER INFORMATION: Leu or Thr
<220> FEATURE:
<221> NAME/KEY: MISC_FEATURE
<222> LOCATION: (10)..(10)
<223> OTHER INFORMATION: Gly, His, or Gln
<220> FEATURE:
<221> NAME/KEY: MISC_FEATURE
<222> LOCATION: (11)..(11)
<223> OTHER INFORMATION: Lys, Gln, or Arg
<220> FEATURE:
<221> NAME/KEY: MISC_FEATURE
<222> LOCATION: (12)..(12)
<223> OTHER INFORMATION: Ley, Trp, or Tyr
<220> FEATURE:
<221> NAME/KEY: MISC_FEATURE
<222> LOCATION: (13)..(13)
<223> OTHER INFORMATION: Ala, Asn, Gln, Ser, or Thr
<220> FEATURE:
<221> NAME/KEY: MISC_FEATURE
<222> LOCATION: (14)..(14)
<223> OTHER INFORMATION: Ala, Asp, Glu, Gly, Lys, Asn, Gln, or Arg
<220> FEATURE:
<221> NAME/KEY: MISC_FEATURE
<222> LOCATION: (15)..(15)
<223> OTHER INFORMATION: Ala, Asp, Glu, Phe, Leu, Ser, or Tyr
<220> FEATURE:
<221> NAME/KEY: MISC_FEATURE
<222> LOCATION: (16)..(16)
<223> OTHER INFORMATION: Phe or Leu
<220> FEATURE:
<221> NAME/KEY: MISC_FEATURE
<222> LOCATION: (17)..(17)
<223> OTHER INFORMATION: His, Gln, Ser or Val
<220> FEATURE:
<221> NAME/KEY: MISC_FEATURE
<222> LOCATION: (18)..(18)
<223> OTHER INFORMATION: Lys or Arg
<220> FEATURE:
<221> NAME/KEY: MISC_FEATURE
<222> LOCATION: (19)..(19)
<223> OTHER INFORMATION: Phe, Leu, Ser, or absent
<220> FEATURE:
<221> NAME/KEY: MISC_FEATURE
```

```
<222> LOCATION: (20)..(20)
<223> OTHER INFORMATION: His, Lys, Gln, or absent
<220> FEATURE:
<221> NAME/KEY: MISC_FEATURE
<222> LOCATION: (21)..(21)
<223> OTHER INFORMATION: Gln, Thr, or absent
<220> FEATURE:
<221> NAME/KEY: MISC_FEATURE
<222> LOCATION: (22)..(22)
<223> OTHER INFORMATION: Phe, Leu, or Tyr
<220> FEATURE:
<221> NAME/KEY: MISC_FEATURE
<222> LOCATION: (24)..(24)
<223> OTHER INFORMATION: Pro or Arg
<220> FEATURE:
<221> NAME/KEY: MISC_FEATURE
<222> LOCATION: (27)..(27)
<223> OTHER INFORMATION: Thr or Val
<220> FEATURE:
<221> NAME/KEY: MISC_FEATURE
<222> LOCATION: (30)..(30)
<223> OTHER INFORMATION: Glu, Lys or Asn
<220> FEATURE:
<221> NAME/KEY: MISC_FEATURE
<222> LOCATION: (31)..(31)
<223> OTHER INFORMATION: Ala or Thr
<220> FEATURE:
<221> NAME/KEY: MISC_FEATURE
<222> LOCATION: (32)..(32)
<223> OTHER INFORMATION: Phe, Tyr, or absent

<400> SEQUENCE: 68

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Pro Xaa Thr Asn Xaa Gly Ser Xaa Xaa Xaa
            20                  25                  30

<210> SEQ ID NO 69
<211> LENGTH: 8
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<223> OTHER INFORMATION: residues 1 and 8 are independently selected
      residues having side chains which can be chemically bonded to
      each other to form an intramolecular linkage
<220> FEATURE:
<221> NAME/KEY: MISC_FEATURE
<222> LOCATION: (1)..(1)
<223> OTHER INFORMATION: variable amino acid
<220> FEATURE:
<221> NAME/KEY: MISC_FEATURE
<222> LOCATION: (2)..(2)
<223> OTHER INFORMATION: variable amino acid or absent
<220> FEATURE:
<221> NAME/KEY: MISC_FEATURE
<222> LOCATION: (3)..(3)
<223> OTHER INFORMATION: Ala, Gly, Ser, Asp or absent
<220> FEATURE:
<221> NAME/KEY: MISC_FEATURE
<222> LOCATION: (4)..(4)
<223> OTHER INFORMATION: Asn, Ala, Asp, Gly or absent
<220> FEATURE:
<221> NAME/KEY: MISC_FEATURE
<222> LOCATION: (5)..(5)
<223> OTHER INFORMATION: Ala, Leu, Thr, or Ser
<220> FEATURE:
<221> NAME/KEY: MISC_FEATURE
<222> LOCATION: (6)..(6)
<223> OTHER INFORMATION: Ala, Ser, or Thr
<220> FEATURE:
<221> NAME/KEY: MISC_FEATURE
<222> LOCATION: (7)..(7)
<223> OTHER INFORMATION: Ala, Ser, Val, Hse, Ahb, Ahp, D-Thr, Thr, or
      a derivative thereof
```

```
<220> FEATURE:
<221> NAME/KEY: MISC_FEATURE
<222> LOCATION: (8)..(8)
<223> OTHER INFORMATION: variable amino acid

<400> SEQUENCE: 69

Xaa Xaa Xaa Xaa Xaa Xaa Xaa Xaa
1               5

<210> SEQ ID NO 70
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Variable amino acid or absent
<220> FEATURE:
<221> NAME/KEY: MISC_FEATURE
<222> LOCATION: (2)..(2)
<223> OTHER INFORMATION: Variable amino acid or absent
<220> FEATURE:
<221> NAME/KEY: MISC_FEATURE
<222> LOCATION: (3)..(3)
<223> OTHER INFORMATION: Variable amino acid or absent
<220> FEATURE:
<221> NAME/KEY: MISC_FEATURE
<222> LOCATION: (4)..(4)
<223> OTHER INFORMATION: Variable amino acid or absent
<220> FEATURE:
<221> NAME/KEY: MISC_FEATURE
<222> LOCATION: (7)..(7)
<223> OTHER INFORMATION: Gly or Aib
<220> FEATURE:
<221> NAME/KEY: MISC_FEATURE
<222> LOCATION: (8)..(8)
<223> OTHER INFORMATION: Lys, Arg, Orn, homo-Arg, Cit, homo-Lys, or
      Lys(for)
<220> FEATURE:
<221> NAME/KEY: MISC_FEATURE
<222> LOCATION: (12)..(12)
<223> OTHER INFORMATION: Glu or Phe
<220> FEATURE:
<221> NAME/KEY: MISC_FEATURE
<222> LOCATION: (14)..(14)
<223> OTHER INFORMATION: His or Aib
<220> FEATURE:
<221> NAME/KEY: MISC_FEATURE
<222> LOCATION: (15)..(15)
<223> OTHER INFORMATION: Lys, Arg, Orn, homo-Arg, Cit, homo-Lys,
      Lys(for), or Lys(PEG 5000)
<220> FEATURE:
<221> NAME/KEY: MISC_FEATURE
<222> LOCATION: (19)..(19)
<223> OTHER INFORMATION: Tyr or Leu
<220> FEATURE:
<221> NAME/KEY: MISC_FEATURE
<222> LOCATION: (21)..(21)
<223> OTHER INFORMATION: Arg or Pro
<220> FEATURE:
<221> NAME/KEY: MISC_FEATURE
<222> LOCATION: (25)..(25)
<223> OTHER INFORMATION: Variable amino acid or absent
<220> FEATURE:
<221> NAME/KEY: MISC_FEATURE
<222> LOCATION: (26)..(26)
<223> OTHER INFORMATION: Variable amino acid or absent
<220> FEATURE:
<221> NAME/KEY: MISC_FEATURE
<222> LOCATION: (27)..(27)
<223> OTHER INFORMATION: Variable amino acid or absent
<220> FEATURE:
<221> NAME/KEY: MISC_FEATURE
<222> LOCATION: (28)..(28)
<223> OTHER INFORMATION: Variable amino acid or absent
```

-continued

```
<400> SEQUENCE: 70

Xaa Xaa Xaa Xaa Val Leu Xaa Xaa Leu Ser Gln Xaa Leu Xaa Xaa Leu
1               5                   10                  15

Gln Thr Xaa Pro Xaa Thr Asn Thr Xaa Xaa Xaa Xaa
            20                  25

<210> SEQ ID NO 71
<211> LENGTH: 11
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Lys, Tyr, or absent
<220> FEATURE:
<221> NAME/KEY: MISC_FEATURE
<222> LOCATION: (2)..(2)
<223> OTHER INFORMATION: Ser, Pro, or absent
<220> FEATURE:
<221> NAME/KEY: MISC_FEATURE
<222> LOCATION: (3)..(3)
<223> OTHER INFORMATION: Ser, Pro, Arg, or absent
<220> FEATURE:
<221> NAME/KEY: MISC_FEATURE
<222> LOCATION: (4)..(4)
<223> OTHER INFORMATION: Thr or absent
<220> FEATURE:
<221> NAME/KEY: MISC_FEATURE
<222> LOCATION: (5)..(5)
<223> OTHER INFORMATION: Asn or absent
<220> FEATURE:
<221> NAME/KEY: MISC_FEATURE
<222> LOCATION: (6)..(6)
<223> OTHER INFORMATION: Val, Thr, or absent
<220> FEATURE:
<221> NAME/KEY: MISC_FEATURE
<222> LOCATION: (8)..(8)
<223> OTHER INFORMATION: Ser or Glu
<220> FEATURE:
<221> NAME/KEY: MISC_FEATURE
<222> LOCATION: (9)..(9)
<223> OTHER INFORMATION: Asn, Lys, or Gly
<220> FEATURE:
<221> NAME/KEY: MISC_FEATURE
<222> LOCATION: (10)..(10)
<223> OTHER INFORMATION: Thr, Phe, or Ala
<220> FEATURE:
<221> NAME/KEY: MISC_FEATURE
<222> LOCATION: (11)..(11)
<223> OTHER INFORMATION: Tyr, Phe, Pro, or absent

<400> SEQUENCE: 71

Xaa Xaa Xaa Xaa Xaa Xaa Gly Xaa Xaa Xaa Xaa
1               5                   10

<210> SEQ ID NO 72
<211> LENGTH: 8
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: variable amino acid
<220> FEATURE:
<221> NAME/KEY: MISC_FEATURE
<222> LOCATION: (2)..(2)
<223> OTHER INFORMATION: any amino acid or absent
<220> FEATURE:
<221> NAME/KEY: MISC_FEATURE
<222> LOCATION: (3)..(3)
<223> OTHER INFORMATION: Ala, Gly, Ser, Asp or absent
```

```
<220> FEATURE:
<221> NAME/KEY: MISC_FEATURE
<222> LOCATION: (4)..(4)
<223> OTHER INFORMATION: Asn, Ala, Asp, Gly or absent
<220> FEATURE:
<221> NAME/KEY: MISC_FEATURE
<222> LOCATION: (5)..(5)
<223> OTHER INFORMATION: Ala, Leu, Thr, or Ser
<220> FEATURE:
<221> NAME/KEY: MISC_FEATURE
<222> LOCATION: (6)..(6)
<223> OTHER INFORMATION: Ala, Ser, or Thr
<220> FEATURE:
<221> NAME/KEY: MISC_FEATURE
<222> LOCATION: (7)..(7)
<223> OTHER INFORMATION: Ala, Ser, Val, Hse, Ahb, Ahp, D-Thr, Thr, or
      a derivative thereof
<220> FEATURE:
<221> NAME/KEY: MISC_FEATURE
<222> LOCATION: (8)..(8)
<223> OTHER INFORMATION: variable amino acid

<400> SEQUENCE: 72

Xaa Xaa Xaa Xaa Xaa Xaa Xaa Xaa
1               5

<210> SEQ ID NO 73
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Variable amino acid or absent
<220> FEATURE:
<221> NAME/KEY: MISC_FEATURE
<222> LOCATION: (2)..(2)
<223> OTHER INFORMATION: Variable amino acid or absent
<220> FEATURE:
<221> NAME/KEY: MISC_FEATURE
<222> LOCATION: (3)..(3)
<223> OTHER INFORMATION: Variable amino acid or absent
<220> FEATURE:
<221> NAME/KEY: MISC_FEATURE
<222> LOCATION: (4)..(4)
<223> OTHER INFORMATION: Variable amino acid or absent
<220> FEATURE:
<221> NAME/KEY: MISC_FEATURE
<222> LOCATION: (5)..(5)
<223> OTHER INFORMATION: Ala or Val
<220> FEATURE:
<221> NAME/KEY: MISC_FEATURE
<222> LOCATION: (6)..(6)
<223> OTHER INFORMATION: Thr, Met or Leu
<220> FEATURE:
<221> NAME/KEY: MISC_FEATURE
<222> LOCATION: (7)..(7)
<223> OTHER INFORMATION: Gln, Gly, or His
<220> FEATURE:
<221> NAME/KEY: MISC_FEATURE
<222> LOCATION: (9)..(9)
<223> OTHER INFORMATION: Leu or Thr
<220> FEATURE:
<221> NAME/KEY: MISC_FEATURE
<222> LOCATION: (10)..(10)
<223> OTHER INFORMATION: Ala, Thr, Asn, Phe, Tyr, Ser, or Thr
<220> FEATURE:
<221> NAME/KEY: MISC_FEATURE
<222> LOCATION: (11)..(11)
<223> OTHER INFORMATION: Asn, Arg, Ala, Asp, Glu, Gln, Thr, or Gly
<220> FEATURE:
<221> NAME/KEY: MISC_FEATURE
<222> LOCATION: (12)..(12)
<223> OTHER INFORMATION: Phe, Leu, Ser, Glu, Ala, Asp, or Tyr
<220> FEATURE:
<221> NAME/KEY: MISC_FEATURE
```

```
<222> LOCATION: (13)..(13)
<223> OTHER INFORMATION: Leu or Asp
<220> FEATURE:
<221> NAME/KEY: MISC_FEATURE
<222> LOCATION: (14)..(14)
<223> OTHER INFORMATION: Val, His, Ser, Phe, or Aib
<220> FEATURE:
<221> NAME/KEY: MISC_FEATURE
<222> LOCATION: (15)..(15)
<223> OTHER INFORMATION: His, Arg, Lys, Orn, homo-Arg, Cit, homo-Lys,
      Lys(for), or Lys(PEG5000)
<220> FEATURE:
<221> NAME/KEY: MISC_FEATURE
<222> LOCATION: (16)..(16)
<223> OTHER INFORMATION: Leu, Ser or Phe
<220> FEATURE:
<221> NAME/KEY: MISC_FEATURE
<222> LOCATION: (17)..(17)
<223> OTHER INFORMATION: Gln or His
<220> FEATURE:
<221> NAME/KEY: MISC_FEATURE
<222> LOCATION: (18)..(18)
<223> OTHER INFORMATION: Thr or Asn
<220> FEATURE:
<221> NAME/KEY: MISC_FEATURE
<222> LOCATION: (19)..(19)
<223> OTHER INFORMATION: Tyr, Val, Phe, Leu or Met
<220> FEATURE:
<221> NAME/KEY: MISC_FEATURE
<222> LOCATION: (21)..(21)
<223> OTHER INFORMATION: Arg or Pro
<220> FEATURE:
<221> NAME/KEY: MISC_FEATURE
<222> LOCATION: (25)..(25)
<223> OTHER INFORMATION: Variable amino acid or absent
<220> FEATURE:
<221> NAME/KEY: MISC_FEATURE
<222> LOCATION: (26)..(26)
<223> OTHER INFORMATION: Variable amino acid or absent
<220> FEATURE:
<221> NAME/KEY: MISC_FEATURE
<222> LOCATION: (27)..(27)
<223> OTHER INFORMATION: Variable amino acid or absent
<220> FEATURE:
<221> NAME/KEY: MISC_FEATURE
<222> LOCATION: (28)..(28)
<223> OTHER INFORMATION: Variable amino acid or absent

<400> SEQUENCE: 73

Xaa Xaa Xaa Xaa Xaa Xaa Xaa Arg Xaa Xaa Xaa Xaa Xaa Xaa Xaa Xaa
1               5                   10                  15

Xaa Xaa Xaa Pro Xaa Thr Asn Thr Xaa Xaa Xaa Xaa
            20                  25

<210> SEQ ID NO 74
<211> LENGTH: 11
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Lys, Tyr, or absent
<220> FEATURE:
<221> NAME/KEY: MISC_FEATURE
<222> LOCATION: (2)..(2)
<223> OTHER INFORMATION: Ser, Pro, or absent
<220> FEATURE:
<221> NAME/KEY: MISC_FEATURE
<222> LOCATION: (3)..(3)
<223> OTHER INFORMATION: Ser, Pro, Arg, or absent
<220> FEATURE:
<221> NAME/KEY: MISC_FEATURE
<222> LOCATION: (4)..(4)
<223> OTHER INFORMATION: Thr or absent
<220> FEATURE:
```

```
<221> NAME/KEY: MISC_FEATURE
<222> LOCATION: (5)..(5)
<223> OTHER INFORMATION: Asn or absent
<220> FEATURE:
<221> NAME/KEY: MISC_FEATURE
<222> LOCATION: (6)..(6)
<223> OTHER INFORMATION: Val, Thr, or absent
<220> FEATURE:
<221> NAME/KEY: MISC_FEATURE
<222> LOCATION: (8)..(8)
<223> OTHER INFORMATION: Ser or Glu
<220> FEATURE:
<221> NAME/KEY: MISC_FEATURE
<222> LOCATION: (9)..(9)
<223> OTHER INFORMATION: Asn, Lys, or Gly
<220> FEATURE:
<221> NAME/KEY: MISC_FEATURE
<222> LOCATION: (10)..(10)
<223> OTHER INFORMATION: Thr, Phe, or Ala
<220> FEATURE:
<221> NAME/KEY: MISC_FEATURE
<222> LOCATION: (11)..(11)
<223> OTHER INFORMATION: Tyr, Phe, Pro, or absent

<400> SEQUENCE: 74

Xaa Xaa Xaa Xaa Xaa Xaa Gly Xaa Xaa Xaa Xaa
1               5                   10

<210> SEQ ID NO 75
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 75

Lys Cys Asn Thr Ala Thr Cys Val Leu Gly Lys Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 76
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 76

Lys Cys Asn Thr Ala Thr Cys Val Leu Gly Arg Leu Ser Gln Glu Leu
1               5                   10                  15

His Arg Leu Gln Thr Leu Pro Arg Thr Asn Thr Gly Ser Asn Thr Tyr
            20                  25                  30

<210> SEQ ID NO 77
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 77

Lys Cys Asn Thr Ala Thr Cys Val Leu Gly Arg Leu Ser Gln Glu Leu
1               5                   10                  15

His Arg Leu Gln Thr Tyr Pro Pro Thr Asn Thr Gly Ser Asn Thr Tyr
            20                  25                  30

<210> SEQ ID NO 78
<211> LENGTH: 32
```

```
<212> TYPE: PRT
<213> ORGANISM: Artificial Sequence
<220> FEATURE:
<223> OTHER INFORMATION: Synthetic peptide construct

<400> SEQUENCE: 78

Lys Cys Asn Thr Ala Thr Cys Val Leu Gly Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 79
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 79

Lys Cys Asn Thr Ala Thr Cys Val Leu Gly Arg Leu Ser Gln Glu Leu
1               5                   10                  15

His Arg Leu Gln Thr Leu Pro Pro Thr Asn Val Gly Ser Asn Thr Tyr
            20                  25                  30

<210> SEQ ID NO 80
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 80

Lys Cys Asn Thr Ala Thr Cys Val Leu Gly Arg Leu Ala Asn Phe Leu
1               5                   10                  15

His Leu Leu Gln Thr Tyr Pro Arg Thr Asn Thr Gly Ser Asn Thr Tyr
            20                  25                  30

<210> SEQ ID NO 81
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 81

Ala Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 82
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 82

Lys Cys Asn Ala Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 83
<211> LENGTH: 32
```

```
<212> TYPE: PRT
<213> ORGANISM: Artificial Sequence
<220> FEATURE:
<223> OTHER INFORMATION: Synthetic peptide construct

<400> SEQUENCE: 83

Lys Cys Asn Thr Ala Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 84

Cys Ala Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 85
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser

<400> SEQUENCE: 85

Ser Thr Ala Val Leu Gly Arg Leu Ser Gln Glu Leu His Arg Leu Gln
1               5                   10                  15

Thr Tyr Pro Arg Thr Asn Thr Gly Ser Asn Thr Tyr
            20                  25

<210> SEQ ID NO 86
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 86

Cys Ser Asn Ala Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 87

Cys Ser Asn Leu Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30
```

```
<210> SEQ ID NO 88
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 88

Cys Ser Asn Leu Ser Ala Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 89

Lys Cys Asn Thr Ala Thr Cys Val Leu Gly Arg Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 90
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 90

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Gly Thr Pro
            20                  25                  30

<210> SEQ ID NO 91
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 91

Cys Ser Ala Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 92
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Ac-Agy
<220> FEATURE:
<221> NAME/KEY: MISC_FEATURE
<222> LOCATION: (7)..(7)
<223> OTHER INFORMATION: Agy
```

<400> SEQUENCE: 92

Xaa Ser Asn Leu Ser Thr Xaa Val Leu Gly Arg Leu Ser Gln Glu Leu
1               5                   10                  15

His Arg Leu Gln Thr Tyr Pro Arg Thr Asn Thr Gly Ser Asn Thr Tyr
                20                  25                  30

<210> SEQ ID NO 93
<211> LENGTH: 27
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MISC_FEATURE
<222> LOCATION: (6)..(6)
<223> OTHER INFORMATION: Aib

<400> SEQUENCE: 93

Ser Thr Ala Val Leu Xaa Arg Leu Ser Gln Glu Leu Arg Leu Gln Thr
1               5                   10                  15

Tyr Pro Arg Thr Asn Thr Gly Ser Gly Thr Pro
                20                  25

<210> SEQ ID NO 94
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (14)..(14)
<223> OTHER INFORMATION: Lys(For)

<400> SEQUENCE: 94

Ser Thr Ala Val Leu Gly Lys Leu Ser Gln Glu Leu His Lys Leu Gln
1               5                   10                  15

Thr Tyr Pro Arg Thr Asn Thr Gly Ser Gly Thr Pro
                20                  25

<210> SEQ ID NO 95
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MISC_FEATURE
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)

```
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 95

Ser Thr Ala Val Leu Xaa Lys Leu Ser Gln Glu Leu Xaa Lys Leu Gln
1               5                   10                  15

Thr Tyr Pro Arg Thr Asn Thr Gly Ser Asn Thr Tyr
            20                  25

<210> SEQ ID NO 96
<211> LENGTH: 28
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Ser
<220> FEATURE:
<221> NAME/KEY: MISC_FEATURE
<222> LOCATION: (6)..(6)
<223> OTHER INFORMATION: Aib
<220> FEATURE:
<221> NAME/KEY: MOD_RES
<222> LOCATION: (7)..(7)
<223> OTHER INFORMATION: Lys(For)
<220> FEATURE:
<221> NAME/KEY: MOD_RES
<222> LOCATION: (13)..(13)
<223> OTHER INFORMATION: Aib
<220> FEATURE:
<221> NAME/KEY: MOD_RES
<222> LOCATION: (14)..(14)
<223> OTHER INFORMATION: Lys(For)

<400> SEQUENCE: 96

Ser Thr Ala Val Leu Xaa Lys Leu Ser Gln Glu Leu Xaa Lys Leu Gln
1               5                   10                  15

Thr Tyr Pro Arg Thr Asn Val Gly Ser Asn Thr Tyr
            20                  25

<210> SEQ ID NO 97
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 97

Lys Cys Asn Thr Ala Thr Cys Leu Leu Gln Gln Leu Gln Lys Leu Leu
1               5                   10                  15

Gln Lys Leu Lys Gln Tyr Pro Arg Thr Asn Thr Gly Ser Asn Thr Tyr
            20                  25                  30

<210> SEQ ID NO 98
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 98

Lys Cys Asn Thr Ala Ser Cys Val Leu Gly Arg Leu Ser Gln Glu Leu
```

```
                1               5                  10                  15
His Arg Leu Gln Thr Tyr Pro Arg Thr Asn Thr Gly Ser Asn Thr Tyr
            20                  25                  30

<210> SEQ ID NO 99
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 99

Lys Cys Asn Thr Ala Val Cys Val Leu Gly Arg Leu Ser Gln Glu Leu
1               5                  10                  15

His Arg Leu Gln Thr Tyr Pro Arg Thr Asn Thr Gly Ser Asn Thr Tyr
            20                  25                  30

<210> SEQ ID NO 100
<211> LENGTH: 29
<212> TYPE: PRT
<213> ORGANISM: Artificial Sequence
<220> FEATURE:
<223> OTHER INFORMATION: Synthetic peptide construct

<400> SEQUENCE: 100

Lys Cys Asn Thr Ala Thr Cys Val Leu Gly Arg Leu Ser Gln Glu Leu
1               5                  10                  15

His Arg Tyr Pro Arg Thr Asn Thr Gly Ser Asn Thr Tyr
            20                  25

<210> SEQ ID NO 101
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (11)..(11)
<223> OTHER INFORMATION: Lys(For)
<220> FEATURE:
<221> NAME/KEY: MOD_RES
<222> LOCATION: (18)..(18)
<223> OTHER INFORMATION: Lys(For)

<400> SEQUENCE: 101

Lys Cys Asn Thr Ala Thr Cys Val Leu Gly Lys Leu Ser Gln Glu Leu
1               5                  10                  15

His Lys Leu Gln Thr Tyr Pro Arg Thr Asn Thr Gly Ser Asn Thr Tyr
            20                  25                  30

<210> SEQ ID NO 102
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (6)..(6)
<223> OTHER INFORMATION: D-Thr

<400> SEQUENCE: 102

Lys Cys Asn Thr Ala Xaa Cys Val Leu Gly Arg Leu Ser Gln Glu Leu
1               5                  10                  15

His Arg Leu Gln Thr Tyr Pro Arg Thr Asn Thr Gly Ser Asn Thr Tyr
            20                  25                  30
```

```
<210> SEQ ID NO 103
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (6)..(6)
<223> OTHER INFORMATION: dAh

<400> SEQUENCE: 103

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 104
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Ac-Ala
<220> FEATURE:
<221> NAME/KEY: MOD_RES
<222> LOCATION: (18)..(18)
<223> OTHER INFORMATION: Lys(PEG5000)

<400> SEQUENCE: 104

Ala Cys Asn Thr Ala Thr Cys Val Leu Gly Arg Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 105
<211> LENGTH: 35
<212> TYPE: PRT
<213> ORGANISM: Artificial Sequence
<220> FEATURE:
<223> OTHER INFORMATION: Synthetic peptide construct

<400> SEQUENCE: 105

Lys Cys Asn Thr Ala Thr Cys Val Leu Gly Arg Leu Ser Gln Glu Leu
1               5                   10                  15

His Arg Leu Gln Thr Leu Gln Thr Tyr Pro Arg Thr Asn Thr Gly Ser
            20                  25                  30

Asn Thr Tyr
        35

<210> SEQ ID NO 106
<211> LENGTH: 36
<212> TYPE: PRT
<213> ORGANISM: Artificial Sequence
<220> FEATURE:
<223> OTHER INFORMATION: Synthetic peptide construct

<400> SEQUENCE: 106

Lys Cys Asn Thr Ala Thr Cys Val Leu Gly Arg Leu Ser Gln Glu Leu
1               5                   10                  15

His Arg Leu Gln Thr Leu Leu Gln Thr Tyr Pro Arg Thr Asn Thr Gly
            20                  25                  30
```

Ser Asn Thr Tyr
        35

<210> SEQ ID NO 107
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 107

Lys Cys Asn Thr Ala Thr Cys Val Leu Gly Lys Leu Ser Gln Glu Leu
1               5                   10                  15

His Lys Leu Gln Thr Tyr Pro Arg Thr Asn Thr Gly Ser Asn Thr Tyr
            20                  25                  30

<210> SEQ ID NO 108
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 108

Lys Cys Asn Thr Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 109
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 109

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 110
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 110

Lys Cys Asn Thr Ala Thr Cys Ala Thr Gln Arg Leu Ser Gln Glu Leu
1               5                   10                  15

His Arg Leu Gln Thr Tyr Pro Arg Thr Asn Val Gly Ser Asn Thr Tyr
            20                  25                  30

<210> SEQ ID NO 111
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 111

Lys Cys Asn Thr Ser Thr Cys Ala Thr Gln Arg Leu Ala Asn Glu Leu
1               5                   10                  15

```
Val Arg Leu Gln Thr Tyr Pro Arg Thr Asn Val Gly Ser Asn Thr Tyr
        20                  25                  30

<210> SEQ ID NO 112
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (6)..(6)
<223> OTHER INFORMATION: Hse

<400> SEQUENCE: 112

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
        20                  25                  30

<210> SEQ ID NO 113
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (6)..(6)
<223> OTHER INFORMATION: Ahb

<400> SEQUENCE: 113

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
        20                  25                  30

<210> SEQ ID NO 114
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (6)..(6)
<223> OTHER INFORMATION: Ahp

<400> SEQUENCE: 114

Lys Cys Asn Thr Ala Xaa Cys Val Leu Gly Arg Leu Ser Gln Glu Leu
1               5                   10                  15

His Arg Leu Gln Thr Tyr Pro Arg Thr Asn Thr Gly Ser Asn Thr Tyr
        20                  25                  30

<210> SEQ ID NO 115
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (6)..(6)
<223> OTHER INFORMATION: Thr(OPO3H2)

<400> SEQUENCE: 115

Lys Cys Asn Thr Ala Thr Cys Val Leu Gly Arg Leu Ser Gln Glu Leu
1               5                   10                  15
```

His Arg Leu Gln Thr Tyr Pro Arg Thr Asn Thr Gly Ser Asn Thr Tyr
            20                  25                  30

<210> SEQ ID NO 116
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (11)..(11)
<223> OTHER INFORMATION: Orn
<220> FEATURE:
<221> NAME/KEY: MISC_FEATURE
<222> LOCATION: (18)..(18)
<223> OTHER INFORMATION: Orn

<400> SEQUENCE: 116

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 117
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (11)..(11)
<223> OTHER INFORMATION: Cit
<220> FEATURE:
<221> NAME/KEY: MISC_FEATURE
<222> LOCATION: (18)..(18)
<223> OTHER INFORMATION: Cit

<400> SEQUENCE: 117

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 118
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (11)..(11)
<223> OTHER INFORMATION: homo-Lys
<220> FEATURE:
<221> NAME/KEY: MISC_FEATURE
<222> LOCATION: (18)..(18)
<223> OTHER INFORMATION: homo-Lys

<400> SEQUENCE: 118

Lys Cys Asn Thr Ala Thr Cys Val Leu Gly Xaa Leu Ser Gln Glu Leu
1               5                   10                  15

His Xaa Leu Gln Thr Tyr Pro Arg Thr Asn Thr Gly Ser Asn Thr Tyr
            20                  25                  30

<210> SEQ ID NO 119
<211> LENGTH: 33
<212> TYPE: PRT
<213> ORGANISM: Artificial Sequence

```
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: L-Octylglycine

<400> SEQUENCE: 119
```

Xaa Lys Cys Asn Thr Ala Thr Cys Val Leu Gly Arg Leu Ser Gln Glu
1               5                   10                  15

Leu His Arg Leu Gln Thr Tyr Pro Arg Thr Asn Thr Gly Ser Asn Thr
            20                  25                  30

Tyr

```
<210> SEQ ID NO 120
<211> LENGTH: 31
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: N-3,6-dioxaoctanoyl-Cys

<400> SEQUENCE: 120
```

Cys Asn Thr Ala Thr Cys Val Leu Gly Arg Leu Ser Gln Glu Leu His
1               5                   10                  15

Arg Leu Gln Thr Val Pro Arg Thr Asn Thr Gly Ser Asn Thr Tyr
            20                  25                  30

```
<210> SEQ ID NO 121
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 121
```

Lys Cys Asn Thr Ala Thr Cys Met Leu Gly Arg Tyr Thr Gln Asp Phe
1               5                   10                  15

His Arg Leu Gln Thr Tyr Pro Arg Thr Asn Thr Gly Ser Asn Thr Tyr
            20                  25                  30

```
<210> SEQ ID NO 122
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 122
```

Asp Ser Asn Leu Ser Thr Lys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

```
<210> SEQ ID NO 123
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 123
```

Lys Asp Asn Thr Ala Thr Lys Val Leu Gly Arg Leu Ser Gln Glu Leu

```
                1               5                  10                  15
His Arg Leu Gln Thr Tyr Pro Arg Thr Asn Thr Gly Ser Asn Thr Tyr
            20                  25                  30
```

<210> SEQ ID NO 124
<211> LENGTH: 31
<212> TYPE: PRT
<213> ORGANISM: Artificial Sequence
<220> FEATURE:
<223> OTHER INFORMATION: Synthetic peptide construct

<400> SEQUENCE: 124

```
Cys Asn Thr Ala Thr Cys Val Leu Gly Arg Leu Ser Gln Glu Leu His
1               5                   10                  15
Arg Leu Gln Thr Tyr Pro Arg Thr Asn Thr Gly Ser Asn Thr Tyr
            20                  25                  30
```

<210> SEQ ID NO 125
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (33)..(33)
<223> OTHER INFORMATION: 9Anc

<400> SEQUENCE: 125

```
Lys Cys Asn Thr Ala Thr Cys Val Leu Gly Arg Leu Ser Gln Glu Leu
1               5                   10                  15
His Arg Leu Gln Thr Tyr Pro Arg Thr Asn Thr Gly Ser Asn Thr Tyr
            20                  25                  30
Xaa
```

<210> SEQ ID NO 126
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (33)..(33)
<223> OTHER INFORMATION: L-octylglycine

<400> SEQUENCE: 126

```
Lys Cys Asn Thr Ala Thr Cys Val Leu Gly Arg Leu Ser Gln Glu Leu
1               5                   10                  15
His Arg Leu Gln Thr Tyr Pro Arg Thr Asn Thr Gly Ser Asn Thr Tyr
            20                  25                  30
Xaa
```

<210> SEQ ID NO 127
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: N-isocaproyl-Lys

<400> SEQUENCE: 127

Lys Cys Asn Thr Ala Thr Cys Val Leu Gly Arg Leu Ser Gln Glu Leu

```
                1               5                   10                  15
His Arg Leu Gln Thr Tyr Pro Arg Thr Asn Thr Gly Ser Asn Thr Tyr
            20                  25                  30

<210> SEQ ID NO 128
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (11)..(11)
<223> OTHER INFORMATION: homo-Arg
<220> FEATURE:
<221> NAME/KEY: MISC_FEATURE
<222> LOCATION: (18)..(18)
<223> OTHER INFORMATION: homo-Arg

<400> SEQUENCE: 128

Lys Cys Asn Thr Ala Thr Cys Val Leu Gly Xaa Leu Ser Gln Glu Leu
1               5                   10                  15
His Xaa Leu Gln Thr Tyr Pro Arg Thr Asn Thr Gly Ser Asn Thr Tyr
            20                  25                  30

<210> SEQ ID NO 129
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 129

Phe Cys Asn Thr Ala Thr Cys Val Leu Gly Arg Leu Ser Gln Glu Leu
1               5                   10                  15
His Arg Leu Gln Thr Tyr Pro Arg Thr Asn Thr Gly Ser Asn Thr Tyr
            20                  25                  30

<210> SEQ ID NO 130
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (18)..(18)
<223> OTHER INFORMATION: Cit

<400> SEQUENCE: 130

Lys Cys Asn Thr Ala Thr Cys Val Leu Gly Arg Leu Ser Gln Glu Leu
1               5                   10                  15
His Xaa Leu Gln Thr Tyr Pro Arg Thr Asn Thr Gly Ser Asn Thr Tyr
            20                  25                  30

<210> SEQ ID NO 131
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (18)..(18)
<223> OTHER INFORMATION: Orn

<400> SEQUENCE: 131

Lys Cys Asn Thr Ala Thr Cys Val Leu Gly Arg Leu Ser Gln Glu Leu
```

```
                1               5                  10                  15

His Xaa Leu Gln Thr Tyr Pro Arg Thr Asn Thr Gly Ser Asn Thr Tyr
                        20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 132

Ile Cys Asn Thr Ala Thr Cys Val Leu Gly Arg Leu Ser Gln Glu Leu
1               5                  10                  15

His Arg Leu Gln Thr Tyr Pro Arg Thr Asn Thr Gly Ser Asn Thr Tyr
                        20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: L-Octylglycine

<400> SEQUENCE: 133

Xaa Cys Asn Thr Ala Thr Cys Val Leu Gly Arg Leu Ser Gln Glu Leu
1               5                  10                  15

His Arg Leu Gln Thr Tyr Pro Arg Thr Asn Thr Gly Ser Asn Thr Tyr
                        20                  25                  30

<210> SEQ ID NO 134
<211> LENGTH: 31
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Cys

<400> SEQUENCE: 134

Cys Asn Thr Ala Thr Cys Val Leu Gly Arg Leu Ser Gln Glu Leu His
1               5                  10                  15

Arg Leu Gln Thr Tyr Pro Arg Thr Asn Thr Gly Ser Asn Thr Tyr
                        20                  25                  30

<210> SEQ ID NO 135
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (11)..(11)
<223> OTHER INFORMATION: Cit

<400> SEQUENCE: 135

Lys Cys Asn Thr Ala Thr Cys Val Leu Gly Xaa Leu Ser Gln Glu Leu
1               5                  10                  15

His Arg Leu Gln Thr Tyr Pro Arg Thr Asn Thr Gly Ser Asn Thr Tyr
                        20                  25                  30
```

<210> SEQ ID NO 136
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (33)..(33)
<223> OTHER INFORMATION: 4ABU

<400> SEQUENCE: 136

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 137
<211> LENGTH: 33
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Isocaproyl-Lys
<220> FEATURE:
<221> NAME/KEY: MISC_FEATURE
<222> LOCATION: (33)..(33)
<223> OTHER INFORMATION: 4ABU

<400> SEQUENCE: 137

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

Xaa

<210> SEQ ID NO 138
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 138

Lys Cys Asn Thr Ser Thr Cys Ala Thr Gln Arg Leu Ala Asn Glu Leu
1               5                   10                  15

Val Arg Leu Gln Thr Tyr Pro Arg Thr Asn Val Gly Ser Glu Ala Phe
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: Synthetic peptide construct

<400> SEQUENCE: 139

Lys Cys Asn Thr Ala Thr Cys Val Leu Gly Arg Leu Ser Gln Glu Leu
1               5                   10                  15

His Arg Leu Gln Thr Tyr Pro Thr Asn Val Gly Ser Glu Ala Phe
            20                  25                  30

<210> SEQ ID NO 140
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 140

Lys Cys Asn Thr Ala Thr Cys Val Leu Gly Arg Leu Ser Arg Ser Leu
1               5                   10                  15

His Arg Leu Gln Thr Tyr Pro Arg Thr Asn Thr Gly Ser Asn Thr Tyr
            20                  25                  30

<210> SEQ ID NO 141
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 141

Lys Cys Asn Thr Ala Thr Cys Val Thr His Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 142
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 142

Lys Cys Asn Thr Ala Thr Cys Val Leu Gly Arg Leu Ala Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 143
<211> LENGTH: 30
<212> TYPE: PRT
<213> ORGANISM: Artificial Sequence
<220> FEATURE:
<223> OTHER INFORMATION: Synthetic peptide construct

<400> SEQUENCE: 143

Cys Asn Thr Ala Thr Cys Val Leu Gly Arg Leu Ser Gln Glu Leu His
1               5                   10                  15

Arg Leu Gln Thr Tyr Pro Arg Thr Asn Thr Gly Ser Asn Thr
            20                  25                  30

<210> SEQ ID NO 144
<211> LENGTH: 33
<212> TYPE: PRT
<213> ORGANISM: Artificial Sequence
<220> FEATURE:
<223> OTHER INFORMATION: Synthetic peptide construct

<400> SEQUENCE: 144

Lys Cys Asn Thr Ala Thr Cys Val Leu Gly Arg Leu Ser Gln Glu Leu
1               5                   10                  15

His Arg Leu Gln Asn Phe Val Pro Arg Thr Asn Thr Gly Ser Asn Thr
            20                  25                  30

Tyr

<210> SEQ ID NO 145
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 145

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Glu Thr Phe
            20                  25                  30

<210> SEQ ID NO 146
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 146

Ala Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 147
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 147

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Lys Ala Phe
            20                  25                  30

<210> SEQ ID NO 148
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 148

Lys Cys Asp Thr Ala Thr Cys Val Thr His Arg Leu Ala Gly Leu Leu
1               5                   10                  15

Ser Arg Ser Gln Thr Tyr Pro Arg Thr Asn Thr Gly Ser Asn Thr Tyr
            20                  25                  30

<210> SEQ ID NO 149
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 149

Lys Cys Asn Thr Ala Thr Cys Val Leu Gly Arg Leu Ala Asp Ala Leu
1               5                   10                  15

His Arg Leu Gln Thr Tyr Pro Arg Thr Asn Thr Gly Ser Asn Thr Tyr
            20                  25                  30

<210> SEQ ID NO 150
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 150

Lys Cys Asn Thr Ala Thr Cys Val Leu Gly Arg Leu Ala Ala Phe Leu
1               5                   10                  15

His Arg Leu Gln Thr Tyr Pro Arg Thr Asn Thr Gly Ser Asn Thr Tyr
            20                  25                  30

<210> SEQ ID NO 151
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 151

Ser Cys Asn Thr Ala Thr Cys Val Leu Gly Arg Leu Ala Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 152
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 152

Lys Cys Asn Thr Ala Thr Cys Val Leu Gly Arg Leu Ser Gln Glu Leu
1               5                   10                  15

His Arg Leu Gln Thr Met Pro Arg Thr Asn Thr Gly Ser Asn Thr Tyr
            20                  25                  30

<210> SEQ ID NO 153
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 153

Lys Cys Asn Thr Ala Thr Cys Val Leu Gly Arg Leu Ser Gln Glu Leu
1               5                   10                  15

His Arg Leu Gln Thr Val Pro Arg Thr Asn Thr Gly Ser Asn Thr Tyr
            20                  25                  30

<210> SEQ ID NO 154
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 154

Lys Cys Asn Thr Ala Thr Cys Val Leu Gly Arg Leu Asn Glu Tyr Leu
1               5                   10                  15

His Arg Leu Gln Thr Tyr Pro Arg Thr Asn Thr Gly Ser Asn Thr Tyr
            20                  25                  30

<210> SEQ ID NO 155
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 155

Ser Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 156
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 156

Lys Cys Asn Thr Ala Thr Cys Val Leu Gly Arg Leu Thr Glu Phe Leu
1               5                   10                  15

His Arg Leu Gln Thr Tyr Pro Arg Thr Asn Thr Gly Ser Asn Thr Tyr
            20                  25                  30

<210> SEQ ID NO 157
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 157

Lys Cys Asn Thr Ala Thr Cys Val Leu Gly Arg Leu Ala Glu Phe Leu
1               5                   10                  15

His Arg Leu Gln Thr Tyr Pro Arg Thr Asn Thr Gly Ser Asn Thr Tyr
            20                  25                  30

<210> SEQ ID NO 158
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 158

Lys Cys Asn Thr Ala Thr Cys Val Leu Gly Arg Leu Thr Asp Tyr Leu
1               5                   10                  15

His Arg Leu Gln Thr Tyr Pro Arg Thr Asn Thr Gly Ser Asn Thr Tyr
            20                  25                  30

<210> SEQ ID NO 159
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 159

Lys Cys Asn Thr Ala Thr Cys Val Leu Gly Arg Leu Ala Gln Phe Leu
1               5                   10                  15

His Arg Leu Gln Thr Tyr Pro Arg Thr Asn Thr Gly Ser Asn Thr Tyr
            20                  25                  30

<210> SEQ ID NO 160
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 160

Lys Cys Asn Thr Ala Thr Cys Val Leu Gly Arg Leu Ala Asp Phe Leu
1               5                   10                  15

His Arg Phe Gln Thr Phe Pro Arg Thr Asn Thr Gly Ser Asn Thr Tyr
            20                  25                  30

<210> SEQ ID NO 161
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 161

Lys Cys Asn Thr Ala Thr Cys Val Leu Gly Arg Leu Ala Asp Phe Leu
1               5                   10                  15

His Arg Phe His Thr Phe Pro Arg Thr Asn Thr Gly Ser Asn Thr Tyr
            20                  25                  30

<210> SEQ ID NO 162
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 162

Lys Cys Asn Thr Ala Thr Cys Val Leu Gly Arg Leu Ala Asp Phe Leu
1               5                   10                  15

His Arg Phe Gln Thr Phe Pro Arg Thr Asn Thr Gly Ser Gly Thr Pro
            20                  25                  30

<210> SEQ ID NO 163
<211> LENGTH: 31
<212> TYPE: PRT
<213> ORGANISM: Artificial Sequence
<220> FEATURE:
<223> OTHER INFORMATION: Synthetic peptide construct

<400> SEQUENCE: 163

Cys Asn Thr Ala Thr Cys Val Leu Gly Arg Leu Ala Asp Phe Leu His
1               5                   10                  15

Arg Leu Gln Thr Tyr Pro Arg Thr Asn Thr Gly Ser Asn Thr Tyr
            20                  25                  30

<210> SEQ ID NO 164
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 164

Lys Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 165
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 165

Lys Cys Asn Thr Ala Thr Cys Val Leu Gly Arg Leu Phe Asp Phe Leu
1               5                   10                  15

His Arg Leu Gln Thr Tyr Pro Arg Thr Asn Thr Gly Ser Asn Thr Tyr
            20                  25                  30

<210> SEQ ID NO 166
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 166

Lys Cys Asn Thr Ala Thr Cys Val Leu Gly Arg Leu Ala Ala Ala Leu
1               5                   10                  15

His Arg Leu Gln Thr Tyr Pro Arg Thr Asn Thr Gly Ser Asn Thr Tyr
            20                  25                  30

<210> SEQ ID NO 167
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 167

Thr Cys Asp Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 168
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 168

Cys Ser Asn Leu Ser Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 169
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 169

Lys Cys Asn Thr Ala Thr Cys Ala Thr Gln Arg Leu Ala Asn Glu Leu
1               5                   10                  15

Val Arg Leu Gln Thr Tyr Pro Arg Thr Asn Val Gly Ser Asn Thr Tyr
            20                  25                  30

<210> SEQ ID NO 170
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 170

Cys Ser Asn Leu Ser Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 171
<211> LENGTH: 32
<212> TYPE: PRT
<213> ORGANISM: Artificial Sequence
<220> FEATURE:
<223> OTHER INFORMATION: Synthetic peptide construct

<400> SEQUENCE: 171

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 172
<211> LENGTH: 25
<212> TYPE: PRT
<213> ORGANISM: Artificial Sequence
<220> FEATURE:
<223> OTHER INFORMATION: Synthetic peptide construct

<400> SEQUENCE: 172

Val Leu Gly Lys Leu Ser Gln Glu Leu His Lys Leu Gln Thr Tyr Pro
1               5                   10                  15

Arg Thr Asn Thr Gly Ser Gly Thr Pro
            20                  25

<210> SEQ ID NO 173
<211> LENGTH: 25
<212> TYPE: PRT
<213> ORGANISM: Artificial Sequence
<220> FEATURE:
<223> OTHER INFORMATION: Synthetic peptide construct

<400> SEQUENCE: 173

Val Leu Gly Lys Leu Ser Gln Glu Leu His Lys Leu Gln Thr Tyr Pro
1               5                   10                  15

Arg Thr Asn Thr Gly Ser Asn Thr Tyr
            20                  25

<210> SEQ ID NO 174
<211> LENGTH: 25
<212> TYPE: PRT
<213> ORGANISM: Artificial Sequence
<220> FEATURE:
<223> OTHER INFORMATION: Synthetic peptide construct
<220> FEATURE:
<221> NAME/KEY: MISC_FEATURE
<222> LOCATION: (1)..(1)
<223> OTHER INFORMATION: Ala or absent
<220> FEATURE:
<221> NAME/KEY: MISC_FEATURE

```
<222> LOCATION: (4)..(4)
<223> OTHER INFORMATION: Arg, Gln, Lys, Asn or Leu
<220> FEATURE:
<221> NAME/KEY: MISC_FEATURE
<222> LOCATION: (8)..(8)
<223> OTHER INFORMATION: Gln, Glu, Asn, Asp or Phe
<220> FEATURE:
<221> NAME/KEY: MISC_FEATURE
<222> LOCATION: (22)..(22)
<223> OTHER INFORMATION: Ala or Ser

<400> SEQUENCE: 174

Xaa Thr Gln Xaa Leu Ala Asn Xaa Leu Val Arg Leu Gln Thr Tyr Pro
 1               5                  10                  15

Arg Thr Asn Val Gly Xaa Asn Thr Tyr
            20                  25

<210> SEQ ID NO 175
<211> LENGTH: 25
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: acetyl-Ala

<400> SEQUENCE: 175

Ala Thr Gln Arg Leu Ala Asn Glu Leu Val Arg Leu Gln Thr Tyr Pro
 1               5                  10                  15

Arg Thr Asn Val Gly Ser Asn Thr Tyr
            20                  25

<210> SEQ ID NO 176
<211> LENGTH: 25
<212> TYPE: PRT
<213> ORGANISM: Artificial Sequence
<220> FEATURE:
<223> OTHER INFORMATION: Synthetic peptide construct

<400> SEQUENCE: 176

Ala Thr Gln Gln Leu Ala Asn Gln Leu Val Arg Leu Gln Thr Tyr Pro
 1               5                  10                  15

Arg Thr Asn Val Gly Ser Asn Thr Tyr
            20                  25

<210> SEQ ID NO 177
<211> LENGTH: 25
<212> TYPE: PRT
<213> ORGANISM: Artificial Sequence
<220> FEATURE:
<223> OTHER INFORMATION: Synthetic peptide construct

<400> SEQUENCE: 177

Ala Thr Gln Leu Leu Ala Asn Gln Leu Val Arg Leu Gln Thr Tyr Pro
 1               5                  10                  15

Arg Thr Asn Val Gly Ser Asn Thr Tyr
            20                  25

<210> SEQ ID NO 178
<211> LENGTH: 25
<212> TYPE: PRT
<213> ORGANISM: Artificial Sequence
<220> FEATURE:
<223> OTHER INFORMATION: Synthetic peptide construct

<400> SEQUENCE: 178
```

```
Ala Thr Gln Arg Leu Ala Asn Gln Leu Val Arg Leu Gln Thr Tyr Pro
1               5                   10                  15

Arg Thr Asn Val Gly Ser Asn Thr Tyr
            20                  25

<210> SEQ ID NO 179
<211> LENGTH: 25
<212> TYPE: PRT
<213> ORGANISM: Artificial Sequence
<220> FEATURE:
<223> OTHER INFORMATION: Synthetic peptide construct

<400> SEQUENCE: 179

Ala Thr Gln Leu Leu Ala Asn Glu Leu Val Arg Leu Gln Thr Tyr Pro
1               5                   10                  15

Arg Thr Asn Val Gly Ser Asn Thr Tyr
            20                  25

<210> SEQ ID NO 180
<211> LENGTH: 25
<212> TYPE: PRT
<213> ORGANISM: Artificial Sequence
<220> FEATURE:
<223> OTHER INFORMATION: Synthetic peptide construct

<400> SEQUENCE: 180

Ala Thr Gln Gln Leu Ala Asn Glu Leu Val Arg Leu Gln Thr Tyr Pro
1               5                   10                  15

Arg Thr Asn Val Gly Ser Asn Thr Tyr
            20                  25

<210> SEQ ID NO 181
<211> LENGTH: 39
<212> TYPE: PRT
<213> ORGANISM: Heloderma horridum

<400> SEQUENCE: 181

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 182
<211> LENGTH: 39
<212> TYPE: PRT
<213> ORGANISM: Heloderma spectum

<400> SEQUENCE: 182

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 183
<211> LENGTH: 39
<212> TYPE: PRT
<213> ORGANISM: Artificial Sequence
<220> FEATURE:
<223> OTHER INFORMATION: Synthetic peptide construct
```

```
<400> SEQUENCE: 183

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 184
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 184

His Gly Glu Gly Ala Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 185
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 185

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn Gly Gly Pro Ser
            20                  25                  30

Ser Gly Ala Pro Pro Ser
        35

<210> SEQ ID NO 186
<211> LENGTH: 30
<212> TYPE: PRT
<213> ORGANISM: Artificial Sequence
<220> FEATURE:
<223> OTHER INFORMATION: Synthetic peptide construct

<400> SEQUENCE: 186

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 187
<211> LENGTH: 28
<212> TYPE: PRT
<213> ORGANISM: Artificial Sequence
<220> FEATURE:
<223> OTHER INFORMATION: Synthetic peptide construct

<400> SEQUENCE: 187

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25
```

```
                     20                  25

<210> SEQ ID NO 188
<211> LENGTH: 28
<212> TYPE: PRT
<213> ORGANISM: Artificial Sequence
<220> FEATURE:
<223> OTHER INFORMATION: Synthetic peptide construct

<400> SEQUENCE: 188

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 189
<211> LENGTH: 28
<212> TYPE: PRT
<213> ORGANISM: Artificial Sequence
<220> FEATURE:
<223> OTHER INFORMATION: Synthetic peptide construct

<400> SEQUENCE: 189

His Gly Glu Gly Thr Phe Thr Ser Asp Leu Ser Lys Gln Leu Glu Glu
1               5                   10                  15

Glu Ala Val Arg Leu Ala Ile Glu Phe Leu Lys Asn
            20                  25

<210> SEQ ID NO 190
<211> LENGTH: 39
<212> TYPE: PRT
<213> ORGANISM: Artificial Sequence
<220> FEATURE:
<223> OTHER INFORMATION: Synthetic peptide construct

<400> SEQUENCE: 190

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 191
<211> LENGTH: 147
<212> TYPE: PRT
<213> ORGANISM: Artificial Sequence
<220> FEATURE:
<223> OTHER INFORMATION: Synthetic peptide construct

<400> SEQUENCE: 191

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95
```

```
Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
        130                 135                 140

Pro Gly Cys
145

<210> SEQ ID NO 192
<211> LENGTH: 32
<212> TYPE: PRT
<213> ORGANISM: Artificial Sequence
<220> FEATURE:
<223> OTHER INFORMATION: Synthetic peptide construct
<220> FEATURE:
<221> NAME/KEY: MOD_RES
<222> LOCATION: (1)..(1)
<223> OTHER INFORMATION: Ac-Lys
<220> FEATURE:
<221> NAME/KEY: MISC_FEATURE
<222> LOCATION: (2)..(2)
<223> OTHER INFORMATION: Agy
<220> FEATURE:
<221> NAME/KEY: MISC_FEATURE
<222> LOCATION: (7)..(7)
<223> OTHER INFORMATION: Agy

<400> SEQUENCE: 192

Lys Xaa Asn Thr Ala Thr Xaa Val Leu Gly Arg Leu Ser Gln Glu Leu
1                5                   10                  15

His Arg Leu Gln Thr Tyr Pro Arg Thr Asn Thr Gly Ser Asn Thr Tyr
                20                  25                  30
```